United States Patent
Zeng et al.

(10) Patent No.: US 7,919,504 B2
(45) Date of Patent: Apr. 5, 2011

(54) THIADIAZOLE MODULATORS OF PKB

(75) Inventors: Qingping Zeng, Thousand Oaks, CA (US); Chester Chenguang Yuan, Newbury Park, CA (US); Guomin Yao, Newbury Park, CA (US); Xianghong Wang, Moorpark, CA (US); Seifu Tadesse, Simi Valley, CA (US); Andreas Reichelt, Moorpark, CA (US); Qingyian Liu, Camarillo, CA (US); Matthew R. Lee, Calabasas, CA (US); Xin Huang, Roslindale, MA (US); Fang-Tsao Hong, Thousand Oaks, CA (US); Nianhe Han, Thousand Oaks, CA (US); Christopher H. Fotsch, Thousand Oaks, CA (US); Celia Dominguez, Los Angeles, CA (US); Matthew P. Bourbeau, Woodland Hills, CA (US); John G. Allen, Newbury Park, CA (US)

(73) Assignee: Amgen Inc., Thousand Oaks, CA (US)

(*) Notice: Subject to any disclaimer, the term of this patent is extended or adjusted under 35 U.S.C. 154(b) by 409 days.

(21) Appl. No.: 12/218,523

(22) Filed: Jul. 15, 2008

(65) Prior Publication Data
US 2009/0298836 A1    Dec. 3, 2009

Related U.S. Application Data

(60) Provisional application No. 60/959,974, filed on Jul. 17, 2007.

(51) Int. Cl.
A61K 31/47    (2006.01)
C07D 401/04   (2006.01)
(52) U.S. Cl. .................... 514/307; 546/144
(58) Field of Classification Search .......... None
See application file for complete search history.

(56) References Cited

U.S. PATENT DOCUMENTS

| | | |
|---|---|---|
| 3,452,035 A | 6/1969 | Berkelhammer et al. |
| 3,591,600 A | 7/1971 | Francher |
| 3,666,860 A | 5/1972 | Berkelhammer et al. |
| 3,740,434 A | 6/1973 | Berkelhammer et al. |
| 3,830,924 A | 8/1974 | Berkelhammer et al. |
| 3,842,174 A | 10/1974 | Berkelhammer et al. |
| 3,904,756 A | 9/1975 | Berkelhammer et al. |
| 3,932,400 A | 1/1976 | Hibino et al. |
| 3,991,200 A | 11/1976 | Berkelhammer et al. |
| 4,086,238 A | 4/1978 | Krenzer |
| 4,086,239 A | 4/1978 | Fancher |
| 4,146,400 A | 3/1979 | Lowski et al. |
| 4,297,365 A | 10/1981 | Rajappa et al. |
| 4,451,471 A | 5/1984 | Ferrini et al. |
| 4,496,560 A | 1/1985 | Farge et al. |
| 4,596,802 A | 6/1986 | Wermuth et al. |
| 4,851,418 A | 7/1989 | Sanchez |
| 4,886,833 A | 12/1989 | Gayer et al. |
| 5,057,520 A | 10/1991 | Chu et al. |
| 5,086,053 A | 2/1992 | Brodin et al. |
| 5,145,860 A | 9/1992 | Takasugi et al. |
| 5,232,921 A | 8/1993 | Biziere et al. |
| 5,254,685 A | 10/1993 | Yokomoto et al. |
| 5,290,794 A | 3/1994 | Mehta et al. |
| 5,302,608 A | 4/1994 | Sohda et al. |
| 5,410,024 A | 4/1995 | Pettit et al. |
| 5,550,138 A | 8/1996 | Sohda et al. |
| 5,693,643 A | 12/1997 | Gilbert et al. |
| 5,834,401 A | 11/1998 | Kawamura et al. |
| 5,856,347 A | 1/1999 | Hashiguchi et al. |
| 5,977,027 A | 11/1999 | Kawamura et al. |
| 6,323,315 B1 | 11/2001 | Pettit et al. |
| 6,420,400 B1 | 7/2002 | Zhang et al. |
| 6,521,643 B1 | 2/2003 | Tomishima et al. |

(Continued)

FOREIGN PATENT DOCUMENTS

CA    1045136    12/1978

(Continued)

OTHER PUBLICATIONS

Aoyama, T. et al., "One Pot Synthesis using Supported Reagents System KSCN/SiO$_2$—RNH$_3$OAc/Al$_2$O$_3$: synthesis of 2-aminothiazoles and N-Allylthioureas," Tetrahedron, 62(14), 3201-3213 (2006).

Arevalo, M. J. et al., "Expeditious Formation of 1,2,4-Triazine Derivatives via a Thioisomunchnone Cycloaddition Reaction," Tet. Lett., 40, 8675-8678 (1999).

Bellacosa, A. et al., "Molecular Alterations of the AKT2 Oncogene in Ovarian and Breast Carcinomas," Int. J. Cancer (Pred. Oncol.), 64, 280-285 (1995).

Besson, A. et al., "PTEN/MMAC1/TEP1 in Signal Transduction and Tumorigenesis," Eur. J. Biochem., 263, 605-611 (1999).

(Continued)

*Primary Examiner* — Zinna N Davis
(74) *Attorney, Agent, or Firm* — Bernard P. Friedrichsen

(57) ABSTRACT

The invention relates to thiazole compounds of Formula I and Formula II and compositions thereof useful for treating diseases mediated by protein kinase B (PKB) where the variables have the definitions provided herein.

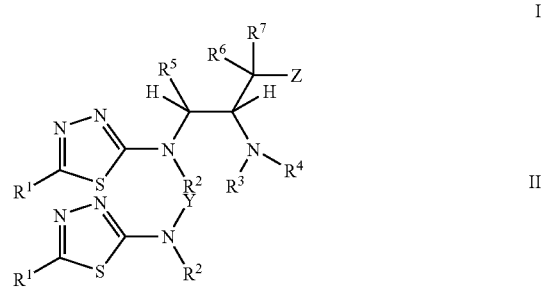

The invention also relates to the therapeutic use of such thiazole compounds and compositions thereof in treating disease states associated with abnormal cell growth, cancer, inflammation, and metabolic disorders.

16 Claims, No Drawings

U.S. PATENT DOCUMENTS

| | | | |
|---|---|---|---|
| 6,525,052 | B2 | 2/2003 | Bekkali et al. |
| 6,620,911 | B1 | 9/2003 | Pettit et al. |
| 6,720,427 | B2 | 4/2004 | Sanner et al. |
| 6,894,054 | B2 | 5/2005 | Laborde et al. |
| 6,962,933 | B1 | 11/2005 | Ohkawa et al. |
| 6,982,272 | B2 | 1/2006 | Emmanuel et al. |
| 2001/0044545 | A1 | 11/2001 | Dhanca et al. |
| 2002/0025976 | A1 | 2/2002 | Chu et al. |
| 2002/0115863 | A1 | 8/2002 | Patel et al. |
| 2002/0119962 | A1 | 8/2002 | Jacobs et al. |
| 2003/0078252 | A1 | 4/2003 | Sanner et al. |
| 2003/0216403 | A1 | 11/2003 | Lively et al. |
| 2004/0053948 | A1 | 3/2004 | McDonald et al. |
| 2004/0053973 | A1 | 3/2004 | Ohkawa et al. |
| 2004/0097555 | A1 | 5/2004 | Ohkawa et al. |
| 2004/0102360 | A1 | 5/2004 | Barnett et al. |
| 2004/0106540 | A1 | 6/2004 | Barnett et al. |
| 2004/0116439 | A1 | 6/2004 | Lively et al. |
| 2004/0122016 | A1 | 6/2004 | Cao et al. |
| 2004/0152747 | A1 | 8/2004 | Chen et al. |
| 2004/0157827 | A1 | 8/2004 | Pevarello et al. |
| 2004/0171643 | A1 | 9/2004 | De Cointet et al. |
| 2005/0004134 | A1 | 1/2005 | Tsutsumi et al. |
| 2005/0038059 | A1 | 2/2005 | Mueller et al. |
| 2005/0043372 | A1 | 2/2005 | Chen |
| 2005/0053594 | A1 | 3/2005 | Alessi et al. |
| 2005/0080113 | A1 | 4/2005 | Ohkawa et al. |
| 2005/0119320 | A1 | 6/2005 | Bruce et al. |
| 2005/0143384 | A1 | 6/2005 | Sartori et al. |
| 2005/0148640 | A1 | 7/2005 | Come et al. |
| 2005/0176789 | A1 | 8/2005 | Hadida Ruah et al. |
| 2005/0182104 | A1 | 8/2005 | Balter et al. |
| 2005/0192300 | A1 | 9/2005 | Wang et al. |
| 2005/0222219 | A1 | 10/2005 | Chen et al. |
| 2005/0256121 | A1 | 11/2005 | Jefferson et al. |
| 2006/0003944 | A1 | 1/2006 | Glinka et al. |
| 2006/0052426 | A1 | 3/2006 | Despeyroux et al. |
| 2006/0154961 | A1 | 7/2006 | Zeng et al. |
| 2006/0178388 | A1 | 8/2006 | Wrobleski et al. |
| 2006/0205731 | A1 | 9/2006 | Kodama et al. |
| 2006/0287317 | A1 | 12/2006 | Smith et al. |
| 2006/0293365 | A1 | 12/2006 | Baltzer et al. |
| 2006/0293366 | A1 | 12/2006 | Baltzer et al. |
| 2007/0032487 | A1 | 2/2007 | Bruce et al. |
| 2007/0173506 | A1 | 7/2007 | Zeng et al. |
| 2008/0255145 | A1 | 10/2008 | Monenschein et al. |
| 2008/0269243 | A1 | 10/2008 | Monenschein et al. |
| 2009/0099221 | A1 | 4/2009 | Vanotti et al. |
| 2009/0203690 | A1 | 8/2009 | Akritopoulou-Zanze et al. |

FOREIGN PATENT DOCUMENTS

| | | |
|---|---|---|
| DE | 3407505 A1 | 9/1985 |
| GB | 2022085 A | 12/1979 |
| JP | 64-75475 A2 | 3/1989 |
| JP | 5117280 | 5/1993 |
| JP | 8073460 | 3/1996 |
| JP | 9221424 | 8/1997 |
| JP | 2002-53565 | 2/2002 |
| JP | 20020-53566 | 2/2002 |
| WO | WO 93/19054 | 9/1993 |
| WO | WO 96/38419 | 12/1996 |
| WO | WO 97/22360 | 6/1997 |
| WO | WO 99/31096 | 6/1999 |
| WO | WO 99/65884 | 12/1999 |
| WO | WO 00/45635 | 8/2000 |
| WO | WO 01/44178 A1 | 6/2001 |
| WO | WO 01/44179 A1 | 6/2001 |
| WO | WO 01/87877 A1 | 11/2001 |
| WO | WO 03/014095 A1 | 2/2003 |
| WO | WO 03/068227 A1 | 8/2003 |
| WO | WO 02/083064 A2 | 10/2003 |
| WO | WO 03/084473 A2 | 10/2003 |
| WO | WO 03/094831 A2 | 11/2003 |
| WO | WO 2004/014864 A1 | 2/2004 |
| WO | WO 2004/041813 A1 | 5/2004 |
| WO | WO 2004/046120 A2 | 6/2004 |
| WO | WO 2004/056789 A1 | 7/2004 |
| WO | WO 2004/089937 A1 | 10/2004 |
| WO | WO 2004/096131 A2 | 11/2004 |
| WO | WO 2005/014554 A1 | 2/2005 |
| WO | WO 2005/046678 A1 | 5/2005 |
| WO | WO 2005/052147 A2 | 6/2005 |
| WO | WO 2005/068444 A2 | 7/2005 |
| WO | WO 2005/089443 A2 | 9/2005 |
| WO | WO 2005/113762 | 12/2005 |
| WO | WO 2005/116025 A2 | 12/2005 |
| WO | WO 2006/020767 A2 | 2/2006 |
| WO | WO 2006/038734 A1 | 4/2006 |
| WO | WO 2006/044860 A2 | 4/2006 |
| WO | WO 2006/045716 A1 | 5/2006 |
| WO | WO 2006/051270 A1 | 5/2006 |
| WO | WO 2007/008541 A2 | 1/2007 |
| WO | WO 2007/033780 A2 | 3/2007 |
| WO | WO 2007/066805 A1 | 6/2007 |
| WO | WO 2007/070600 A2 | 6/2007 |
| WO | WO 2007/084391 A2 | 7/2007 |
| WO | WO 2007/110344 A1 | 10/2007 |
| WO | WO 2008/036308 A2 | 3/2008 |
| WO | WO 2008/154241 A1 | 12/2008 |
| WO | WO 2009/133170 A1 | 11/2009 |

OTHER PUBLICATIONS

Beyer, H. et al., "Folgeprodukte der Thiazolyl-(2)-cyanamide," Chem. Ber., 99(9), 2937-2943 (1966). This in in German. English language abstract is attached.

Blume-Jensen, P. et al., "OncogenicKinase Signalling," Nature, 411, 355-365 (2001).

Brazil, D. P. et al., "Ten Years of Protein Kinase B Signalling: a hard Akt to follow," Trends Biochem Sci., 11, 657-664 (2001).

Brodbeck, D. et al., "A Human Protein Kinase Bγ with Regulatory Phosphorylation Sites in the Activation Loop and in the C-terminal Hydrophobic Domain," J. Biol. Chem., 274, 9133-9136 (1999).

Cheng, J. Q. et al., "AKT2, a Putative Oncogene Encoding a Member of a Subfamily of Protein-Serine/Threonine Kinases, is Amplified in Human Ovarian Carcinomas", PNAS, 89, 9267-9271 (1992).

Cheng, J. Q. et al.,"Amplification of AKT2 in Human Pancreatic Cancer Cells and Inhibition of AKT2 Expression and Tumorigenicity by Antisense RNA", PNAS, 93, 3636-3641 (1996).

Czech, M. P. et al., "Signaling Mechanisms that Regulate Glucose Transport," J. Biol. Chem., 274, 1865-1868 (1999).

Datta, S. R. et al., "Cellular Survival: a Play in Three Akts," Genes Dev., 13, 2905-2927 (1999).

Duan, C. et al., "Phosphatidylinositol 3-Kinase Is Required for Insulin-Like Growth Factor-I—Induced Vascular Smooth Muscle Cell Proliferation and Migration," Circ. Res., 86, 15-23 (2000).

Fathalla et al., "Synthesis of Some New 1,8-Naphthyridine Derivatives of Expected Biological Activity", Egypt. J. Chem., 46(1), 135-152 (2003).

Fennel, B. J. et al., "Effects of the Antimitotic Natural Product Dolastatin 10, and Related Peptides, on the Human Malarial Parasite Plasmodium Falciparum", J. Antimicrob. Chemo., 51(4), 833-841 (2003).

Ghattas, A.G. et al., "Synthesis of Some New Heterocyclic 1,3,4-Oxadiazoles with Antibacterial Activity," Fac. Sci., Assuit University, 37(6), 410-412 (1982).

Ghodousi, A. et al., "Pyrrolobenzimidazoles Linked to Heterocycles and Peptides. Design of DNA Base Pair Specific Phosphate Hydrolyzing Agents and Novel Cytotoxic Agents", J. Med. Chem., 47(1), 90-100 (2004).

Gommaa, A. M. et al., "Synthesis of Some New Substituted Aminoacylthiazoles and Dipeptide Derivatives", Asian J. Chem., 4(3), 527-533 (1992).

Grehn, Leif, "A Method for Nitration of Thiazoles," J. Heterocyc. Chem., 14, 917-919 (1977).

Hackbarth, C. J. et al., "N-Alkyl Urea Hydroxamic Acids as a New Class of Peptide Deformylase Inhibitors with Antibacterial Activity," Antimicrob. Agents and Chemo., 46(9), 2752-2764 (2002).

Hassan, H. M. et al., "Synthesis and Antimicrobial Activity of Some New N-Aminoacyl Derivatives of 2-Amino-4-phenylthiazole", Acta Pharm., 47, 159-166 (1997).

Hemmings,, B. A. "Akt Signaling: Linking Membrane Events to Life and Death Decisions," Science, 275, 628-630 (1997).

Hill, M. M. et al., "Identification of a Plasma Membrane Raft-Associated PKB Ser473 Kinase Activity that Is Distinct from ILK and PDK1," Current Biol., 12, 1251-1255 (2002).
Hiremath, S. P. et al., "Synthesis of 2-Phenyl(indol-3-yl)Isothiocyanates, 1-Substituted-3-(Substituted-2'-Phenylindol-3'-yl) Thiosemicarbazides and their Reacations," Ind. J. Heterocyc. Chem., 2, 119-124 (1992).
Hiremath, S. P. et al., "Synthesis of Substituted indolylthiadiazolines and indolylisoxazolines," Ind. J. Chem., 30B, 744-748 (1991).
Hresko, R. C. et al., "Phosphionositide-dependent Kinase-2 is a Distinct Protein Kinase Enriched in a Novel Cytoskeletal Fraction Associated with Adipocyte Plasma Membranes," J. Biol. Chem., 278, 21615-21622 (2003).
Jeske, J. et al., "Preliminary Evaluation of Analgesic Effect of Amino Acid 4-Aminoantipyrine Derivatives", Pol. Med. Sci. Hist. Bull., 17(6) 475-480 (1974).
Jeske, J. et al., "Some Pharmacological Effects of Amino Acid 4-Aminoantipyrine Derivatives", Pol. Med. Sci. Hist. Bull., 17(6) 481-485 (1974).
Jeske, J. et al., "The Effect of Amino Acid Substituents in 4-Antipyrineamide on the LD50 Value", Pol. Med. Sci. Hist. Bull., 17(4) 323-325 (1974).
Jeske, J. et al., "Evaluation of Spasmolytic Action of Amino Acid 4-Aminoantipyrine Derivatives", Pol. Med. Sci. Hist. Bull., 17(6) 487-490 (1974).
Khwaja, A. "AKT Is More Than Just a Bad Kinase", Nature, 401, 33-34 (1999).
Kidwai, M. et al., "Microwave Induced Synthesis and Antibacterial Activity of Cephalosporin Derivatives Using Solid Support," Bioorg. Chem., 29, 380-386 (2001).
Kidwai, M. et al., "Solid Supported Reaction of Substituted 2-Oxazoline with Amines under Microwave Irradiation," J. Chin. Chem. Soc., 50, 1075-1078 (2003).
Kodomari, M. et al., "One-Pot Synthesis of 2-Aminothiazoles using Supported Reagents," Tet. Lett., 43(9), 1717-1720 (2002).
Komori, T. et al., "Structure Activity Relationships of Synthetic Antibiotic Analogs of Chryscandin", J. of Antibiotics, 38(9). 1182-1203 (1985).
Kulik, G. et al., "Antiapoptotic Signalling by the Insulin-Like Growth Factor I Receptor, Phosphatidylinositol 3-Kinase, and Akt," Mol. and Cell. Biol., 17, 1595-1606 (1997).
Kulkarni, R.A. et al., "O,O-Dialkyl-S-(4-substituted-phenyl-5-phenylacetamido-thiazol-2-yl)phosphorothiaotes and O,O-Dialkyl-s-(4-substituted-phenyl-5-phenylthiazol-2-yl)phosphorothioate," J. Ind. Chem. Soc., 65(6), 432-434 (1988).
Kureishi, Y. et al., "The HMG-CoA Reductase Inhibitor Simvastatin Activates the Protein Kinase Akt and Promotes Angiogenesis in Normocholesterolemic Animals," Nat. Med., 6, 1004-1010 (2000).
Kwapiszewski, W. et al., "4-Antipyrinylamides of Amino Acids. II. 4-Antipyrinylamides of DL-Leucine, Phenylalanine, Tyrosine, Glutamic Acid, and ε-Aminocaproic Acid", Acta Poloniae Pharmaceutica, 34(1), 45-50 (1977). This is in Polish, but an English Language Abstract is provided.
Kwapiszewski, W. et al., "Preparation of the Aminoacyl Derivatives of 4-Aminoantipyrine. IV. Derivatives of D-Amino Acids", Acta Poloniae Pharmaceutica, 41(1), 21-24 (1984). This is in Polish, but an English Language Abstract is provided.
Lawlor, M. A. et al., "PKB/Akt: a Key Mediator of Cell Proliferation, Survival and Insulin Responses?" J. Cell Sci., 114, 2903-2910 (2001).
Li , D-M. et al., "TEP1, Encoded by a Candidate Tumor Suppressor Locus, Is a Novel Protein Tyrosine Phosphatase Regulated by Transforming Growth Factor $\beta^1$," Cancer Res., 57, 2124-2129 (1997).
Lin, H-K et al., "Akt Suppresses Androgen-Induced Apoptosis by Phosphorylating and Inhibiting Androgen Receptor," PNAS, 98, 7200-7205 (2001).
Luo, Z. et al., "Acute Modulation of Endothelial Akt/PKB Activity Alters Nitric Oxide-Dependent Vasomotor Activity in vivo," J. Clin. Invest., 106, 493-499 (2000).
Mankad, P. R. et al., "Analgesic & Muscle Tension Relaxing Agents: Part I—Synthesis of Some New 2-β-Hydroxyphenethylaminothiazoles," Ind. J. Chem., 1 (10), 441-442 (1963).
Masakazu, B. et al., "Novel Antiallergic and Antiinflammatory Agents. Part I: Synthesis and Pharmacology of Glycolic Amide Derivatives," Bioorg. and Med. Chem., 6, 1069-1076 (1998).

Mazzone, G. et al., "Synthesis and Local Anesthetic Activity of Alkylaminoacyl Derivatives of 2-Amino-1,3,4-Thiadiazole", II Farmaco, 48(9), 1207-1224 (1993).
Miao, W. et al., "Intracoronary, Adenovirus-mediated Akt Gene Transfer in Heart Limits Infarct Size Following Ischemia-reperfusion Injury in Vivo," J. Mol. Cell. Cardiol., 32, 2397-2402 (2000).
Misterek, K, et al., "Effects of Pyrazolone-5 Derivatives on Amphetamine-Induced Hyperthermia and Behavioral Changes in Rats", Pol. J. Pharmacology Pharmacy, 28(6), 593-599 (1976).
U.S. Appl. No. 12/218,754, filed Jul. 16, 2008, Zeng et al.
U.S. Appl. No. 12/378,195, filed Feb. 11, 2009, Zeng et al.
Hanada, Masahito, et al., "Structure, Regulation and Function of PKB/AKT-A Major Therapeutic Target," Biochim. et Biophys. Acta 1697, pp. 3-16 (2004).
Supplementary European Search Report for EP 05812533 dated Oct. 16, 2009.
International Search Report from co-pending PCT Application No. PCT/US2008/008690 (WO 2009/011871 A3) mailed on Mar. 3, 2009.
Mishra L., et al., "Synthesis and Fungicidal Activity of Some 5-Membered Heterocyclic Derivatives Containing Benzimidazoles," Biosci. Biotech. and Biochem. 57(6), pp. 989-991 (1993).
Zhuravel, I. O. et al., "Synthesis of Substituted 3-(5-Amino-[1,3,4]thiadiazol-2-yl)-2H-pyrano [2,3-c]pyridin-2-ones," J. Heterocyc. Chem. 41(4), pp. 517-524 (2004).
Murer, P. et al., "Combinatorial Library On-Bead" Approach to Polymeric Materials with Vastly Enhanced Chiral Recognition, Chem. Commun., 23, 2559-2560 (1998).
Murer, P. et al., "On-Bead Combinatorial Approach to the Design of Chiral Stationary Phases for HPLC", Anal. Chem., 71, 1278-1284 (1999).
Namikawa, K. et al., "AKT/Protein Kinase B Prevents Injury-Induced Motoneuron Death and Accelerates Axonal Regeneration", J. Neurosci., 20, 2875-2886 (2000).
Nicholson, K. M. et al., "The Protein Kinase B/AKT Signalling Pathway in Human Malignancy", Cell. Signal., 14, 381-395 (2002).
Pachhaimia, V. L. et al., "Studies on Thiadiazoles: Part I: Preparation and Antimicrobial Activity of 2-(α Carbamylarylmethylamino)-5-(4'-Pyridyl)-1, 3, 4-Thiadiazoles," J. Instit. Chem.. (India), 61, 54-56 (1989).
Pande, K. et al., "Anti-Inflammatory and AntiProteolytic Activities of Substituted Imidazolones," Indian Drugs, 23(1), 13-17 (1985).
Park, C-M. et al., "Non-peptidic Small Molecule Inhibitors of XIAP," Bioorg. and Med. Chem. Lett., 15(3), 771-775 (2005).
Pathak,V.N. et al., "Synthesis and Biological Activities of Some New 2-(N-Arylamino)-4-(Fluoroaryl)thiazoles," J. Ind. Chem. Soc., vol. LVI, pp. 1010-1012 (1979).
Pettit, R. K. et al., "Specific Activities of Dolastatin 10 and Peptide Derivatives against *Cryptococcus neoformans*," Antimicrob. Agents and Chemo., 42, 2961-2965 (1998).
Sanchez, J. P. et al., "Quinolone Antibacterial Agents. Synthesis and Structure-Activity Relationships of a Series of Amino Acid Prodrugs of Racemic and Chiral 7-(3-Amino-1-pyrrolidinyl)quinolones. Highly Soluble Quinolone Prodrugs with In Vivo Pseudomonas Activity", J. Med. Chem., 35 (10), 1764-1773 (1992).
Senapti, R. M. et al., "Studies on Thiadiazoles," Proc. Instit. Chem. (India), 37(3), 111-113 (1965).
Shah, V. H. et al., "Studies on Acetamide Derivatives: Preparation and Antimicrobial Activity of 2-α-Arylaminoacetamido/α-Carbamoyl benzylamino/Arylcarbamoylmethylamino-5-o-Nitrophenyl/Benzoylaminomethyl-1,3,4-Thiadiazole," J. Ind. Chem. Soc., LIX, 678-690 (1982).
Singh, H. et al., "Synthesis, Characterization and Fungitoxicity of Manganese (II), Iron (II), Colbalt (II), Nickel (II), Copper (II), and Zinc (II) Complexes of N-Phenyl-5-phenyl-1,3,4-oxadiazole-2-sulphonamide and 5-Phenyl-1,3,4-oxadiazole-2-imino Sulphonamide," Ind. J. Chem., 33A, 350-353 (1994).
Suzuki, N. et al., "Synthesis and Antiallergy Activity of [1,3,4]Thiadizolo[3,2-a]-1,2,3,-triazolo[4,5-d]pyrimidin-9(3H)-one", Chem. Pharm. Bull., 40(2), 357-363 (1992).
Tanaka, A. et al., "Antiplatelet Agents Based on Cyclooxygenase Inhibition without Ulcerogenesis. Evaluation and Synthesis of 4,5-Bis (4-methoxyphenyl)-2-substituted-thiazoles," J. Med. Chem., 37(8), 1189-1199 (1994).

Testa, J. R. et al., "AKT Plays a Central Role in Tumorigenesis," PNAS, 98, 10983-10985 (2001).

Tripathi, M, et al., "Antipyrine Congeners as Antidepressant Agents", Arzneimittel-Forschung, 43(10), 1045-1049 (1993).

Verdu, J. et al., "Cell-Autonomous Regulation of Cell and Organ Growth in Drosophila by Akt/PKB," Nat. Cell Biol., 1, 500-506 (1999).

Vivanco, I. et al., "The Phosphatidylinositol 3-Kinase-AKT Pathway In Human Cancer," Nat. Rev. Cancer, 2, 489-501 (2002).

Wengel, J. et al. "Analogs of the Antibiotic Puromycin as Potential Prodrugs of 3'-Amino-3'-deoxythymidine", J. Heterocyc. Chem., 29(1), 5-9 (1992).

Yadav, L. D. S. et al., "A Facile Ring Transformation of 5-Oxazolone Derivatives to New 1,3,4-Oxa(thia)diazolo[3,2-a]pyrirnidin-5-ones", Ind. J. Chem., 34B, 500-503 (1995).

Yadav L. et al., "One-Pot Annulation of Pyrimidine Ring on Azoles Under Microwave Irradiation and Solvent-Free Conditions," Synthesis, 1, 63-66 (2003).

Yang, L. et al., "Akt/Protein Kinase B Signaling Inhibitor-2, a Selective Small Molecule Inhibitor of Akt Signaling with Antitumor Activity in Cancer Cells Overexpressing Akt," Cancer Res., 64, 4394-4399 (2004).

Yuan, Z. Q. et al., "Frequent Activation of AKT2 and Induction of Apoptosis by Inhibition of Phosphoinositide-3-OH Kinase/Akt Pathway in Human Ovarian Cancer," Oncogene, 19, 2324-2330 (2000).

THIADIAZOLE MODULATORS OF PKB

CROSS REFERENCES TO RELATED APPLICATIONS

This application claims the benefit of U.S. Provisional Application No. 60/959,974, filed on Jul. 17, 2007, which is hereby incorporated by reference in its entirety and for all purposes as if fully set forth herein.

FIELD OF THE INVENTION

The invention relates to thiadiazole compounds useful for treating diseases mediated by protein kinase B (PKB). The invention also relates to the therapeutic use of such thiadiazole compounds and compositions thereof in treating disease states associated with abnormal cell growth, cancer, inflammation, and metabolic disorders.

BACKGROUND OF THE INVENTION

Protein kinases represent a large family of proteins which play a central role in the regulation of a wide variety of cellular processes, maintaining control over cellular function. A partial list of such kinases includes ab1, bcr-ab1, Blk, Brk, Btk, c-kit, c-met, c-src, c-fms, CDK1, CDK2, CDK3, CDK4, CDK5, CDK6, CDK7, CDK8, CDK9, CDK10, cRaf1, CSF1R, CSK, EGFR, ErbB2, ErbB3, ErbB4, Erk, Fak, fes, FGFR1, FGFR2, FGFR3, FGFR4, FGFR5, Fgr, flt-1, Fps, Frk, Fyn, GSK3α, GSK3β, Hck, IGF-1R, INS-R, Jak, KDR, Lck, Lyn, MEK, MK2, MSK1, p38, PDGFR, PIK, PKB, PKA, PIM1, PIM2, PRAK, PRK2, PKC, PYK2, P70S6, ROCK2, ros, tie, tie2, TRK, Yes, and Zap70. Inhibition of such kinases has become an important therapeutic approach.

AKT (also known as protein kinase B (PKB) or RAC-PK), including three isoforms AKT1/PKBα/RAC-PKα, AKT2/PKBα/RAC-PKβ, AKT3/PKBγ/RAC-PKγ, has been identified as a serine/threonine protein kinase. Testa et al., Proc. Natl. Acad. Sci., 2001, 98, 10983-10985; Brazil et al., Trends Biochem Sci., 2001, 11, 657-64; Lawlor et al., J. Cell Sci., 2001, 114, 2903-2910; Cheng, Proc. Natl. Acad. Sci. USA, 1992, 89, 9267-9271; Brodbeck, et al., J. Biol. Chem. 1999, 274, 9133-9136. PKB mediates many effects of IGF-1 and other growth factors on tumor growth and inhibition of apoptosis. Nicholson, et al., Cell. Signal., 2002, 14, 381-395. PKB plays an important role in cell proliferation, apoptosis and response to insulin. For these reasons, modulation of PKBs is of interest in the treatment of tumorigenesis, abnormal cell proliferation, and diabetes.

The molecular structure of the PKBs comprises a regulatory site near the carboxy terminus of the polypeptide, a catalytic domain with an activation loop having a threonine, and an amino-terminal pleckstrin homology domain. The pleckstrin homology domain permits anchorage of the enzyme to the cell membrane through interaction with phospholipids, which triggers the activation of the PKBs. The role of the pleckstrin homology domain requires phosphorylation of phosphatidylinositol at the D-3 position via phosphatidylinositol 3-kinase PI3K, an SH2 domain protein that associates with activated receptor tyrosine kinases, particularly IGF-1R. In particular, phosphoinositol-3-kinase, when activated by receptor tyrosine kinase, catalyzes the synthesis of phosphoinositol-3,4-diphosphate and phosphatidylinositol 3,4,5-triphosphate. The pleckstrin homology domain binds 3-phosphoinositides, which are synthesized by PI3K upon stimulation by growth factors such as platelet derived growth factor (PDGF), nerve growth factor (NGF) and insulin-like growth factor (IGF-1). Kulik et al., Mol. Cell. Biol., 1997, 17, 1595-1606; Hemmings, Science, 1997, 275, 628-630; Datta, et al. Genes Dev., 1999, 13, 2905-2927. Lipid binding to the pleckstrin homology domain promotes translocation of PKB to the plasma membrane. Further activation of PKB occurs by phosphorylation by another protein kinase, PDK1 at Thr308, Thr309, and Thr305 for the PKB isoforms α, β and γ, respectively. A third step of activation is catalyzed by a kinase that phosphorylates Ser473, Ser474 or Ser472 in the C-terminal tails of PKBα, β, and γ respectively. The Ser473 kinase activity has been identified to be associated with plasma membrane and is not due to PKB and PDK1 kinase activity. Hill et al., Current Biology, 2002, 12, 1251-1255; Hresko et al., J. Biol. Chem., 2003, 278, 21615-21622. The process produces the fully activated form of PKB.

Activation of PKB can also occur by inhibiting the D-3 phosphoinositide specific phosphatase, PTEN, which is a membrane-associated FYVE finger phosphatase commonly inactivated in many cancers due to genetic alteration, including prostate cancer. Besson, et al., Eur. J. Biochem., 1999, 263, 605-611; Li, et al., Cancer Res., 1997, 57, 2124-2129.

The catalytic domain of PKB is responsible for the phosphorylation of serine or threonine in the target protein.

Once activated, PKB mediates several cellular functions including proliferation, cell growth, and promotion of survival. Intracoronary, adenovirus-mediated akt gene transfer in heart limits infarct size following ischemia-reperfusion injury in vivo. Miao et al., J. Mol. Cell. Cardiol., 2000, 32, 2397-2402. The antiapoptotic function of PKB is reported to be mediated by its ability to phosphorylate apoptosis regulatory molecules including BAD, caspase 9, IKK-, and the forkhead transcriptional factor FKHRL1. Datta et al., at 2905. PKB signaling is also implicated in the physiological regulation of organ size (Verdu, et al., Nat. Cell Biol., 1999, 1, 500-506), glucose homeostasis (Czech, et al., J. Biol. Chem., 1999, 274, 1865-1868), vasomotor tone (Luo, et al. J. Clin. Invest. 1999, 106, 493-499), and angiogenesis (Kureishi, et al., Nat. Med., 2000, 6, 1004-1010).

Manifestations of altered PKB regulation appear in both injury and disease, the most important role being in cancer. PKB kinase activity is constitutively activated in tumors with PTEN mutation, PI 3-kinase mutation and overexpression, and receptor tyrosine kinase overexpression. PKB is also a mediator of normal cell functions in response to growth factor signaling. Expression of the PKB gene was found to be amplified in 15% of human ovarian carcinoma cases. Cheng, et al., Proc. Natl. Acad. Sci. U.S.A., 1992, 89, 9267-9271. PKB has also been found to be over expressed in 12% of pancreatic cancers. Cheng, et al., Proc. Natl. Acad. Sci. U.S.A., 1996, 93, 3636-3641. In particular, PKBβ is over-expressed in 12% of ovarian carcinomas and in 50% of undifferentiated tumors, suggesting that PKB may be associated with tumor aggressiveness. Bellacosa, et al., Int. J. Cancer, 1995, 64, 280-285. PKB is also a mediator of normal cell functions. Khwaja, Nature, 1999, 401, 33-34; Yuan, et al., Oncogene, 2000, 19, 2324-2330; Namikawa, et al., J. Neurosci., 2000, 20, 2875-2886.

Elucidation of the role of PKB in the increase of growth and inhibition of apoptosis is complicated by the many protein substrates of PKB, including BAD, Forkhead (FOXO family), GSK3, Tuberin (TSC2), p27 Kip1, p21Cip1/WAF1, Raf, Caspase-9, and Mdm2. Lin, et al., Proc. Natl. Acad. Sci. U.S.A., 2001, 98, 7200-7205; Blume-Jensen, et al., Nature 2001, 411, 355-365; Vivanco, et al., Nat. Rev. Cancer, 2002, 2, 489-501.

The various PKBs vary in their abundance in different mammalian cell types. For example, PKBβ is especially abundant in highly insulin-responsive tissues, including brown fat; PKBα is widely expressed in most of the tissues; and PKBγ is more abundant in brain and testes.

Modulation of PKB by small molecules can be achieved by identifying compounds that bind to and activate or inhibit one or more PKBs. Cao et al. in United States Publication No. 2004/0122016, published Jun. 24, 2004, disclose certain thiophene derivatives and thiophene analogs as inhibitors of protein kinases. In particular, the disclosure addresses compositions effective as inhibitors of Rho-associated coiled-coil forming protein serine/threonine kinase (ROCK), extracellular signal regulated kinase (ERK), glycogen synthase kinase (GSK), and members of the AGC sub-family of protein kinases. Id. at 4. The AGC sub-family of kinases includes protein kinase A (PKA), PDK, $p70^{S6K}$-1, $p70^{S6K}$-2, and PKB. Id.

Triciribine has been reported to inhibit cell growth in PKBβ overexpressing cells, transformed cells, and was effective at a concentration of 50 nM. Yang et al., Cancer Res., 2004, 64, 4394-4399.

In other work, U.S. Pat. No. 5,232,921, issued Aug. 3, 1993, discloses thiazole derivatives that are active on the cholinergic system. The patent does not address modulation of PKB.

U.S. Patent Publication No. US 2005/0004134, published Jan. 6, 2005, discloses certain thiazole derivatives, a method of obtaining them, and pharmaceutical compositions containing them. The derivatives are described as adenosine antagonists useful in the prevention and/or treatment of cardiac and circulatory disorders, degenerative disorders of the central nervous system, respiratory disorders, and many diseases for which diuretic treatment is suitable.

Derivatives of thiazole were synthesized and used in treating conditions alleviated by antagonism of a 5-HT2b receptor in International Publication No. WO 03/068227. Thiazolyl substituted aminopyrimidines were also made and tested as fungicides in U.S. Patent Publication No. US 2005/0038059, published February, 2005. Derivatives of thiazole were also synthesized by Sanner et al. and indicated to have activity inhibiting cdk5, cdk2, and GSK-3. U.S. Patent Publication No. US 2003/0078252, published Apr. 24, 2003.

Thiadiazole compounds useful for treating diseases mediated by PKB are disclosed in WO 2006/044860, published on Apr. 27, 2006, and in U.S. Patent Publication No. U.S. Patent Application Publication No. 2006/0154961, published on Jul. 13, 2006 both of which are hereby incorporated by reference in their entireties and for all purposes as if specifically set forth herein. Thiazole compounds useful treating disease mediated by PKB are disclosed in U.S. Patent Application Publication No. 2007/0173506, published on Jul. 26, 2007, which is hereby incorporated by reference in its entirety and for all purposes as if specifically set forth herein. Various heterocycle compounds including certain thiadiazole compounds are disclosed in WO 2008/036308, published on Mar. 27, 2008, which are reportedly useful in inhibiting the PKB pathway.

A need exists for new compounds that can be used to modulate PKB and can be used to treat various disease conditions associated with PKB.

SUMMARY OF THE INVENTION

This invention encompasses novel compounds useful for treating diseases or conditions mediated by PKB. The invention also encompasses the therapeutic use of such compounds and compositions thereof in the treatment of disease states associated with abnormal cell growth, such as cancer, or metabolic disease states, such as diabetes, or inflammation. The invention further provides pharmaceutical compositions that include the compounds of the invention and the use of the compounds in the preparation of medicaments for treating various conditions and disease states.

In one aspect the invention comprises a compound of Formula I $R^1$ is selected from a carbocyclic ring system or a heterocyclic ring system;

$R^2$ is selected from —H, $C_1$-$C_8$ alkyl, —($C_1$-$C_6$ alkyl)aryl, or —C(O)($C_1$-$C_6$ alkyl);

$R^3$ is selected from —H, $C_1$-$C_8$ alkyl, —C(O)($CR^8R^9$)$_t$N($R^7$)$_2$, —($CR^8R^9$)$_t$(aryl), —($CR^8R^9$)$_t$(heteroaryl), —($CR^8R^9$)$_t$(cycloalkyl), or —($CR^8R^9$)$_t$(heterocyclyl);

$R^4$ is selected from —H, $C_1$-$C_8$ alkyl, —($C_1$-$C_6$ alkyl)aryl, or —C(O)($C_1$-$C_6$ alkyl);

$R^5$ is selected from —H, —$OR^{10}$, —O—($C_1$-$C_6$ alkyl)—O—$R^{10}$, $C_1$-$C_6$ alkyl, $C_1$-$C_6$ alkenyl, —($C_1$-$C_6$ alkyl)—O—$R^{10}$, or —($C_1$-$C_6$ alkyl)—O—C(O)—$R^{10}$;

$R^6$ is selected from —H, or $C_1$-$C_6$ alkyl;

$R^7$ is selected from —H, —$OR^{10}$, —O—($C_1$-$C_6$ alkyl)—O—$R^{10}$, $C_1$-$C_6$ alkyl, $C_1$-$C_6$ alkenyl, —($C_1$-$C_6$ alkyl)—O—$R^{10}$, or —($C_1$-$C_6$ alkyl)—O—C(O)—$R^{10}$;

$R^8$ and $R^9$, in each instance, are independently selected from —H, $C_1$-$C_6$ alkyl, or aryl;

$R^{10}$ is selected from —H, $C_1$-$C_6$ alkyl, $C_1$-$C_6$ haloalkyl, —($C_1$-$C_6$ alkyl)aryl, aryl, heteroaryl, $C_1$-$C_6$ hydroxyalkyl, or —($C_1$-$C_6$ alkyl)—O—($C_1$-$C_6$ alkyl), cycloalkyl, or heterocyclyl;

each t is independently selected from 0, 1, 2, or 3; and

Z is selected from aryl or heteroaryl;

wherein each of the above alkyl, aryl, heteroaryl, cycloalkyl, and heterocyclyl moieties and heterocyclic and carbocyclic rings are optionally and independently substituted by 1-3 substituents selected from amino, aryl, heteroaryl, cycloalkyl, or heterocyclyl optionally substituted by 1-5 substituents selected from
$C_1$-$C_6$ alkoxy,
$C_1$-$C_6$ alkyl optionally substituted by halo,
aryl,
halo,
hydroxyl,
heteroaryl,
$C_1$-$C_6$ hydroxyalkyl, or
—NHS(O)$_2$—$C_1$-$C_6$ alkyl);

$C_1$-$C_6$ alkyl, $C_1$-$C_6$ haloalkyl, $C_1$-$C_6$ hydroxyalkyl, $C_1$-$C_6$ alkoxy, $C_1$-$C_6$ haloalkoxy, $C_1$-$C_6$ hydroxyalkoxy, $C_1$-$C_6$ alkylamino, $C_2$-$C_6$ alkenyl, or $C_2$-$C_6$ alkynyl, wherein each of which may be interrupted by one or more hetero atoms, cyano,
halo,
hydroxyl,
nitro,
oxo,
—NH(CO)—O—($C_1$-$C_6$ alkyl)aryl, —NH(CO)—O—($C_1$-$C_6$ alkyl), —N($C_1$-$C_6$ alkyl)(CO)—O—($C_1$-$C_6$ alkyl)aryl, —N($C_1$-$C_6$ alkyl)(CO)—O—($C_1$-$C_6$ alkyl), —C(O)OH, —C(O)O($C_1$-$C_6$ alkyl), —C(O)NH$_2$, —C(O)N(H)—($C_1$-$C_6$ alkyl), —C(O)N($C_1$-$C_6$ alkyl)$_2$, —NH($C_1$-$C_6$ alkyl), —N($C_1$-$C_6$ alkyl)$_2$, —($C_2$-$C_4$ alkenyl)heterocyclyl, or —($C_2$-$C_4$ alkenyl)cycloalkyl, or —O-aryl;

or a pharmaceutically acceptable salt, hydrate, stereoisomer, or mixture thereof, wherein at least one of the following is true:

(a) $R^5$ is selected from —$OR^{10}$, —O—($C_1$-$C_6$ alkyl)—O—$R^{10}$, $C_1$-$C_6$ alkyl, $C_1$-$C_6$ alkenyl, —($C_1$-$C_6$ alkyl)—O—$R^{10}$, or —($C_1$-$C_6$ alkyl)—O—C(O)—$R^{10}$; or (b) $R^7$ is selected from —$OR^{10}$, —O—($C_1$-$C_6$ alkyl)—O—$R^{10}$, $C_1$-$C_6$ alkenyl, —($C_1$-$C_6$ alkyl)—O—$R^{10}$, or —($C_1$-$C_6$ alkyl)—O—C(O)—$R^{10}$.

In some embodiments of the compound of Formula I, the compound of Formula I has the Formula IA

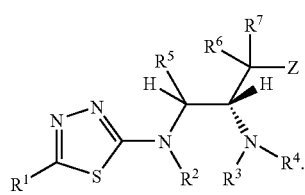

IA

In some embodiments of the compound of Formula I, the compound of Formula I has the Formula IB

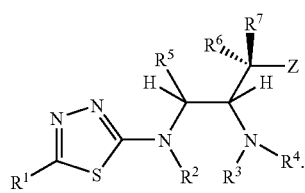

IB

In some embodiments of the compound of Formula I, the compound of Formula I has the Formula IC

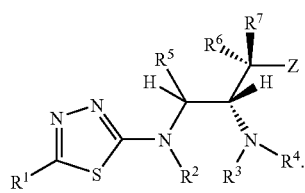

IC

In some embodiments of the compound of Formula I, the compound of Formula I has the Formula ID

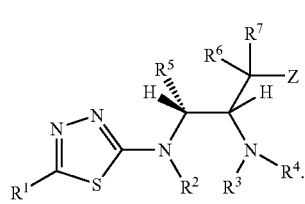

ID

In some embodiments of the compound of Formula I, the compound of Formula I has the Formula IE

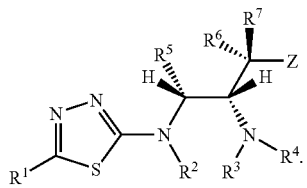

IE

In some embodiments of the compound of Formula I, $R^5$ is —H or $C_1$-$C_6$ alkyl. In some such embodiments, $R^5$ is —H or methyl. In some such embodiments, $R^5$ is —H.

In some embodiments of the compound of Formula I, $R^6$ is —H.

In some embodiments of the compound of Formula I, $R^7$ is —H.

In some embodiments of the compound of Formula I, $R^7$ is —$OR^{10}$, —O—($C_1$-$C_6$ alkyl)—O—$R^{10}$, $C_1$-$C_6$ alkyl, $C_1$-$C_6$ alkenyl, —($C_1$-$C_6$ alkyl)—O—$R^{10}$, or —($C_1$-$C_6$ alkyl)—O—C(O)—$R^{10}$. In some embodiments, $R^7$ is selected from —H, methyl, ethyl, propyl, ethenyl, propenyl, hydroxymethyl, methoxymethyl, —$CH_2$—O—C(O)—($C_1$-$C_6$ alkyl), 1-hydroxyethyl, or methoxymethoxy.

In some embodiments of the compound of Formula I, Z is selected from optionally substituted phenyl, optionally substituted indolyl, optionally substituted naphthyl, optionally substituted pyridyl, or optionally substituted thiophenyl. In some embodiments, Z is selected from phenyl, indolyl, naphthyl, pyridyl, or thiophenyl, each of which is optionally substituted with 1-3 substituents selected from —Cl, —F, —$CF_3$, —OH, —O—($C_1$-$C_6$ alkyl), —O—($C_1$-$C_6$ alkyl)-Cl, —O—($C_1$-$C_6$ alkyl)—OH, —$C_1$-$C_6$ alkyl, —$OCF_3$, —NH(CO)—O—($C_1$-$C_6$ alkyl)aryl, or —NH(CO)—O—($C_1$-$C_6$ alkyl). In other embodiments, Z is selected from phenyl, indolyl, naphthyl, pyridyl, thiophenyl, 4-chlorophenyl, 4-trifluoromethylphenyl, 3-chlorophenyl, 3-trifluoromethylphenyl, 4-methoxyphenyl, 3-fluoro-4-trifluoromethylphenyl, 4-chloro-3-fluorophenyl, 4-(3-chloropropoxy)phenyl, 4-(3-hydroxypropoxy)phenyl, 3,4-dichlorophenyl, 4-fluorophenyl, 2,4-dichlorophenyl, 4-methylphenyl, 3,4-difluorophenyl, 3-fluoro-4-methoxyphenyl, 3,5-difluorophenyl, 6-trifluoromethylpyridin-3-yl, 5-methoxy-6-trifluoromethylpyridin-3-yl, 2-fluoro-4-trifluoromethylphenyl, 4-trifluoromethoxyphenyl, 2,3-difluoro-4-trifluoromethylphenyl, 4-hydroxyphenyl, 3-methoxy-4-trifluoromethylphenyl, 3-hydroxy-4-trifluoromethylphenyl, 5-chlorothiophen-2-yl, 3-fluoro-4-hydroxyphenyl, or a phenyl substituted in the 4 position with —NH—C(O)—O—$CH_2$-phenyl.

In some embodiments of the compound of Formula I, $R^2$ is —H.

In some embodiments of the compound of Formula I, $R^3$ is —H. In some embodiments, both $R^3$ and $R^4$ are —H. In still other embodiments, $R^2$, $R^3$, and $R^4$ are all —H. In some such embodiments, at least one of $R^3$ and $R^4$ is —H.

In some embodiments of the compound of Formula I, $R^4$ is —H.

In some embodiments of the compound of Formula I, the carbocyclic ring system or the heterocyclic ring system of $R^1$ comprises at least one aromatic ring.

In some embodiments of the compound of Formula I, the carbocyclic ring system or the heterocyclic ring system of $R^1$ comprises a bicyclic ring system.

In some embodiments of the compound of Formula I, the carbocyclic ring system or the heterocyclic ring system of $R^1$ comprises two rings that are fused to one another, wherein at least one of the rings is a 6-membered ring.

In some embodiments of the compound of Formula I, the carbocyclic ring system or the heterocyclic ring system of $R^1$ comprises at least one ring that is not aromatic.

In some embodiments of the compound of Formula I, the carbocyclic ring system or the heterocyclic ring system of $R^1$ is selected from a group other than an unsubstituted or optionally substituted group of one of the following where the wavy line indicates the point of attachment to the thiadiazole ring:

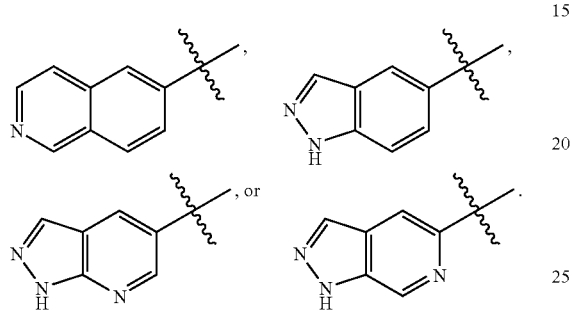

In some embodiments of the compound of Formula I, $R^1$ is selected from optionally substituted phenyl, pyridyl, indazolyl, isoquinolinyl, thiazolopyridinyl, benzothiazolonyl, dihydroquinolinonyl, benzoisoxazolyl, benzooxazolonyl, indolinonyl, benzoimidazolonyl, phthalazinyl, naphthyridinyl, thienopyridinyl, benzodioxolyl, isoindolinonyl, quinazolinyl, or cinnolinyl.

In some embodiments of the compound of Formula I, $R^1$ is selected from one of the following groups which may optionally be substituted and where the wavy line indicates the point of attachment to the thiadiazole:

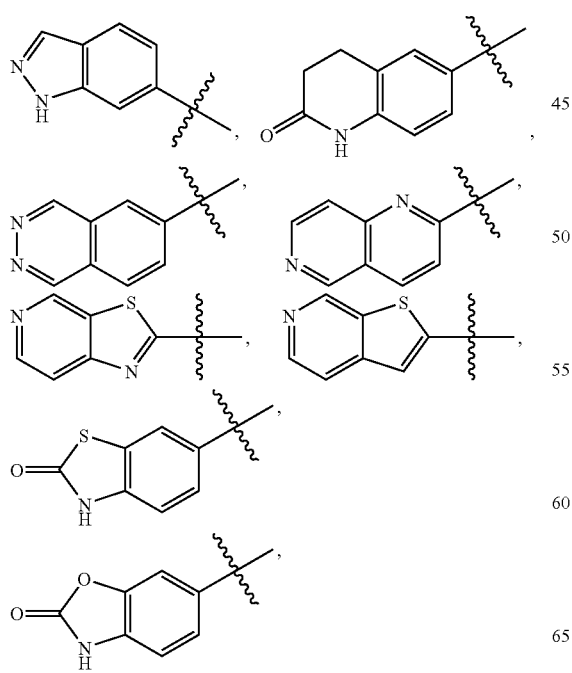

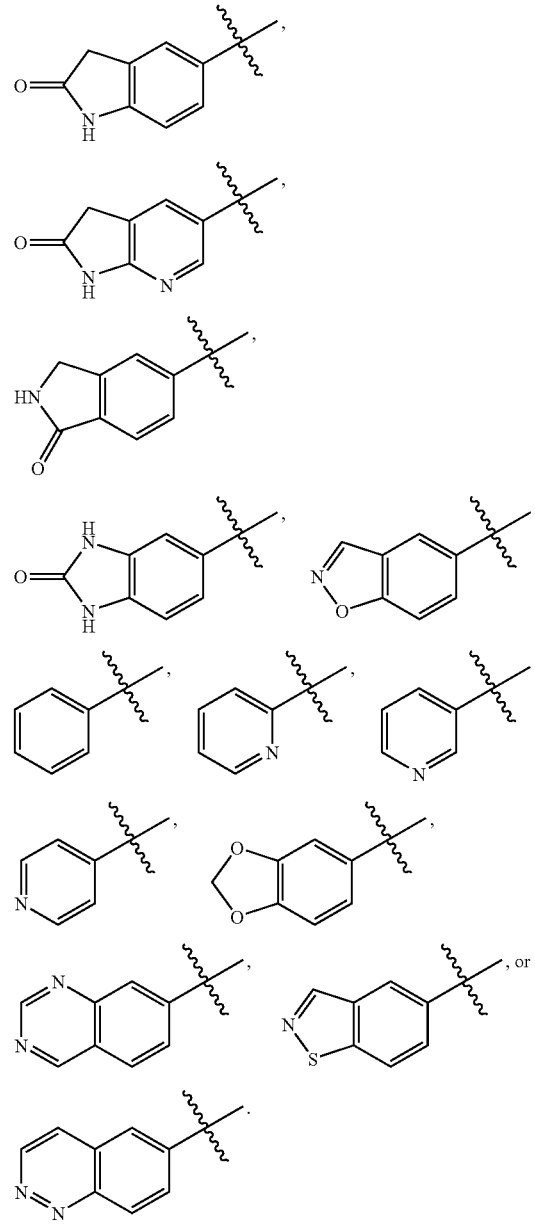

In some embodiments of the compound of Formula I, $R^1$ is selected from one of the following groups which may optionally be substituted and where the wavy line indicates the point of attachment to the thiadiazole:

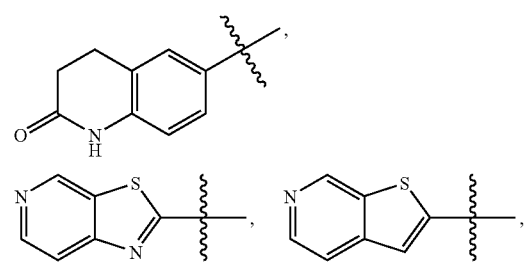

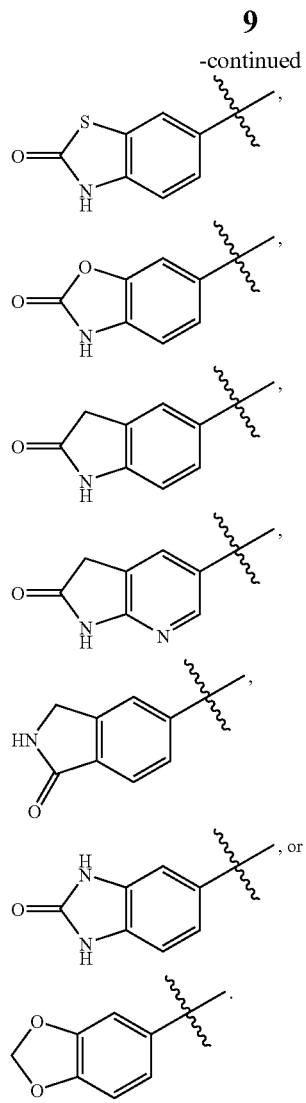
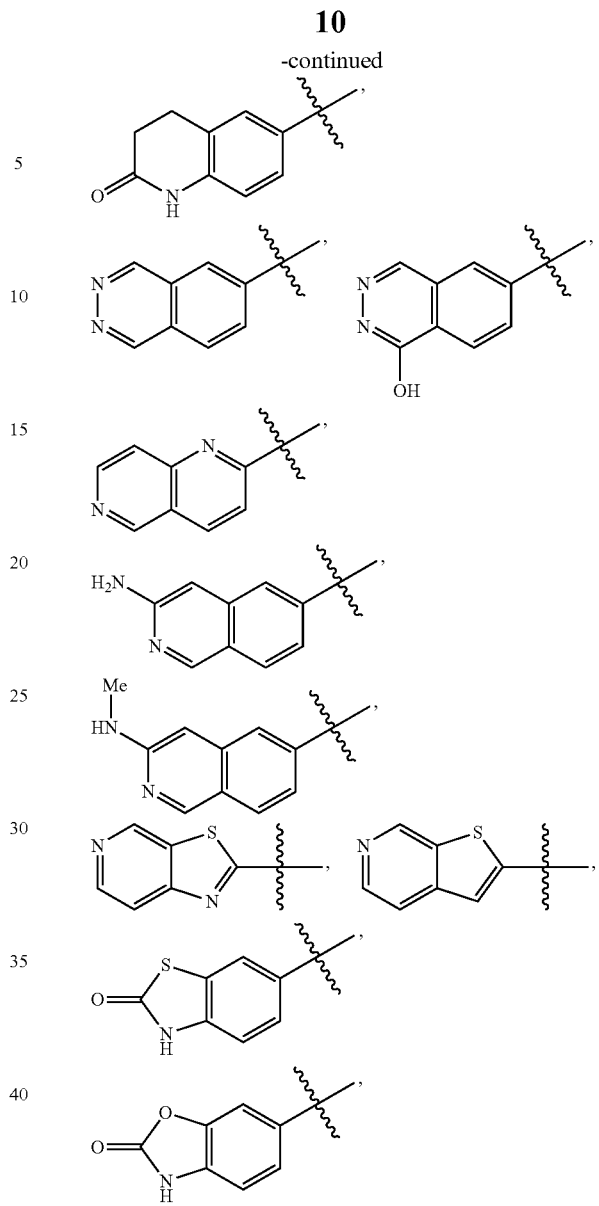
In some embodiments of the compound of Formula I, $R^1$ is selected from one of the following groups, where the wavy line indicates the point of attachment to the thiadiazole:
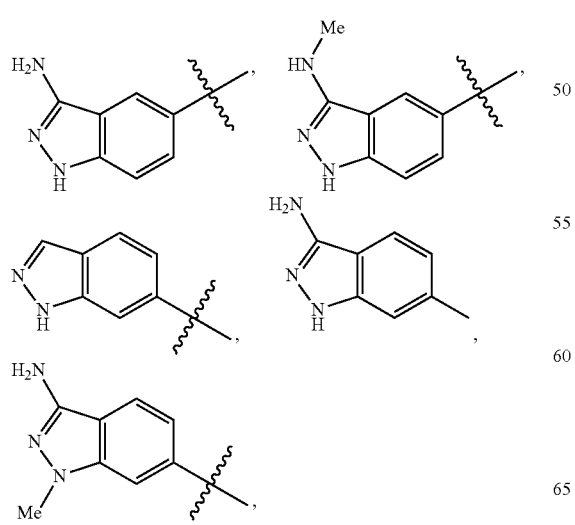
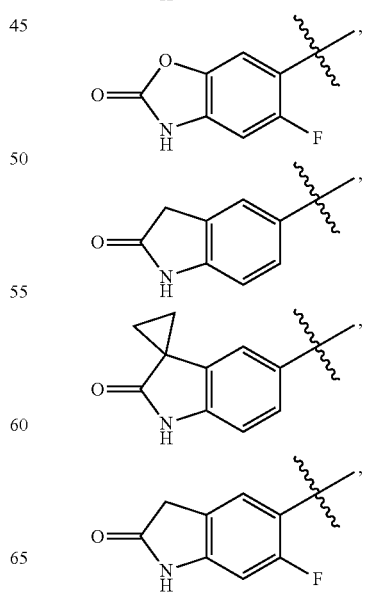

-continued
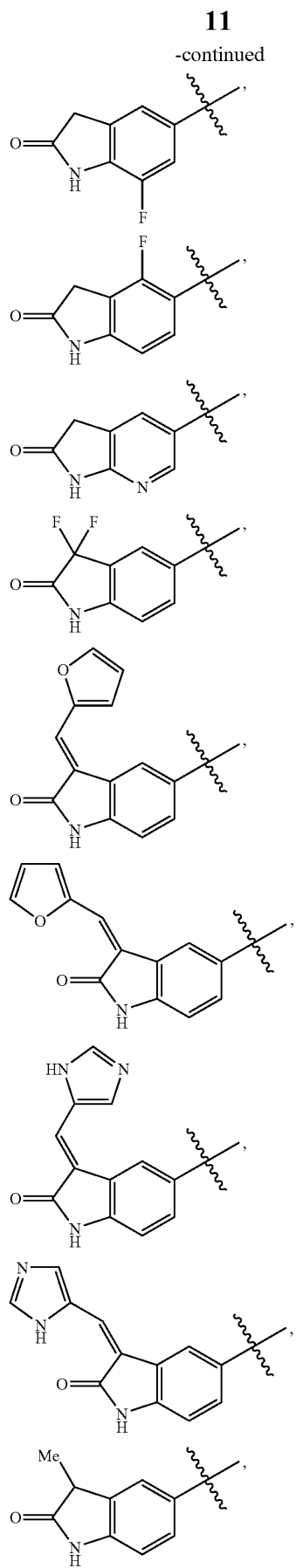
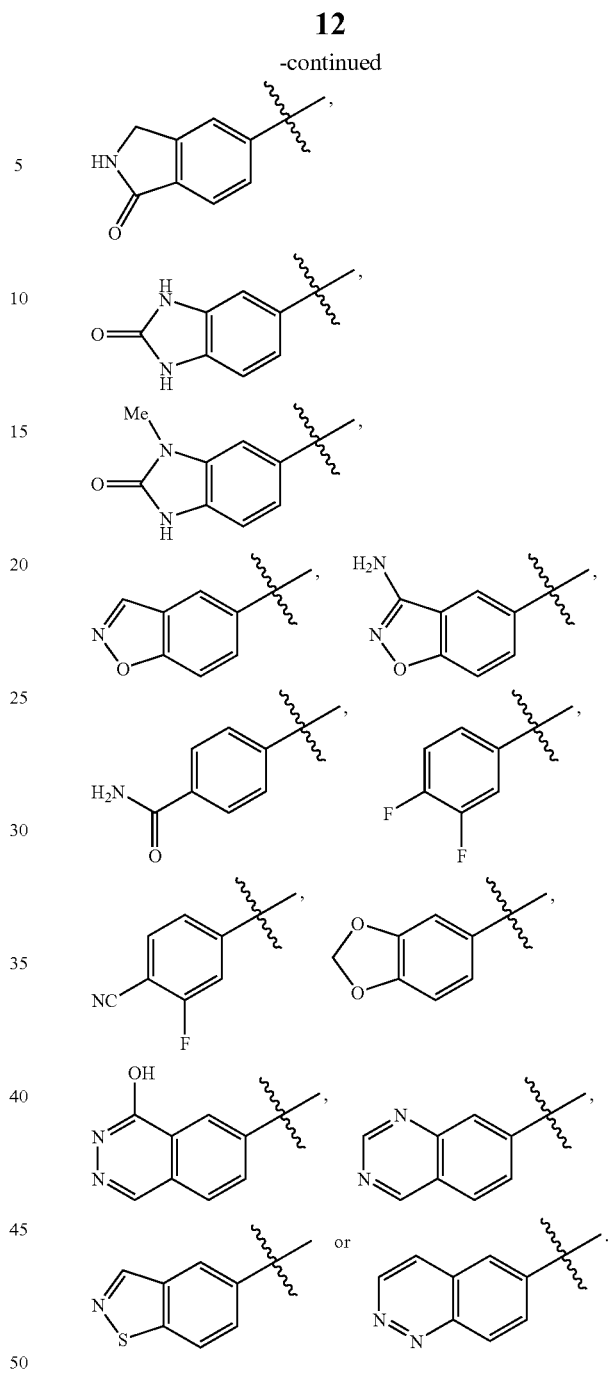
In another aspect, the invention provides a compound of Formula II
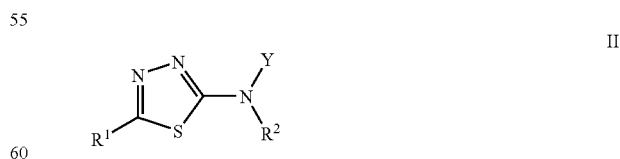
wherein:
R$^1$ is selected from a carbocyclic ring system or a heterocyclic ring system;
R$^2$ is selected from —H, C$_1$-C$_8$ alkyl, —(C$_1$-C$_6$ alkyl)aryl, or —C(O)(C$_1$-C$_6$ alkyl); and Y is selected from a group having the following formula:

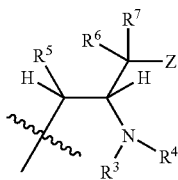

R³ is selected from —H, C₁-C₈ alkyl, —C(O)(CR⁸R⁹)ₜN(R⁷)₂, —(CR⁸R⁹)ₜ(aryl), —(CR⁸R⁹)ₜ(heteroaryl), —(CR⁸R⁹)ₜ(cycloalkyl), or —(CR⁸R⁹)ₜ(heterocyclyl);
R⁴ is selected from —H, C₁-C₈ alkyl, —(C₁-C₆ alkyl)aryl, or —C(O)(C₁-C₆ alkyl);
R⁵ is selected from —H, —OR¹⁰, —O—(C₁-C₆ alkyl)—O—R¹⁰, C₁-C₆ alkyl, C₁-C₆ alkenyl, —(C₁-C₆ alkyl)—O—R¹⁰, or —(C₁-C₆ alkyl)—O—C(O)—R¹⁰;
R⁶ is selected from —H, or C₁-C₆ alkyl;
R⁷ is selected from —H, —OR¹⁰, —O—(C₁-C₆ alkyl)—O—R¹⁰, C₁-C₆ alkyl, C₁-C₆ alkenyl, —(C₁-C₆ alkyl)—O—R¹⁰, or —(C₁-C₆ alkyl)—O—C(O)—R¹⁰;
R⁸ and R⁹, in each instance, are independently selected from —H, C₁-C₆ alkyl, or aryl;
R¹⁰ is selected from —H, C₁-C₆ alkyl, C₁-C₆ haloalkyl, —(C₁-C₆ alkyl)aryl, aryl, heteroaryl, C₁-C₆ hydroxyalkyl, or —(C₁-C₆ alkyl)—O—(C₁-C₆ alkyl), cycloalkyl, or heterocyclyl;
each t is independently selected from 0, 1, 2, or 3; and
Z is selected from aryl or heteroaryl;
wherein each of the above alkyl, aryl, heteroaryl, cycloalkyl, and heterocyclyl moieties and heterocyclic and carbocyclic rings are optionally and independently substituted by 1-3 substituents selected from
amino,
aryl, heteroaryl, cycloalkyl, or heterocyclyl optionally substituted by 1-5 substituents selected from
C₁-C₆ alkoxy,
C₁-C₆ alkyl optionally substituted by halo,
aryl,
halo,
hydroxyl,
heteroaryl,
C₁-C₆ hydroxyalkyl, or
—NHS(O)₂—C₁-C₆ alkyl);
C₁-C₆ alkyl, C₁-C₆ haloalkyl, C₁-C₆ hydroxyalkyl, C₁-C₆ alkoxy, C₁-C₆ haloalkoxy, C₁-C₆ hydroxyalkoxy, C₁-C₆ alkylamino, C₂-C₆ alkenyl, or C₂-C₆ alkynyl, wherein each of which may be interrupted by one or more hetero atoms,
cyano,
halo,
hydroxyl,
nitro,
oxo,
—NH(CO)—O—(C₁-C₆ alkyl)aryl, —NH(CO)—O—(C₁-C₆ alkyl), —N(C₁-C₆ alkyl)(CO)—O—(C₁-C₆ alkyl)aryl, —N(C₁-C₆ alkyl)(CO)—O—(C₁-C₆ alkyl), —C(O)OH, —C(O)O(C₁-C₆ alkyl), —C(O)NH₂, —C(O)N(H)—(C₁-C₆ alkyl), —C(O)N(C₁-C₆ alkyl)₂, —NH(C₁-C₆ alkyl), —N(C₁-C₆ alkyl)₂, —(C₂-C₄ alkenyl)heterocyclyl, or —(C₂-C₄ alkenyl)cycloalkyl, or —O-aryl;
or a pharmaceutically acceptable salt, hydrate, stereoisomer, or mixture thereof,
wherein the carbocyclic ring system or the heterocyclic ring system of R¹ is selected from a group other than one of the following or a substituted form of one of the following:

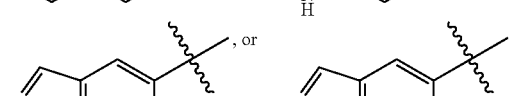

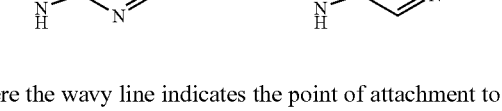

where the wavy line indicates the point of attachment to the thiadiazole ring.

In some embodiments of the compound of Formula II, the carbocyclic ring system or the heterocyclic ring system of R¹ comprises at least one ring that is not aromatic. In some such embodiments, the ring that is not aromatic includes an oxo group.

In some embodiments of the compound of Formula II, the carbocyclic ring system or the heterocyclic ring system of R¹ comprises at least one aromatic ring.

In some embodiments of the compound of Formula II, the carbocyclic ring system or the heterocyclic ring system of R¹ comprises a bicyclic ring system.

In some embodiments of the compound of Formula II, the carbocyclic ring system or the heterocyclic ring system of R¹ comprises two rings that are fused to one another, wherein at least one of the rings is a 6-membered ring. In some such embodiments, one of the rings is a 5-membered ring. In some such embodiments, the 5-membered ring is not aromatic and in some embodiments includes an oxo group.

In some embodiments of the compound of Formula II, R¹ is selected from optionally substituted phenyl, pyridyl, thiazolopyridinyl, benzothiazolonyl, dihydroquinolinonyl, benzoisoxazolyl, benzooxazolonyl, indolinonyl, benzoimidazolonyl, phthalazinyl, naphthyridinyl, thienopyridinyl, benzodioxolyl, isoindolinonyl, quinazolinyl, or cinnolinyl.

In some embodiments of the compound of Formula II, R¹ is selected from one of the following groups which may optionally be substituted and where the wavy line indicates the point of attachment to the thiadiazole:

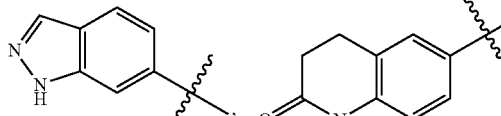

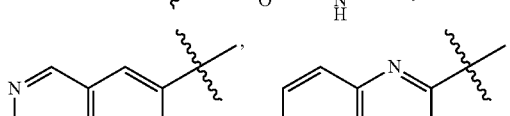

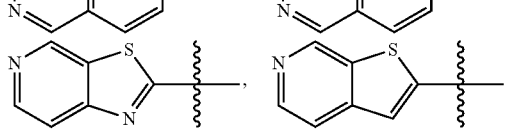

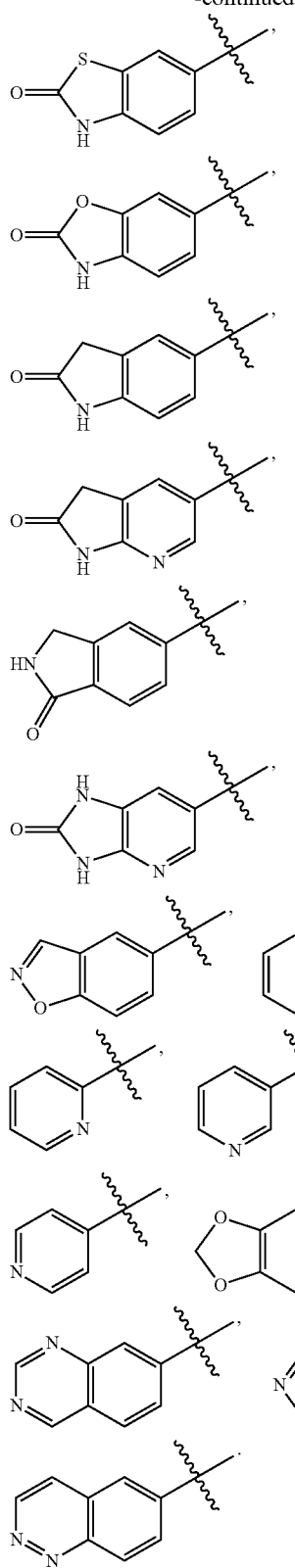

In some embodiments of the compound of Formula II, R$^1$ is selected from one of the following groups which may optionally be substituted and where the wavy line indicates the point of attachment to the thiadiazole:

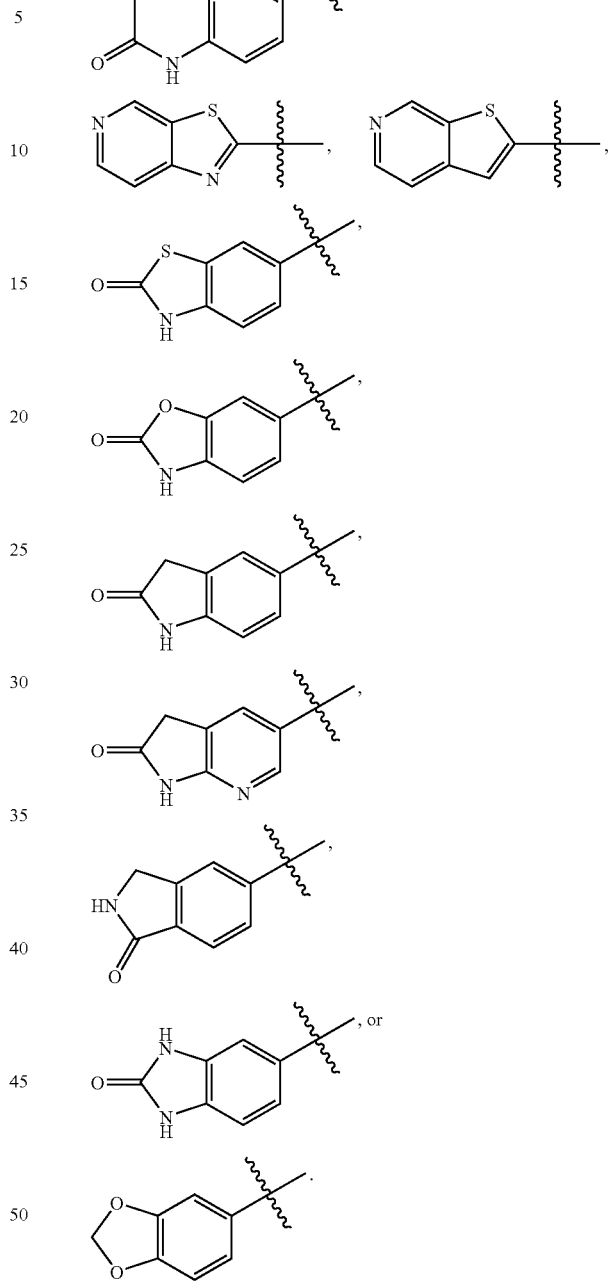

In some embodiments of the compound of Formula II, R$^1$ is selected from one of the following groups, where the wavy line indicates the point of attachment to the thiadiazole:

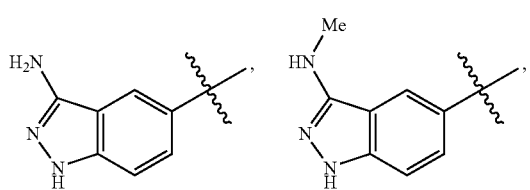

-continued
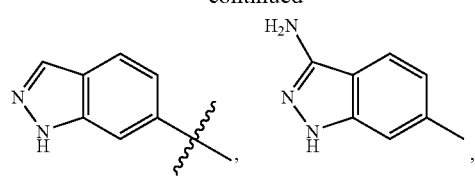
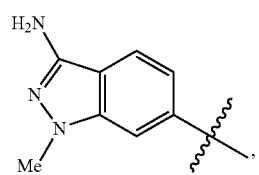
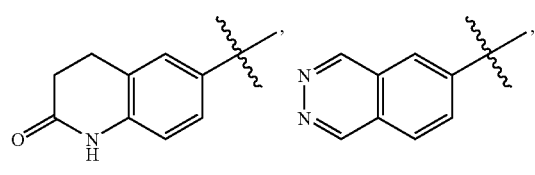
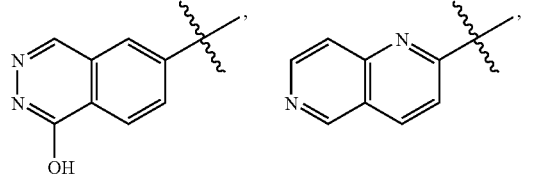
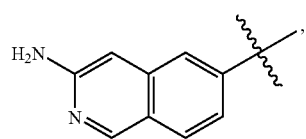
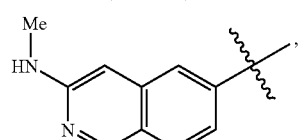
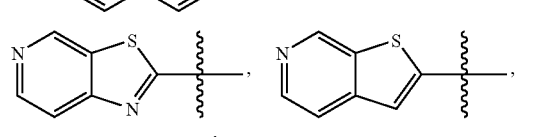
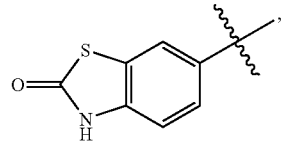
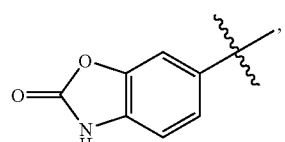
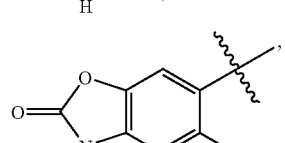
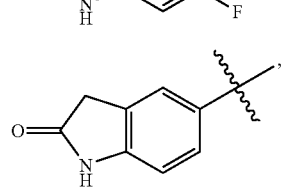
-continued
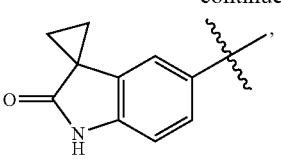
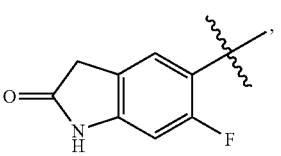
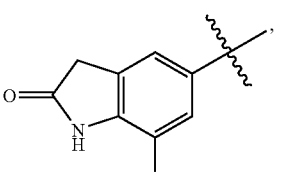
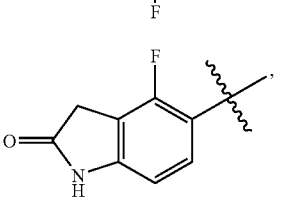
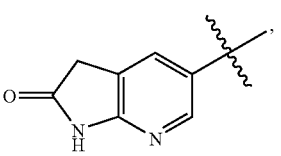
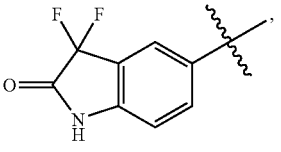
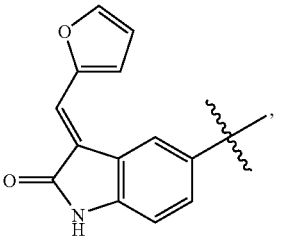
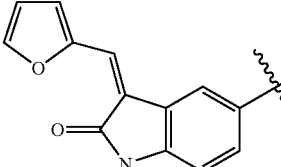
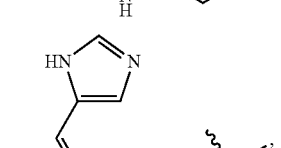
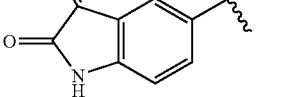

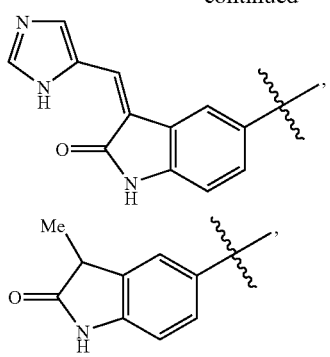
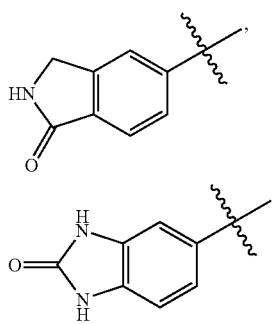
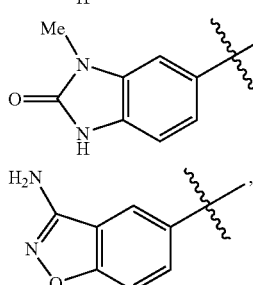
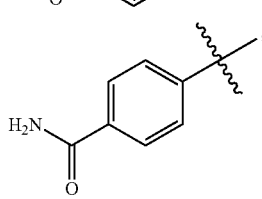
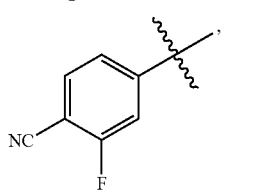
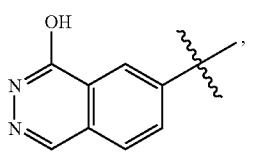
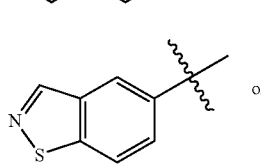

In some embodiments of the compound of Formula II, the compound has the Formula IA

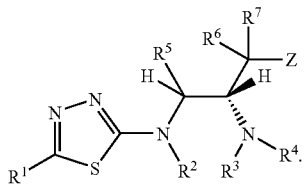

IA

In some embodiments of the compound of Formula II, the compound has the Formula IB

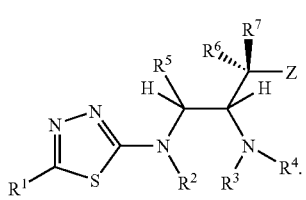

IB

In some embodiments of the compound of Formula II, the compound has the Formula IC

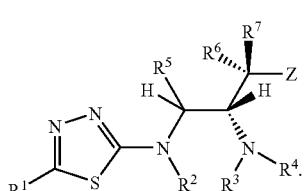

IC

In some embodiments of the compound of Formula II, the compound has the Formula ID

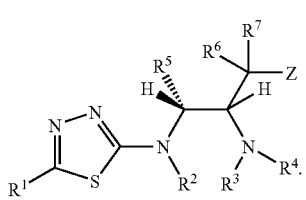

ID

In some embodiments of the compound of Formula II, the compound has the Formula IE

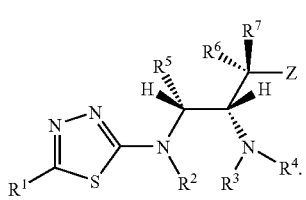

IE

In some embodiments of the compound of Formula II, $R^5$ is —H or $C_1$-$C_6$ alkyl. In some such embodiments, $R^5$ is —H or methyl.

In some embodiments of the compound of Formula II, $R^6$ is —H.

In some embodiments of the compound of Formula II, $R^7$ is —H.

In some embodiments of the compound of Formula II, $R^7$ is —$OR^{10}$, —O—($C_1$-$C_6$ alkyl)—O—$R^{10}$, $C_1$-$C_6$ alkyl, $C_1$-$C_6$ alkenyl, —($C_1$-$C_6$ alkyl)—O—$R^{10}$, or —($C_1$-$C_6$ alkyl)—O—C(O)—$R^{10}$.

In some embodiments of the compound of Formula II, $R^7$ is selected from —H, methyl, ethyl, propyl, ethenyl, propenyl, hydroxymethyl, methoxymethyl, —$CH_2$—O—C(O)—($C_1$-$C_6$ alkyl), 1-hydroxyethyl, or methoxymethoxy.

In some embodiments of the compound of Formula II, Z is selected from optionally substituted phenyl, optionally substituted indolyl, optionally substituted naphthyl, optionally substituted pyridyl, or optionally substituted thiophenyl.

In some embodiments of the compound of Formula II, Z is selected from phenyl, indolyl, naphthyl, pyridyl, or thiophenyl, each of which is optionally substituted with 1-3 substituents selected from —Cl, —F, —$CF_3$, —OH, —O—($C_1$-$C_6$ alkyl), —O—($C_1$-$C_6$ alkyl)-Cl, —O—($C_1$-$C_6$ alkyl)—OH, —$C_1$-$C_6$ alkyl, —$OCF_3$, —NH(CO)—O—($C_1$-$C_6$ alkyl)aryl, or —NH(CO)—O—($C_1$-$C_6$ alkyl).

In some embodiments of the compound of Formula II, Z is selected from phenyl, indolyl, naphthyl, pyridyl, thiophenyl, 4-chlorophenyl, 4-trifluoromethylphenyl, 3-chlorophenyl, 3-trifluoromethylphenyl, 4-methoxyphenyl, 3-fluoro-4-trifluoromethylphenyl, 4-chloro-3-fluorophenyl, 4-(3-chloropropoxy)phenyl, 4-(3-hydroxypropoxy)phenyl, 3,4-dichlorophenyl, 4-fluorophenyl, 2,4-dichlorophenyl, 4-methylphenyl, 3,4-difluorophenyl, 3-fluoro-4-methoxyphenyl, 3,5-difluorophenyl, 6-trifluoromethylpyridin-3-yl, 5-methoxy-6-trifluoromethylpyridin-3-yl, 2-fluoro-4-trifluoromethylphenyl, 4-trifluoromethoxyphenyl, 2,3-difluoro-4-trifluoromethylphenyl, 4-hydroxyphenyl, 3-methoxy-4-trifluoromethylphenyl, 3-hydroxy-4-trifluoromethylphenyl, 5-chlorothiophen-2-yl, 3-fluoro-4-hydroxyphenyl, or a phenyl substituted in the 4 position with —NH—C(O)—O—$CH_2$-phenyl.

In some embodiments of the compound of Formula II, $R^2$ is —H.

In some embodiments of the compound of Formula II, $R^3$ is —H. In some embodiments, both $R^3$ and $R^4$ are —H. In still other embodiments, $R^2$, $R^3$, and $R^4$ are all —H. In some such embodiments, at least one of $R^3$ and $R^4$ is —H.

In some embodiments of the compound of Formula II, $R^4$ is —H.

In another aspect, the invention provides a compound of Formula IV

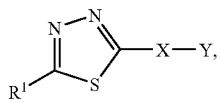

IV wherein:
X is selected from O, S, $NR^2$, or $CR^{2a}R^{2b}$;
$R^1$ is selected from a carbocyclic ring system or a heterocyclic ring system;
$R^2$ may be absent or is selected from —H, $C_1$-$C_8$ alkyl, —($C_1$-$C_6$ alkyl)aryl, or —C(O)($C_1$-$C_6$ alkyl);
$R^{2a}$ and $R^{2b}$ may be absent or are independently selected from —H, $C_1$-$C_8$ alkyl, —($C_1$-$C_6$ alkyl)aryl, or —C(O)($C_1$-$C_6$ alkyl);
Y is selected from one of the following when X is O, S, $NR^2$, or $CR^{2a}R^{2b}$:

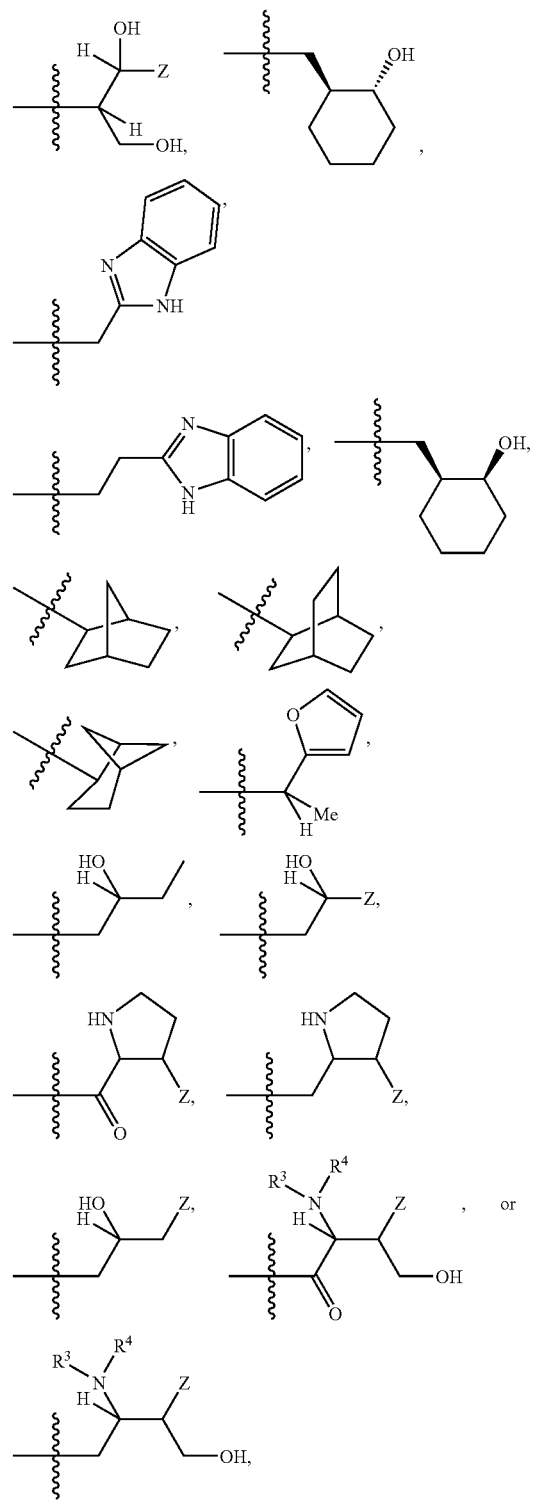

wherein the wavy line indicates the point of attachment to X and any of the carbons with unspecified substituents in the alkyl, cycloalkyl, aryl, or heteroaryl groups in the above selections for Y may be substituted with —H, halo, $C_1$-$C_6$ alkyl, or —$OR^{10}$ groups;

or Y is optionally selected from the following when X is O, S, or $CR^{2a}R^{2b}$:

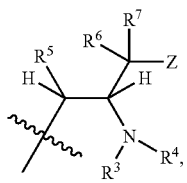

and the wavy line indicates the point of attachment to X;

$R^3$ may be absent or is selected from —H, $C_1$-$C_8$ alkyl, —C(O)(CR$^1$R$^9$)$_t$)N(R$^7$)$_2$, —(CR$^8$R$^9$)$_t$(aryl), —(CR$^8$R$^9$)$_t$(heteroaryl), —(CR$^8$R$^9$)$_t$(cycloalkyl), or —(CR$^8$R$^9$)$_t$(heterocyclyl);

$R^4$ may be absent or is selected from —H, $C_1$-$C_8$ alkyl, —($C_1$-$C_6$ alkyl)aryl, or —C(O)($C_1$-$C_6$ alkyl);

$R^5$ may be absent or is selected from —H, —OR$^{10}$, —O—($C_1$-$C_6$ alkyl)—O—R$^{10}$, $C_1$-$C_6$ alkyl, $C_1$-$C_6$ alkenyl, —($C_1$-$C_6$ alkyl)—O—R$^{10}$, or —($C_1$-$C_6$ alkyl)—O—C(O)—R$^{10}$;

$R^6$ may be absent or is selected from —H, or $C_1$-$C_6$ alkyl;

$R^7$ may be absent or is selected from —H, —OR$^{10}$, —O—($C_1$-$C_6$ alkyl)—O—R$^{10}$, $C_1$-$C_6$ alkyl, $C_1$-$C_6$ alkenyl, —($C_1$-$C_6$ alkyl)—O—R$^{10}$, or —($C_1$-$C_6$ alkyl)—O—C(O)—R$^{10}$;

$R^8$ and $R^9$, in each instance, may be absent or are independently selected from —H, $C_1$-$C_6$ alkyl, or aryl;

$R^{10}$ may be absent or is selected from —H, $C_1$-$C_6$ alkyl, $C_1$-$C_6$ haloalkyl, —($C_1$-$C_6$ alkyl)aryl, aryl, heteroaryl, $C_1$-$C_6$ hydroxyalkyl, or —($C_1$-$C_6$ alkyl)—O—($C_1$-$C_6$ alkyl), cycloalkyl, or heterocyclyl;

each t is independently selected from 0, 1, 2, or 3; and

Z may be absent or is selected from aryl or heteroaryl;

wherein each of the above alkyl, aryl, heteroaryl, cycloalkyl, and heterocyclyl moieties and heterocyclic and carbocyclic rings are optionally and independently substituted by 1-3 substituents selected from amino, aryl, heteroaryl, cycloalkyl, or heterocyclyl optionally substituted by 1-5 substituents selected from $C_1$-$C_6$ alkoxy, $C_1$-$C_6$ alkyl optionally substituted by halo, aryl, halo, hydroxyl, heteroaryl, $C_1$-$C_6$ hydroxyalkyl, or —NHS(O)$_2$—$C_1$-$C_6$ alkyl);

$C_1$-$C_6$ alkyl, $C_1$-$C_6$ haloalkyl, $C_1$-$C_6$ hydroxyalkyl, $C_1$-$C_6$ alkoxy, $C_1$-$C_6$ haloalkoxy, $C_1$-$C_6$ hydroxyalkoxy, $C_1$-$C_6$ alkylamino, $C_2$-$C_6$ alkenyl, or $C_2$-$C_6$ alkynyl, wherein each of which may be interrupted by one or more hetero atoms, cyano, halo, hydroxyl, nitro, oxo, —NH(CO)—O—($C_1$-$C_6$ alkyl)aryl, —NH(CO)—O—($C_1$-$C_6$ alkyl), —N($C_1$-$C_6$ alkyl)(CO)—O—($C_1$-$C_6$ alkyl)aryl, —N($C_1$-$C_6$ alkyl)(CO)—O—($C_1$-$C_6$ alkyl), —C(O)OH, —C(O)O($C_1$-$C_6$ alkyl), —C(O)NH$_2$, —C(O)N(H)—($C_1$-$C_6$ alkyl), —C(O)N($C_1$-$C_6$ alkyl)$_2$, —NH($C_1$-$C_6$ alkyl), —N($C_1$-$C_6$ alkyl)$_2$, —($C_2$-$C_4$ alkenyl)heterocyclyl, or —($C_2$-$C_4$ alkenyl)cycloalkyl, or —O-aryl;

or a pharmaceutically acceptable salt, hydrate, stereoisomer, or mixture thereof.

In some embodiments of the compound of Formula IV,

X is selected from O, S, NR$^2$, or CR$^{2a}$R$^{2b}$;

$R^1$ is selected from a carbocyclic ring system or a heterocyclic ring system;

$R^2$ may be absent or is selected from —H, $C_1$-$C_8$ alkyl, —($C_1$-$C_6$ alkyl)aryl, or —C(O)($C_1$-$C_6$ alkyl);

$R^{2a}$ and $R^{2b}$ may be absent or are independently selected from —H, $C_1$-$C_8$ alkyl, —($C_1$-$C_6$ alkyl)aryl, or —C(O)($C_1$-$C_6$ alkyl);

Y is selected from one of the following:

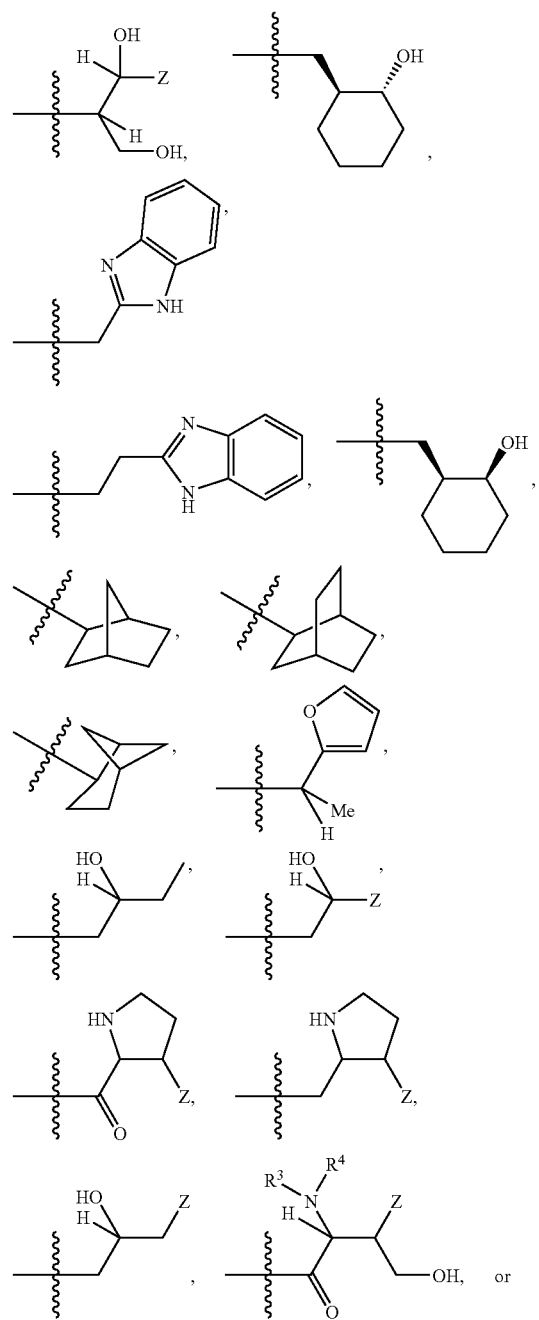

-continued

[structure with $R^3$, $R^4$, N, H, Z, OH]

wherein the wavy line indicates the point of attachment to X and any of the carbons with unspecified substituents in the alkyl, cycloalkyl, aryl, or heteroaryl groups in the above selections for Y may be substituted with —H, halo, $C_1$-$C_6$ alkyl, or —$OR^{10}$ groups;

$R^3$ may be absent or is selected from —H, $C_1$-$C_8$ alkyl, —C(O)(C$R^8R^9$)$_t$)N($R^7$)$_2$, —(C$R^8R^9$)$_t$(aryl), —(C$R^8R^9$)$_t$(heteroaryl), —(C$R^8R^9$)$_t$(cycloalkyl), or —(C$R^8R^9$)$_t$(heterocyclyl);

$R^4$ may be absent or is selected from —H, $C_1$-$C_8$ alkyl, —($C_1$-$C_6$ alkyl)aryl, or —C(O)($C_1$-$C_6$ alkyl);

$R^7$ may be absent or is selected from —H, —$OR^{10}$, —O—($C_1$-$C_6$ alkyl)—O—$R^{10}$, $C_1$-$C_6$ alkyl, $C_1$-$C_6$ alkenyl, —($C_1$-$C_6$ alkyl)—O—$R^{10}$, or —($C_1$-$C_6$ alkyl)—O—C(O)—$R^{10}$;

$R^8$ and $R^9$, in each instance, may be absent or are independently selected from —H, $C_1$-$C_6$ alkyl, or aryl;

$R^{10}$ may be absent or is selected from —H, $C_1$-$C_6$ alkyl, $C_1$-$C_6$ haloalkyl, —($C_1$-$C_6$ alkyl)aryl, aryl, heteroaryl, $C_1$-$C_6$ hydroxyalkyl, or —($C_1$-$C_6$ alkyl)—O—($C_1$-$C_6$ alkyl), cycloalkyl, or heterocyclyl;

each t is independently selected from 0, 1, 2, or 3; and
Z may be absent or is selected from aryl or heteroaryl;
wherein each of the above alkyl, aryl, heteroaryl, cycloalkyl, and heterocyclyl moieties and heterocyclic and carbocyclic rings are optionally and independently substituted by 1-3 substituents selected from
 amino,
 aryl, heteroaryl, cycloalkyl, or heterocyclyl optionally substituted by 1-5 substituents selected from
  $C_1$-$C_6$ alkoxy,
  $C_1$-$C_6$ alkyl optionally substituted by halo,
  aryl,
  halo,
  hydroxyl,
  heteroaryl,
  $C_1$-$C_6$ hydroxyalkyl, or
  —NHS(O)$_2$—$C_1$-$C_6$ alkyl);
 $C_1$-$C_6$ alkyl, $C_1$-$C_6$ haloalkyl, $C_1$-$C_6$ hydroxyalkyl, $C_1$-$C_6$ alkoxy, $C_1$-$C_6$ haloalkoxy, $C_1$-$C_6$ hydroxyalkoxy, $C_1$-$C_6$ alkylamino, $C_2$-$C_6$ alkenyl, or $C_2$-$C_6$ alkynyl, wherein each of which may be interrupted by one or more hetero atoms,
 cyano,
 halo,
 hydroxyl,
 nitro,
 oxo,
 —NH(CO)—O—($C_1$-$C_6$ alkyl)aryl, —NH(CO)—O—($C_1$-$C_6$ alkyl), —N($C_1$-$C_6$ alkyl)(CO)—O—($C_1$-$C_6$ alkyl)aryl, —N($C_1$-$C_6$ alkyl)(CO)—O—($C_1$-$C_6$ alkyl), —C(O)OH, —C(O)O($C_1$-$C_6$ alkyl), —C(O)NH$_2$, —C(O)N(H)—($C_1$-$C_6$ alkyl), —C(O)N($C_1$-$C_6$ alkyl)$_2$, —NH($C_1$-$C_6$ alkyl), —N($C_1$-$C_6$ alkyl)$_2$, —($C_2$-$C_4$ alkenyl)heterocyclyl, or —($C_2$-$C_4$ alkenyl)cycloalkyl, or —O-aryl;
or a pharmaceutically acceptable salt, hydrate, stereoisomer, or mixture thereof.

In some embodiments of the compound of Formula UV,
X is selected from O, S, or C$R^{2a}R^{2b}$;
$R^1$ is selected from a carbocyclic ring system or a heterocyclic ring system;
$R^{2a}$ and $R^{2b}$ may be absent or are independently selected from —H, $C_1$-$C_8$ alkyl, —($C_1$-$C_6$ alkyl)aryl, or —C(O)($C_1$-$C_6$ alkyl);
Y is:

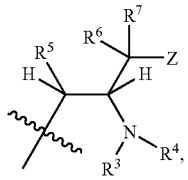

and the wavy line indicates the point of attachment to X;
$R^3$ may be absent or is selected from —H, $C_1$-$C_8$ alkyl, —C(O)(C$R^8R^9$)$_t$)N($R^7$)$_2$, —(C$R^8R^9$)$_t$(aryl), —(C$R^8R^9$)$_t$(heteroaryl), —(C$R^8R^9$)$_t$(cycloalkyl), or —(C$R^8R^9$)$_t$(heterocyclyl);

$R^4$ may be absent or is selected from —H, $C_1$-$C_8$ alkyl, —($C_1$-$C_6$ alkyl)aryl, or —C(O)($C_1$-$C_6$ alkyl);

$R^5$ may be absent or is selected from —H, —$OR^{10}$, —O—($C_1$-$C_6$ alkyl)—O—$R^{10}$, $C_1$-$C_6$ alkyl, $C_1$-$C_6$ alkenyl, —($C_1$-$C_6$ alkyl)—O—$R^{10}$, or —($C_1$-$C_6$ alkyl)—O—C(O)—$R^{10}$;

$R^6$ may be absent or is selected from —H, or $C_1$-$C_6$ alkyl;

$R^7$ may be absent or is selected from —H, —$OR^{10}$, —O—($C_1$-$C_6$ alkyl)—O—$R^{10}$, $C_1$-$C_6$ alkyl, $C_1$-$C_6$ alkenyl, —($C_1$-$C_6$ alkyl)—O—$R^{10}$, or —($C_1$-$C_6$ alkyl)—O—C(O)—$R^{10}$;

$R^8$ and $R^9$, in each instance, may be absent or are independently selected from —H, $C_1$-$C_6$ alkyl, or aryl;

$R^{10}$ may be absent or is selected from —H, $C_1$-$C_6$ alkyl, $C_1$-$C_6$ haloalkyl, —($C_1$-$C_6$ alkyl)aryl, aryl, heteroaryl, $C_1$-$C_6$ hydroxyalkyl, or —($C_1$-$C_6$ alkyl)—O—($C_1$-$C_6$ alkyl), cycloalkyl, or heterocyclyl;

each t is independently selected from 0, 1, 2, or 3; and
Z may be absent or is selected from aryl or heteroaryl;
wherein each of the above alkyl, aryl, heteroaryl, cycloalkyl, and heterocyclyl moieties and heterocyclic and carbocyclic rings are optionally and independently substituted by 1-3 substituents selected from
 amino,
 aryl, heteroaryl, cycloalkyl, or heterocyclyl optionally substituted by 1-5 substituents selected from
  $C_1$-$C_6$ alkoxy,
  $C_1$-$C_6$ alkyl optionally substituted by halo,
  aryl,
  halo,
  hydroxyl,
  heteroaryl,
  $C_1$-$C_6$ hydroxyalkyl, or
  —NHS(O)$_2$—$C_1$-$C_6$ alkyl);
 $C_1$-$C_6$ alkyl, $C_1$-$C_6$ haloalkyl, $C_1$-$C_6$ hydroxyalkyl, $C_1$-$C_6$ alkoxy, $C_1$-$C_6$ haloalkoxy, $C_1$-$C_6$ hydroxyalkoxy, $C_1$-$C_6$ alkylamino, $C_2$-$C_6$ alkenyl, or $C_2$-$C_6$ alkynyl, wherein each of which may be interrupted by one or more hetero atoms,
 cyano,
 halo,
 hydroxyl,
 nitro, oxo, —NH(CO)—O—(C$_1$-C$_6$ alkyl)aryl, —NH(CO)—O—(C$_1$-C$_6$ alkyl), —N(C$_1$-C$_6$ alkyl)(CO)—O—(C$_1$-C$_6$ alkyl)aryl, —N(C$_1$-C$_6$ alkyl)(CO)—O—(C$_1$-C$_6$ alkyl), —C(O)OH, —C(O)O(C$_1$-C$_6$ alkyl), —C(O)NH$_2$, —C(O)N(H)—(C$_1$-C$_6$ alkyl), —C(O)N(C$_1$-C$_6$ alkyl)$_2$, —NH(C$_1$-C$_6$ alkyl), —N(C$_1$-C$_6$ alkyl)$_2$, —(C$_2$-C$_4$ alkenyl)heterocyclyl, or —(C$_2$-C$_4$ alkenyl)cycloalkyl, or —O-aryl;

or a pharmaceutically acceptable salt, hydrate, stereoisomer, or mixture thereof.

In some embodiments of the compound of Formula IV, Y is

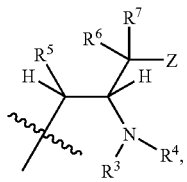

and one of the following is true:
(a) R$^5$ is selected from —OR$^{10}$, —O—(C$_1$-C$_6$ alkyl)—O—R$^{10}$, C$_1$-C$_6$ alkyl, C$_1$-C$_6$ alkenyl, —(C$_1$-C$_6$ alkyl)—O—R$^{10}$, or —(C$_1$-C$_6$ alkyl)—O—C(O)—R$^{10}$; or
(b) R$^7$ is selected from —OR$^{10}$, —O—(C$_1$-C$_6$ alkyl)—O—R$^{10}$, C$_1$-C$_6$ alkenyl, —(C$_1$-C$_6$ alkyl)—O—R$^{10}$, or —(C$_1$-C$_6$ alkyl)—O—C(O)—R$^{10}$.

In some embodiments of the compound of Formula IV, the compound is a compound other than

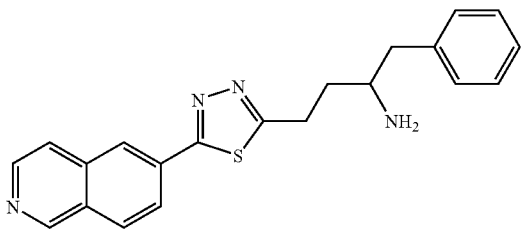

or a pharmaceutically acceptable salt, polymorph, clathrate, solvate, hydrate, stereoisomer, enantiomer, or prodrug thereof.

In some embodiments of the compound of Formula IV, X is NR$^2$. In some such embodiments, R$^2$ is —H.

In some embodiments of the compound of Formula IV, X is O.

In some embodiments of the compound of Formula IV, X is S.

In some embodiments of the compound of Formula IV, X is CR$^{2a}$R$^{2b}$. In some such embodiments, R$^{2a}$ and R$^{2b}$ are both H.

In some embodiments of the compound of Formula IV, R$^5$ is —H or C$_1$-C$_6$ alkyl. In some such embodiments, R$^5$ is —H or methyl.

In some embodiments of the compound of Formula IV, R$^6$ is —H.

In some embodiments of the compound of Formula IV, R$^7$ is —H

In some embodiments of the compound of Formula IV, R$^7$ is —OR$^{10}$, —O—(C$_1$-C$_6$ alkyl)—O—R$^{10}$, C$_1$-C$_6$ alkyl, C$_1$-C$_6$ alkenyl, —(C$_1$-C$_6$ alkyl)—O—R$^{10}$, or —(C$_1$-C$_6$ alkyl)—O—C(O)—R$^{10}$.

In some embodiments of the compound of Formula IV, R$^7$ is selected from —H, methyl, ethyl, propyl, ethenyl, propenyl, hydroxymethyl, methoxymethyl, —CH$_2$—O—C(O)—(C$_1$-C$_6$ alkyl), 1-hydroxyethyl, or methoxymethoxy.

In some embodiments of the compound of Formula IV, Z is selected from optionally substituted phenyl, optionally substituted indolyl, optionally substituted naphthyl, optionally substituted pyridyl, or optionally substituted thiophenyl.

In some embodiments of the compound of Formula IV, Z is selected from phenyl, indolyl, naphthyl, pyridyl, or thiophenyl, each of which is optionally substituted with 1-3 substituents selected from —Cl, —F, —CF$_3$, —OH, —O—(C$_1$-C$_6$ alkyl), —O—(C$_1$-C$_6$ alkyl)-Cl, —O—(C$_1$-C$_6$ alkyl)—OH, —C$_1$-C$_6$ alkyl, —OCF$_3$, —NH(CO)—O—(C$_1$-C$_6$ alkyl)aryl, or —NH(CO)—O—(C$_1$-C$_6$ alkyl).

In some embodiments of the compound of Formula IV, Z is selected from phenyl, indolyl, naphthyl, pyridyl, thiophenyl, 4-chlorophenyl, 4-trifluoromethylphenyl, 3-chlorophenyl, 3-trifluoromethylphenyl, 4-methoxyphenyl, 3-fluoro-4-trifluoromethylphenyl, 4-chloro-3-fluorophenyl, 4-(3-chloropropoxy)phenyl, 4-(3-hydroxypropoxy)phenyl, 3,4-dichlorophenyl, 4-fluorophenyl, 2,4-dichlorophenyl, 4-methylphenyl, 3,4-difluorophenyl, 3-fluoro-4-methoxyphenyl, 3,5-difluorophenyl, 6-trifluoromethylpyridin-3-yl, 5-methoxy-6-trifluoromethylpyridin-3-yl, 2-fluoro-4-trifluoromethylphenyl, 4-trifluoromethoxyphenyl, 2,3-difluoro-4-trifluoromethylphenyl, 4-hydroxyphenyl, 3-methoxy-4-trifluoromethylphenyl, 3-hydroxy-4-trifluoromethylphenyl, 5-chlorothiophen-2-yl, 3-fluoro-4-hydroxyphenyl, or a phenyl substituted in the 4 position with —NH—C(O)—O—CH$_2$-phenyl.

In some embodiments of the compound of Formula IV, R$^3$ and R$^4$ are each H. In some such embodiments, R$^2$, R$^3$, and R$^4$ are all H. In other such embodiments, R$^{2a}$, R$^{2b}$, R$^3$, and R$^4$ are all H.

In some embodiments of the compound of Formula IV, the carbocyclic ring system or the heterocyclic ring system of R$^1$ comprises at least one aromatic ring.

In some embodiments of the compound of Formula IV, the carbocyclic ring system or the heterocyclic ring system of R$^1$ comprises a bicyclic ring system.

In some embodiments of the compound of Formula IV, the carbocyclic ring system or the heterocyclic ring system of R$^1$ comprises two rings that are fused to one another, wherein at least one of the rings is a 6-membered ring.

In some embodiments of the compound of Formula IV, the carbocyclic ring system or the heterocyclic ring system of R$^1$ comprises at least one ring that is not aromatic.

In some embodiments of the compound of Formula IV, the carbocyclic ring system or the heterocyclic ring system of R$^1$ is selected from a group other than an unsubstituted or optionally substituted group of one of the following where the wavy line indicates the point of attachment to the thiadiazole ring:

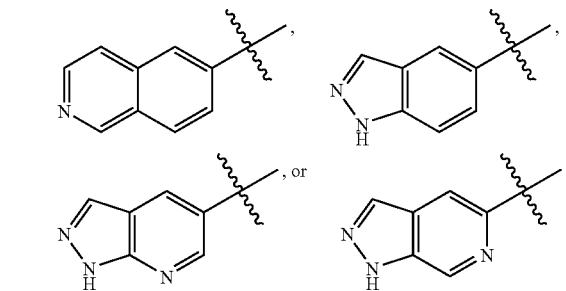

In some embodiments of the compound of Formula IV, $R^1$ is selected from optionally substituted phenyl, pyridyl, indazolyl, isoquinolinyl, thiazolopyridinyl, benzothiazolonyl, dihydroquinolinonyl, benzoisoxazolyl, benzooxazolonyl, indolinonyl, benzoimidazolonyl, phthalazinyl, naphthyridinyl, thienopyridinyl, benzodioxolyl, isoindolinonyl, quinazolinyl, or cinnolinyl.

In some embodiments of the compound of Formula IV, $R^1$ is selected from one of the following groups which may optionally be substituted and where the wavy line indicates the point of attachment to the thiadiazole:

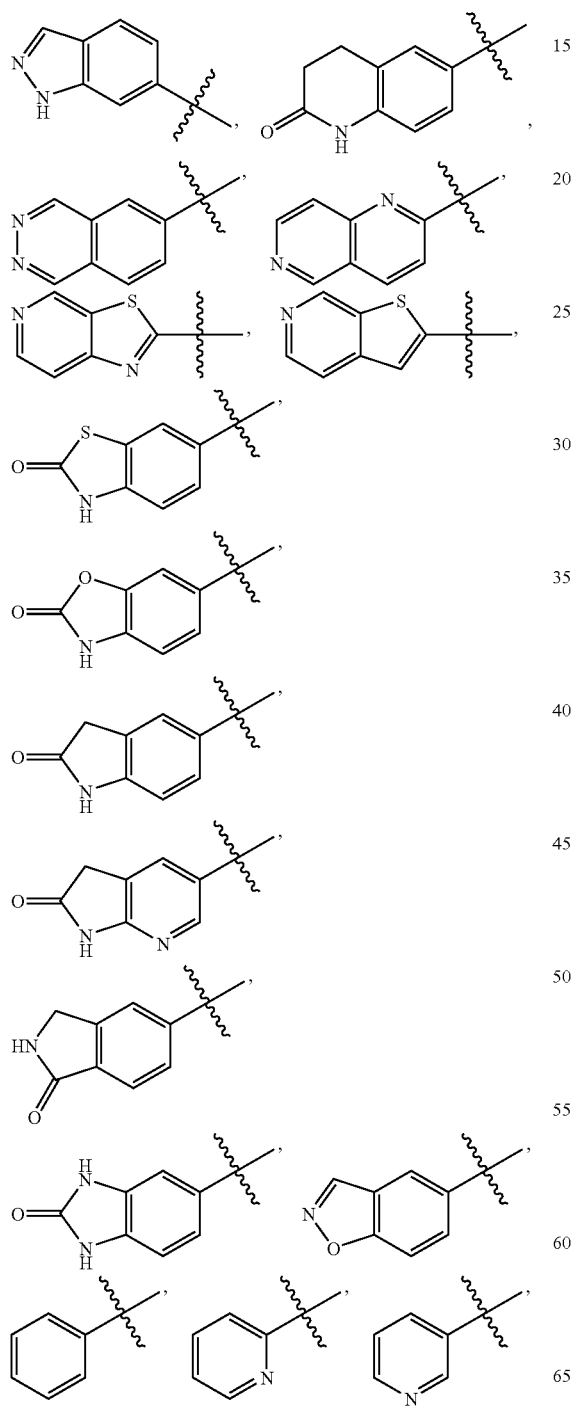

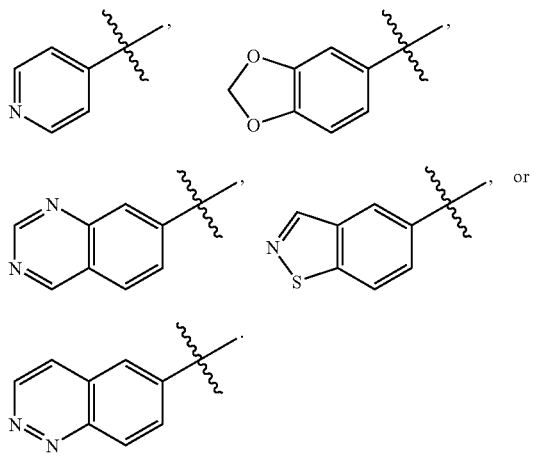

In some embodiments of the compound of Formula IV, $R^1$ is selected from one of the following groups which may optionally be substituted and where the wavy line indicates the point of attachment to the thiadiazole:

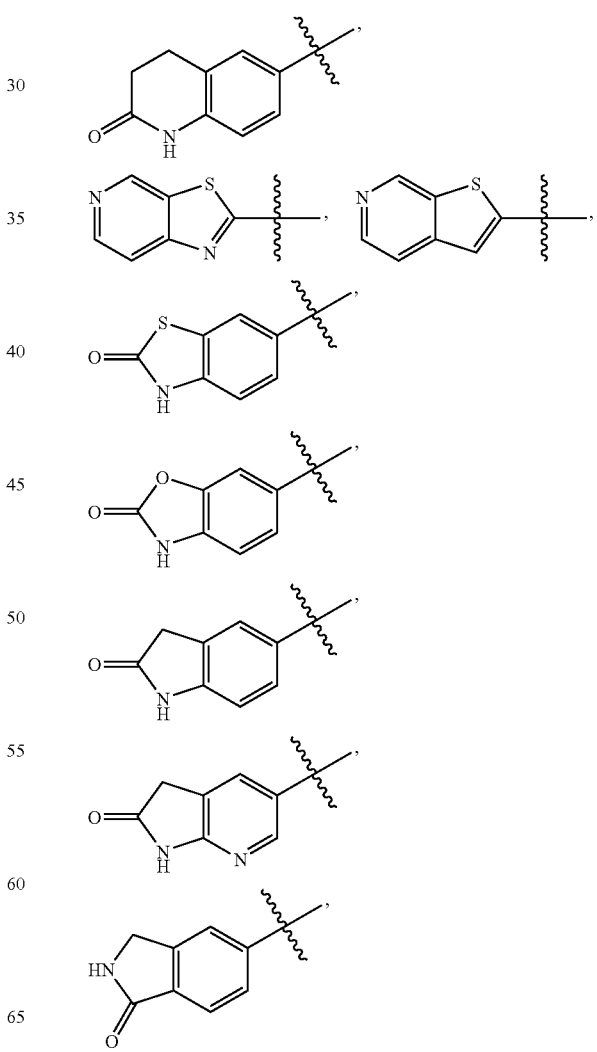

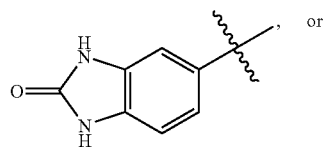
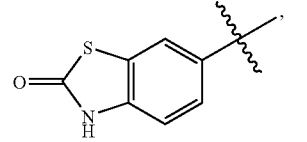
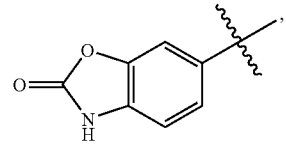
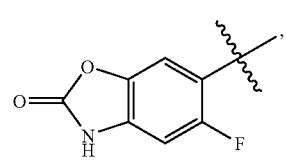
In some embodiments of the compound of Formula IV, R$^1$ is selected from one of the following groups, where the wavy line indicates the point of attachment to the thiadiazole:
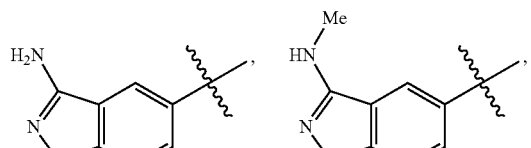
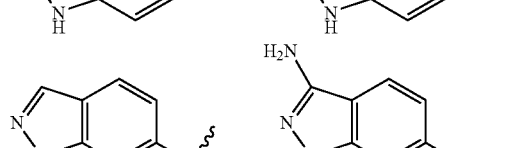
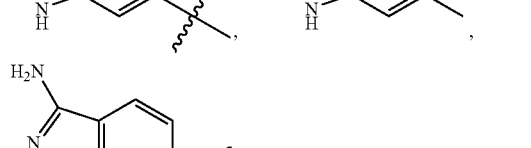
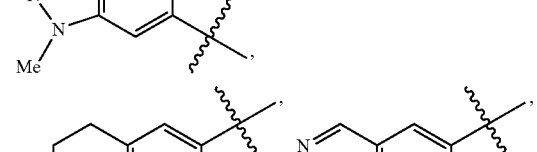
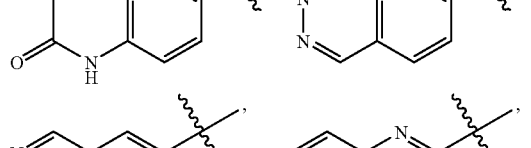
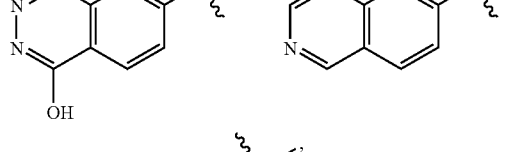
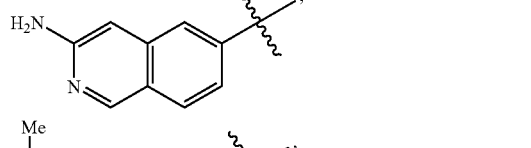
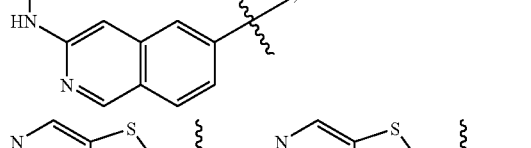

-continued

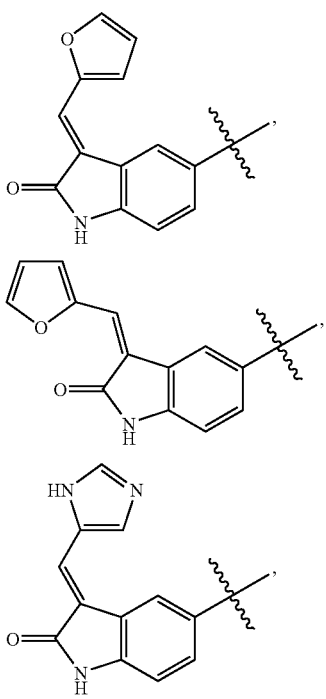

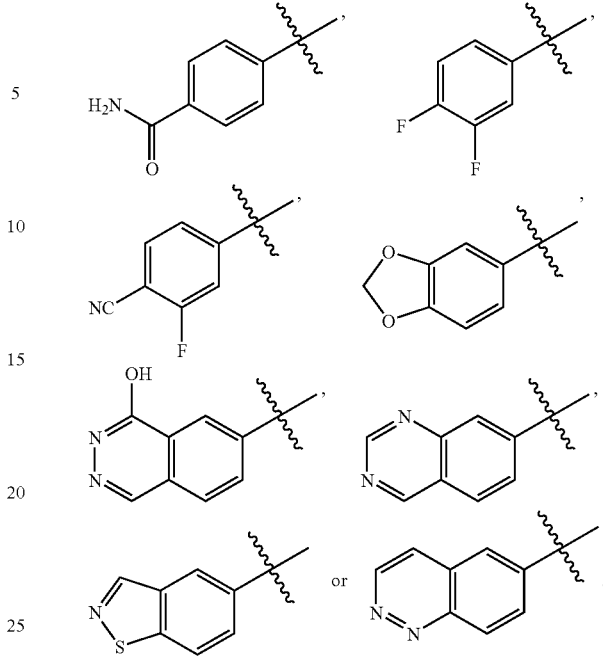

In another aspect, the invention provides a compound of Formula V

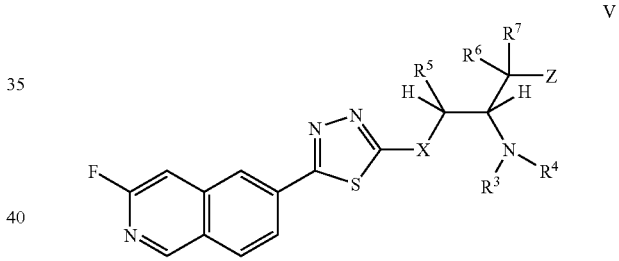

wherein:
X is selected from $NR^2$ or $CR^{2a}R^{2b}$;
$R^2$ may be absent or is selected from —H, $C_1$-$C_8$ alkyl, —($C_1$-$C_6$ alkyl)aryl, or —C(O)($C_1$-$C_6$ alkyl);
$R^{2a}$ and $R^{2b}$ may both be absent or are independently selected from —H, $C_1$-$C_8$ alkyl, —($C_1$-$C_6$)alkyl)aryl, or —C(O)($C_1$-$C_6$ alkyl);
$R^3$ is selected from —H, $C_1$-$C_8$ alkyl, —C(O)$(CR^8R^9)_t$N$(R^7)_2$, —$(CR^8R^9)_t$(aryl), —$(CR^8R^9)_t$(heteroaryl), —$(CR^8R^9)_t$(cycloalkyl), or —$(CR^8R^9)_t$(heterocyclyl);
$R^4$ is selected from —H, $C_1$-$C_8$ alkyl, —($C_1$-$C_6$ alkyl)aryl, or —C(O)($C_1$-$C_6$ alkyl);
$R^5$ is selected from —H, —$OR^{10}$, —O—($C_1$-$C_6$ alkyl)—O—$R^{10}$, $C_1$-$C_6$ alkyl, $C_1$-$C_6$ alkenyl, —($C_1$-$C_6$ alkyl)—O—$R^{10}$, or —($C_1$-$C_6$ alkyl)—O—C(O)—$R^{10}$;
$R^6$ is selected from —H, or $C_1$-$C_6$ alkyl;
$R^7$ is selected from —H, —$OR^{10}$, —O—($C_1$-$C_6$ alkyl)—O—$R^{10}$, $C_1$-$C_6$ alkyl, $C_1$-$C_6$ alkenyl, —($C_1$-$C_6$ alkyl)—O—$R^{10}$, or —($C_1$-$C_6$ alkyl)—O—C(O)—$R^{10}$;
$R^8$ and $R^9$, in each instance, are independently selected from —H, $C_1$-$C_6$ alkyl, or aryl;
$R^{10}$ is selected from —H, $C_1$-$C_6$ alkyl, $C_1$-$C_6$ haloalkyl, —($C_1$-$C_6$ alkyl)aryl, aryl, heteroaryl, $C_1$-$C_6$ hydroxyalkyl, or —($C_1$-$C_6$ alkyl)—O—($C_1$-$C_6$ alkyl), cycloalkyl, or heterocyclyl;

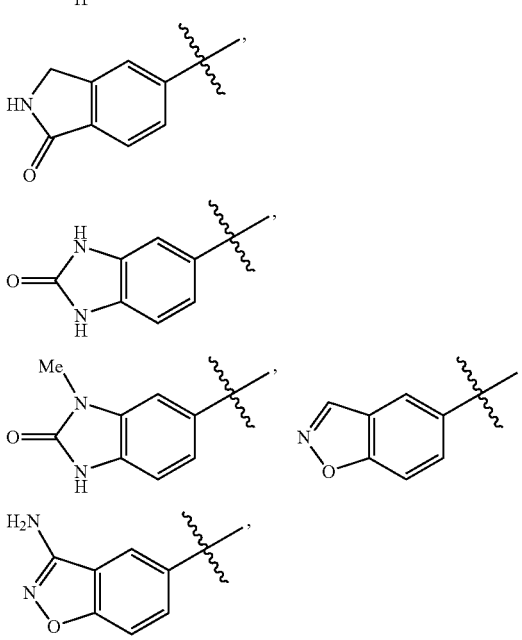

each t is independently selected from 0, 1, 2, or 3; and
Z is selected from aryl or heteroaryl;
wherein each of the above alkyl, aryl, heteroaryl, cycloalkyl, and heterocyclyl moieties and heterocyclic and carbocyclic rings are optionally and independently substituted by 1-3 substituents selected from
amino,
aryl, heteroaryl, cycloalkyl, or heterocyclyl optionally substituted by 1-5 substituents selected from
$C_1$-$C_6$ alkoxy,
$C_1$-$C_6$ alkyl optionally substituted by halo,
aryl,
halo,
hydroxyl,
heteroaryl,
$C_1$-$C_6$ hydroxyalkyl, or
—NHS(O)$_2$—$C_1$-$C_6$ alkyl);
$C_1$-$C_6$ alkyl, $C_1$-$C_6$ haloalkyl, $C_1$-$C_6$ hydroxyalkyl, $C_1$-$C_6$ alkoxy, $C_1$-$C_6$ haloalkoxy, $C_1$-$C_6$ hydroxyalkoxy, $C_1$-$C_6$ alkylamino, $C_2$-$C_6$ alkenyl, or $C_2$-$C_6$ alkynyl, wherein each of which may be interrupted by one or more hetero atoms,
cyano,
halo,
hydroxyl,
nitro,
oxo,
—NH(CO)—O—($C_1$-$C_6$ alkyl)aryl, —NH(CO)—O—($C_1$-$C_6$ alkyl), —N($C_1$-$C_6$ alkyl)(CO)—O—($C_1$-$C_6$ alkyl)aryl, —N($C_1$-$C_6$ alkyl)(CO)—O—($C_1$-$C_6$ alkyl), —C(O)OH, —C(O)O($C_1$-$C_6$ alkyl), —C(O)NH$_2$, —C(O)N(H)—($C_1$-$C_6$ alkyl), —C(O)N($C_1$-$C_6$ alkyl)$_2$, —NH($C_1$-$C_6$ alkyl), —N($C_1$-$C_6$ alkyl)$_2$, —($C_2$-$C_4$ alkenyl)heterocyclyl, or —($C_2$-$C_4$ alkenyl)cycloalkyl, or —O-aryl;
or a pharmaceutically acceptable salt, hydrate, stereoisomer, or mixture thereof.

In some embodiments of the compound of Formula V, the compound has the Formula VA

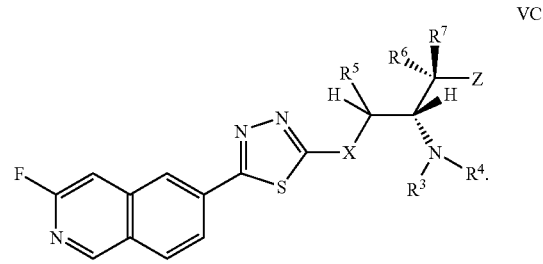

In some embodiments of the compound of Formula V, the compound has the Formula VB

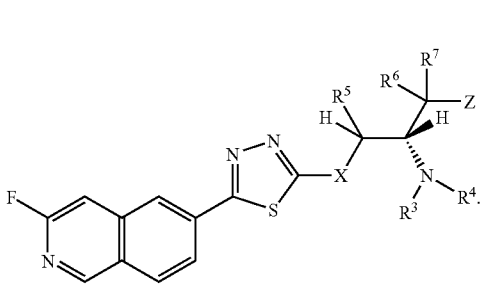

In some embodiments of the compound of Formula V, the compound has the Formula VC

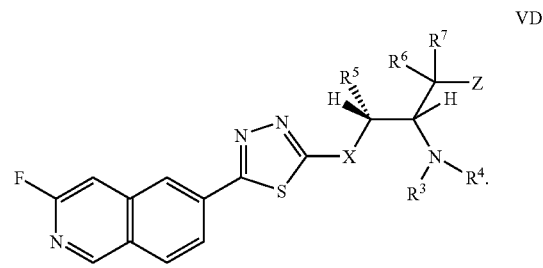

In some embodiments of the compound of Formula V, the compound has the Formula VD

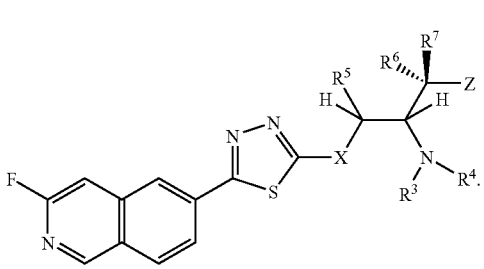

In some embodiments of the compound of Formula V, the compound has the Formula VE

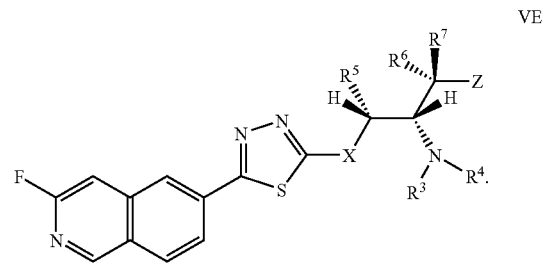

In some embodiments of the compound of Formula V, X is NR$^2$. In some such embodiments R$^2$ is —H.
In some embodiments of the compound of Formula V, X is CR$^{2a}$R$^{2b}$. In some such embodiments, R$^{2a}$ and R$^{2b}$ are both —H.
In some embodiments of the compound of Formula V, R$^5$ is —H or $C_1$-$C_6$ alkyl. In some such embodiments, R$^5$ is —H or methyl. In other such embodiments, R$^5$ is —H.
In some embodiments of the compound of Formula V, R$^6$ is —H.
In some embodiments of the compound of Formula V, R$^7$ is —H. In other embodiments, R$^7$ is —OR$^{10}$, —O—($C_1$-$C_6$ alkyl)—O—R$^{10}$, $C_1$-$C_6$ alkyl, $C_1$-$C_6$ alkenyl, —($C_1$-$C_6$ alkyl)—O—R$^{10}$, or —($C_1$-$C_6$ alkyl)—O—C(O)—R$^{10}$. In still other embodiments, R$^7$ is selected from —H, methyl, ethyl, propyl, ethenyl, propenyl, hydroxymethyl, methoxymethyl, —CH$_2$—O—C(O)—($C_1$-$C_6$ alkyl), 1-hydroxyethyl, or methoxymethoxy.
In some embodiments of the compound of Formula V, Z is selected from optionally substituted phenyl, optionally substituted indolyl, optionally substituted naphthyl, optionally substituted pyridyl, or optionally substituted thiophenyl.

In some embodiments of the compound of Formula V, Z is selected from phenyl, indolyl, naphthyl, pyridyl, or thiophenyl, each of which is optionally substituted with 1-3 substituents selected from —Cl, —F, —CF$_3$, —OH, —O—(C$_1$-C$_6$ alkyl), —O—(C$_1$-C$_6$ alkyl)-Cl, —O—(C$_1$-C$_6$ alkyl)—OH, —C$_1$-C$_6$ alkyl, —OCF$_3$, —NH(CO)—O—(C$_1$-C$_6$ alkyl)aryl, or —NH(CO)—O—(C$_1$-C$_6$ alkyl).

In some embodiments of the compound of Formula V, Z is selected from phenyl, indolyl, naphthyl, pyridyl, thiophenyl, 4-chlorophenyl, 4-trifluoromethylphenyl, 3-chlorophenyl, 3-trifluoromethylphenyl, 4-methoxyphenyl, 3-fluoro-4-trifluoromethylphenyl, 4-chloro-3-fluorophenyl, 4-(3-chloropropoxy)phenyl, 4-(3-hydroxypropoxy)phenyl, 3,4-dichlorophenyl, 4-fluorophenyl, 2,4-dichlorophenyl, 4-methylphenyl, 3,4-difluorophenyl, 3-fluoro-4-methoxyphenyl, 3,5-difluorophenyl, 6-trifluoromethylpyridin-3-yl, 5-methoxy-6-trifluoromethylpyridin-3-yl, 2-fluoro-4-trifluoromethylphenyl, 4-trifluoromethoxyphenyl, 2,3-difluoro-4-trifluoromethylphenyl, 4-hydroxyphenyl, 3-methoxy-4-trifluoromethylphenyl, 3-hydroxy-4-trifluoromethylphenyl, 5-chlorothiophen-2-yl, 3-fluoro-4-hydroxyphenyl, or a phenyl substituted in the 4 position with —NH—C(O)—O—CH$_2$-phenyl. In some such embodiments, Z is 4-trifluoromethylphenyl. In other embodiments, Z is 6-trifluoromethylpyridin-3-yl.

In some embodiments of the compound of Formula V, R$^3$ is —H. In some embodiments, R$^4$ is —H. In some embodiments R$^3$ and R$^4$ are each —H.

In another aspect, the invention comprises a pharmaceutically acceptable salt, hydrate, or solvate of a compound of Formula I, Formula II, Formula IV, or Formula V, or any of the compounds listed above. In one embodiment, the pharmaceutically acceptable salts of Formula I compounds, Formula II compounds, Formula IV compounds, or Formula V compounds are selected from ammonium trifluoroacetate and ammonium chloride.

In another aspect, the invention comprises a pharmaceutical composition comprising a pharmaceutically-acceptable carrier and a compound of Formula I, Formula II, Formula IV, or Formula V, or a compound of any of the embodiments described herein, and/or a salt of any of the compounds of any of the embodiments. In some embodiments, the invention also provides the use of a compound of any of the embodiments in the manufacture of a medicament for carrying out any of the methods of any of the embodiments of the invention. Such compositions and medicaments may further include one or more additional therapeutic agent. Therefore, in some embodiments, the composition or medicament includes at least one additional therapeutic agent.

In another aspect, the invention comprises a method for treating a kinase-mediated disorder in a mammal comprising administering to the mammal a therapeutically effective amount of a compound of Formula I, Formula II, Formula IV, or Formula V, or a pharmaceutical composition of the invention. In some embodiments, the invention provides the use of a compound of Formula I, Formula II, Formula IV, or Formula V, or a pharmaceutical composition of the invention for treating a kinase-mediated disorder in a mammal. The disorder can be one that is mediated by kinases including IGF-1R, Insulin Receptor, KDR, Tie2, EGFR, PKA, PKB, PKC, FKHR, TSC1/2, SGK, LCK, BTK, Erk, MSK, MK2, MSK, p38, P70S6K, PIM1, PIM2, ROCK2, GSK3, or a CDK complex. In some embodiments, the disorder is mediated by PKB, and in some embodiments is mediated by PKBα. In some embodiments, the method comprises selective inhibition of PKB. In some such embodiments, the method comprises selective inhibition of PKBα.

In another embodiment, the invention encompasses Formula I compounds, Formula II compounds, Formula IV compounds, or Formula V compounds that have selective kinase activity—i.e., they possess significant activity against one specific kinase while possessing less or minimal activity against a different kinase. In some embodiments, the compounds have selective PKB inhibition activity. In some such embodiments, the compounds have selective PKBα inhibition activity. In other embodiments, the invention provides the use of a compound of Formula I, Formula II, Formula IV, or Formula V, or a pharmaceutical composition of the invention for selectively inhibiting a kinase activity. In some embodiments, PKB is selectively inhibited. In some such embodiments, PKBα is selectively inhibited.

In one embodiment, the invention provides a method of treating a proliferation-related disorder in a mammal in need thereof. Such methods include administering to the mammal a therapeutically effective amount of a compound of any of the embodiments described herein or a pharmaceutical composition comprising the compound. Another embodiment of the invention comprises treating abnormal cell growth by administering a therapeutically effective amount of a compound of the invention or a pharmaceutical composition of the invention to a subject in need thereof. In some embodiments, the invention provides the use of a compound of Formula I, Formula II, Formula IV, or Formula V, or a pharmaceutical composition of the invention for treating abnormal cell growth. The abnormal cell growth can be a benign growth or a malignant growth. In particular, the abnormal cell growth can be a carcinoma, sarcoma, lymphoma, or leukemia. In one embodiment of this method, the abnormal cell growth is a cancer, including, but not limited to, lung cancer, bone cancer, pancreatic cancer, skin cancer, cancer of the head or neck, cutaneous or intraocular melanoma, uterine cancer, ovarian cancer, rectal cancer, cancer of the anal region, stomach cancer, colon cancer, breast cancer, uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, chronic or acute leukemia, lymphocytic lymphomas, cancer of the bladder, cancer of the kidney or ureter, renal cell carcinoma, carcinoma of the renal pelvis, neoplasms of the central nervous system (CNS), primary CNS lymphoma, spinal axis tumors, brain stem glioma, pituitary adenoma, or a combination of one or more of the foregoing cancers. The method of the invention also comprises treating a patient having cancer wherein the cancer is selected from the group consisting of small cell lung carcinoma, non-small cell lung carcinoma, esophageal cancer, kidney cancer, pancreatic cancer, melanoma, bladder cancer, breast cancer, colon cancer, liver cancer, lung cancer, sarcoma, stomach cancer, cholangiocarcinoma, mesothelioma, or prostate cancer. In another embodiment of said method, said abnormal cell growth is a benign proliferative disease, including, but not limited to, psoriasis, benign prostatic hypertrophy or restenosis.

In another embodiment, the invention comprises a method of administering a therapeutically effective amount of a Formula I, Formula II, Formula Iv, or Formula V compound to a mammal for treating disease states or conditions selected from diabetes, inflammation, and metabolic disorders. In other embodiments, the invention provides the use of a compound of Formula I, Formula II, Formula IV, or Formula V, or a pharmaceutical composition of the invention for treating a disease state or a condition selected from diabetes, inflammation, and metabolic disorders.

In another embodiment, the invention encompasses a method for treating or preventing cancer in a patient in need thereof, comprising administering to the patient a therapeutically or prophylactically effective amount of a compound according to Formula I, Formula II, Formula IV, or Formula V, and a pharmaceutically acceptable excipient, carrier, or vehicle. In other embodiments, the invention provides the use of a compound of Formula I, Formula II, Formula IV, or Formula V, or a pharmaceutical composition of the invention for treating or preventing cancer in a patient such as in a human cancer patient. In some embodiments, the cancer is a tumor.

In another aspect, the invention encompasses a method for treating or preventing cancer in a patient in need thereof, comprising administering to the patient a therapeutically or prophylactically effective amount of a Formula I, Formula II, Formula IV, or Formula V compound and at least one additional therapeutic agent.

In another aspect, the invention provides a compound of any of the embodiments described herein for use in a method for treating a kinase mediated disorder in a mammal in need thereof. In some embodiments, the disorder is mediated by IGF-1R, Insulin Receptor, KDR, Tie2, EGFR, PKA, PKB, PKC, FKHR, TSC1/2, SGK, LCK, BTK, Erk, MSK, MK2, MSK, p38, P70S6K, PIM1, PIM2, ROCK2, GSK3, or a CDK complex. In some embodiments, the method comprises selective inhibition of PKB, and in some embodiments the method comprises selective inhibition of PKBα. In some embodiments, the disorder is cancer, and in some such embodiments is a solid tumor.

In another aspect, the invention provides a compound of any of the embodiments described herein for use in a method of treating a proliferation-related disorder in a mammal in need thereof. In some embodiments, the disorder is abnormal cell growth. In some embodiments, the disorder is inflammation or an inflammation-related disorder. In other embodiments, the disorder is a metabolic disease such as diabetes. In other embodiments, the disorder is cancer, and in some such embodiments the cancer is a solid tumor.

Further objects, features, and advantages of the invention will be apparent from the following detailed description.

DETAILED DESCRIPTION OF THE INVENTION 1.1 Definitions

Where the following terms are used in this specification, they are used as defined below:

The terms "comprising" and "including" are used herein in their open, non-limiting sense. For example, a composition comprising or including components A and B may also include any one or all of components C, D, and E.

As used herein, unless otherwise specified, the term "alkyl" means a saturated straight chain or branched non-cyclic hydrocarbon having from 1 to 20 carbon atoms, preferably 1-10 carbon atoms and most preferably 1-4 carbon atoms. Representative saturated straight chain alkyls include, but are not limited to, -methyl, -ethyl, -n-propyl, -n-butyl, -n-pentyl, -n-hexyl, -n-heptyl, -n-octyl, -n-nonyl and -n-decyl; while saturated branched alkyls include, but are not limited to, -isopropyl, -sec-butyl, -isobutyl, -tert-butyl, -isopentyl, 2-methylbutyl, 3-methylbutyl, 2-methylpentyl, 3-methylpentyl, 4-methylpentyl, 2-methylhexyl, 3-methylhexyl, 4-methylhexyl, 5-methylhexyl, 2,3-dimethylbutyl, 2,3-dimethylpentyl, 2,4-dimethylpentyl, 2,3-dimethylhexyl, 2,4-dimethylhexyl, 2,5-dimethylhexyl, 2,2-dimethylpentyl, 2,2-dimethylhexyl, 3,3-dimethylpentyl, 3,3-dimethylhexyl, 4,4-dimethylhexyl, 2-ethylpentyl, 3-ethylpentyl, 2-ethylhexyl, 3-ethylhexyl, 4-ethylhexyl, 2-methyl-2-ethylpentyl, 2-methyl-3-ethylpentyl, 2-methyl-4-ethylpentyl, 2-methyl-2-ethylhexyl, 2-methyl-3-ethylhexyl, 2-methyl-4-ethylhexyl, 2,2-diethylpentyl, 3,3-diethylhexyl, 2,2-diethylhexyl, 3,3-diethylhexyl and the like. An alkyl group can be unsubstituted or substituted. An alkyl group may be designated as having a certain number of carbon atoms. For example, an alkyl group having from 1 to 8 carbon atoms may be designated as a $C_1$-$C_8$ alkyl group whereas an alkyl group having from 1 to 6 carbon atoms may be designated as a $C_1$-$C_6$ alkyl group. When such terms are used in conjunction with others such as in the term "—($C_1$-$C_6$ alkyl)aryl", the "—" symbol indicates the point of attachment to the rest of the molecule, and the term indicates that one of the hydrogens of the alkyl group is replaced by a bond to an aryl group. For example, a —($C_1$-$C_2$ alkyl)aryl includes such groups as —$CH_2$Ph, —$H_2CH_2$Ph, and —CH(Ph)$CH_3$.

When so designated, an alkyl group can be interrupted by one or more heteroatoms such as N, O, S, or Si atoms. Insertion of a heteroatom in the alkyl group forms a heteroalkyl group. In some embodiments, the heteroatom is a N, O, or S atom. The term "heteroalkyl," by itself or in combination with another term, means, unless otherwise stated, a stable straight or branched chain radical, or combination thereof, that includes carbon atoms and from one to three heteroatoms selected from the group consisting of O, N, and S. The nitrogen and sulfur atoms may optionally be oxidized, and the nitrogen heteroatom may optionally be quaternized. The heteroatom(s) O, N, and S may be placed at any position in the heteroalkyl group. Examples include —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$—S(O)—$CH_3$, and —$CH_2$—$CH_2$—S(O)$_2$—$CH_3$. Up to two heteroatoms may be consecutive or adjacent to one another, such as, for example, in —$CH_2$—NH—$OCH_3$. When a prefix such as ($C_2$-$C_8$) is used to refer to a heteroalkyl group, the number of carbons (2 to 8, in this example) is meant to include the heteroatoms as well. For example, a $C_2$-heteroalkyl group is meant to include, for example, —$CH_2$OH (one carbon atom and one heteroatom replacing a carbon atom) and —$CH_2$SH.

To further illustrate the definition of a heteroalkyl group, where the heteroatom is oxygen, a heteroalkyl group is an oxyalkyl group. For instance, ($C_2$-$C_5$)oxyalkyl is meant to include, for example —$CH_2$—O—$CH_3$ (a $C_3$-oxyalkyl group with two carbon atoms and one oxygen replacing a carbon atom), —$CH_2CH_2CH_2CH_2$OH, and the like.

As used herein, unless otherwise specified, the term "alkenyl" means an unsaturated straight chain or branched non-cyclic hydrocarbon having from 2 to 20 carbon atoms and at least one carbon-carbon double bond. Preferably, an alkenyl has 2 to 10 carbon atoms and most preferably has 2 to 4 carbon atoms. Exemplary straight chain alkenyls include, but are not limited to, -but-3-ene, -hex-4-ene, and -oct-1-ene. Exemplary branched chain alkenyls include, but are not limited to, -2-methyl-but-2-ene, -1-methyl-hex-4-ene, and -4-ethyl-oct-1-ene. An alkenyl group can be substituted or unsubstituted. An alkenyl group may be designated as having a certain number of carbon atoms. For example, an alkenyl group having from 2 to 8 carbon atoms may be designated as a $C_2$-$C_8$ alkenyl group whereas an alkenyl group having from 2 to 6 carbon atoms may be designated as a $C_2$-$C_6$ alkenyl group.

As used herein, and unless otherwise specified, the term "alkynyl" means an alkyl group in which one or more carbon-carbon single bonds is replaced with an equivalent number of carbon-carbon triple bonds. An alkynyl group must comprise at least two carbon atoms, and can be substituted or unsubstituted. An alkynyl group may be designated as having a certain number of carbon atoms. For example, an alkynyl group having from 2 to 8 carbon atoms may be designated as a $C_2$-$C_8$ alkynyl group whereas an alkynyl group having from 2 to 6 carbon atoms may be designated as a $C_2$-$C_6$ alkynyl group.

As used herein, the term "halo" means a halogen atom such as a fluorine, chlorine, bromine, or iodine atom (—F, —Cl, —Br, or —I).

As used herein, unless otherwise specified, the term "haloalkyl" means an alkyl group in which one or more hydrogens has been replaced by a halogen atom. A halogen atom is a fluorine, chlorine, bromine, or iodine atom. The number of halogen atoms in a haloalkyl group may range from one to (2m'+1), where m' is the total number of carbon atoms in the alkyl group. For example, the term "halo($C_1$-$C_4$) alkyl" is meant to include trifluoromethyl, 2,2,2-trifluoroethyl, 4-chlorobutyl, 3-bromopropyl, and the like. Thus, the term "haloalkyl" includes monohaloalkyl (alkyl substituted with one halogen atom) and polyhaloalkyl (alkyl substituted with halogen atoms in a number ranging from two to (2m'+1) halogen atoms). The term "perhaloalkyl" means, unless otherwise stated, an alkyl substituted with (2m'+1) halogen atoms, where m' is the total number of carbon atoms in the alkyl group. For example, the term "perhalo($C_1$-$C_4$)alkyl", is meant to include trifluoromethyl, pentachloroethyl, 1,1,1-trifluoro-2-bromo-2-chloroethyl, and the like.

As used herein, the term "cyano" means a —C≡N group.

As used herein, the term "nitro" means a —$NO_2$ group.

As used herein, the term "oxo" means a =O group.

As used herein, the terms "hydroxy" and "hydroxyl" mean an —OH group.

As used herein, unless otherwise specified, the term "hydroxyalkyl" means an alkyl group in which one or more hydrogens has been replaced with a hydroxyl group.

The term "alkoxy" means a structure of the formula —O-alkyl where alkyl has the meaning set forth above.

The term "haloalkoxy" means an alkoxy group in which one or more hydrogen is replaced by a halogen atom.

The term "hydroxyalkoxy" means an alkoxy group in which one or more hydrogen is replaced by a hydroxy group.

The term "amino" means an —$NH_2$ group.

The terms "alkylamino" and "dialkylamino" mean a structure of the formula —NH-alkyl and —N(alkyl)alkyl, respectively, wherein the alkyl is as defined above. The alkyl groups in dialkylamino groups may be the same or different.

As used herein, the terms "carbocyclic ring system" and "carbocyclic" mean a ring system in which all the ring members are carbon atoms. Carbocyclic ring systems typically include from 3 to 14 ring atoms. Carbocyclic ring systems may be aromatic or may be non-aromatic. Carbocyclic ring systems include cycloalkyl rings and may also include fused ring systems. Examples of fused ring carbocyclic ring systems include, but are not limited to, decalin, norbornane, tetrahydronaphthalene, naphthalene, indene, and adamantane. The ring atoms in a carbocyclic ring system may be substituted or unsubstituted.

As used herein, the terms "heterocyclic ring system", "heterocyclic" and "heterocyclyl" means a carbocyclic ring system in which at least one ring atom is a heteroatom such as a N, O, S, or Si. In some embodiments, the heterocyclic ring system includes from 1 to 4 heteroatoms. In some embodiments, the heteroatom is selected from N, O, or S. Heterocyclic ring systems may include one ring or may include fused ring systems. By way of nonlimiting example, heterocyclic ring systems may include two six membered rings that are fused to one another or may include one five membered ring and one six membered ring that are fused to one another. Heterocyclic ring systems may be aromatic or may be non-aromatic and may be unsaturated, partially unsaturated, or saturated. The ring atoms in a heterocyclic ring system may be substituted or unsubstituted.

As used herein, unless otherwise specified the term "aryl" means a carbocyclic ring or ring system containing from 6 to 14 ring atoms wherein at least one ring is aromatic. The ring atoms of a carbocyclic aryl group are all carbon atoms. Aryl groups include mono-, bi-, and tricyclic groups as well as benzo-fused carbocyclic moieties such as, but not limited to, 5,6,7,8-tetrahydronaphthyl and the like. In some embodiments, the aryl group is a monocyclic ring or is a bicyclic ring. Representative aryl groups include, but are not limited to, phenyl, tolyl, anthracenyl, fluorenyl, indenyl, azulenyl, phenanthrenyl and naphthyl. An aryl group can be unsubstituted or substituted.

The term "heteroaryl" means an aryl group in which one or more, but not all, of the ring carbon atoms in any ring, whether aromatic or not, is replaced by a hetero atom. For example pyridine is a heteroaryl group as is a compound in which benzene is fused to a nonaromatic ring that includes at least one heteroatom. Exemplary heteroatoms are N, O, S, and Si. In some embodiments, the heteroatoms are N, O, or S. A heteroaryl group can be unsubstituted or substituted. Non-limiting examples of aryl and heteroaryl groups include phenyl, 1-naphthyl, 2-naphthyl, 4-biphenyl, 1-pyrrolyl, 2-pyrrolyl, 3-pyrrolyl, 1-pyrazolyl, 3-pyrazolyl, 5-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furanyl, 3-furanyl, dibenzofuryl, 2-thienyl (2-thiophenyl), 3-thienyl (3-thiophenyl), 2-pyridyl, 3-pyridyl, 4-pyridyl, 2-pyrimidinyl, 4-pyrimidinyl, 5-pyrimidinyl, 3-pyridazinyl, 4-pyridazinyl, 5-benzothiazolyl, 2-benzoxazolyl, 5-benzoxazolyl, benzo[c][1,2,5]oxadiazolyl, purinyl, 2-benzimidazolyl, 5-indolyl, 1H-indazolyl, carbazolyl, α-carbolinyl, β-carbolinyl, γ-carbolinyl, 1-isoquinolyl, 5-isoquinolyl, 2-quinoxalinyl, 5-quinoxalinyl, 2-quinolyl, 3-quinolyl, 4-quinolyl, 5-quinolyl, 6-quinolyl, 7-quinolyl, and 8-quinolyl. Non-limiting examples of other heteroaryl groups include pyridyl, indazolyl, isoquinolinyl, thiazolopyridinyl, benzothiazolonyl, dihydroquinolinonyl, benzoisoxazolyl, benzooxazolonyl, indolinonyl, benzoimidazolonyl, phthalazinyl, naphthyridinyl, thienopyridinyl, benzodioxolyl, isoindolinonyl, quinazolinyl, or cinnolinyl. The nonaromatic rings in aryl and heteroaryl groups that include nonaromatic rings may be substituted with various groups as described herein including the oxo (=O) group for example in groups such as, but not limited to, the benzo[d]thiazol-2 (3H)-onyl group.

The term "cycloalkyl" means an unsaturated or saturated hydrocarbon that forms at least one ring, having from 3 to 20 ring carbon atoms, and in some embodiments, from 3 to 10 ring, from 3 to 8, or from 3 to 6 carbon atoms. The rings in a cycloalkyl group are not aromatic. A cycloalkyl group can be unsubstituted or substituted.

As described herein, compounds of the invention may optionally be substituted with one or more substituents, such as are illustrated generally above, or as exemplified by particular classes, subclasses, and species of the invention. It will be appreciated that the phrase "optionally substituted" is used interchangeably with the phrase "substituted or unsubstituted." In general, the term "substituted", whether preceded by the term "optionally" or not, refers to the replacement of hydrogen radicals in a given structure with the radical of a specified substituent. Unless otherwise indicated, an optionally substituted group may have a substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds.

The term "PKB" refers to protein kinase B, also known as AKT.

The term "treating" refers to:

(i) preventing a disease, disorder, or condition from occurring in a mammal that may be predisposed to the disease, disorder and/or condition, but may not yet have been diagnosed as having it;

(ii) inhibiting the disease, disorder, or condition, i.e., arresting its development; and (iii) relieving the disease, disorder, or condition, i.e., causing regression of the disease, disorder, and/or condition, or one or more of its symptoms.

The term "preventing" refers to the ability of a compound or composition of the invention to prevent a disease identified herein in mammals diagnosed as having the disease or who are at risk of developing such disease. The term also encompasses preventing further progression of the disease in mammals that are already suffering from or have symptoms of the disease.

The term "mammal" refers to non-human animals or humans.

As used herein, the term "patient" or "subject" means an animal (e.g., cow, horse, sheep, pig, chicken, turkey, quail, cat, dog, mouse, rat, rabbit, guinea pig, etc.) or a mammal, including chimeric and transgenic animals and mammals. In the treatment or prevention of a cancer, the term "patient" or "subject" preferably means a monkey or a human, most preferably a human. In a specific embodiment, the patient or subject is afflicted by a cancer.

As used herein, a "therapeutically effective amount" refers to an amount of a compound of the invention, or prodrug thereof, sufficient to provide a benefit in the treatment or prevention of a condition or disease such as cancer, to delay or minimize symptoms associated with the condition or disease, or to cure or ameliorate the disease or cause thereof. In particular, a therapeutically effective amount means an amount sufficient to provide a therapeutic benefit in vivo. Used in connection with an amount of a compound of the invention, the term preferably encompasses a non-toxic amount that improves overall therapy, reduces or avoids symptoms or causes of disease, or enhances the therapeutic efficacy of or synergies with another therapeutic agent.

As used herein, a "prophylactically effective amount" refers to an amount of a compound of the invention or other active ingredient sufficient to result in the prevention of a condition or disease such as cancer, or recurrence or metastasis of cancer. A prophylactically effective amount may refer to an amount sufficient to prevent initial disease or the recurrence or spread of the disease. The term preferably encompasses a non-toxic amount that improves overall prophylaxis or enhances the prophylactic efficacy of or synergies with another prophylactic or therapeutic agent.

As used herein, "in combination" refers to the use of more than one prophylactic and/or therapeutic agents simultaneously or sequentially. The agents may be selected and administered in such a manner that their respective effects are additive or synergistic.

As used herein, the term "pharmaceutically acceptable salts" refers to salts prepared from pharmaceutically acceptable non-toxic acids or bases including inorganic and organic acids and bases. If the Formula I or Formula II compound is a base, the desired pharmaceutically acceptable salt may be prepared by any suitable method available in the art, for example, treatment of the free base with an inorganic acid, such as hydrochloric acid, hydrobromic acid, sulfuric acid, nitric acid, phosphoric acid and the like, or with an organic acid, such as acetic acid, maleic acid, succinic acid, mandelic acid, fumaric acid, malonic acid, pyruvic acid, oxalic acid, glycolic acid, salicylic acid, a pyranosidyl acid, such as glucuronic acid or galacturonic acid, an alpha-hydroxy acid, such as citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, or the like. If the Formula I or Formula II compound is an acid, the desired pharmaceutically acceptable salt may be prepared by any suitable method, for example, treatment of the free acid with an inorganic or organic base, such as an amine (primary, secondary or tertiary), an alkali metal hydroxide or alkaline earth metal hydroxide, or the like. Illustrative examples of suitable salts include organic salts derived from amino acids, such as glycine and arginine, ammonia, primary, secondary, and tertiary amines, and cyclic amines, such as piperidine, morpholine and piperazine, and inorganic salts derived from sodium, calcium, potassium, magnesium, manganese, iron, copper, zinc, aluminum and lithium.

The neutral forms of the compounds may be regenerated from the salt by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the invention.

In addition to salt forms, the invention provides compounds which are in a prodrug form. The term "prodrug" is intended to mean any chemical entity that, after administration, is converted to a different therapeutically effective chemical entity. Prodrugs of the compounds described herein are those compounds that readily undergo chemical changes under physiological conditions to provide the compounds of the invention. Additionally, prodrugs can be converted to the compounds of the invention by chemical or biochemical methods in an ex vivo environment. For example, prodrugs can be slowly converted to the compounds of the invention when placed in a transdermal patch reservoir with a suitable enzyme or chemical reagent. Prodrugs are often useful because, in some situations, they may be easier to administer than the parent drug. They may, for instance, be bioavailable by oral administration whereas the parent drug is not. The prodrug may also have improved solubility in pharmaceutical compositions over the parent drug. A wide variety of prodrug derivatives are known in the art, such as those that rely on hydrolytic cleavage or oxidative activation of the prodrug. An example, without limitation, of a prodrug would be a compound of the invention which is administered as an ester (the "prodrug"), but then is metabolically hydrolyzed to the carboxylic acid, the active entity. Additional examples include peptidyl derivatives of a compound.

As used herein, "solvate" refers to a compound of the present invention or a salt thereof, that further includes a stoichiometric or non-stoichiometric amount of solvent bound by non-covalent intermolecular forces. Where the solvent is water, the solvate is a hydrate.

The compounds of this invention may contain one or more asymmetric centers and thus occur as racemates and racemic mixtures, scalemic mixtures, single enantiomers, individual diastereomers, and diastereomeric mixtures. All such isomeric forms of these compounds are expressly included in the present invention.

As used herein and unless otherwise indicated, the term "optically pure" or "stereomerically pure" means a composition that comprises one stereoisomer of a compound and is substantially free of other stereoisomers of that compound. For example, a stereomerically pure compound having one chiral center will be substantially free of the opposite enantiomer of the compound. A typical stereomerically pure compound comprises greater than about 80% by weight of one stereoisomer of the compound and less than about 20% by weight of other stereoisomers of the compound, more preferably greater than about 90% by weight of one stereoisomer of the compound and less than about 10% by weight of the other stereoisomers of the compound, even more preferably greater than about 95% by weight of one stereoisomer of the compound and less than about 5% by weight of the other stereoisomers of the compound, and most preferably greater than about 97% by weight of one stereoisomer of the compound and less than about 3% by weight of the other stereoisomers of the compound. This invention encompasses the use of stereomerically pure forms of such compounds, as well as the use of mixtures of those forms. For example, mixtures comprising equal or unequal amounts of the enantiomers of a particular compound of the invention may be used in methods and compositions of the invention. These isomers may be asymmetrically synthesized or resolved using standard techniques such as chiral columns or chiral resolving agents. See, e.g., Jacques, J., et al., Enantiomers, Racemates and Resolutions (Wiley-Interscience, New York, 1981); Wilen, S. H., et al. (1997) Tetrahedron 33:2725; Eliel, E. L., Stereochemistry of Carbon Compounds (McGraw-Hill, NY, 1962); and Wilen, S. H., Tables of Resolving Agents and Optical Resolutions p. 268 (E. L. Eliel, Ed., Univ. of Notre Dame Press, Notre Dame, Ind., 1972).

The compounds of the invention may exhibit the phenomenon of tautomerism. While the structural formulas set forth herein cannot expressly depict all possible tautomeric forms, it is to be understood that these structures are intended to represent all tautomeric forms of the depicted compound and are not to be limited merely to the specific compound form depicted by the formula drawings.

Certain compounds of the invention may exist in multiple crystalline or amorphous forms. In general, all physical forms are equivalent for the uses contemplated by the invention and are intended to be within the scope of the invention.

The compounds of the invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). Radiolabeled compounds are useful as therapeutic or prophylactic agents, research reagents, e.g., assay reagents, and diagnostic agents, e.g., in vivo imaging agents. All isotopic variations of the compounds of the invention, whether radioactive or not, are intended to be encompassed within the scope of the invention.

1.2 Compounds

The compounds described herein are useful for treating diseases or conditions mediated by various kinases such as PKB. The invention encompasses the therapeutic use of such compounds and compositions thereof in the treatment of disease states associated with abnormal cell growth, such as cancer, or metabolic disease states, such as diabetes, or inflammation. The invention further provides pharmaceutical compositions that include the compounds of the invention and the use of the compounds in the preparation of medicaments or pharmaceutical formulations or compositions for treating various conditions and disease states.

In one aspect the invention comprises a compound of Formula I $R^1$ is selected from a carbocyclic ring system or a heterocyclic ring system;

$R^2$ is selected from —H, $C_1$-$C_8$ alkyl, —($C_1$-$C_6$ alkyl)aryl, or —C(O)($C_1$-$C_6$ alkyl);

$R^3$ is selected from —H, $C_1$-$C_8$ alkyl, —C(O)(CR$^8$R$^9$)$_t$N(R$^7$)$_2$, —(CR$^8$R$^9$)$_t$(aryl), —(CR$^8$R$^9$)$_t$(heteroaryl), —(CR$^8$R$^9$)$_t$(cycloalkyl), or —(CR$^8$R$^9$)$_t$(heterocyclyl);

$R^4$ is selected from —H, $C_1$-$C_8$ alkyl, —($C_1$-$C_6$ alkyl)aryl, or —C(O)($C_1$-$C_6$ alkyl);

$R^5$ is selected from —H, —OR$^{10}$, —O—($C_1$-$C_6$ alkyl)—O—R$^{10}$, $C_1$-$C_6$ alkyl, $C_1$-$C_6$ alkenyl, —($C_1$-$C_6$ alkyl)—O—R$^{10}$, or —($C_1$-$C_6$ alkyl)—O—C(O)—R$^{10}$;

$R^6$ is selected from —H, or $C_1$-$C_6$ alkyl;

$R^7$ is selected from —H, —OR$^{10}$, —O—($C_1$-$C_6$ alkyl)—O—R$^{10}$, $C_1$-$C_6$ alkyl, $C_1$-$C_6$ alkenyl, —($C_1$-$C_6$ alkyl)—O—R$^{10}$, or —($C_1$-$C_6$ alkyl)—O—C(O)—R$^{10}$;

$R^8$ and $R^9$, in each instance, are independently selected from —H, $C_1$-$C_6$ alkyl, or aryl;

$R^{10}$ is selected from —H, $C_1$-$C_6$ alkyl, $C_1$-$C_6$ haloalkyl, —($C_1$-$C_6$ alkyl)aryl, aryl, heteroaryl, $C_1$-$C_6$ hydroxyalkyl, or —($C_1$-$C_6$ alkyl)—O—($C_1$-$C_6$ alkyl), cycloalkyl, or heterocyclyl;

each t is independently selected from 0, 1, 2, or 3; and

Z is selected from aryl or heteroaryl;

wherein each of the above alkyl, aryl, heteroaryl, cycloalkyl, and heterocyclyl moieties and heterocyclic and carbocyclic rings are optionally and independently substituted by 1-3 substituents selected from
 amino,
 aryl, heteroaryl, cycloalkyl, or heterocyclyl optionally substituted by 1-5 substituents selected from
  $C_1$-$C_6$ alkoxy,
  $C_1$-$C_6$ alkyl optionally substituted by halo,
  aryl,
  halo,
  hydroxyl,
  heteroaryl,
  $C_1$-$C_6$ hydroxyalkyl, or
  —NHS(O)$_2$—$C_1$-$C_6$ alkyl);
 $C_1$-$C_6$ alkyl, $C_1$-$C_6$ haloalkyl, $C_1$-$C_6$ hydroxyalkyl, $C_1$-$C_6$ alkoxy, $C_1$-$C_6$ haloalkoxy, $C_1$-$C_6$ hydroxyalkoxy, $C_1$-$C_6$ alkylamino, $C_2$-$C_6$ alkenyl, or $C_2$-$C_6$ alkynyl, wherein each of which may be interrupted by one or more hetero atoms,
 cyano,
 halo,
 hydroxyl,
 nitro,
 oxo,
 —NH(CO)—O—($C_1$-$C_6$ alkyl)aryl, —NH(CO)—O—($C_1$-$C_6$ alkyl), —N($C_1$-$C_6$ alkyl)(CO)—O—($C_1$-$C_6$ alkyl)aryl, —N($C_1$-$C_6$ alkyl)(CO)—O—($C_1$-$C_6$ alkyl), —C(O)OH, —C(O)O($C_1$-$C_6$ alkyl), —C(O)NH$_2$, —C(O)N(H)—(C$_1$-C$_6$ alkyl), —C(O)N(C$_1$-C$_6$ alkyl)$_2$, —NH(C$_1$-C$_6$ alkyl), —N(C$_1$-C$_6$ alkyl)$_2$, —(C$_2$-C$_4$ alkenyl)heterocyclyl, or —(C$_2$-C$_4$ alkenyl)cycloalkyl, or —O-aryl;

or a pharmaceutically acceptable salt, hydrate, stereoisomer, or mixture thereof, wherein at least one of the following is true:
(a) R$^5$ is selected from —OR$^{10}$, —O—(C$_1$-C$_6$ alkyl)—O—R$^{10}$, C$_1$-C$_6$ alkyl, C$_1$-C$_6$ alkenyl, —(C$_1$-C$_6$ alkyl)—O—R$^{10}$, or —(C$_1$-C$_6$ alkyl)—O—C(O)—R$^{10}$; or
(b) R$^7$ is selected from —OR$^{10}$, —O—(C$_1$-C$_6$ alkyl)—O—R$^{10}$, C$_1$-C$_6$ alkenyl, —(C$_1$-C$_6$ alkyl)—O—R$^{10}$, or —(C$_1$-C$_6$ alkyl)—O—C(O)—R$^{10}$.

In some embodiments of the compound of Formula I, the compound of Formula I has the Formula IA

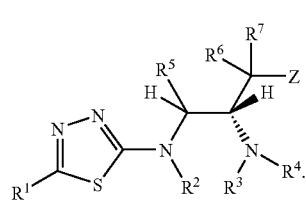

IA

In some embodiments of the compound of Formula I, the compound of Formula I has the Formula IB

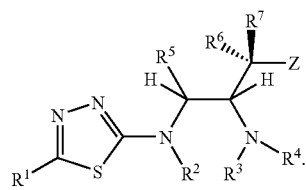

IB

In some embodiments of the compound of Formula I, the compound of Formula I has the Formula IC

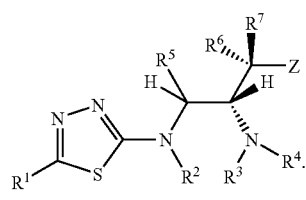

IC

In some embodiments of the compound of Formula I, the compound of Formula I has the Formula ID

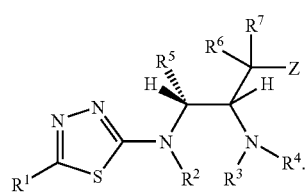

ID

In some embodiments of the compound of Formula I, the compound of Formula I has the Formula IE

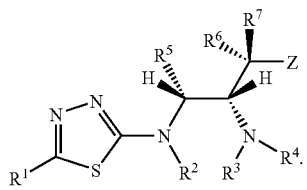

IE

In some embodiments of the compound of Formula I, R$^5$ is —H or C$_1$-C$_6$ alkyl. In some such embodiments, R$^5$ is —H or methyl. In some such embodiments, R$^5$ is —H.

In some embodiments, the compound of Formula I is selected from one of the following:

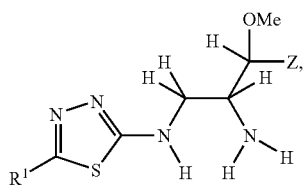

IIIA

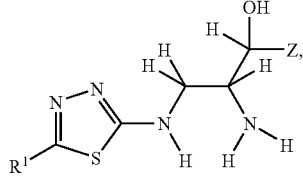

IIIB

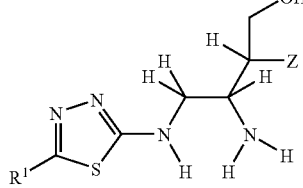

IIIC

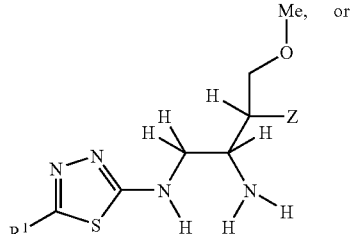

IIID

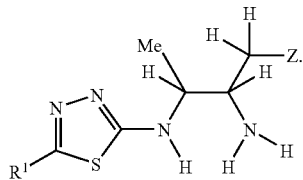

IIIE

In some embodiments of the compound of Formula I, R$^6$ is —H.

In some embodiments of the compound of Formula I, R$^7$ is —H.

In some embodiments of the compound of Formula I, R$^7$ is —OR$^{10}$, —O—(C$_1$-C$_6$ alkyl)—O—R$^{10}$, C$_1$-C$_6$ alkyl, C$_1$-C$_6$ alkenyl, —(C$_1$-C$_6$ alkyl)—O—R$^{10}$, or —(C$_1$-C$_6$ alkyl)—O—C(O)—R$^{10}$. In some embodiments, R$^7$ is selected from —H, methyl, ethyl, propyl, ethenyl, propenyl, hydroxymethyl, methoxymethyl, —CH$_2$—O—C(O)—(C$_1$-C$_6$ alkyl), 1-hydroxyethyl, or methoxymethoxy.

In some embodiments of the compound of Formula I, Z is selected from optionally substituted phenyl, optionally substituted indolyl, optionally substituted naphthyl, optionally substituted pyridyl, or optionally substituted thiophenyl. In some embodiments, Z is selected from phenyl, indolyl, naphthyl, pyridyl, or thiophenyl, each of which is optionally substituted with 1-3 substituents selected from —Cl, —F, —CF$_3$, —OH, —O—(C$_1$-C$_6$ alkyl), —O—(C$_1$-C$_6$ alkyl)-Cl, —O—(C$_1$-C$_6$ alkyl)—OH, —C$_1$-C$_6$ alkyl, —OCF$_3$, —NH(CO)—O—(C$_1$-C$_6$ alkyl)aryl, or —NH(CO)—O—(C$_1$-C$_6$ alkyl). In other embodiments, Z is selected from phenyl, indolyl, naphthyl, pyridyl, thiophenyl, 4-chlorophenyl, 4-trifluoromethylphenyl, 3-chlorophenyl, 3-trifluoromethylphenyl, 4-methoxyphenyl, 3-fluoro-4-trifluoromethylphenyl, 4-chloro-3-fluorophenyl, 4-(3-chloropropoxy)phenyl, 4-(3-hydroxypropoxy)phenyl, 3,4-dichlorophenyl, 4-fluorophenyl, 2,4-dichlorophenyl, 4-methylphenyl, 3,4-difluorophenyl, 3-fluoro-4-methoxyphenyl, 3,5-difluorophenyl, 6-trifluoromethylpyridin-3-yl, 5-methoxy-6-trifluoromethylpyridin-3-yl, 2-fluoro-4-trifluoromethylphenyl, 4-trifluoromethoxyphenyl, 2,3-difluoro-4-trifluoromethylphenyl, 4-hydroxyphenyl, 3-methoxy-4-trifluoromethylphenyl, 3-hydroxy-4-trifluoromethylphenyl, 5-chlorothiophen-2-yl, 3-fluoro-4-hydroxyphenyl, or a phenyl substituted in the 4 position with —NH—C(O)—O—CH$_2$-phenyl.

In some embodiments of the compound of Formula I, R$^2$ is —H.

In some embodiments of the compound of Formula I, R$^3$ is —H. In some embodiments, both R$^3$ and R$^4$ are —H. In still other embodiments, R$^2$, R$^3$, and R$^4$ are all —H. In some such embodiments, at least one of R$^3$ and R$^4$ is —H.

In some embodiments of the compound of Formula I, R$^4$ is —H.

In some embodiments of the compound of Formula I, the carbocyclic ring system or the heterocyclic ring system of R$^1$ comprises at least one aromatic ring.

In some embodiments of the compound of Formula I, the carbocyclic ring system or the heterocyclic ring system of R$^1$ comprises a bicyclic ring system.

In some embodiments of the compound of Formula I, the carbocyclic ring system or the heterocyclic ring system of R$^1$ comprises two rings that are fused to one another, wherein at least one of the rings is a 6-membered ring.

In some embodiments of the compound of Formula I, the carbocyclic ring system or the heterocyclic ring system of R$^1$ comprises at least one ring that is not aromatic.

In some embodiments of the compound of Formula I, the carbocyclic ring system or the heterocyclic ring system of R$^1$ is selected from a group other than an unsubstituted or optionally substituted group of one of the following where the wavy line indicates the point of attachment to the thiadiazole ring:

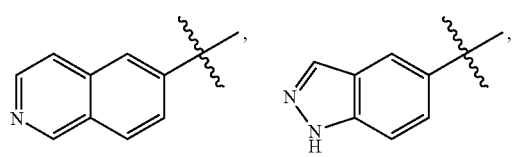

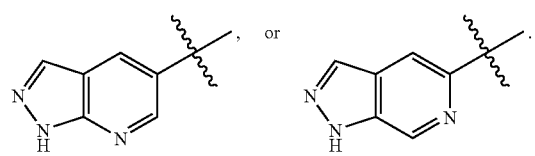

In some embodiments of the compound of Formula I, R$^1$ is selected from optionally substituted phenyl, pyridyl, indazolyl, isoquinolinyl, thiazolopyridinyl, benzothiazolonyl, dihydroquinolinonyl, benzoisoxazolyl, benzooxazolonyl, indolinonyl, benzoimidazolonyl, phthalazinyl, naphthyridinyl, thienopyridinyl, benzodioxolyl, isoindolinonyl, quinazolinyl, or cinnolinyl.

In some embodiments of the compound of Formula I, R$^1$ is selected from one of the following groups which may optionally be substituted and where the wavy line indicates the point of attachment to the thiadiazole:

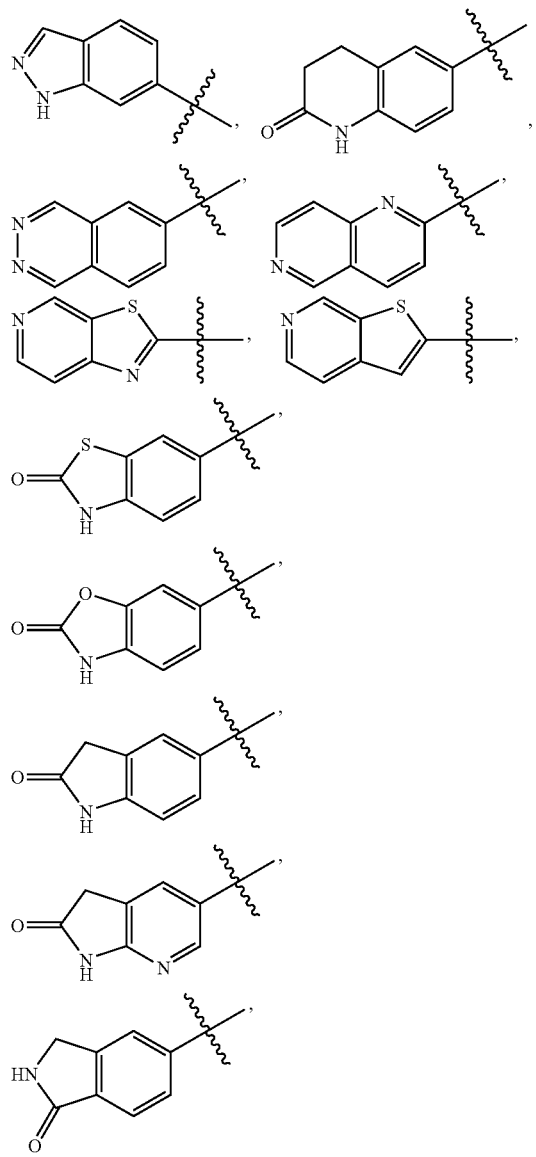

-continued

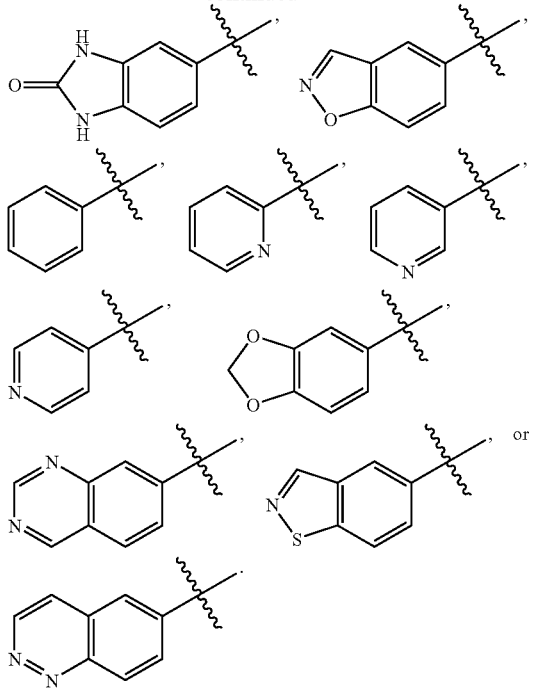

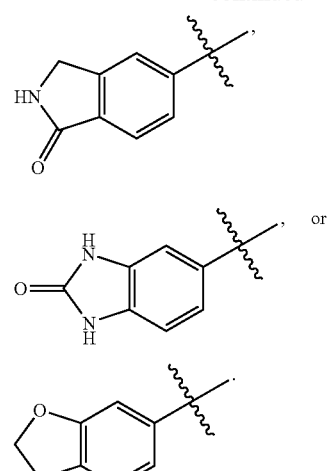

In some embodiments of the compound of Formula I, $R^1$ is selected from one of the following groups which may optionally be substituted and where the wavy line indicates the point of attachment to the thiadiazole:

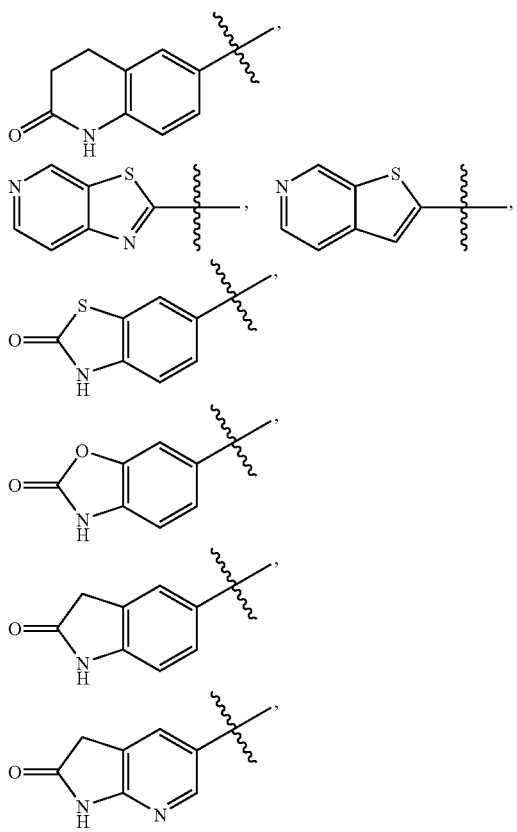

-continued

In some embodiments of the compound of Formula I, $R^1$ is selected from one of the following groups, where the wavy line indicates the point of attachment to the thiadiazole:

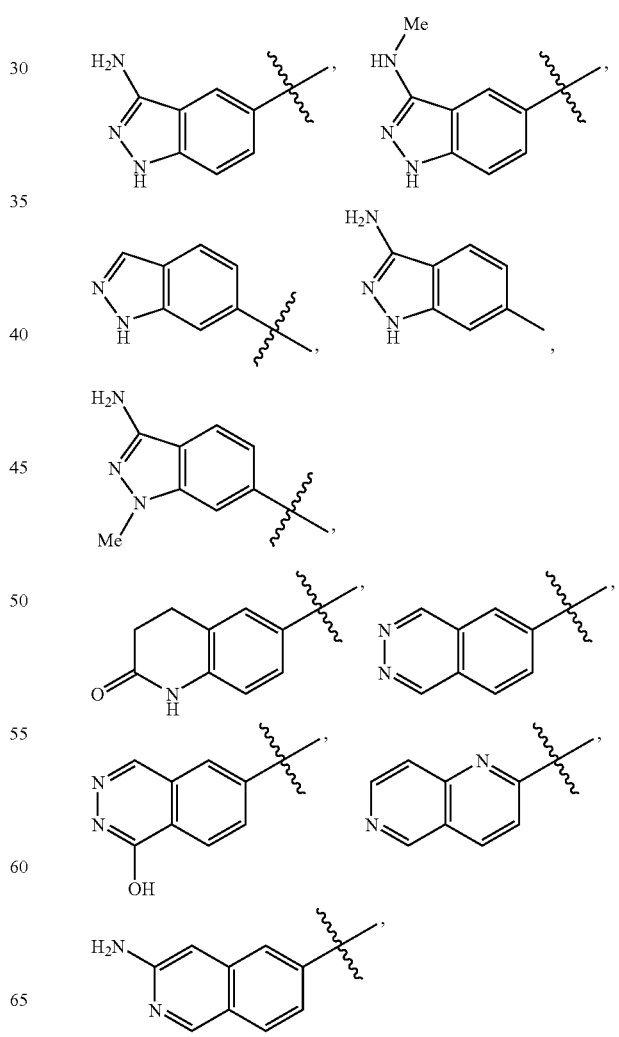

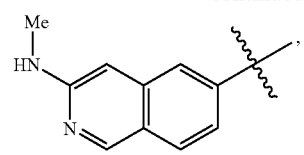
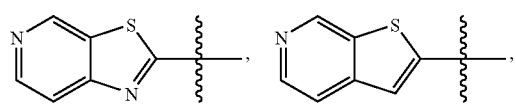
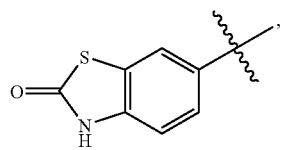
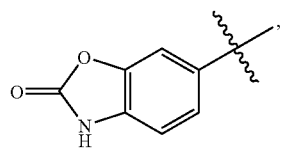
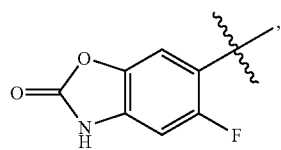
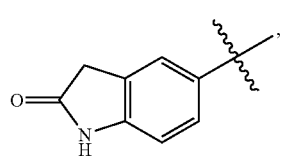
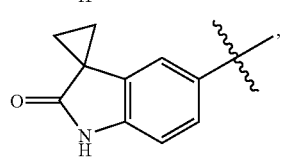
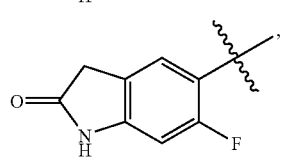
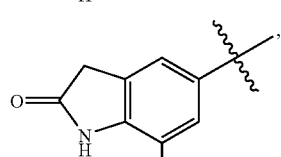
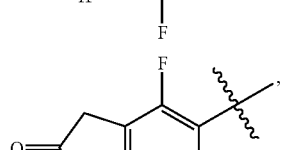
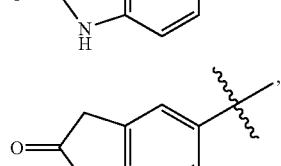
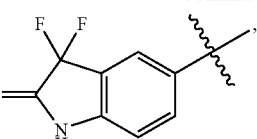
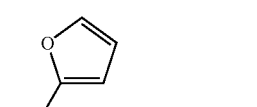
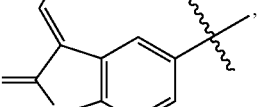
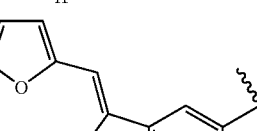
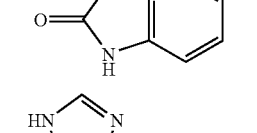
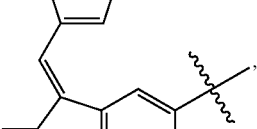
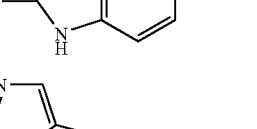
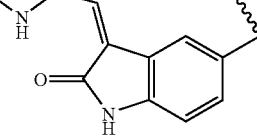
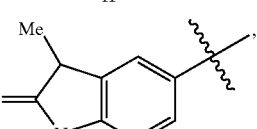
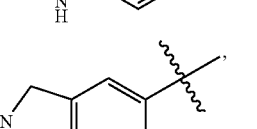
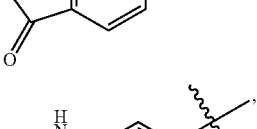
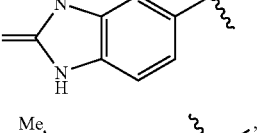
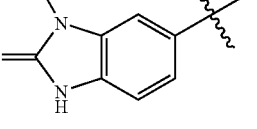

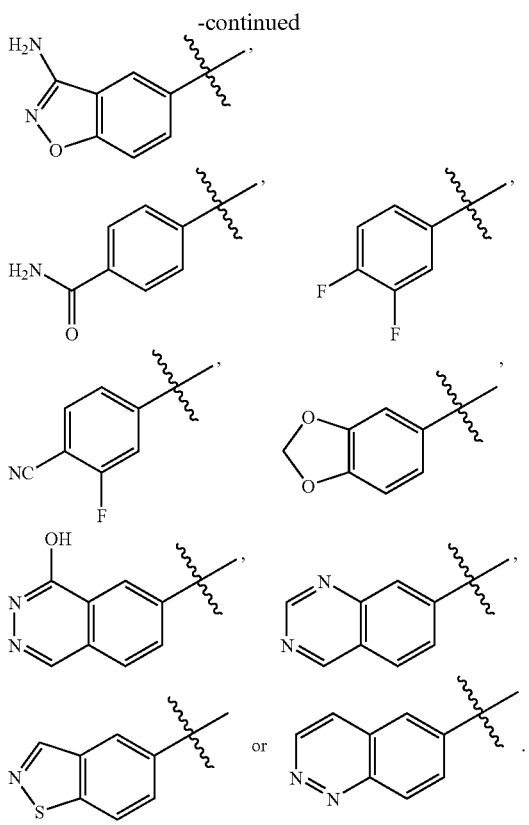

In another aspect, the invention provides a compound of Formula II

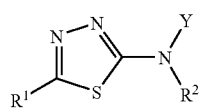

II wherein:
$R^1$ is selected from a carbocyclic ring system or a heterocyclic ring system;
$R^2$ is selected from —H, $C_1$-$C_8$ alkyl, —($C_1$-$C_6$ alkyl)aryl, or —C(O)($C_1$-$C_6$ alkyl); and
Y is selected from a group having the following formula:

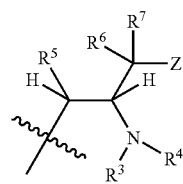

$R^3$ is selected from —H, $C_1$-$C_8$ alkyl, —C(O)($CR^8R^9$)$_t$N($R^7$)$_2$, —($CR^8R^9$)$_t$(aryl), —($CR^8R^9$)$_t$(heteroaryl), —($CR^8R^9$)$_t$(cycloalkyl), or —($CR^8R^9$)$_t$(heterocyclyl);
$R^4$ is selected from —H, $C_1$-$C_8$ alkyl, —($C_1$-$C_6$ alkyl)aryl, or —C(O)($C_1$-$C_6$ alkyl);
$R^5$ is selected from —H, —$OR^{10}$, —O—($C_1$-$C_6$ alkyl)—O—$R^{10}$, $C_1$-$C_6$ alkyl, $C_1$-$C_6$ alkenyl, —($C_1$-$C_6$ alkyl)—O—$R^{10}$, or —($C_1$-$C_6$ alkyl)—O—C(O)—$R^{10}$;
$R^6$ is selected from —H, or $C_1$-$C_6$ alkyl;
$R^7$ is selected from —H, —$OR^{10}$, —O—($C_1$-$C_6$ alkyl)—O—$R^{10}$, $C_1$-$C_6$ alkyl, $C_1$-$C_6$ alkenyl, —($C_1$-$C_6$ alkyl)—O—$R^{10}$, or —($C_1$-$C_6$ alkyl)—O—C(O)—$R^{10}$;
$R^8$ and $R^9$, in each instance, are independently selected from —H, $C_1$-$C_6$ alkyl, or aryl;
$R^{10}$ is selected from —H, $C_1$-$C_6$ alkyl, $C_1$-$C_6$ haloalkyl, —($C_1$-$C_6$ alkyl)aryl, aryl, heteroaryl, $C_1$-$C_6$ hydroxyalkyl, or —($C_1$-$C_6$ alkyl)—O—($C_1$-$C_6$ alkyl), cycloalkyl, or heterocyclyl;
each t is independently selected from 0, 1, 2, or 3; and
Z is selected from aryl or heteroaryl;
wherein each of the above alkyl, aryl, heteroaryl, cycloalkyl, and heterocyclyl moieties and heterocyclic and carbocyclic rings are optionally and independently substituted by 1-3 substituents selected from
amino,
aryl, heteroaryl, cycloalkyl, or heterocyclyl optionally substituted by 1-5 substituents selected from
$C_1$-$C_6$ alkoxy,
$C_1$-$C_6$ alkyl optionally substituted by halo,
aryl,
halo,
hydroxyl,
heteroaryl,
$C_1$-$C_6$ hydroxyalkyl, or
—NHS(O)$_2$—($C_1$-$C_6$ alkyl);
$C_1$-$C_6$ alkyl, $C_1$-$C_6$ haloalkyl, $C_1$-$C_6$ hydroxyalkyl, $C_1$-$C_6$ alkoxy, $C_1$-$C_6$ haloalkoxy, $C_1$-$C_6$ hydroxyalkoxy, $C_1$-$C_6$ alkylamino, $C_2$-$C_6$ alkenyl, or $C_2$-$C_6$ alkynyl, wherein each of which may be interrupted by one or more hetero atoms,
cyano,
halo,
hydroxyl,
nitro,
oxo,
—NH(CO)—O—($C_1$-$C_6$ alkyl)aryl, —NH(CO)—O—($C_1$-$C_6$ alkyl), —N($C_1$-$C_6$ alkyl)(CO)—O—($C_1$-$C_6$ alkyl)aryl, —N($C_1$-$C_6$ alkyl)(CO)—O—($C_1$-$C_6$ alkyl), —C(O)OH, —C(O)O($C_1$-$C_6$ alkyl), —C(O)NH$_2$, —C(O)N(H)—($C_1$-$C_6$ alkyl), —C(O)N($C_1$-$C_6$ alkyl)$_2$, —NH($C_1$-$C_6$ alkyl), —N($C_1$-$C_6$ alkyl)$_2$, —($C_2$-$C_4$ alkenyl)heterocyclyl, or —($C_2$-$C_4$ alkenyl)cycloalkyl, or —O-aryl;
or a pharmaceutically acceptable salt, hydrate, stereoisomer, or mixture thereof,
wherein the carbocyclic ring system or the heterocyclic ring system of $R^1$ is selected from a group other than one of the following or a substituted form of one of the following:

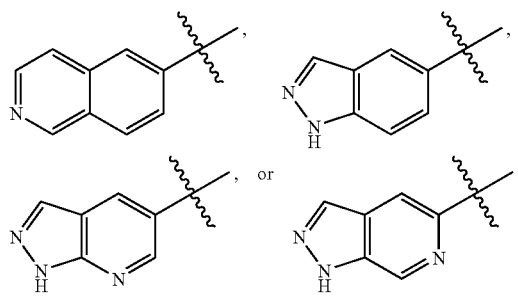

where the wavy line indicates the point of attachment to the thiadiazole ring.

In some embodiments of the compound of Formula II, the carbocyclic ring system or the heterocyclic ring system of $R^1$ comprises at least one ring that is not aromatic. In some such embodiments, the ring that is not aromatic includes an oxo group.

In some embodiments of the compound of Formula II, the carbocyclic ring system or the heterocyclic ring system of $R^1$ comprises at least one aromatic ring.

In some embodiments of the compound of Formula II, the carbocyclic ring system or the heterocyclic ring system of $R^1$ comprises a bicyclic ring system.

In some embodiments of the compound of Formula II, the carbocyclic ring system or the heterocyclic ring system of $R^1$ comprises two rings that are fused to one another, wherein at least one of the rings is a 6-membered ring. In some such embodiments, one of the rings is a 5-membered ring. In some such embodiments, the 5-membered ring is not aromatic and in some embodiments includes an oxo group.

In some embodiments of the compound of Formula II, $R^1$ is selected from optionally substituted phenyl, pyridyl, thiazolopyridinyl, benzothiazolonyl, dihydroquinolinonyl, benzoisoxazolyl, benzooxazolonyl, indolinonyl, benzoimidazolonyl, phthalazinyl, naphthyridinyl, thienopyridinyl, benzodioxolyl, isoindolinonyl, quinazolinyl, or cinnolinyl.

In some embodiments of the compound of Formula II, $R^1$ is selected from one of the following groups which may optionally be substituted and where the wavy line indicates the point of attachment to the thiadiazole:

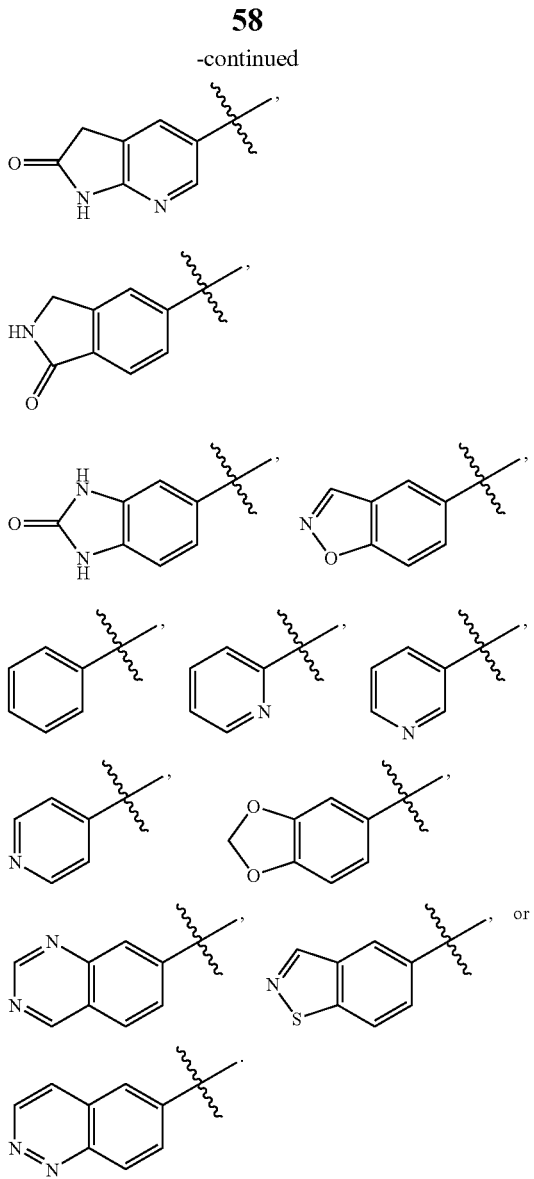

In some embodiments of the compound of Formula II, $R^1$ is selected from one of the following groups which may optionally be substituted and where the wavy line indicates the point of attachment to the thiadiazole:

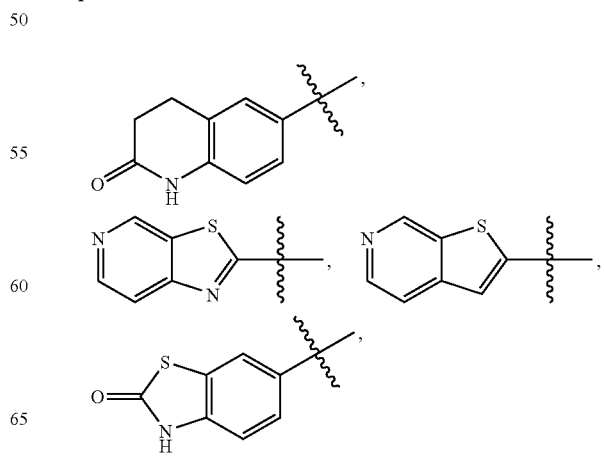

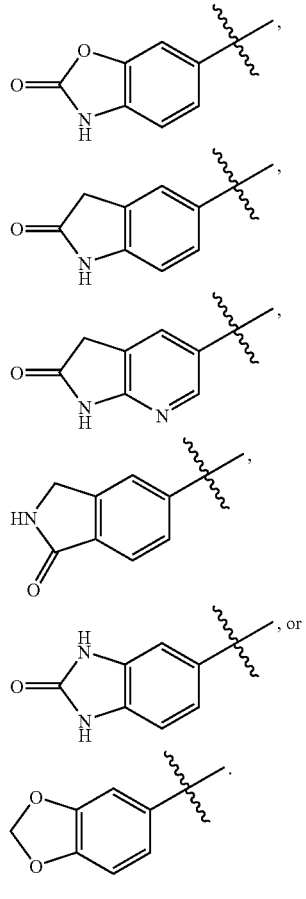
In some embodiments of the compound of Formula II, $R^1$ is selected from one of the following groups, where the wavy line indicates the point of attachment to the thiadiazole:
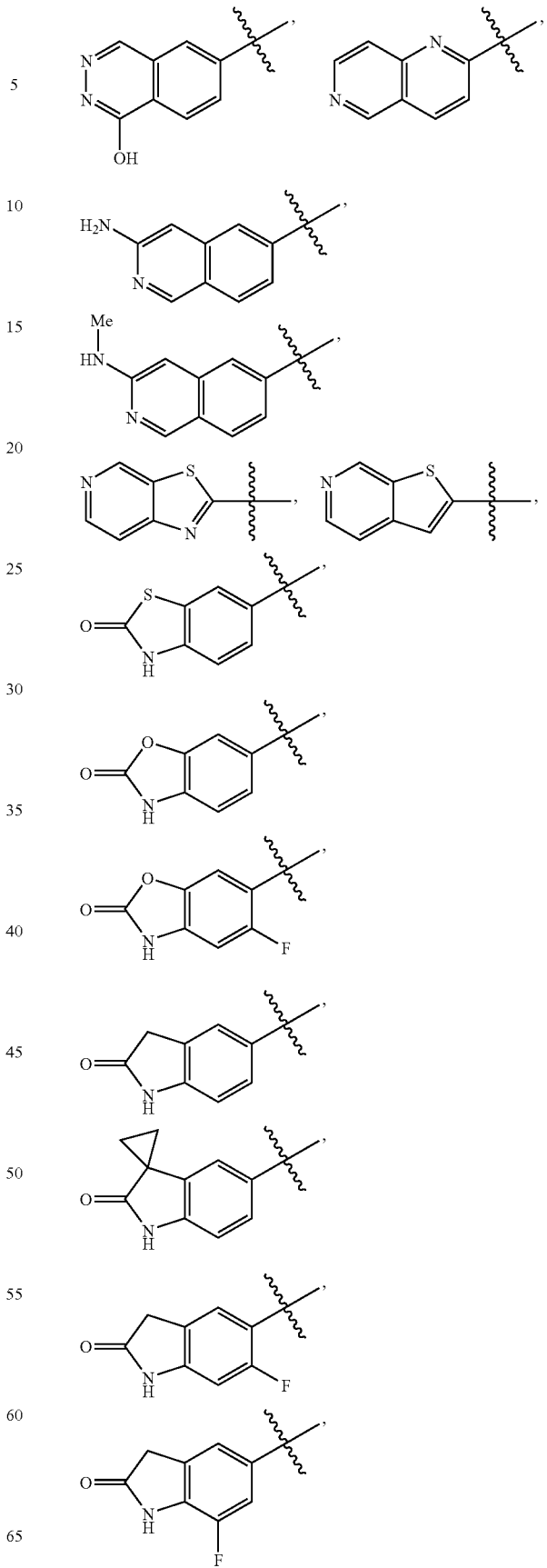

-continued
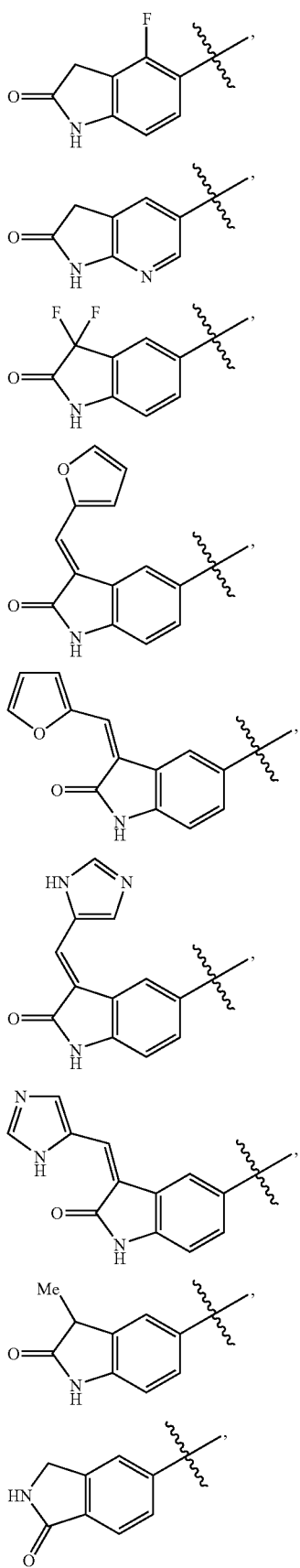
-continued
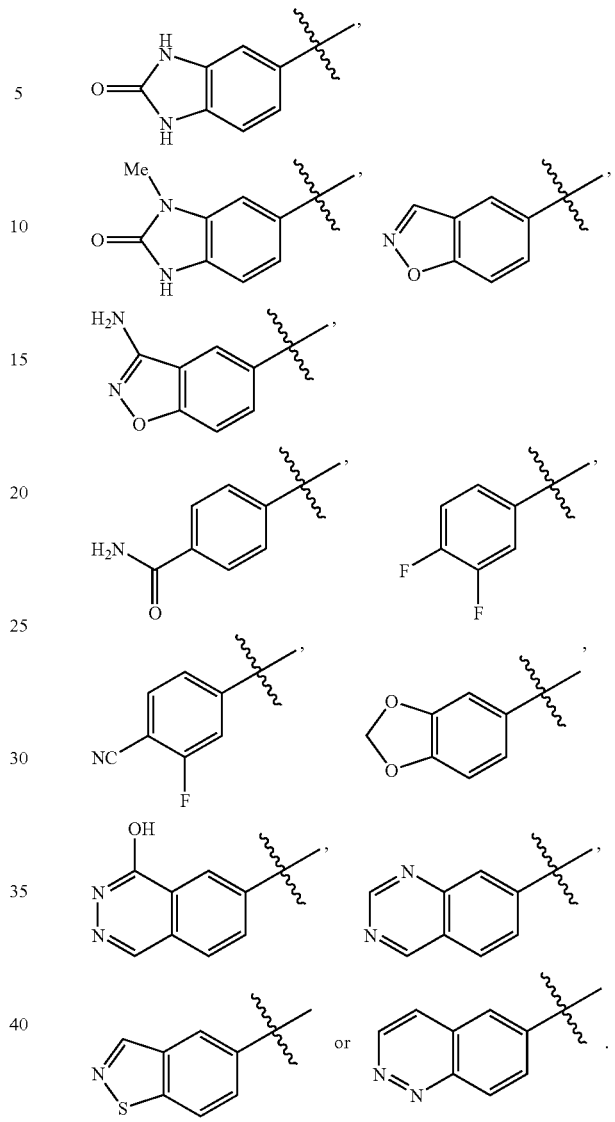
In some embodiments of the compound of Formula II, the compound has the Formula IA
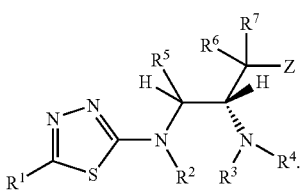
IA
In some embodiments of the compound of Formula II, the compound has the Formula IB
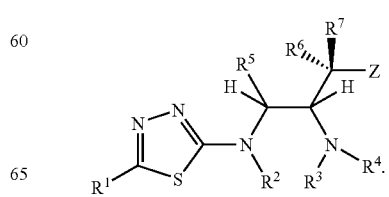
IB In some embodiments of the compound of Formula II, the compound has the Formula IC

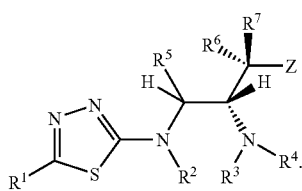

IC

In some embodiments of the compound of Formula II, the compound has the Formula ID

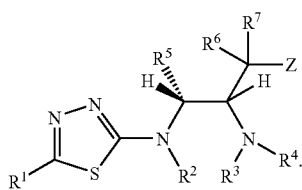

ID

In some embodiments of the compound of Formula II, the compound has the Formula IE

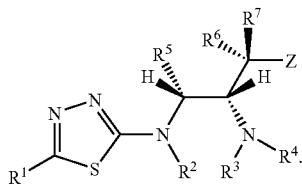

IE

In some embodiments of the compound of Formula II, $R^5$ is —H or $C_1$-$C_6$ alkyl. In some such embodiments, $R^5$ is —H or methyl.

In some embodiments of the compound of Formula II, $R^6$ is —H.

In some embodiments of the compound of Formula II, $R^7$ is —H.

In some embodiments of the compound of Formula II, $R^7$ is —$OR^{10}$, —O—($C_1$-$C_6$ alkyl)—O—$R^{10}$, $C_1$-$C_6$ alkyl, $C_1$-$C_6$ alkenyl, —($C_1$-$C_6$ alkyl)—O—$R^{10}$, or —($C_1$-$C_6$ alkyl)—O—C(O)—$R^{10}$.

In some embodiments of the compound of Formula II, $R^7$ is selected from —H, methyl, ethyl, propyl, ethenyl, propenyl, hydroxymethyl, methoxymethyl, —$CH_2$—O—C(O)—($C_1$-$C_6$ alkyl), 1-hydroxyethyl, or methoxymethoxy.

In some embodiments of the compound of Formula II, Z is selected from optionally substituted phenyl, optionally substituted indolyl, optionally substituted naphthyl, optionally substituted pyridyl, or optionally substituted thiophenyl.

In some embodiments of the compound of Formula II, Z is selected from phenyl, indolyl, naphthyl, pyridyl, or thiophenyl, each of which is optionally substituted with 1-3 substituents selected from —Cl, —F, —$CF_3$, —OH, —O—($C_1$-$C_6$ alkyl), —O—($C_1$-$C_6$ alkyl)-Cl, —O—($C_1$-$C_6$ alkyl)—OH, —$C_1$-$C_6$ alkyl, —$OCF_3$, —NH(CO)—O—($C_1$-$C_6$ alkyl)aryl, or —NH(CO)—O—($C_1$-$C_6$ alkyl).

In some embodiments of the compound of Formula II, Z is selected from phenyl, indolyl, naphthyl, pyridyl, thiophenyl, 4-chlorophenyl, 4-trifluoromethylphenyl, 3-chlorophenyl, 3-trifluoromethylphenyl, 4-methoxyphenyl, 3-fluoro-4-trifluoromethylphenyl, 4-chloro-3-fluorophenyl, 4-(3-chloropropoxy)phenyl, 4-(3-hydroxypropoxy)phenyl, 3,4-dichlorophenyl, 4-fluorophenyl, 2,4-dichlorophenyl, 4-methylphenyl, 3,4-difluorophenyl, 3-fluoro-4-methoxyphenyl, 3,5-difluorophenyl, 6-trifluoromethylpyridin-3-yl, 5-methoxy-6-trifluoromethylpyridin-3-yl, 2-fluoro-4-trifluoromethylphenyl, 4-trifluoromethoxyphenyl, 2,3-difluoro-4-trifluoromethylphenyl, 4-hydroxyphenyl, 3-methoxy-4-trifluoromethylphenyl, 3-hydroxy-4-trifluoromethylphenyl, 5-chlorothiophen-2-yl, 3-fluoro-4-hydroxyphenyl, or a phenyl substituted in the 4 position with —NH—C(O)—O—$CH_2$-phenyl.

In some embodiments of the compound of Formula II, $R^2$ is —H.

In some embodiments of the compound of Formula II, $R^3$ is —H. In some embodiments, both $R^3$ and $R^4$ are —H. In still other embodiments, $R^2$, $R^3$, and $R^4$ are all —H. In some such embodiments, at least one of $R^3$ and $R^4$ is —H.

In some embodiments of the compound of Formula II, $R^4$ is —H.

In another aspect, the invention provides a compound of Formula IV

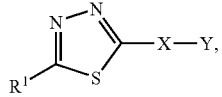

IV wherein:
X is selected from O, S, $NR^2$, or $CR^{2a}R^{2b}$;
$R^1$ is selected from a carbocyclic ring system or a heterocyclic ring system;
$R^2$ may be absent or is selected from —H, $C_1$-$C_8$ alkyl, —($C_1$-$C_6$ alkyl)aryl, or —C(O)($C_1$-$C_6$ alkyl);
$R^{2a}$ and $R^{2b}$ may be absent or are independently selected from —H, $C_1$-$C_8$ alkyl, —($C_1$-$C_6$ alkyl)aryl, or —C(O)($C_1$-$C_6$ alkyl);
Y is selected from one of the following when X is O, S, $NR^2$, or $CR^{2a}R^{2b}$:

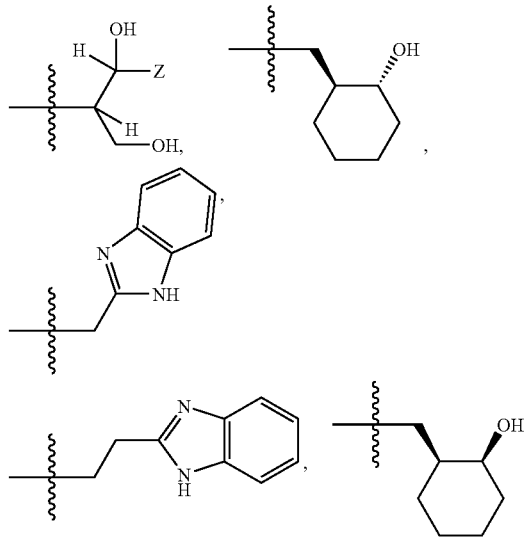

wherein the wavy line indicates the point of attachment to X and any of the carbons with unspecified substituents in the alkyl, cycloalkyl, aryl, or heteroaryl groups in the above selections for Y may be substituted with —H, halo, $C_1$-$C_6$ alkyl, or —$OR^{10}$ groups;

or Y is optionally selected from the following when X is O, S, or $CR^{2a}R^{2b}$:

and the wavy line indicates the point of attachment to X;

$R^3$ may be absent or is selected from —H, $C_1$-$C_8$ alkyl, —C(O)($CR^8R^9$)$_t$)N($R^7$)$_2$, —($CR^8R^9$)$_t$(aryl), —($CR^8R^9$)$_t$(heteroaryl), —($CR^8R^9$)$_t$(cycloalkyl), or —($CR^8R^9$)$_t$(heterocyclyl);

$R^4$ may be absent or is selected from —H, $C_1$-$C_8$ alkyl, —($C_1$-$C_6$ alkyl)aryl, or —C(O)($C_1$-$C_6$ alkyl);

$R^5$ may be absent or is selected from —H, —$OR^{10}$, —O—($C_1$-$C_6$ alkyl)—O—$R^{10}$, $C_1$-$C_6$ alkyl, $C_1$-$C_6$ alkenyl, —($C_1$-$C_6$ alkyl)—O—$R^{10}$, or —($C_1$-$C_6$ alkyl)—O—C(O)—$R^{10}$;

$R^6$ may be absent or is selected from —H, or $C_1$-$C_6$ alkyl;

$R^7$ may be absent or is selected from —H, —$OR^{10}$, —O—($C_1$-$C_6$ alkyl)—O—$R^{10}$, $C_1$-$C_6$ alkyl, $C_1$-$C_6$ alkenyl, —($C_1$-$C_6$ alkyl)—O—$R^{10}$, or —($C_1$-$C_6$ alkyl)—O—C(O)—$R^{10}$;

$R^8$ and $R^9$, in each instance, may be absent or are independently selected from —H, $C_1$-$C_6$ alkyl, or aryl;

$R^{10}$ may be absent or is selected from —H, $C_1$-$C_6$ alkyl, $C_1$-$C_6$ haloalkyl, —($C_1$-$C_6$ alkyl)aryl, aryl, heteroaryl, $C_1$-$C_6$ hydroxyalkyl, or —($C_1$-$C_6$ alkyl)—O—($C_1$-$C_6$ alkyl), cycloalkyl, or heterocyclyl;

each t is independently selected from 0, 1, 2, or 3; and

Z may be absent or is selected from aryl or heteroaryl;

wherein each of the above alkyl, aryl, heteroaryl, cycloalkyl, and heterocyclyl moieties and heterocyclic and carbocyclic rings are optionally and independently substituted by 1-3 substituents selected from amino, aryl, heteroaryl, cycloalkyl, or heterocyclyl optionally substituted by 1-5 substituents selected from
$C_1$-$C_6$ alkoxy,
$C_1$-$C_6$ alkyl optionally substituted by halo,
aryl,
halo,
hydroxyl,
heteroaryl,
$C_1$-$C_6$ hydroxyalkyl, or
—NHS(O)$_2$—($C_1$-$C_6$ alkyl);

$C_1$-$C_6$ alkyl, $C_1$-$C_6$ haloalkyl, $C_1$-$C_6$ hydroxyalkyl, $C_1$-$C_6$ alkoxy, $C_1$-$C_6$ haloalkoxy, $C_1$-$C_6$ hydroxyalkoxy, $C_1$-$C_6$ alkylamino, $C_2$-$C_6$ alkenyl, or $C_2$-$C_6$ alkynyl, wherein each of which may be interrupted by one or more hetero atoms, cyano,
halo,
hydroxyl,
nitro,
oxo,
—NH(CO)—O—($C_1$-$C_6$ alkyl)aryl, —NH(CO)—O—($C_1$-$C_6$ alkyl), —N($C_1$-$C_6$ alkyl)(CO)—O—($C_1$-$C_6$ alkyl)aryl, —N($C_1$-$C_6$ alkyl)(CO)—O—($C_1$-$C_6$ alkyl), —C(O)OH, —C(O)O($C_1$-$C_6$ alkyl), —C(O)NH$_2$, —C(O)N(H)—($C_1$-$C_6$ alkyl), —C(O)N($C_1$-$C_6$ alkyl)$_2$, —NH($C_1$-$C_6$ alkyl), —N($C_1$-$C_6$ alkyl)$_2$, —($C_2$-$C_4$ alkenyl)heterocyclyl, or —($C_2$-$C_4$ alkenyl)cycloalkyl, or —O-aryl;

or a pharmaceutically acceptable salt, hydrate, stereoisomer, or mixture thereof.

In some embodiments of the compound of Formula IV,

X is selected from O, S, $NR^2$, or $CR^{2a}R^{2b}$;

$R^1$ is selected from a carbocyclic ring system or a heterocyclic ring system;

$R^2$ may be absent or is selected from —H, $C_1$-$C_8$ alkyl, —($C_1$-$C_6$ alkyl)aryl, or —C(O)($C_1$-$C_6$ alkyl);

$R^{2a}$ and $R^{2b}$ may be absent or are independently selected from —H, $C_1$-$C_8$ alkyl, —($C_1$-$C_6$ alkyl)aryl, or —C(O)($C_1$-$C_6$ alkyl);

Y is selected from one of the following:

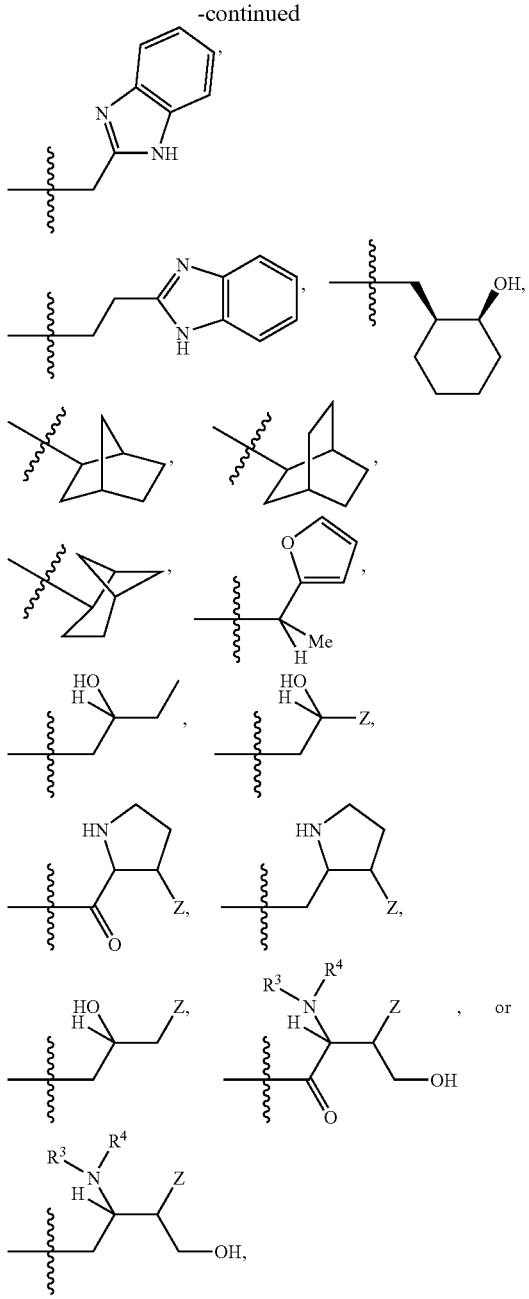

wherein the wavy line indicates the point of attachment to X and any of the carbons with unspecified substituents in the alkyl, cycloalkyl, aryl, or heteroaryl groups in the above selections for Y may be substituted with —H, halo, $C_1$-$C_6$ alkyl, or —$OR^{10}$ groups;

$R^3$ may be absent or is selected from —H, $C_1$-$C_8$ alkyl, —C(O)($CR^8R^9$)$_t$N($R^7$)$_2$, —($CR^8R^9$)$_t$(aryl), —($CR^8R^9$)$_t$(heteroaryl), —($CR^8R^9$)$_t$(cycloalkyl), or —($CR^8R^9$)$_t$(heterocyclyl);

$R^4$ may be absent or is selected from —H, $C_1$-$C_8$ alkyl, —($C_1$-$C_6$ alkyl)aryl, or —C(O)($C_1$-$C_6$ alkyl);

$R^7$ may be absent or is selected from —H, —$OR^{10}$, —O—($C_1$-$C_6$ alkyl)—O—$R^{10}$, $C_1$-$C_6$ alkyl, $C_1$-$C_6$ alkenyl, —($C_1$-$C_6$ alkyl)—O—$R^{10}$, or —($C_1$-$C_6$ alkyl)—O—C(O)—$R^{10}$;

$R^8$ and $R^9$, in each instance, may be absent or are independently selected from —H, $C_1$-$C_6$ alkyl, or aryl;

$R^{10}$ may be absent or is selected from —H, $C_1$-$C_6$ alkyl, $C_1$-$C_6$ haloalkyl, —($C_1$-$C_6$ alkyl)aryl, aryl, heteroaryl, $C_1$-$C_6$ hydroxyalkyl, or —($C_1$-$C_6$ alkyl)—O—($C_1$-$C_6$ alkyl), cycloalkyl, or heterocyclyl;

each t is independently selected from 0, 1, 2, or 3; and

Z may be absent or is selected from aryl or heteroaryl;

wherein each of the above alkyl, aryl, heteroaryl, cycloalkyl, and heterocyclyl moieties and heterocyclic and carbocyclic rings are optionally and independently substituted by 1-3 substituents selected from
amino,
aryl, heteroaryl, cycloalkyl, or heterocyclyl optionally substituted by 1-5 substituents selected from
  $C_1$-$C_6$ alkoxy,
  $C_1$-$C_6$ alkyl optionally substituted by halo,
  aryl,
  halo,
  hydroxyl,
  heteroaryl,
  $C_1$-$C_6$ hydroxyalkyl, or
  —NHS(O)$_2$—$C_1$-$C_6$ alkyl);
$C_1$-$C_6$ alkyl, $C_1$-$C_6$ haloalkyl, $C_1$-$C_6$ hydroxyalkyl, $C_1$-$C_6$ alkoxy, $C_1$-$C_6$ haloalkoxy, $C_1$-$C_6$ hydroxyalkoxy, $C_1$-$C_6$ alkylamino, $C_2$-$C_6$ alkenyl, or $C_2$-$C_6$ alkynyl, wherein each of which may be interrupted by one or more hetero atoms,
cyano,
halo,
hydroxyl,
nitro,
oxo,
—NH(CO)—O—($C_1$-$C_6$ alkyl)aryl, —NH(CO)—O—($C_1$-$C_6$ alkyl), —N($C_1$-$C_6$ alkyl)(CO)—O—($C_1$-$C_6$ alkyl)aryl, —N($C_1$-$C_6$ alkyl)(CO)—O—($C_1$-$C_6$ alkyl), —C(O)OH, —C(O)O($C_1$-$C_6$ alkyl), —C(O)NH$_2$, —C(O)N(H)—($C_1$-$C_6$ alkyl), —C(O)N($C_1$-$C_6$ alkyl)$_2$, —NH($C_1$-$C_6$ alkyl), —N($C_1$-$C_6$ alkyl)$_2$, —($C_2$-$C_4$ alkenyl)heterocyclyl, or —($C_2$-$C_4$ alkenyl)cycloalkyl, or —O-aryl;

or a pharmaceutically acceptable salt, hydrate, stereoisomer, or mixture thereof.

In some embodiments of the compound of Formula IV,

X is selected from O, S, or $CR^{2a}R^{2b}$;

$R^1$ is selected from a carbocyclic ring system or a heterocyclic ring system;

$R^{2a}$ and $R^{2b}$ may be absent or are independently selected from —H, $C_1$-$C_8$ alkyl, —($C_1$-$C_6$ alkyl)aryl, or —C(O)($C_1$-$C_6$ alkyl);

Y is:

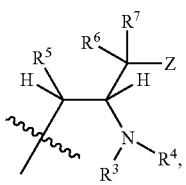

and the wavy line indicates the point of attachment to X;

$R^3$ may be absent or is selected from —H, $C_1$-$C_8$ alkyl, —C(O)($CR^8R^9$)$_t$N($R^7$)$_2$, —($CR^8R^9$)$_t$(aryl), —($CR^8R^9$)$_t$(heteroaryl), —($CR^8R^9$)$_t$(cycloalkyl), or —($CR^8R^9$)$_t$(heterocyclyl);

$R^4$ may be absent or is selected from —H, $C_1$-$C_8$ alkyl, —($C_1$-$C_6$ alkyl)aryl, or —C(O)($C_1$-$C_6$ alkyl);

R⁵ may be absent or is selected from —H, —OR¹⁰, —O—(C₁-C₆ alkyl)—O—R¹⁰, C₁-C₆ alkyl, C₁-C₆ alkenyl, —(C₁-C₆ alkyl)—O—R¹⁰, or —(C₁-C₆ alkyl)—O—C(O)—R¹⁰;

R⁶ may be absent or is selected from —H, or C₁-C₆ alkyl;

R⁷ may be absent or is selected from —H, —OR¹⁰, —O—(C₁-C₆ alkyl)—O—R¹⁰, C₁-C₆ alkyl, C₁-C₆ alkenyl, —(C₁-C₆ alkyl)—O—R¹⁰, or —(C₁-C₆ alkyl)—O—C(O)—R¹⁰;

R⁸ and R⁹, in each instance, may be absent or are independently selected from —H, C₁-C₆ alkyl, or aryl;

R¹⁰ may be absent or is selected from —H, C₁-C₆ alkyl, C₁-C₆ haloalkyl, —(C₁-C₆ alkyl)aryl, aryl, heteroaryl, C₁-C₆ hydroxyalkyl, or —(C₁-C₆ alkyl)—O—(C₁-C₆ alkyl), cycloalkyl, or heterocyclyl;

each t is independently selected from 0, 1, 2, or 3; and

Z may be absent or is selected from aryl or heteroaryl;

wherein each of the above alkyl, aryl, heteroaryl, cycloalkyl, and heterocyclyl moieties and heterocyclic and carbocyclic rings are optionally and independently substituted by 1-3 substituents selected from amino,
aryl, heteroaryl, cycloalkyl, or heterocyclyl optionally substituted by 1-5 substituents selected from
  C₁-C₆ alkoxy,
  C₁-C₆ alkyl optionally substituted by halo,
  aryl,
  halo,
  hydroxyl,
  heteroaryl,
  C₁-C₆ hydroxyalkyl, or
  —NHS(O)₂—(C₁-C₆ alkyl);
C₁-C₆ alkyl, C₁-C₆ haloalkyl, C₁-C₆ hydroxyalkyl, C₁-C₆ alkoxy, C₁-C₆ haloalkoxy, C₁-C₆ hydroxyalkoxy, C₁-C₆ alkylamino, C₂-C₆ alkenyl, or C₂-C₆ alkynyl, wherein each of which may be interrupted by one or more hetero atoms,
cyano,
halo,
hydroxyl,
nitro,
oxo,
—NH(CO)—O—(C₁-C₆ alkyl)aryl, —NH(CO)—O—(C₁-C₆ alkyl), —N(C₁-C₆ alkyl)(CO)—O—(C₁-C₆ alkyl)aryl, —N(C₁-C₆ alkyl)(CO)—O—(C₁-C₆ alkyl), —C(O)OH, —C(O)O(C₁-C₆ alkyl), —C(O)NH₂, —C(O)N(H)—(C₁-C₆ alkyl), —C(O)N(C₁-C₆ alkyl)₂, —NH(C₁-C₆ alkyl), —N(C₁-C₆ alkyl)₂, —(C₂-C₄ alkenyl)heterocyclyl, or —(C₂-C₄ alkenyl)cycloalkyl, or —O-aryl;

or a pharmaceutically acceptable salt, hydrate, stereoisomer, or mixture thereof.

In some embodiments of the compound of Formula IV, Y is

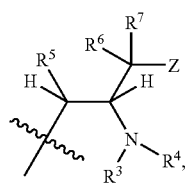

and one of the following is true:
(a) R⁵ is selected from —OR¹⁰, —O—(C₁-C₆ alkyl)—O—R¹⁰, C₁-C₆ alkyl, C₁-C₆ alkenyl, —(C₁-C₆ alkyl)—O—R¹⁰, or —(C₁-C₆ alkyl)—O—C(O)—R¹⁰; or (b) R⁷ is selected from —OR¹⁰, —O—(C₁-C₆ alkyl)—O—R¹⁰, C₁-C₆ alkenyl, —(C₁-C₆ alkyl)—O—R¹⁰, or —(C₁-C₆ alkyl)—O—C(O)—R¹⁰.

In some embodiments of the compound of Formula IV, the compound is a compound other than

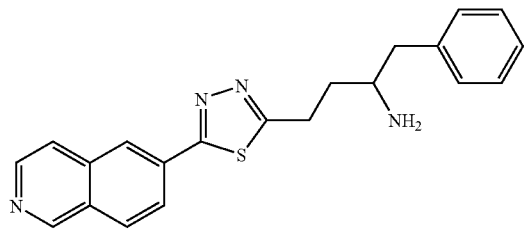

or a pharmaceutically acceptable salt, polymorph, clathrate, solvate, hydrate, stereoisomer, enantiomer, or prodrug thereof.

In some embodiments of the compound of Formula IV, X is NR². In some such embodiments, R² is —H.

In some embodiments of the compound of Formula IV, X is O.

In some embodiments of the compound of Formula IV, X is S.

In some embodiments of the compound of Formula IV, X is CR²ᵃR²ᵇ. In some such embodiments, R²ᵃ and R²ᵇ are both H.

In some embodiments of the compound of Formula IV, R⁵ is —H or C₁-C₆ alkyl. In some such embodiments, R⁵ is —H or methyl.

In some embodiments of the compound of Formula IV, R⁶ is —H.

In some embodiments of the compound of Formula IV, R⁷ is —H

In some embodiments of the compound of Formula IV, R⁷ is —OR¹⁰, —O—(C₁-C₆ alkyl)—O—R¹⁰, C₁-C₆ alkyl, C₁-C₆ alkenyl, —(C₁-C₆ alkyl)—O—R¹⁰, or —(C₁-C₆ alkyl)—O—C(O)—R¹⁰.

In some embodiments of the compound of Formula IV, R⁷ is selected from —H, methyl, ethyl, propyl, ethenyl, propenyl, hydroxymethyl, methoxymethyl, —CH₂—O—C(O)—(C₁-C₆ alkyl), 1-hydroxyethyl, or methoxymethoxy.

In some embodiments of the compound of Formula IV, Z is selected from optionally substituted phenyl, optionally substituted indolyl, optionally substituted naphthyl, optionally substituted pyridyl, or optionally substituted thiophenyl.

In some embodiments of the compound of Formula IV, Z is selected from phenyl, indolyl, naphthyl, pyridyl, or thiophenyl, each of which is optionally substituted with 1-3 substituents selected from —Cl, —F, —CF₃, —OH, —O—(C₁-C₆ alkyl), —O—(C₁-C₆ alkyl)-Cl, —O—(C₁-C₆ alkyl)—OH, —C₁-C₆ alkyl, —OCF₃, —NH(CO)—O—(C₁-C₆ alkyl)aryl, or —NH(CO)—O—(C₁-C₆ alkyl).

In some embodiments of the compound of Formula IV, Z is selected from phenyl, indolyl, naphthyl, pyridyl, thiophenyl, 4-chlorophenyl, 4-trifluoromethylphenyl, 3-chlorophenyl, 3-trifluoromethylphenyl, 4-methoxyphenyl, 3-fluoro-4-trifluoromethylphenyl, 4-chloro-3-fluorophenyl, 4-(3-chloropropoxy)phenyl, 4-(3-hydroxypropoxy)phenyl, 3,4-dichlorophenyl, 4-fluorophenyl, 2,4-dichlorophenyl, 4-methylphenyl, 3,4-difluorophenyl, 3-fluoro-4-methoxyphenyl, 3,5-difluorophenyl, 6-trifluoromethylpyridin-3-yl, 5-methoxy-6-trifluoromethylpyridin-3-yl, 2-fluoro-4-trifluoromethylphenyl, 4-trifluoromethoxyphenyl, 2,3-difluoro-4-trifluoromethylphenyl, 4-hydroxyphenyl, 3-methoxy-4-trifluoromethylphenyl, 3-hydroxy-4-trifluoromethylphenyl, 5-chlorothiophen-2-yl, 3-fluoro-4-hydroxyphenyl, or a phenyl substituted in the 4 position with —NH—C(O)—O—CH$_2$-phenyl.

In some embodiments of the compound of Formula IV, R$^3$ and R$^4$ are each H. In some such embodiments, R$^2$, R$^3$, and R$^4$ are all H. In other such embodiments, R$^{2a}$, R$^{2b}$, R$^3$, and R$^4$ are all H.

In some embodiments of the compound of Formula IV, the carbocyclic ring system or the heterocyclic ring system of R$^1$ comprises at least one aromatic ring.

In some embodiments of the compound of Formula IV, the carbocyclic ring system or the heterocyclic ring system of R$^1$ comprises a bicyclic ring system.

In some embodiments of the compound of Formula IV, the carbocyclic ring system or the heterocyclic ring system of R$^1$ comprises two rings that are fused to one another, wherein at least one of the rings is a 6-membered ring.

In some embodiments of the compound of Formula IV, the carbocyclic ring system or the heterocyclic ring system of R$^1$ comprises at least one ring that is not aromatic.

In some embodiments of the compound of Formula IV, the carbocyclic ring system or the heterocyclic ring system of R$^1$ is selected from a group other than an unsubstituted or optionally substituted group of one of the following where the wavy line indicates the point of attachment to the thiadiazole ring:

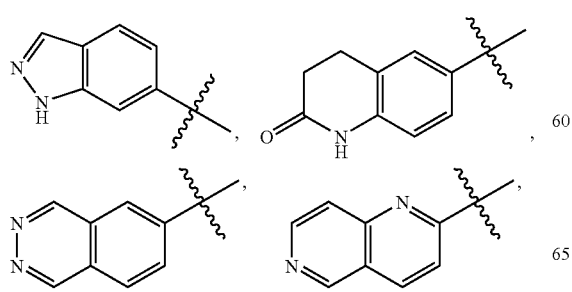

In some embodiments of the compound of Formula IV, R$^1$ is selected from optionally substituted phenyl, pyridyl, indazolyl, isoquinolinyl, thiazolopyridinyl, benzothiazolonyl, dihydroquinolinonyl, benzoisoxazolyl, benzooxazolonyl, indolinonyl, benzoimidazolonyl, phthalazinyl, naphthyridinyl, thienopyridinyl, benzodioxolyl, isoindolinonyl, quinazolinyl, or cinnolinyl.

In some embodiments of the compound of Formula IV, R$^1$ is selected from one of the following groups which may optionally be substituted and where the wavy line indicates the point of attachment to the thiadiazole:

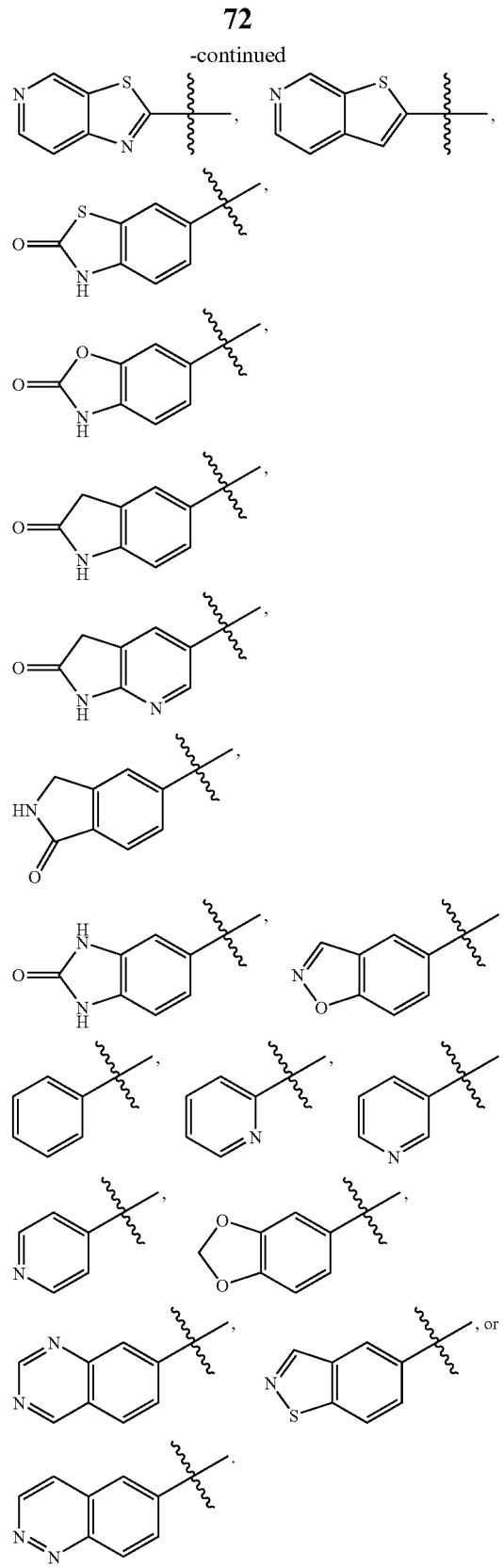

In some embodiments of the compound of Formula IV, R$^1$ is selected from one of the following groups which may optionally be substituted and where the wavy line indicates the point of attachment to the thiadiazole:

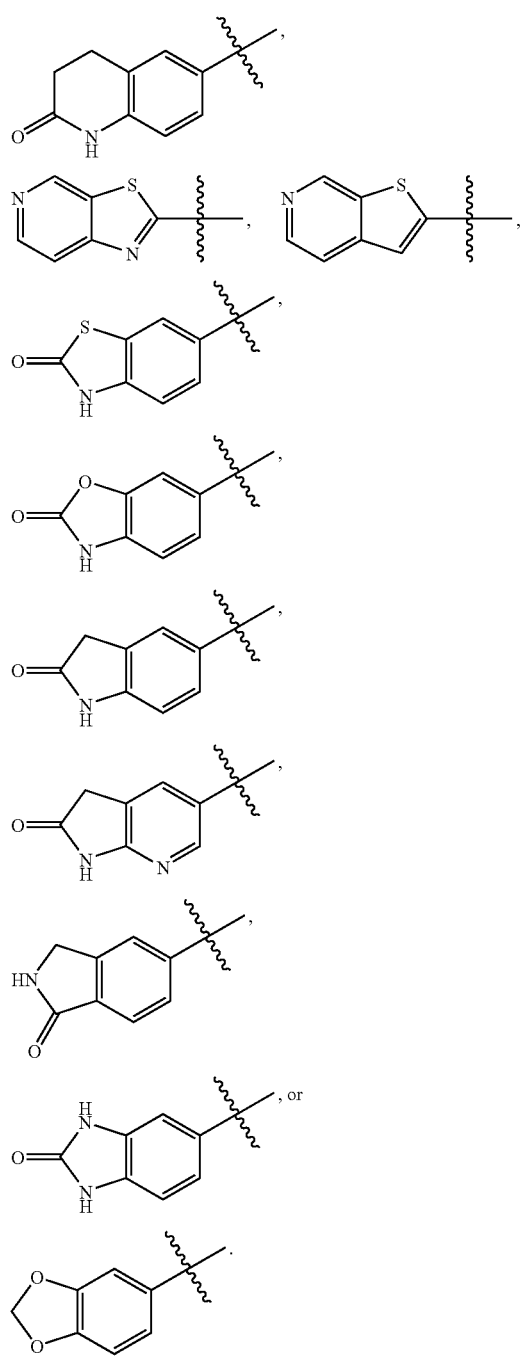
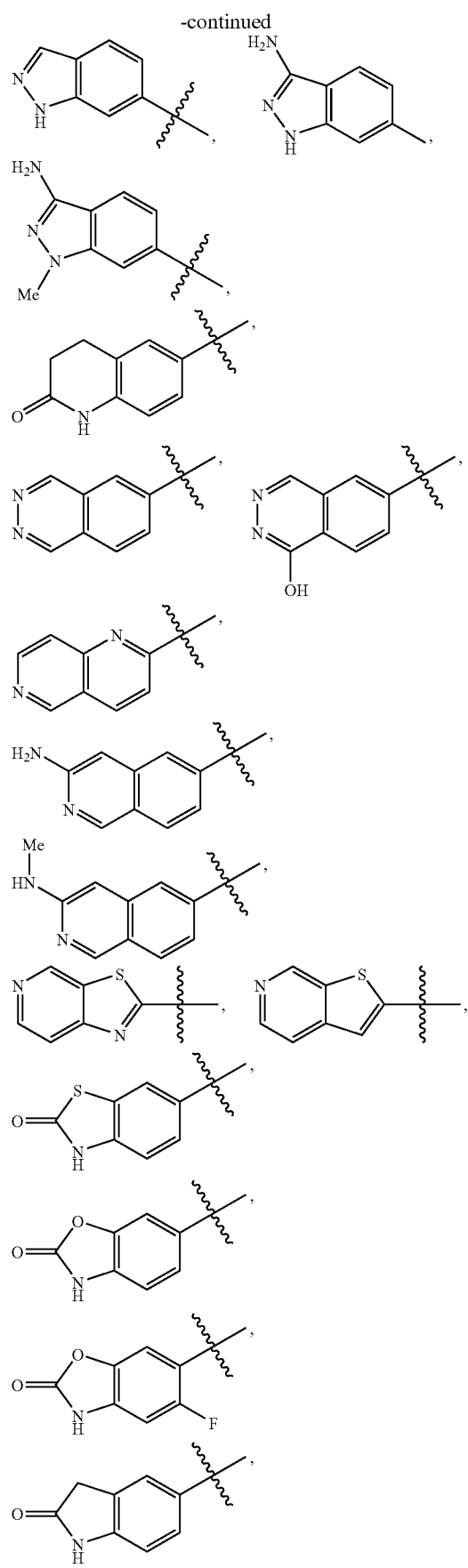
In some embodiments of the compound of Formula IV, R[1] is selected from one of the following groups, where the wavy line indicates the point of attachment to the thiadiazole:
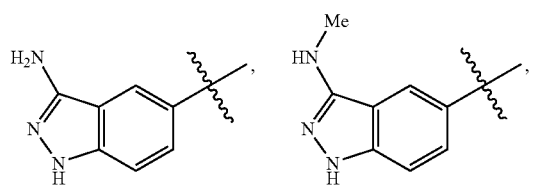

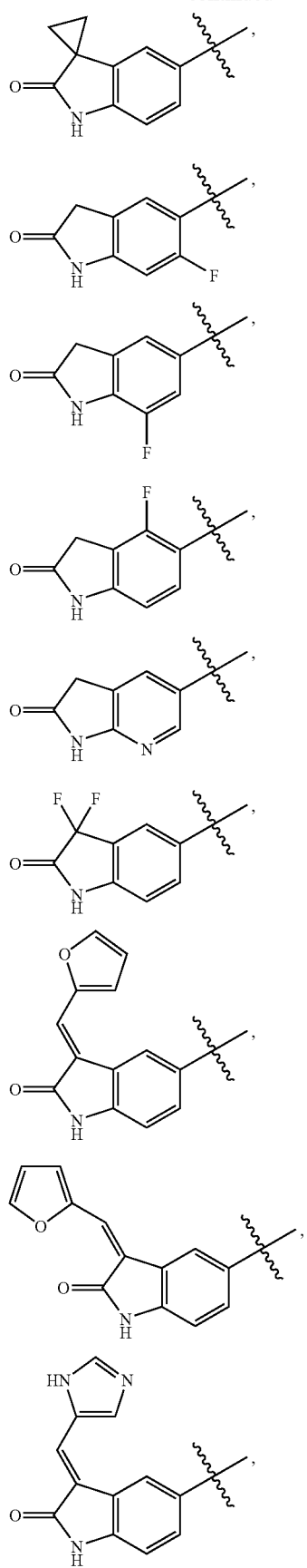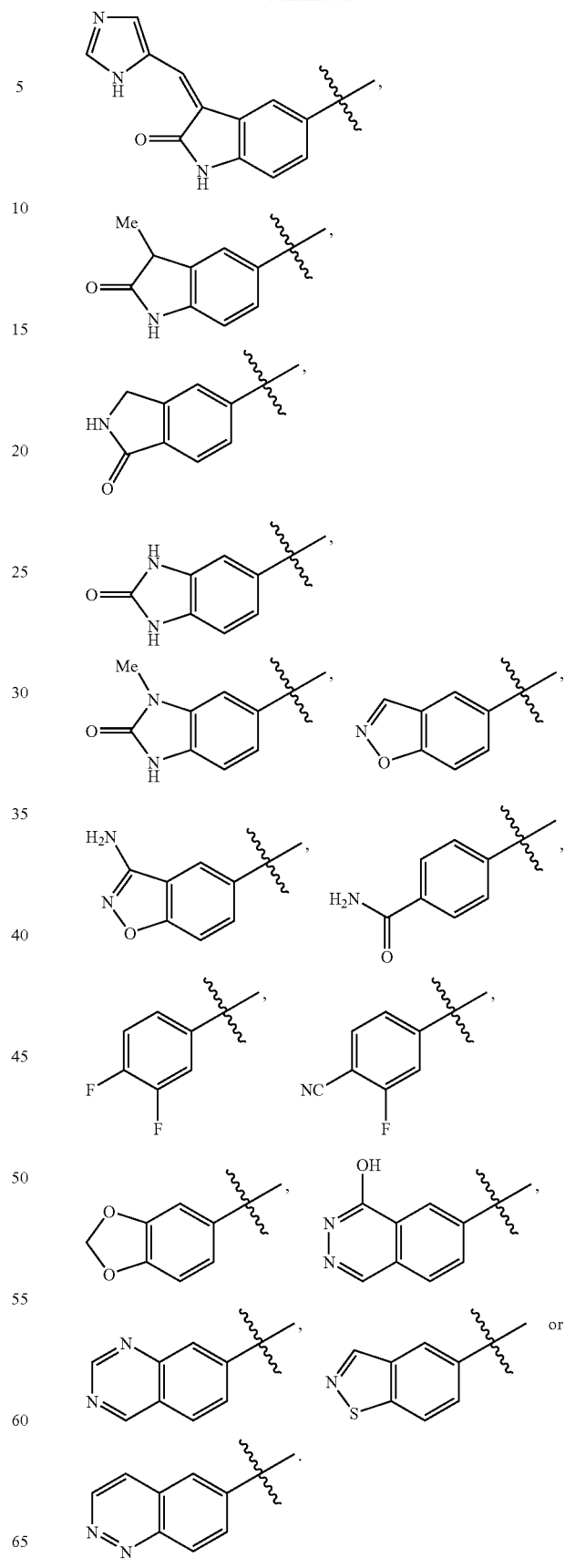

In another aspect, the invention provides a compound of Formula V

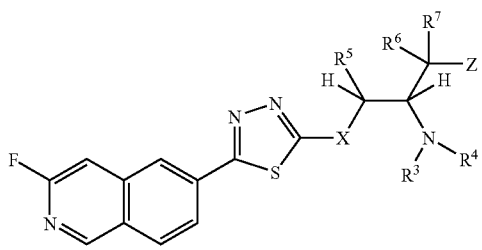

wherein:
X is selected from $NR^2$ or $CR^{2a}R^{2b}$;
$R^2$ may be absent or is selected from —H, $C_1$-$C_8$ alkyl, —($C_1$-$C_6$ alkyl)aryl, or —C(O)($C_1$-$C_6$ alkyl);
$R^{2a}$ and $R^{2b}$ may both be absent or are independently selected from —H, $C_1$-$C_8$ alkyl, —($C_1$-$C_6$)alkyl)aryl, or —C(O)($C_1$-$C_6$ alkyl);
$R^3$ is selected from —H, $C_1$-$C_8$ alkyl, —C(O)($CR^8R^9)_t$N($R^7)_2$, —($CR^8R^9)_t$(aryl), —($CR^8R^9)_t$(heteroaryl), —($CR^8R^9)_t$(cycloalkyl), or —($CR^8R^9)_t$(heterocyclyl);
$R^4$ is selected from —H, $C_1$-$C_8$ alkyl, —($C_1$-$C_6$ alkyl)aryl, or —C(O)($C_1$-$C_6$ alkyl);
$R^5$ is selected from —H, —$OR^{10}$, —O—($C_1$-$C_6$ alkyl)—O—$R^{10}$, $C_1$-$C_6$ alkyl, $C_1$-$C_6$ alkenyl, —($C_1$-$C_6$ alkyl)—O—$R^{10}$, or —($C_1$-$C_6$ alkyl)—O—C(O)—$R^{10}$;
$R^6$ is selected from —H, or $C_1$-$C_6$ alkyl;
$R^7$ is selected from —H, —$OR^{10}$, —O—($C_1$-$C_6$ alkyl)—O—$R^{10}$, $C_1$-$C_6$ alkyl, $C_1$-$C_6$ alkenyl, —($C_1$-$C_6$ alkyl)—O—$R^{10}$, or —($C_1$-$C_6$ alkyl)—O—C(O)—$R^{10}$;
$R^8$ and $R^9$, in each instance, are independently selected from —H, $C_1$-$C_6$ alkyl, or aryl;
$R^{10}$ is selected from —H, $C_1$-$C_6$ alkyl, $C_1$-$C_6$ haloalkyl, —($C_1$-$C_6$ alkyl)aryl, aryl, heteroaryl, $C_1$-$C_6$ hydroxyalkyl, or —($C_1$-$C_6$ alkyl)—O—($C_1$-$C_6$ alkyl), cycloalkyl, or heterocyclyl;
each t is independently selected from 0, 1, 2, or 3; and
Z is selected from aryl or heteroaryl;
wherein each of the above alkyl, aryl, heteroaryl, cycloalkyl, and heterocyclyl moieties and heterocyclic and carbocyclic rings are optionally and independently substituted by 1-3 substituents selected from
amino,
aryl, heteroaryl, cycloalkyl, or heterocyclyl optionally substituted by 1-5 substituents selected from
$C_1$-$C_6$ alkoxy,
$C_1$-$C_6$ alkyl optionally substituted by halo,
aryl,
halo,
hydroxyl,
heteroaryl,
$C_1$-$C_6$ hydroxyalkyl, or
—NHS(O)$_2$—$C_1$-$C_6$ alkyl);
$C_1$-$C_6$ alkyl, $C_1$-$C_6$ haloalkyl, $C_1$-$C_6$ hydroxyalkyl, $C_1$-$C_6$ alkoxy, $C_1$-$C_6$ haloalkoxy, $C_1$-$C_6$ hydroxyalkoxy, $C_1$-$C_6$ alkylamino, $C_2$-$C_6$ alkenyl, or $C_2$-$C_6$ alkynyl, wherein each of which may be interrupted by one or more hetero atoms,
cyano,
halo,
hydroxyl,
nitro,
oxo,
—NH(CO)—O—($C_1$-$C_6$ alkyl)aryl, —NH(CO)—O—($C_1$-$C_6$ alkyl), —N($C_1$-$C_6$ alkyl)(CO)—O—($C_1$-$C_6$ alkyl)aryl, —N($C_1$-$C_6$ alkyl)(CO)—O—($C_1$-$C_6$ alkyl), —C(O)OH, —C(O)O($C_1$-$C_6$ alkyl), —C(O)NH$_2$, —C(O)N(H)—($C_1$-$C_6$ alkyl), —C(O)N($C_1$-$C_6$ alkyl)$_2$, —NH($C_1$-$C_6$ alkyl), —N($C_1$-$C_6$ alkyl)$_2$, —($C_2$-$C_4$ alkenyl)heterocyclyl, or —($C_2$-$C_4$ alkenyl)cycloalkyl, or —O-aryl;

or a pharmaceutically acceptable salt, hydrate, stereoisomer, or mixture thereof.

In some embodiments of the compound of Formula V, the compound has the Formula VA

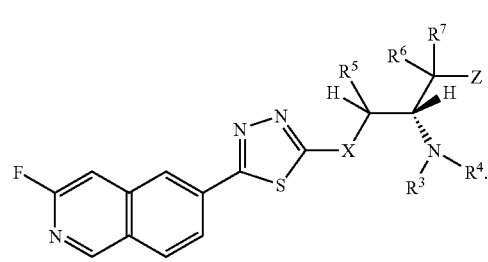

In some embodiments of the compound of Formula V, the compound has the Formula VB

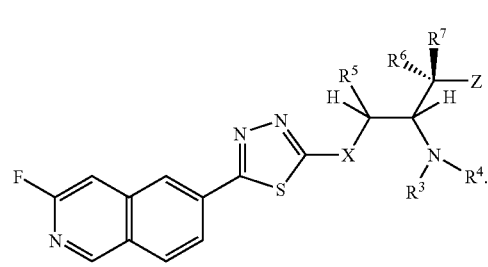

In some embodiments of the compound of Formula V, the compound has the Formula VC

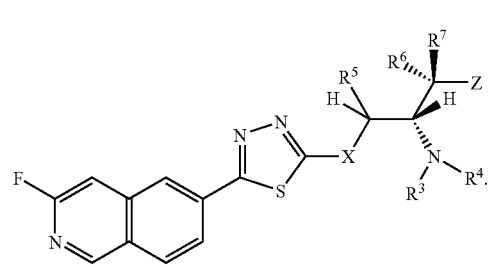

In some embodiments of the compound of Formula V, the compound has the Formula VD

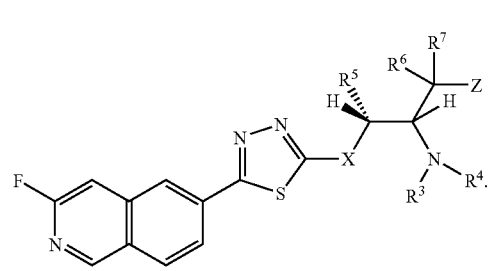

In some embodiments of the compound of Formula V, the compound has the Formula VE

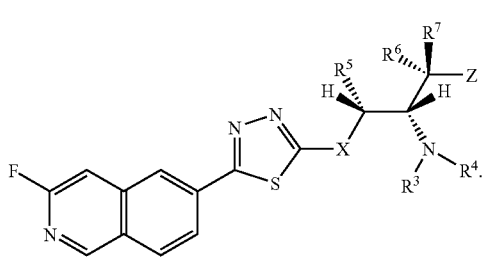

In some embodiments of the compound of Formula V, X is $NR^2$. In some such embodiments $R^2$ is —H.

In some embodiments of the compound of Formula V, X is $CR^{2a}R^{2b}$. In some such embodiments, $R^{2a}$ and $R^{2b}$ are both —H.

In some embodiments of the compound of Formula V, $R^5$ is —H or $C_1$-$C_6$ alkyl. In some such embodiments, $R^5$ is —H or methyl. In other such embodiments, $R^5$ is —H.

In some embodiments of the compound of Formula V, $R^6$ is —H.

In some embodiments of the compound of Formula V, $R^7$ is —H. In other embodiments, $R^7$ is —$OR^{10}$, —O—($C_1$-$C_6$ alkyl)—O—$R^{10}$, $C_1$-$C_6$ alkyl, $C_1$-$C_6$ alkenyl, —($C_1$-$C_6$ alkyl)—O—$R^{10}$, or —($C_1$-$C_6$ alkyl)—O—C(O)—$R^{10}$. In still other embodiments, $R^7$ is selected from —H, methyl, ethyl, propyl, ethenyl, propenyl, hydroxymethyl, methoxymethyl, —$CH_2$—O—C(O)—($C_1$-$C_6$ alkyl), 1-hydroxyethyl, or methoxymethoxy.

In some embodiments of the compound of Formula V, Z is selected from optionally substituted phenyl, optionally substituted indolyl, optionally substituted naphthyl, optionally substituted pyridyl, or optionally substituted thiophenyl.

In some embodiments of the compound of Formula V, Z is selected from phenyl, indolyl, naphthyl, pyridyl, or thiophenyl, each of which is optionally substituted with 1-3 substituents selected from —Cl, —F, —$CF_3$, —OH, —O—($C_1$-$C_6$ alkyl), —O—($C_1$-$C_6$ alkyl)-Cl, —O—($C_1$-$C_6$ alkyl)—OH, —$C_1$-$C_6$ alkyl, —$OCF_3$, —NH(CO)—O—($C_1$-$C_6$ alkyl)aryl, or —NH(CO)—O—($C_1$-$C_6$ alkyl).

In some embodiments of the compound of Formula V, Z is selected from phenyl, indolyl, naphthyl, pyridyl, thiophenyl, 4-chlorophenyl, 4-trifluoromethylphenyl, 3-chlorophenyl, 3-trifluoromethylphenyl, 4-methoxyphenyl, 3-fluoro-4-trifluoromethylphenyl, 4-chloro-3-fluorophenyl, 4-(3-chloropropoxy)phenyl, 4-(3-hydroxypropoxy)phenyl, 3,4-dichlorophenyl, 4-fluorophenyl, 2,4-dichlorophenyl, 4-methylphenyl, 3,4-difluorophenyl, 3-fluoro-4-methoxyphenyl, 3,5-difluorophenyl, 6-trifluoromethylpyridin-3-yl, 5-methoxy-6-trifluoromethylpyridin-3-yl, 2-fluoro-4-trifluoromethylphenyl, 4-trifluoromethoxyphenyl, 2,3-difluoro-4-trifluoromethylphenyl, 4-hydroxyphenyl, 3-methoxy-4-trifluoromethylphenyl, 3-hydroxy-4-trifluoromethylphenyl, 5-chlorothiophen-2-yl, 3-fluoro-4-hydroxyphenyl, or a phenyl substituted in the 4 position with —NH—C(O)—O—$CH_2$-phenyl. In some such embodiments, Z is 4-trifluoromethylphenyl. In other embodiments, Z is 6-trifluoromethylpyridin-3-yl.

In some embodiments of the compound of Formula V, $R^3$ is —H. In some embodiments, $R^4$ is —H. In some embodiments $R^3$ and $R^4$ are each —H.

It is believed that the thiadiazole compounds with the 3-fluoroisoquinolin-6-yl group bonded to the 5 position of the thiadiazole such as in the compounds of Formula V, have several advantageous properties as compared to the analogous isoquinolin-6-yl compounds and some of these advantages may be substantial. For example, it is believed that the compounds of Formula V may have the following advantageous properties: improved reduction in cytochrome P450 inhibition; improved bioavailability following oral dosing in rats; improved reduction in cytochrome P450 3A4 inhibition, and improved efflux ratios. In some embodiments, these advantageous or possibly substantial advantageous properties are found in any one of the specific compounds of Formula V set forth herein.

In one embodiment, the invention comprises one or more compound selected from any one or all of the Example compounds, or a pharmaceutically acceptable salt, hydrate, or stereoisomer thereof. Each of the different groups of the Examples that correspond to any of the variables in the compounds of Formula I, Formula II, Formula IV, and/or Formula V is preferred in some embodiments.

In another aspect, the invention comprises a pharmaceutically acceptable salt, hydrate, or solvate of a compound of Formula I, Formula II, Formula IV, or Formula V or any of the compounds of any of the embodiments described herein. In one embodiment, the pharmaceutically acceptable salt is selected from a chloride or trifluoroacetate salt. In some such embodiments, the salt is an ammonium trifluoroacetate, ammonium chloride, or hydrochloride salt.

1.3 Pharmaceutical Compositions and Dosage Forms

Compounds of Formula I, Formula II, Formula IV, and Formula V, or any of the embodiments thereof, or a pharmaceutically acceptable salt, hydrate, or stereoisomer thereof may be used to prepare pharmaceutical compositions and single unit dosage forms. Therefore, in some embodiments, the invention provides a pharmaceutical composition that includes a compound of Formula I, Formula II, Formula IV, or Formula V, or a pharmaceutically acceptable salt, hydrate, or stereoisomer thereof. Pharmaceutical compositions and individual dosage forms of the invention may be suitable for oral, mucosal (including sublingual, buccal, rectal, nasal, or vaginal), parenteral (including subcutaneous, intramuscular, bolus injection, intra-arterial, or intravenous), transdermal, or topical administration. Pharmaceutical compositions and dosage forms of the invention typically also comprise one or more pharmaceutically acceptable carrier, excipient, or diluent. Sterile dosage forms are also contemplated.

The term "composition" as used herein is intended to encompass a product comprising the specified ingredients (and in the specified amounts, if indicated), as well as any product which results, directly or indirectly, from combination of the specified ingredients. The term "pharmaceutically acceptable" carrier, excipient, or diluent means that the carrier, excipient, or diluent is compatible with the other ingredients of the formulation and is not deleterious to the recipient thereof. Composition formulation may improve one or more pharmacokinetic properties (e.g., oral bioavailability, membrane permeability) of a compound of the invention (herein referred to as the active ingredient).

The pharmaceutical compositions of the invention may conveniently be presented in unit dosage form and may be prepared by any of the methods well known in the art. All methods include the step of bringing the active ingredient such as a compound of any of the embodiments into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition, the active object compound is included in an amount sufficient to produce the desired effect in the subject.

In some embodiments, pharmaceutical compositions include a Formula I or Formula II compound of the invention, or a pharmaceutically acceptable salt, hydrate or stereoisomer thereof, and at least one additional therapeutic agent. Examples of additional therapeutic agents include, but are not limited to, those listed above. Such compositions may include one or more pharmaceutically acceptable carrier, excipient, or diluent.

The composition, shape, and type of dosage forms of the invention will typically vary depending on their use. For example, a dosage form used in the acute treatment of a disease or a related disease may contain larger amounts of one or more of the active ingredients it comprises than a dosage form used in the chronic treatment of the same disease. Similarly, a parenteral dosage form may contain smaller amounts of one or more of the active ingredients it comprises than an oral dosage form used to treat the same disease or disorder. These and other ways in which specific dosage forms encompassed by this invention will vary from one another will be readily apparent to those skilled in the art. See, e.g., Remington's Pharmaceutical Sciences, 20th ed., Mack Publishing, Easton Pa. 2000. Examples of dosage forms include, but are not limited to, tablets; caplets; capsules, such as soft elastic gelatin capsules; cachets; troches; lozenges; dispersions; suppositories; ointments; cataplasms (poultices); pastes; powders; dressings; creams; plasters; solutions; patches; aerosols (e.g., nasal sprays or inhalers); gels; liquid dosage forms suitable for oral or mucosal administration to a patient, including suspensions (e.g., aqueous or non-aqueous liquid suspensions, oil-in-water emulsions, or a water-in-oil liquid emulsions), solutions, and elixirs; liquid dosage forms particularly suitable for parenteral administration to a patient; and sterile solids (e.g., crystalline or amorphous solids) that can be reconstituted to provide liquid dosage forms suitable for parenteral administration to a patient.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions. Such compositions may contain one or more agents selected from sweetening agents, flavoring agents, coloring agents and preserving agents in order to provide pharmaceutically elegant and palatable preparations. Tablets contain the active ingredient in admixture with other non-toxic pharmaceutically acceptable excipients which are suitable for the manufacture of tablets. These excipients may be, for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid, or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in U.S. Pat. Nos. 4,256,108, 4,160,452, and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate, or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxy-propylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil, or coconut oil, or in a mineral oil such as liquid paraffin. The oily suspensions may contain a thickening agent, for example beeswax, hard paraffin, or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative, and flavoring and coloring agents.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, for example as a solution in 1,3-butane diol. Among the acceptable vehicles and solvents that may be employed are water, Ringer's solution, and isotonic sodium chloride solution. In addition, sterile, fixed oils are conventionally employed as a solvent or suspending medium. For this purpose, any bland fixed oil may be employed including synthetic mono- or diglycerides. In addition, fatty acids such as oleic acid find use in the preparation of injectables.

The pharmaceutical compositions may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials include, for example, cocoa butter and polyethylene glycols.

For topical use, creams, ointments, jellies, solutions, or suspensions, etc., containing the compounds of the invention are employed. As used herein, topical application is also meant to include the use of mouthwashes and gargles.

Like the amounts and types of excipients, the amounts and specific types of active ingredients in a dosage form may differ depending on factors such as, but not limited to, the route by which it is to be administered to patients. However, typical dosage forms of the invention comprise a Formula I, Formula II, Formula IV, or Formula V compound of the invention, or a pharmaceutically acceptable salt, hydrate, or stereoisomer thereof in an amount of from 0.1 mg to 1500 mg per unit to provide doses of about 0.01 to 200 mg/kg per day.

The invention further provides the use of a compound of Formula I, Formula II, Formula IV, or Formula V, or any of the embodiments thereof, or a pharmaceutically acceptable salt, hydrate, or stereoisomer thereof, in the preparation of a pharmaceutical composition or medicament. In some embodiments, the composition or medicament may be used to treat a disease mediated by a kinase such as PKB. In some embodiments, the disease is mediated by PKBα. In some embodiments, the disease is cancer and in some such embodiments, the cancer is a solid tumor.

The invention also provides a compound of any of the embodiments described herein for use in a method for treating a kinase mediated disorder in a mammal in need thereof. In some embodiments, the disorder is mediated by IGF-1R, Insulin Receptor, KDR, Tie2, EGFR, PKA, PKB, PKC, FKHR, TSC1/2, SGK, LCK, BTK, Erk, MSK, MK2, MSK, p38, P70S6K, PIM1, PIM2, ROCK2, GSK3, or a CDK complex. In some embodiments, the method comprises selective inhibition of PKB, and in some embodiments the method comprises selective inhibition of PKBα. In some embodiments, the disorder is cancer, and in some such embodiments is a solid tumor.

The invention also provides a compound of any of the embodiments described herein for use in a method of treating a proliferation-related disorder in a mammal in need thereof. In some embodiments, the disorder is abnormal cell growth. In some embodiments, the disorder is inflammation or an inflammation-related disorder. In other embodiments, the is a metabolic disease such as diabetes. In other embodiments, the disorder is cancer, and in some such embodiments the cancer is a solid tumor.

1.4 Methods of Treatment and Prevention of Disease States

The compounds of the invention may be used to treat or prevent various kinase-related disorders. Thus, the present invention provides methods for treating or preventing such disorders. In some embodiments, the invention provides a method for treating a kinase-mediated disorder in a subject that includes administering a therapeutically effective amount of a compound of any of the embodiments of the invention or a pharmaceutical composition to the subject. In some embodiments, the subject is a mammal, and in some such embodiments is a human. In some embodiments the disorder is mediated by IGF-1R, Insulin Receptor, KDR, Tie2, EGFR, PKA, PKB, PKC, FKHR, TSC1/2, SGK, LCK, BTK, Erk, MSK, MK2, MSK, p38, P70S6K, PIM1, PIM2, ROCK2, GSK3, or a CDK complex. In some such embodiments, the disorder is mediated by PKB. In some such embodiments, the administration of the compound or pharmaceutical composition produces selective inhibition of PKB, and in some cases PKBα, in the subject after administration. In some embodiments, the disorder is cancer. The present invention thus provides methods for treating or preventing PKB-mediated disease states, such as cancer. In some embodiments, the cancer is a tumor such as a solid tumor.

The compounds of the invention may also be used to treat proliferation-related disorders. Thus, the invention further provides methods for treating such proliferation-related disorders in a subject. Such methods include administering to a subject in need thereof a therapeutically effective amount of the compound or pharmaceutical composition of any of the embodiments. In some embodiments, the subject is a mammal. In some such embodiments, the mammal is a human. In some embodiments, the proliferation-related disorder is abnormal cell growth. In other embodiments, the disorder is inflammation or an inflammation-related disorder. In still other embodiments, the disorder is a metabolic disease such as diabetes. In still other embodiments, the disorder is cancer. In some such embodiments, the cancer is a solid tumor.

The magnitude of a prophylactic or therapeutic dose of a Formula I, Formula II, Formula IV, or Formula V compound of the invention or a pharmaceutically acceptable salt, solvate, hydrate, or stereoisomer thereof in the acute or chronic treatment or prevention of a cancer or other disease or condition will vary with the nature and aggressiveness of the condition, and the route by which the active ingredient is administered. The dose, and in some cases the dose frequency, will also vary according to the condition to be treated, the age, body weight, and response of the individual patient. Suitable dosing regimens can be readily selected by those skilled in the art with due consideration of such factors. In one embodiment, the dose administered depends upon the specific compound to be used, and the weight and condition of the patient. In general, the dose per day is in the range of from about 0.001 to 100 mg/kg, preferably about 1 to 25 mg/kg, more preferably about 1 to about 5 mg/kg. For treatment of humans having a cancer, about 0.1 mg to about 15 g per day is administered in about one to four divisions a day, preferably 10 mg to 12 g per day, more preferably from 40 mg to 500 mg per day. In one embodiment the compounds of the invention are administered from 40 mg to 500 mg per day in about one to four divisions a day. Additionally, the recommended daily dose can be administered in cycles as single agents or in combination with other therapeutic agents. In one embodiment, the daily dose is administered in a single dose or in equally divided doses. In a related embodiment, the recommended daily dose can be administered one time per week, two times per week, three times per week, four times per week or five times per week.

The compounds of the invention can be administered to provide systemic distribution of the compound within the patient. Therefore, in some embodiments, the compounds of the invention are administered to produce a systemic effect in the body.

The compounds of the invention may also be administered directly to a site affected by a condition, as, for example, an in the treatment of an accessible area of skin or an esophageal cancer.

As indicated above, the compounds of the invention may be administered via oral, mucosal (including sublingual, buccal, rectal, nasal, or vaginal), parenteral (including subcutaneous, intramuscular, bolus injection, intra-arterial, or intravenous), transdermal, or topical administration. In some embodiments, the compounds of the invention are administered via mucosal (including sublingual, buccal, rectal, nasal, or vaginal), parenteral (including subcutaneous, intramuscular, bolus injection, intra-arterial, or intravenous), transdermal, or topical administration. In other embodiments, the compounds of the invention are administered via oral administration. In still other embodiments, the compounds of the invention are not administered via oral administration.

Different therapeutically effective amounts may be applicable for different conditions, as will be readily known by those of ordinary skill in the art. Similarly, amounts sufficient to treat or prevent such conditions, but insufficient to cause, or sufficient to reduce, adverse effects associated with conventional therapies are also encompassed by the above described dosage amounts and dose frequency schedules.

Some methods of the invention comprise the administration of a compound of the invention and an additional therapeutic agent (i.e., a therapeutic agent other than a compound of the invention). Thus, the compounds of the invention can be used in combination with at least one other therapeutic agent. Examples of additional therapeutic agents include, but are not limited to, antibiotics, anti-emetic agents, antidepressants, antifungal agents, anti-inflammatory agents, antineoplastic agents, antiviral agents, cytotoxic agents, and other anticancer agents, immunomodulatory agents, alpha-interferons, β-interferons, alkylating agents, hormones, and cytokines. In one embodiment, the invention encompasses administration of an additional therapeutic agent that demonstrates anti-cancer activity. In another embodiment, an additional therapeutic agent that demonstrates cytotoxic activity is administered to a subject such as a cancer patient.

The compounds of the invention and the other therapeutics agent can act additively or, preferably, synergistically. In some embodiments, a composition comprising a compound of the invention is administered concurrently with the administration of another therapeutic agent, which can be part of the same composition or can be in a different composition from the one that comprises the compound of the invention. In other embodiments, a compound of the invention is administered prior to, or subsequent to, administration of another therapeutic agent. In still other embodiments, a compound of the invention is administered to a patient who has not previously undergone or is not currently undergoing treatment with another therapeutic agent. A compound of the invention may be administered to a subject that has had, is currently undergoing, or is scheduled to receive radiation therapy. In some such embodiments, the subject is a cancer patient.

When administered as a combination, the therapeutic agents can be formulated as separate compositions that are administered at the same time or sequentially at different times, or the therapeutic agents can be given as a single composition. The phrase "co-therapy" (or "combination-therapy"), in defining use of a compound of the present invention and another pharmaceutical agent, is intended to embrace administration of each agent in a sequential manner in a regimen that will provide beneficial effects of the drug combination, and is intended as well to embrace co-administration of these agents in a substantially simultaneous manner, such as in a single capsule having a fixed ratio of these active agents or in multiple, separate capsules for each agent. Specifically, the administration of compounds of the present invention may be in conjunction with additional therapies known to those skilled in the art in the prevention or treatment of neoplasia, such as with radiation therapy or with cytostatic or cytotoxic agents.

If formulated as a fixed dose, such combination products employ the compounds of this invention within the accepted dosage ranges. Compounds of Formula I or Formula II may also be administered sequentially with known anticancer or cytotoxic agents when a combination formulation is inappropriate. The invention is not limited in the sequence of administration as compounds of the invention may be administered either prior to, simultaneous with, or after administration of a known anticancer or cytotoxic agent.

There are large numbers of antineoplastic agents available in commercial use, in clinical evaluation and in pre-clinical development, which may be selected for treatment of neoplasia by combination drug chemotherapy. Such antineoplastic agents fall into several major categories, namely, antibiotic-type agents, alkylating agents, antimetabolite agents, hormonal agents, immunological agents, interferon-type agents and a category of miscellaneous agents.

A first family of antineoplastic agents which may be used in combination with compounds of the present invention consists of antimetabolite-type/thymidilate synthase inhibitor antineoplastic agents. Suitable antimetabolite antineoplastic agents may be selected from, but are not limited to, the group consisting of 5-FU-fibrinogen, acanthifolic acid, aminothiadiazole, brequinar sodium, carmofur, Ciba-Geigy CGP-30694, cyclopentyl cytosine, cytarabine phosphate stearate, cytarabine conjugates, Lilly DATHF, Merrel Dow DDFC, dezaguanine, dideoxycytidine, dideoxyguanosine, didox, Yoshitomi DMDC, doxifluridine, Wellcome EHNA, Merck & Co. EX-015, fazarabine, floxuridine, fludarabine phosphate, 5-fluorouracil, N-(2'-furanidyl)-5-fluorouracil, Daiichi Seiyaku FO-152, isopropyl pyrrolizine, Lilly LY-188011, Lilly LY-264618, methobenzaprim, methotrexate, Wellcome MZPES, norspermidine, NCI NSC-127716, NCI NSC-264880, NCI NSC-39661, NCI NSC-612567, Warner-Lambert PALA, pentostatin, piritrexim, plicamycin, Asahi Chemical PL-AC, Takeda TAC-788, thioguanine, tiazofurin, Erbamont TIF, trextrimetrexate, tyrosine kinase inhibitors, Taiho UFT, and uricytin.

A second family of antineoplastic agents which may be used in combination with compounds of the present invention consists of alkylating-type antineoplastic agents. Suitable alkylating-type antineoplastic agents may be selected from, but are not limited to, the group consisting of Shionogi 254-S, aldo-phosphamide analogues, altretamine, anaxirone, Boehringer Mannheim BBR-2207, bestrabucil, budotitane, Wakunaga CA-102, carboplatin, carmustine, Chinoin-139, Chinoin-153, chlorambucil, cisplatin, cyclophosphamide, American Cyanamid CL-286558, Sanofi CY-233, cyplatate, Degussa D-19-384, Sumimoto DACHP(Myr)2, diphenylspiromustine, diplatinum cytostatic, Erba distamycin derivatives, Chugai DWA-2114R, ITI E09, elmustine, Erbamont FCE-24517, estramustine phosphate sodium, fotemustine, Unimed G-6-M, Chinoin GYKI-17230, hepsul-fam, ifosfamide, iproplatin, lomustine, mafosfamide, mitolactol, Nippon Kayaku NK-121, NCI NSC-264395, NCI NSC-342215, oxaliplatin, Upjohn PCNU, prednimustine, Proter PTT-119, ranimustine, semustine, SmithKline SK&F-101772, Yakult Honsha SN-22, spiromus-tine, Tanabe Seiyaku TA-077, tauromustine, temozolomide, teroxirone, tetraplatin, and trimelamol.

A third family of antineoplastic agents which may be used in combination with compounds of the present invention consists of antibiotic-type antineoplastic agents. Suitable antibiotic-type antineoplastic agents may be selected from, but are not limited to, the group consisting of Taiho 4181-A, aclarubicin, actinomycin D, actinoplanone, Erbamont ADR-456, aeroplysinin derivative, Ajinomoto AN-201-II, Ajinomoto AN-3, Nippon Soda anisomycins, anthracycline, azino-mycin-A, bisucaberin, Bristol-Myers BL-6859, Bristol-Myers BMY-25067, Bristol-Myers BMY-25551, Bristol-Myers BMY-26605, Bristol-Myers BMY-27557, Bristol-Myers BMY-28438, bleomycin sulfate, bryostatin-1, Taiho C-1027, calichemycin, chromoximycin, dactinomycin, daunorubicin, Kyowa Hakko DC-102, Kyowa Hakko DC-79, Kyowa Hakko DC-88A, Kyowa Hakko DC89-A1, Kyowa Hakko DC92-B, ditrisarubicin B, Shionogi DOB-41, doxorubicin, doxorubicin-fibrinogen, elsamicin-A, epirubicin, erbstatin, esorubicin, esperamicin-A1, esperamicin-Alb, Erbamont FCE-21954, Fujisawa FK-973, fostriecin, Fujisawa FR-900482, glidobactin, gregatin-A, grincamycin, herbimycin, idarubicin, illudins, kazusamycin, kesarirhodins, Kyowa Hakko KM-5539, Kirin Brewery KRN-8602, Kyowa Hakko KT-5432, Kyowa Hakko KT-5594, Kyowa Hakko KT-6149, American Cyanamid LL-D49194, Meiji Seika ME 2303, menogaril, mitomycin, mitoxantrone, SmithKline M-TAG, neoenactin, Nippon Kayaku NK-313, Nippon Kayaku NKT-01, SRI International NSC-357704, oxalysine, oxaunomycin, peplomycin, pilatin, pirarubicin, porothramycin, pyrindanycin A, Tobishi RA-I, rapamycin, rhizoxin, rodorubicin, sibanomicin, siwenmycin, Sumitomo SM-5887, Snow Brand SN-706, Snow Brand SN-07, sorangicin-A, sparsomycin, SS Pharmaceutical SS-21020, SS Pharmaceutical SS-7313B, SS Pharmaceutical SS-9816B, steffimycin B, Taiho 4181-2, talisomycin, Takeda TAN-868A, terpentecin, thrazine, tricrozarin A, Upjohn U-73975, Kyowa Hakko UCN-10028A, Fujisawa WF-3405, Yoshitomi Y-25024, and zorubicin.

A fourth family of antineoplastic agents which may be used in combination with compounds of the present invention consists of a miscellaneous family of antineoplastic agents, including tubulin interacting agents, topoisomerase II inhibitors, topoisomerase I inhibitors and hormonal agents, selected from, but not limited to, the group consisting of α-carotene, α-difluoromethyl-arginine, acitretin, Biotec AD-5, Kyorin AHC-52, alstonine, amonafide, amphethinile, amsacrine, Angiostat, ankinomycin, anti-neoplaston A10, antineoplaston A2, antineoplaston A3, antineoplaston A5, antineoplaston AS2-1, Henkel APD, aphidicolin glycinate, asparaginase, Avarol, baccharin, batracylin, benfluoron, benzotript, Ipsen-Beaufour BIM-23015, bisantrene, Bristol-Myers BMY-40481, Vestar boron-10, bromofosfamide, Wellcome BW-502, Wellcome BW-773, caracemide, carmethizole hydrochloride, Ajinomoto CDAF, chlorsulfaquinoxalone, Chemes CHX-2053, Chemex CHX-100, Warner-Lambert CI-921, Warner-Lambert CI-937, Warner-Lambert CI-941, Warner-Lambert CI-958, clanfenur, claviridenone, ICN compound 1259, ICN compound 4711, Contracan, Yakult Honsha CPT-11, crisnatol, curaderm, cytochalasin B, cytarabine, cytocytin, Merz D-609, DABIS maleate, dacarbazine, datelliptinium, didemnin-B, dihaematoporphyrin ether, dihydrolenperone, dinaline, distamycin, Toyo Pharmar DM-341, Toyo Pharmar DM-75, Daiichi Seiyaku DN-9693, docetaxel ellprabin, elliptinium acetate, Tsumura EPMTC, the epothilones, ergotamine, etoposide, etretinate, fenretinide, Fujisawa FR-57704, gallium nitrate, genkwadaphnin, Chugai GLA-43, Glaxo GR-63178, grifolan NMF-5N, hexadecylphosphocholine, Green Cross HO-221, homoharringtonine, hydroxyurea, BTG ICRF-187, ilmofosine, isoglutamine, isotretinoin, Otsuka JI-36, Ramot K-477, Otsuak K-76COONa, Kureha Chemical K-AM, MECT Corp KI-8110, American Cyanamid L-623, leukoregulin, lonidamine, Lundbeck LU-23-112, Lilly LY-186641, NCI (US) MAP, marycin, Merrel Dow MDL-27048, Medco MEDR-340, merbarone, merocyanlne derivatives, methylanilinoacridine, Molecular Genetics MGI-136, minactivin, mitonafide, mitoquidone mopidamol, motretinide, Zenyaku Kogyo MST-16, N-(retinoyl)amino acids, Nisshin Flour Milling N-021, N-acylated-dehydroalanines, nafazatrom, Taisho NCU-190, nocodazole derivative, Normosang, NCI NSC-145813, NCI NSC-361456, NCI NSC-604782, NCI NSC-95580, ocreotide, Ono ONO-112, oquizanocine, Akzo Org-10172, paclitaxel, pancratistatin, pazelliptine, Warner-Lambert PD-111707, Warner-Lambert PD-115934, Warner-Lambert PD-131141, Pierre Fabre PE-1001, ICRT peptide D, piroxantrone, polyhaematoporphyrin, polypreic acid, Efamol porphyrin, probimane, procarbazine, proglumide, Invitron protease nexin I, Tobishi RA-700, razoxane, Sapporo Breweries RBS, restrictin-P, retelliptine, retinoic acid, Rhone-Poulenc RP-49532, Rhone-Poulenc RP-56976, SmithKline SK&F-104864, Sumitomo SM-108, Kuraray SMANCS, SeaPharm SP-10094, spatol, spirocyclopropane derivatives, spirogermanium, Unimed, SS Pharmaceutical SS-554, strypoldinone, Stypoldione, Suntory SUN 0237, Suntory SUN 2071, superoxide dismutase, Toyama T-506, Toyama T-680, taxol, Teijin TEI-0303, teniposide, thaliblastine, Eastman Kodak TJB-29, tocotrienol, topotecan, Topostin, Teijin TT-82, Kyowa Hakko UCN-01, Kyowa Hakko UCN-1028, ukrain, Eastman Kodak USB-006, vinblastine sulfate, vincristine, vindesine, vinestramide, vinorelbine, vintriptol, vinzolidine, withanolides, and Yamanouchi YM-534.

Alternatively, the present compounds may also be used in co-therapies with other anti-neoplastic agents, such as acemannan, aclarubicin, aldesleukin, alemtuzumab, alitertinoin, altretamine, amifostine, aminolevulinic acid, amrubicin, amsacrine, anagrelide, anastrozole, ANCER, ancestim, ARGLABIN, arsenic trioxide, BAM 002 (Novelos), bexarotene, bicalutamide, broxuridine, capecitabine, celmoleukin, cetrorelix, cladribine, clotrimazole, cytarabine ocfosfate, DA 3030 (Dong-A), daclizumab, denileukin diftitox, deslorelin, dexrazoxane, dilazep, docetaxel, docosanol, doxercalciferol, doxifluridine, doxorubicin, bromocriptine, carmustine, cytarabine, fluorouracil, HIT diclofenac, interferon alfa, daunorubicin, doxorubicin, tretinoin, edelfosine, edrecolomab, eflornithine, emitefur, epirubicin, epoetin beta, etoposide phosphate, exemestane, exisulind, fadrozole, filgrastim, finasteride, fludarabine phosphate, formestane, fotemustine, gallium nitrate, gemcitabine, gemtuzumab zogamicin, gimeracil/oteracil/tegafur combination, glycopine, goserelin, heptaplatin, human chorionic gonadotropin, human fetal alpha fetoprotein, ibandronic acid, idarubicin, (imiquimod, interferon alfa, interferon alfa, natural, interferon alfa-2, interferon alfa-2a, interferon alfa-2b, interferon alfa-N1, interferon alfa-n3, interferon alfacon-1, interferon alpha, natural, interferon beta, interferon beta-1a, interferon beta-1b, interferon gamma, natural interferon gamma-1a, interferon gamma-1b, interleukin-1 beta, iobenguane, irinotecan, irsogladine, lanreotide, LC 9018 (Yakult), leflunomide, lenograstim, lentinan sulfate, letrozole, leukocyte alpha interferon, leuprorelin, levamisole+fluorouracil, liarozole, lobaplatin, lonidamine, lovastatin, masoprocol, melarsoprol, metoclopramide, mifepristone, miltefosine, mirimostim, mismatched double stranded RNA, mitoguazone, mitolactol, mitoxantrone, molgramostim, nafarelin, naloxone+pentazocine, nartograstim, nedaplatin, nilutamide, noscapine, novel erythropoiesis stimulating protein, NSC 631570 octreotide, oprelvekin, osaterone, oxaliplatin, paclitaxel, pamidronic acid, pegaspargase, peginterferon alfa-2b, pentosan polysulfate sodium, pentostatin, picibanil, pirarubicin, rabbit antithymocyte polyclonal antibody, polyethylene glycol interferon alfa-2a, porfimer sodium, raloxifene, raltitrexed, rasburicase, rhenium Re 186 etidronate, RII retinamide, rituximab, romurtide, samarium (153 Sm) lexidronam, sargramostim, sizofuran, sobuzoxane, sonermin, strontium-89 chloride, suramin, tasonermin, tazarotene, tegafur, temoporfin, temozolomide, teniposide, tetrachlorodecaoxide, thalidomide, thymalfasin, thyrotropin alfa, topotecan, toremifene, tositumomab-iodine 131, trastuzumab, treosulfan, tretinoin, trilostane, trextrimetrexate, triptorelin, tumor necrosis factor alpha, natural, ubenimex, bladder cancer vaccine, Maruyama vaccine, melanoma lysate vaccine, valrubicin, verteporfin, vinorelbine, VIRULIZIN, zinostatin stimalamer, or zoledronic acid; abarelix; AE 941 (Aeterna), ambamustine, antisense oligonucleotide, bcl-2 (Genta), APC 8015 (Dendreon), cetuximab, decitabine, dexaminoglutethimide, diaziquone, EL 532 (Elan), EM 800 (Endorecherche), eniluracil, etanidazole, fenretinide, filgrastim SD01 (Amgen), fulvestrant, galocitabine, gastrin 17 immunogen, HLA-B7 gene therapy (Vical), granulocyte macrophage colony stimulating factor, histamine dihydrochloride, ibritumomab tiuxetan, ilomastat, IM 862 (Cytran), interleukin-2, iproxifene, LDI 200 (Milkhaus), leridistim, lintuzumab, CA 125 MAb (Biomira), cancer MAb (Japan Pharmaceutical Development), HER-2 and Fc MAb (Medarex), idiotypic 105AD7 MAb (CRC Technology), idiotypic CEA MAb (Trilex), LYM-1-iodine 131 MAb (Techniclone), polymorphic epithelial mucin-yttrium 90 MAb (Antisoma), marimastat, menogaril, mitumomab, motexafin gadolinium, MX 6 (Galderma), nelarabine, nolatrexed, P 30 protein, pegvisomant, pemetrexed, porfiromycin, prinomastat, RL 0903 (Shire), rubitecan, satraplatin, sodium phenylacetate, sparfosic acid, SRL 172 (SR Pharma), SU 5416 (SUGEN), TA 077 (Tanabe), tetrathiomolybdate, thaliblastine, thrombopoietin, tin ethyl etiopurpurin, tirapazamine, cancer vaccine (Biomira), melanoma vaccine (New York University), melanoma vaccine (Sloan Kettering Institute), melanoma oncolysate vaccine (New York Medical College), viral melanoma cell lysates vaccine (Royal Newcastle Hospital), or valspodar.

The compounds of the invention may further be used with VEGFR inhibitors. Other compounds described in the following patents and patent applications can be used in combination therapy: U.S. Pat. No. 6,258,812, US 2003/0105091, WO 01/37820, U.S. Pat. No. 6,235,764, WO 01/32651, U.S. Pat. Nos. 6,630,500, 6,515,004, 6,713,485, 5,521,184, 5,770,599, 5,747,498, WO 02/68406, WO 02/66470, WO 02/55501, WO 04/05279, WO 04/07481, WO 04/07458, WO 04/09784, WO 02/59110, WO 99/45009, WO 00/59509, WO 99/61422, U.S. Pat. No. 5,990,141, WO 00/12089, and WO 00/02871.

In some embodiments, the combination comprises a composition of the present invention in combination with at least one anti-angiogenic agent. Agents are inclusive of, but not limited to, in vitro synthetically prepared chemical compositions, antibodies, antigen binding regions, radionuclides, and combinations and conjugates thereof. An agent can be an agonist, antagonist, allosteric modulator, toxin or, more generally, may act to inhibit or stimulate its target (e.g., receptor or enzyme activation or inhibition), and thereby promote cell death or arrest cell growth.

Exemplary anti-tumor agents include HERCEPTIN™ (trastuzumab), which may be used to treat breast cancer and other forms of cancer, and RITUXAN™ (rituximab), ZEVALIN™ (ibritumomab tiuxetan), and LYMPHOCIDE™ (epratuzumab), which may be used to treat non-Hodgkin's lymphoma and other forms of cancer, GLEEVAC™ which may be used to treat chronic myeloid leukemia and gastrointestinal stromal tumors, and BEXXAR™ (iodine 131 tositumomab) which may be used for treatment of non-Hodgkins's lymphoma.

Exemplary anti-angiogenic agents include ERBITUX™ (IMC-C225), KDR (kinase domain receptor) inhibitory agents (e.g., antibodies and antigen binding regions that specifically bind to the kinase domain receptor), anti-VEGF agents (e.g., antibodies or antigen binding regions that specifically bind VEGF, or soluble VEGF receptors or a ligand binding region thereof) such as AVASTIN™ or VEGF-TRAP™, and anti-VEGF receptor agents (e.g., antibodies or antigen binding regions that specifically bind thereto), EGFR inhibitory agents (e.g., antibodies or antigen binding regions that specifically bind thereto) such as ABX-EGF (panitumumab), IRESSA™ (gefitinib), TARCEVA™ (erlotinib), anti-Ang1 and anti-Ang2 agents (e.g., antibodies or antigen binding regions specifically binding thereto or to their receptors, e.g., Tie2/Tek), and anti-Tie2 kinase inhibitory agents (e.g., antibodies or antigen binding regions that specifically bind thereto). The pharmaceutical compositions of the present invention can also include one or more agents (e.g., antibodies, antigen binding regions, or soluble receptors) that specifically bind and inhibit the activity of growth factors, such as antagonists of hepatocyte growth factor (HGF, also known as Scatter Factor), and antibodies or antigen binding regions that specifically bind its receptor "c-met".

Other anti-angiogenic agents include Campath, IL-8, B-FGF, Tek antagonists (Ceretti et al., U.S. Publication No. 2003/0162712; U.S. Pat. No. 6,413,932), anti-TWEAK agents (e.g., specifically binding antibodies or antigen binding regions, or soluble TWEAK receptor antagonists; see, Wiley, U.S. Pat. No. 6,727,225), ADAM distintegrin domain to antagonize the binding of integrin to its ligands (Fanslow et al., U.S. Publication No. 2002/0042368), specifically binding anti-eph receptor and/or anti-ephrin antibodies or antigen binding regions (U.S. Pat. No. 5,981,245; 5,728,813; 5,969,110; 6,596,852; 6,232,447; 6,057,124 and patent family members thereof), and anti-PDGF-BB antagonists (e.g., specifically binding antibodies or antigen binding regions) as well as antibodies or antigen binding regions specifically binding to PDGF-BB ligands, and PDGFR kinase inhibitory agents (e.g., antibodies or antigen binding regions that specifically bind thereto).

Additional anti-angiogenic/anti-tumor agents include: SD-7784 (Pfizer, USA); cilengitide.(Merck KGaA, Germany, EPO 770622); pegaptanib octasodium, (Gilead Sciences, USA); Alphastatin, (BioActa, UK); M-PGA, (Celgene, USA, U.S. Pat. No. 5,712,291); ilomastat, (Arriva, USA, U.S. Pat. No. 5,892,112); emaxanib, (Pfizer, USA, U.S. Pat. No. 5,792,783); vatalanib, (Novartis, Switzerland); 2-methoxyestradiol, (EntreMed, USA); TLC ELL-12, (Elan, Ireland); anecortave acetate, (Alcon, USA); alpha-D148 Mab, (Amgen, USA); CEP-7055, (Cephalon, USA); anti-Vn Mab, (Crucell, Netherlands) DAC:antiangiogenic, (ConjuChem, Canada); Angiocidin, (InKine Pharmaceutical, USA); KM-2550, (Kyowa Hakko, Japan); SU-0879, (Pfizer, USA); CGP-79787, (Novartis, Switzerland, EP 970070); ARGENT technology, (Ariad, USA); Y1GSR-Stealth, (Johnson & Johnson, USA); fibrinogen-E fragment, (BioActa, UK); angiogenesis inhibitor, (Trigen, UK); TBC-1635, (Encysive Pharmaceuticals, USA); SC-236, (Pfizer, USA); ABT-567, (Abbott, USA); Metastatin, (EntreMed, USA); angiogenesis inhibitor, (Tripep, Sweden); maspin, (Sosei, Japan); 2-methoxyestradiol, (Oncology Sciences Corporation, USA); ER-68203-00, (IVAX, USA); Benefin, (Lane Labs, USA); Tz-93, (Tsumura, Japan); TAN-1120, (Takeda, Japan); FR-111142, (Fujisawa, Japan, JP 02233610); platelet factor 4, (RepliGen, USA, EP 407122); vascular endothelial growth factor antagonist, (Borean, Denmark); cancer therapy, (University of South Carolina, USA); bevacizumab (pINN) (Genentech, USA); angiogenesis inhibitors, (SUGEN, USA); XL 784, (Exelixis, USA); XL 647, (Exelixis, USA); MAb, alpha5beta3 integrin, second generation, (Applied Molecular Evolution, USA and MedImmune, USA); gene therapy, retinopathy, (Oxford BioMedica, UK); enzastaurin hydrochloride (USAN), (Lilly, USA); CEP 7055, (Cephalon, USA and Sanofi-Synthelabo, France); BC 1, (Genoa Institute of Cancer Research, Italy); angiogenesis inhibitor, (Alchemia, Australia); VEGF antagonist, (Regeneron, USA); rBPI 21 and BPI-derived antiangiogenic, (XOMA, USA); PI 88, (Progen, Australia); cilengitide (pINN), (Merck KGaA, German; Munich Technical University, Germany, Scripps Clinic and Research Foundation, USA); cetuximab (INN), (Aventis, France); AVE 8062, (Ajinomoto, Japan); AS1404, (Cancer Research Laboratory, New Zealand); SG 292, (Telios, USA); Endostatin, (Boston Childrens Hospital, USA); ATN 161, (Attenuon, USA); ANGIOSTATIN, (Boston Childrens Hospital, USA); 2-methoxyestradiol, (Boston Childrens Hospital, USA); ZD 6474, (AstraZeneca, UK); ZD 6126, (Angiogene Pharmaceuticals, UK); PPI 2458, (Praecis, USA); AZD 9935, (AstraZeneca, UK); AZD 2171, (AstraZeneca, UK); vatalanib (pINN), (Novartis, Switzerland and Schering AG, Germany); tissue factor pathway inhibitors, (EntreMed, USA); pegaptanib (Pinn), (Gilead Sciences, USA); xanthorrhizol, (Yonsei University, South Korea); vaccine, gene-based, VEGF-2, (Scripps Clinic and Research Foundation, USA); SPV5.2, (Supratek, Canada); SDX 103, (University of California at San Diego, USA); PX 478, (ProIX, USA); METASTATIN, (EntreMed, USA); troponin I, (Harvard University, USA); SU 6668, (SUGEN, USA); OXI 4503, (OXiGENE, USA); o-guanidines, (Dimensional Pharmaceuticals, USA); motuporamine C, (British Columbia University, Canada); CDP 791, (Celltech Group, UK); atiprimod (pINN), (GlaxoSmithKline, UK); E 7820, (Eisai, Japan); CYC 381, (Harvard University, USA); AE 941, (Aeterna, Canada); vaccine, angiogenesis, (EntreMed, USA); urokinase plasminogen activator inhibitor, (Dendreon, USA); oglufanide (pINN), (Melmotte, USA); HIF-1alfa inhibitors, (Xenova, UK); CEP 5214, (Cephalon, USA); BAY RES 2622, (Bayer, Germany); Angiocidin, (InKine, USA); A6, (Angstrom, USA); KR 31372, (Korea Research Institute of Chemical Technology, South Korea); GW 2286, (GlaxoSmithKline, UK); EHT 0101, (ExonHit, France); CP 868596, (Pfizer, USA); CP 564959, (OSI, USA); CP 547632, (Pfizer, USA); 786034, (GlaxoSmithKline, UK); KRN 633, (Kirin Brewery, Japan); drug delivery system, intraocular, 2-methoxyestradiol, (EntreMed, USA); anginex, (Maastricht University, Netherlands, and Minnesota University, USA); ABT 510, (Abbott, USA); AAL 993, (Novartis, Switzerland); VEGI, (ProteomTech, USA); tumor necrosis factor-alpha inhibitors, (National Institute on Aging, USA); SU 11248, (Pfizer, USA and SUGEN USA); ABT 518, (Abbott, USA); YH16, (Yantai Rongchang, China); S-3APG, (Boston Childrens Hospital, USA and EntreMed, USA); MAb, KDR, (ImClone Systems, USA); MAb, alpha5 beta1, (Protein Design, USA); KDR kinase inhibitor, (Celltech Group, UK, and Johnson & Johnson, USA); GFB 116, (South Florida University, USA and Yale University, USA); CS 706, (Sankyo, Japan); combretastatin A4 prodrug, (Arizona State University, USA); chondroitinase AC, (IBEX, Canada); BAY RES 2690, (Bayer, Germany); AGM 1470, (Harvard University, USA, Takeda, Japan, and TAP, USA); AG 13925, (Agouron, USA); Tetrathiomolybdate, (University of Michigan, USA); GCS 100, (Wayne State University, USA) CV 247, (Ivy Medical, UK); CKD 732, (Chong Kun Dang, South Korea); MAb, vascular endothelium growth factor, (Xenova, UK); irsogladine (INN), (Nippon Shinyaku, Japan); RG 13577, (Aventis, France); WX 360, (Wilex, Germany); squalamine (pINN), (Genaera, USA); RPI 4610, (Sirna, USA); cancer therapy, (Marinova, Australia); heparanase inhibitors, (InSight, Israel); KL 3106, (Kolon, South Korea); Honokiol, (Emory University, USA); ZK CDK, (Schering AG, Germany); ZK Angio, (Schering AG, Germany); ZK 229561, (Novartis, Switzerland, and Schering AG, Germany); XMP 300, (XOMA, USA); VGA 1102, (Taisho, Japan); VEGF receptor modulators, (Pharmacopeia, USA); VE-cadherin-2 antagonists, (ImClone Systems, USA); Vasostatin, (National Institutes of Health, USA); vaccine, Flk-1, (ImClone Systems, USA); TZ 93, (Tsumura, Japan); TumStatin, (Beth Israel Hospital, USA); truncated soluble FLT 1 (vascular endothelial growth factor receptor 1), (Merck & Co, USA); Tie-2 ligands, (Regeneron, USA); and, thrombospondin 1 inhibitor, (Allegheny Health, Education and Research Foundation, USA).

Alternatively, the present compounds may also be used in co-therapies with other anti-neoplastic agents, such as VEGF antagonists, other kinase inhibitors including p38 inhibitors, KDR inhibitors, EGF inhibitors and CDK inhibitors, TNF inhibitors, matrix metalloproteinases (MMP) inhibitors, COX-2 inhibitors including celecoxib, NSAID's, or $\alpha_v\beta_3$ inhibitors.

EXAMPLES

The compounds of Formula I, Formula II, Formula IV, and Formula V were prepared according to the following synthetic schemes and individual examples detailed herein. The compounds were named using Chemdraw Ultra, v.8.07. These schemes and examples are provided for the purpose of illustration only and are not intended to limit the scope of the invention.

Unless otherwise noted, all materials were obtained from commercial suppliers and were used without further purification. Anhydrous solvents such as DMF, THF, DCM, and toluene were obtained from the Aldrich Chemical Company or EMD Chemicals Inc. All reactions involving air- or moisture-sensitive compounds were performed under a nitrogen atmosphere. Flash chromatography was performed using Aldrich Chemical Company silica gel (200-400 mesh, 60 A) or Biotage pre-packed column or Isco prepacked column. Thin-layer chromatography (TLC) was performed with Analtech gel TLC plates (250 mµ.). Preparative TLC was performed with Analtech silica gel plates (1000-2000.mu.). Preparative HPLC was conducted on a Varian, Shimadzu, Beckman, or Waters HPLC system with 0.1% TFA/$H_2O$ and 0.1% TFA/$CH_3CN$ as mobile phase. The flow rate was at 20 mL/minute and the gradient method was used. $^1H$ NMR spectra were obtained with super conducting FT NMR spectrometers operating at 400 MHz or a Varian 300 MHz instrument. Chemical shifts are expressed in ppm downfield from the tetramethylsilane internal standard. All compounds showed NMR spectra consistent with their assigned structures. Mass spectra (MS) were obtained using a Perkin Elmer-SCIEX API 165 electrospray mass spectrometer (positive and/or negative) or an HP 1100 MSD LC-MS with electrospray ionization and quadrupole detection. All parts are by weight and temperatures are in degrees centigrade unless otherwise indicated.

The following abbreviations are used: AcOH (acetic acid), ATP (adenosine triphosphate), Boc (tert-butyloxycarbonyl), Boc₂O (Boc anhydride), Br₂ (bromine), t-BuOH (tert-butanol), CH₃CN or ACN (acetonitrile), MeI (iodomethane or methyl iodide), CCl₄ (carbon tetrachloride), CHCl₃ (chloroform), CDCl₃ (deuterated chloroform), CDI (1,1'carbonyldiimidazole), CD₃OD (d₄-methanol), CO₂ (carbon dioxide), Cs₂CO₃ (cesium carbonate), CuI (copper iodide), DAST (diethylaminosulfur trifluoride), DCM or CH₂Cl₂ (dichloromethane), DIEA (diisopropylethylamine), dppf (1,1-diphenylphosphinoferrocene), DMAP (4-(dimethylamino) pyridine), DMF (dimethylformamide), DMSO (dimethylsulfoxide), EDC 1-(3-dimethylaminopropyl)-3 (ethylcarbodiimide hydrochloride), EtOAc (ethyl acetate), EtOH (ethanol), Et₂O (diethyl ether), Fe (iron), g (gram), h (hour), HATU (O-(7-azabenzotriazol-1-yl)-N,N,N',N'-tetramethyluronium hexafluorophosphate), H₂ (hydrogen), H₂O (water), HCl (hydrochloric acid), H₂SO₄ (sulfuric acid), HOBt (1-hydroxybenzotriazole), K₂CO₃ (potassium carbonate), KHMDS (potassium hexamethylsilazane), KOAc (potassium acetate), KOH (potassium hydroxide), LAH (lithium aluminum hydride), LCMS (liquid chromatography mass spectrometry), LiCl (lithium chloride), MeOH (methanol), MgSO₄ (magnesium sulfate), mg (milligram), min (minute), mL (milliliter), Na₂SO₄ (sodium sulfate), NaHCO₃ (sodium bicarbonate), Na₂CO₃ (sodium carbonate), NaCl (sodium chloride), NaH (sodium hydride), NaOH (sodium hydroxide), NaBH₄ (sodium borohydride), NH₄Cl (ammonium chloride), Pd/C (palladium on carbon), PdCl₂(PPh₃)₂ (palladium chloride bis(triphenylphosphine)), Pd₂(dba)₃ (palladium dibenzylideneacetone), PdCl₂(dppf) (1,1-bis(diphenylphosphino)ferrocene, palladium chloride), Pd(PPh₃)₄ (palladium tetrakis triphenylphosphine), Pd(OH)₂ (palladium hydroxide), Pd(OAc)₂ (palladium acetate), PPh₃ (triphenylphosphine), RT (room temperature), SiO₂ (silica), SOCl₂ (thionyl chloride), TBAF (tetrabutylammonium fluoride), TEA (triethylamine), TFA (trifluoroacetic acid), THF (tetrahydrofuran), and Zn (zinc).

Example 1

6-(5-((S)-2-Amino-3-(4-(trifluoromethyl)phenyl)propylamino)-1,3,4-thiadiazol-2-yl)-1-methyl-1H-benzo[d]imidazol-2(3H)-one. The title compound was synthesized as shown in Schemes 1a and 1b starting with 3-fluoro-4-nitrobenzenecarboxylic acid purchased from Aldrich.

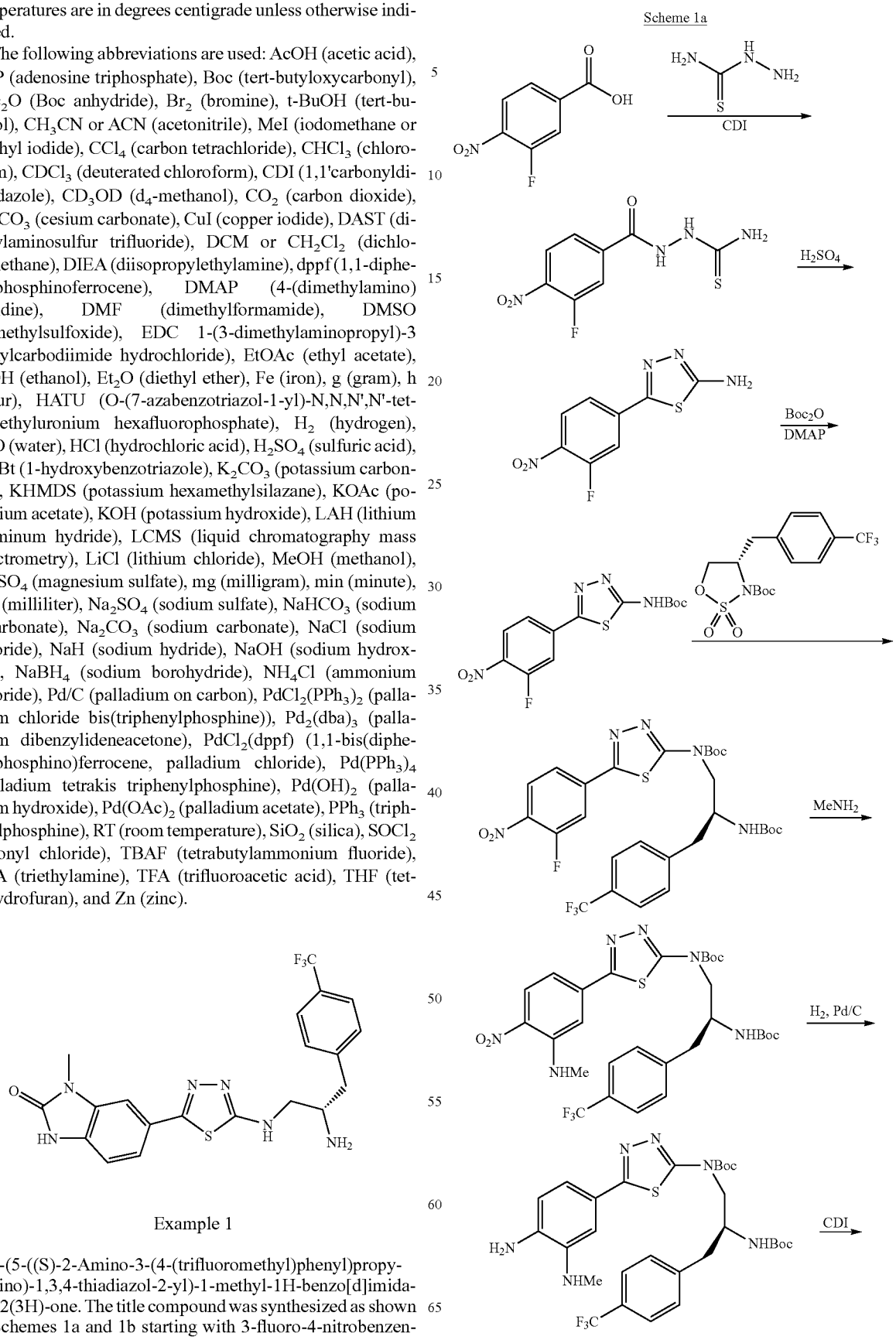

Scheme 1a

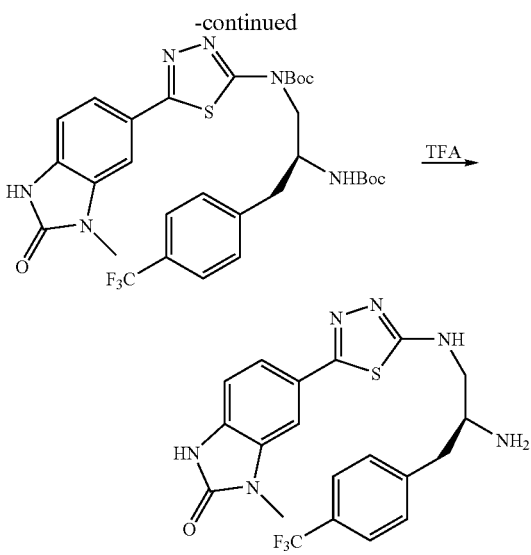

Scheme 1b

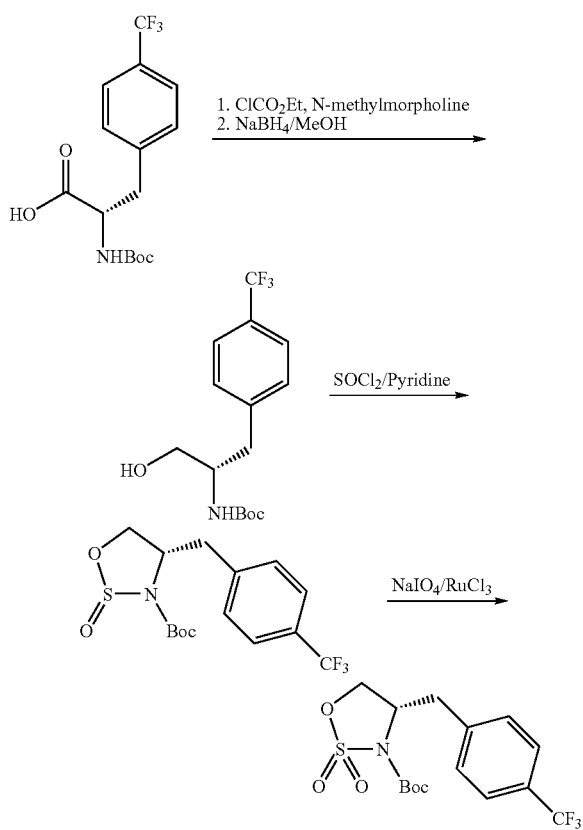

1-(3-Fluoro-4-nitrobenzoyl)thiosemicarbazide. 3-Fluoro-4-nitrobenzenecarboxylic acid (8.4 g, 45 mmol) and 1,1'-carbonyldiimidazole (10 g, 64 mmol) were mixed in 100 mL DMF. The mixture was stirred at 20° C. for 1 hour. A clear yellow solution formed. To this mixture was added thiosemicarbazide (8.3 g, 91 mmol). The resulting mixture was stirred at 20° C. for 30 minutes. The reaction mixture was concentrated under vacuum to remove almost all the DMF. The remaining residue was treated with 2 N HCl with stirring until the solution reached pH 4. Upon standing, a yellow solid formed. The pure product was obtained as a yellow solid after filtering, washing with water, and drying (8.02 g, 68% yield). LCMS (API-ES) m/z (%): 259.1 (100%, M$^+$+H); $^1$H NMR (400 MHz, DMSO-d$_6$) δ ppm 7.81 (s, 1H) 7.90 (d, J=8.41 Hz, 1H) 7.99 (s, 1H) 8.04 (d, J=11.93 Hz, 1H) 8.28 (t, J=8.02 Hz, 1H) 9.47 (s, 1H) 10.76 (s, 1H).

5-(3-Fluoro-4-nitrophenyl)-1,3,4-thiadiazol-2-amine. 1-(3-Fluoro-4-nitrobenzoyl)thiosemicarbazide (6.6 g, 26 mmol) was dissolved in 30 mL concentrated sulfuric acid and stirred at room temperature for 3 hours. The reaction mixture was poured into a mixture of 40 mL 33% aqueous ammonia and 200 mL ice with stirring. The resulting solution was adjusted to pH 8 with an additional amount of the ammonia solution. An orange solid formed during the process. The product was obtained as a yellow solid after filtering, washing with water, and drying in a vacuum for 24 hours at 50° C. LCMS (API-ES) m/z (%): 241.1 (100%, M$^+$+H); $^1$H NMR (400 MHz, DMSO-d$_6$) δ ppm 7.80 (bs, 3H) 7.93 (d, J=12.32 Hz, 1H) 8.22 (t, J=8.12 Hz, 1H).

tert-Butyl 5-(3-fluoro-4-nitrophenyl)-1,3,4-thiadiazol-2-ylcarbamate. 5-(3-Fluoro-4-nitrophenyl)-1,3,4-thiadiazol-2-amine (0.8 g, 3 mmol) and di-tert-butylpyrocarbonate (1 mL, 5 mmol) were mixed in 100 mL THF with 4-(dimethylamino)pyridine (0.002 g, 0.02 mmol). The mixture was heated at 60° C. for 2 hours. The mixture was then mixed with 200 mL EtOAc, washed with saturated aqueous ammonium chloride, and dried over sodium sulfate. During the process of evaporating the solvent, a yellow solid formed. The product was obtained as a yellow solid after filtration and washing with EtOAc (1.01 g, 89% yield). LCMS (API-ES) m/z (%): 341.1 (30%, M$^+$+H), 285.0 (100%, M-55); $^1$H NMR (400 MHz, DMSO-d$_6$) δ ppm 1.52 (s, 9H) 7.99 (d, J=8.41 Hz, 1H) 8.14 (d, J=11.93 Hz, 1H) 8.29 (t, J=8.22 Hz, 1H) 12.30 (s, 1H).

(S)-tert-Butyl 1-hydroxy-3-(4-(trifluoromethyl)phenyl)propan-2-ylcarbamate. In a 1 L round bottom flask, (S)-2-(tert-butoxycarbonyl)-3-(4-(trifluoromethyl)phenyl)propanoic acid purchased from Peptech (CAS No. 114873-07-3) (30.00 g, 90.1 mmol) was dissolved in 300 mL THF and cooled to −10° C. in an acetone-dry ice bath. 4-Methylmorpholine (9.54 g, 94.6 mmol) was then added at one portion. To this mixture was added ethyl chloroformate (19.56 g, 180.2 mmol) drop wise. After addition, the reaction mixture was stirred for 45 minutes at −10° C. To the resulting mixture was added NaBH$_4$ in one portion. The reaction flask was cooled to 0° C. by switching to an ice-water bath. MeOH (100 mL) was then added slowly to the mixture using a dropping funnel over one hour. After addition, the mixture was stirred for an additional three hours as the temperature warmed from 0° C. to room temperature. The reaction mixture was then cooled to 0° C. and quenched with careful addition of 30 mL 1N HCl. After quenching, the cold bath was removed, and the reaction mixture was allowed to warm to room temperature. The reaction mixture was then filtered. The solid obtained was washed with EtOAc until the filtrate was not UV active. After the solvent was evaporated under reduced pressure, the product was re-dissolved in EtOAc. The organic layer was washed with a saturated ammonia chloride solution and saturated sodium bicarbonate and then dried with sodium sulfate. After removing the solvent, the resulting product was subjected to a silica gel column chromatography separation using DCM as the eluant. The product was isolated as a white solid (15 g, yield 63%). LCMS (API-ES) m/z (%): 264.0 (100%, M-55).

(R) and (S)-tert-Butyl-(S)-4-(4-trifluoromethylbenzyl)-1,2,3-oxathiazolidine-3-carboxylate-2-oxide. A 1000 mL round bottom flask was charged with thionyl chloride (22.40 g, 188 mmol) in 200 mL DCM and cooled to between −40° C.

and −50° C. with stirring. (S)-tert-Butyl 1-hydroxy-3-(4-(trifluoromethyl)phenyl)propan-2-ylcarbamate (24.00 g, 75.23 mmol) in 200 mL DCM was dropped into the flask while keeping the bath temperature between −40° C. to −50° C. Pyridine (30.00 g, 375 mmol) was then added dropwise. After addition, the cold bath was removed, and the mixture was stirred for an additional 3 hours. The DCM solution was washed with distilled water three times and once with brine. After removing the solvent, the residue was subjected to a silica gel column chromatography separation to yield a white solid as the mixture of the two diastereomers (23.3 g, yield 85%). This product was used directly in the next step.

(S)-tert-Butyl 4-(4-(trifluoromethyl)benzyl)-1,2,3-oxathiazolidine-3-carboxylate-2,2-dioxide. (R),(S)-tert-Butyl-(S)-4-(4-trifluoromethylbenzyl)-1,2,3-oxathiazolidine-3-carboxylate-2-oxide (4.6 g, 12.6 mmol) was dissolved in 60 mL ACN in a 500 mL round bottom flask. Sodium periodate (10.7 g, 50.44 mmol) was dissolved in 20 mL water and added to the ACN solution. Ruthenium(III) chloride (13.0 mg, 0.063 mmol) was then added to the flask, followed by 10 mL EtOAc. The final solvent ratio was $CH_3CN$:water:EtOAc=30:10:5. The flask was cooled in an ice-water bath, and the mixture was stirred rigorously for 18 hours as it warmed from 0° C. to room temperature. The reaction mixture was filtered through filter paper and the solid obtained was washed with DCM until its solution was not UV active. The filtrate was evaporated under reduced pressure, and the remaining residue was re-dissolved in DCM. The DCM solution was washed with brine three times and dried over sodium sulfate. After removing the solvent, a white solid powder was obtained as the pure product (4.51 g, yield 94%). $^1$H NMR (400 MHz, CDCl$_3$) δ ppm 1.53 (s, 9H) 3.03 (dd, J=13.50, 9.19 Hz, 1H) 3.40 (dd, J=13.50, 4.70 Hz, 1H) 4.29 (d, J=8.61 Hz, 1H) 4.51 (ddd, J=14.28, 9.19, 5.28 Hz, 2H) 7.37 (d, J=7.82 Hz, 2H) 7.62 (d, J=8.02 Hz, 2H).

tert-Butyl (S)-1-(5-(3-fluoro-4-nitrophenyl)-1,3,4-thiadiazol-2-yl-boc-amino)-3-(4-(trifluoromethyl)phenyl)propan-2-ylcarbamate. tert-Butyl 5-(3-fluoro-4-nitrophenyl)-1,3,4-thiadiazol-2-ylcarbamate (0.587 g, 1.72 mmol) and cesium carbonate (1.12 g, 3.45 mmol) were heated to 50° C. in 15 mL THF in a round bottle flask. (S)-tert-Butyl 4-(4-(trifluoromethyl)benzyl)-1,2,3-oxathiazolidine-3-carboxylate-2,2-dioxide (0.855 g, 2.24 mmol) in 10 mL THF was added to the flask dropwise, and the mixture was heated at 50° C. for 30 minutes. The flask was then cooled to 20° C., and 10 mL 1 N HCl was added to the flask. The resulting mixture was stirred at room temperature for 30 minutes. The reaction mixture was combined with 200 mL EtOAc. The organic phase was washed with water, twice with saturated ammonium sulfate, and dried over sodium sulfate. After removing the solvent, the product was obtained as yellow oil. LCMS indicated two major peaks with the same desired product M+1. The product thus obtained was used directly in the next step.

tert-Butyl (S)-1-(5-(3-(methylamino)-4-nitrophenyl)-1,3,4-thiadiazol-2-yl-boc-amino)-3-(4-(trifluoromethyl)phenyl)propan-2-ylcarbamate. The above mentioned tert-butyl (S)-1-(5-(3-fluoro-4-nitrophenyl)-1,3,4-thiadiazol-2-yl-boc-amino)-3-(4-(trifluoromethyl)phenyl)propan-2-ylcarbamate was dissolved in 20 mL 2M THF solution of methanamine (20 mL, 40 mmol) in a microwave heating tube. The tube was heated at 120° C. for 10 minutes. The THF solution was mixed with 200 mL EtOAc. The organic phase was washed with water, twice with saturated aqueous ammonium sulfate twice, and dried over sodium sulfate. After removing the solvent, the product was used directly in the next step.

tert-Butyl (S)-1-(5-(3-(methylamino)-4-aminophenyl)-1,3,4-thiadiazol-2-yl-boc-amino)-3-(4-(trifluoromethyl)phenyl)propan-2-ylcarbamate. The above mentioned tert-butyl (S)-1-(5-(3-(methylamino)-4-nitrophenyl)-1,3,4-thiadiazol-2-yl-boc-amino)-3-(4-(trifluoromethyl)phenyl)propan-2-ylcarbamate (1.13 g, 2 mmol) was dissolved in 200 mL MeOH in a 500 mL round bottle flask. To this flask, was added 10% Pd/C 100 mg pre-wet with water and 2 mL acetic acid. The mixture was stirred under an atmosphere of hydrogen under balloon pressure for 1 hour. After filtration through a pad of celite, the solution was evaporated to dryness. The residue was re-dissolved in 200 mL of EtOAc. The solution was washed with saturated sodium bicarbonate three times and dried over sodium sulfate. The product was obtained after removing the solvent. It was used directly in the next step.

tert-Butyl (S)-1-(5-(3-methyl-2-oxo-2,3-dihydro-1H-benzo[d]imidazol-5-yl)-1,3,4-thiadiazol-2-yl-boc-amino)-3-(4-(trifluoromethyl)phenyl)propan-2-ylcarbamate. The above mentioned crude tert-butyl (S)-1-(5-(3-(methylamino)-4-aminophenyl)-1,3,4-thiadiazol-2-yl-boc-amino)-3-(4-(trifluoromethyl)phenyl)propan-2-ylcarbamate was dissolved in 150 mL THF in a round bottom flask. To this flask was added a 50 mL THF solution of 1,1'-carbonyldiimidazole (1.37 g, 8.45 mmol). The mixture was stirred at 70° C. for 10 hours. After removing the solvent under reduced pressure, the remaining residue was mixed with 200 mL EtOAc. The organic solution was washed with water, three times with saturated ammonium chloride, and dried over sodium sulfate. After removing the solvent, the remaining residue was subjected to silica gel column chromatograph separation using 40% EtOAc in hexane as the eluant. There were two very close major spots on TLC (Rf=0.16, 0.17). The pure fractions for the bottom spot were combined. After removing the solvent, tert-butyl (S)-1-(5-(3-methyl-2-oxo-2,3-dihydro-1H-benzo[d]imidazol-5-yl)-1,3,4-thiadiazol-2-yl-boc-amino)-3-(4-(trifluoromethyl)phenyl)propan-2-ylcarbamate (0.36 g) was obtained as a tan solid. LCMS (API-ES) m/z (%): 649.3 (100%, M$^+$+H); $^1$H NMR (400 MHz, CDCl$_3$) δ ppm 1.21 (s, 9H) 1.42 (s, 9H) 2.83 (m, 1H) 2.98 (m, 1H) 3.40 (s, 3H) 3.93-4.09 (m, 1H) 4.21-4.44 (m, 2H) 4.97-5.13 (m, 1H) 7.05 (d, J=8.02 Hz, 1H) 7.32 (d, J=7.82 Hz, 2H) 7.50 (m, 3H) 7.60 (s, 1H) 9.24 (s, 1H).

6-(5-((S)-2-Amino-3-(4-(trifluoromethyl)phenyl)propylamino)-1,3,4-thiadiazol-2-yl)-1-methyl-1H-benzo[d]imidazol-2(3H)-one. tert-Butyl (S)-1-(5-(3-methyl-2-oxo-2,3-dihydro-1H-benzo[d]imidazol-5-yl)-1,3,4-thiadiazol-2-yl-boc-amino)-3-(4-(trifluoromethyl)phenyl)propan-2-ylcarbamate (0.36 g, 0.6 mmol) in 20 mL DCM was treated with TFA (20 mL, 260 mmol) for 30 minutes. After removing the solvent, the remaining residue was dissolved in 100 mL EtOAc. The resulting solution was washed with a mixture of aqueous saturated sodium bicarbonate and 5% 5N NaOH, and then twice with saturated sodium bicarbonate. After removing the solvent, a tan solid was obtained as the pure product 6-(5-((S)-2-amino-3-(4-(trifluoromethyl)phenyl)propylamino)-1,3,4-thiadiazol-2-yl)-1-methyl-1H-benzo[d]imidazol-2(3H)-one (0.2 g, 79% yield). LCMS (API-ES) m/z (%): 449.1 (100%, M$^+$+H); $^1$H NMR (400 MHz, CDCl$_3$) δ ppm 2.72 (b, 3H), 2.97 (dd, J=13.2, 7.7 Hz, 1H) 3.27 (dd, J=13.2, 7.7 Hz, 1H) 3.36-3.46 (m, 5H) 3.56 (m, 1H) 7.03 (d, J=8.22 Hz, 1H) 7.32-7.37 (m, 3H) 7.49 (s, 1H) 7.57 (d, J=7.82 Hz, 2H).

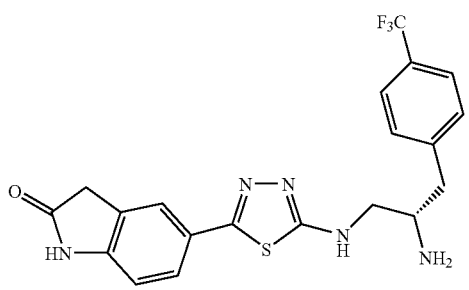

Example 2

5-(5-((S)-2-amino-3-(4-(trifluoromethyl)phenyl)propylamino)-1,3,4-thiadiazol-2-yl)indolin-2-one. The title compound was synthesized as shown in Scheme 2 starting with tert-butyl (S)-1-(5-(3-fluoro-4-nitrophenyl)-1,3,4-thiadiazol-2-yl-boc-amino)-3-(4-(trifluoromethyl)phenyl)propan-2-ylcarbamate that was shown Schemes 1a and 1b.

Scheme 2

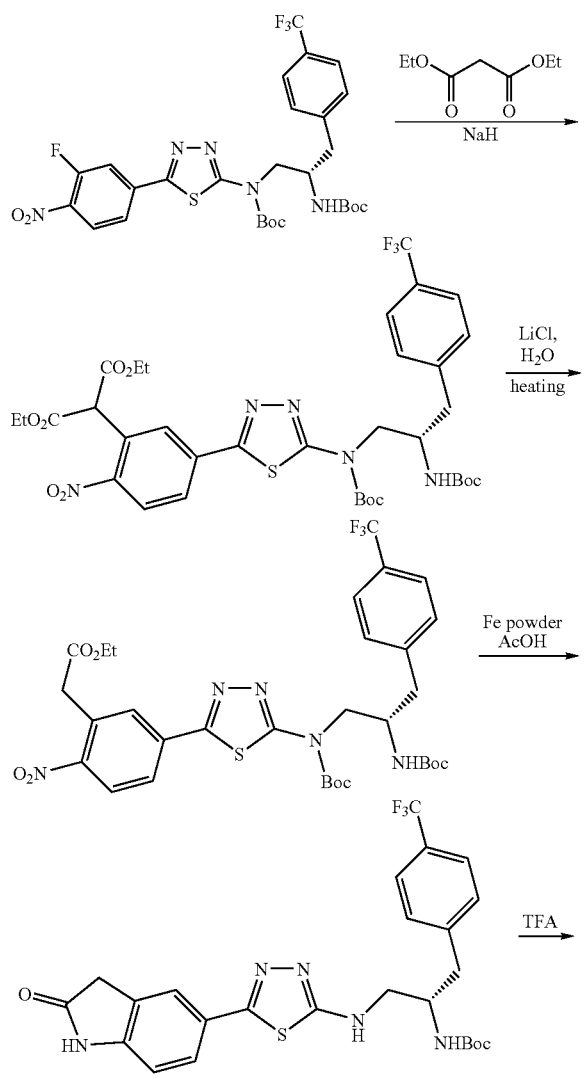

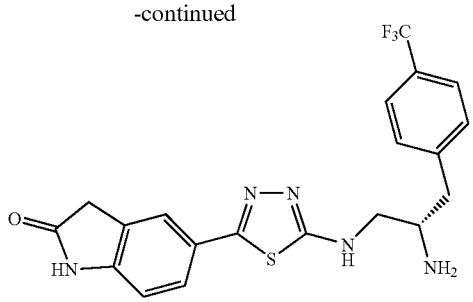

Diethyl 2-(5-(5-((S)-2-(tert-butoxycarbonylamino)-3-(4-(trifluoromethyl)phenyl)propyl-boc-amino)-1,3,4-thiadiazol-2-yl)-2-nitrophenyl)malonate. Diethyl malonate (2.83 mL, 18.7 mmol) in 30 mL of 1,4-dioxane was added to sodium hydride (0.748 g, 60% dispersion in mineral oil, 18.7 mmol) in 10 mL of 1,4-dioxane at room temperature under nitrogen. The mixture became a clear solution within 5 minutes. The mixture was stirred for another 15 minutes followed by addition of the tert-butyl (S)-1-(5-(3-fluoro-4-nitrophenyl)-1,3,4-thiadiazol-2-yl-boc-amino)-3-(4-(trifluoromethyl)phenyl)propan-2-ylcarbamate as described in Schemes 1a and 1b (3.0 g, 4.7 mmol). After overnight stirring, the solvent was removed. The residue was partitioned between EtOAc and saturated NH$_4$Cl. The combined organic portions were washed with brine and dried over sodium sulfate. The crude product was used in the following reaction without purification.

Ethyl (5-(5-(((tert-butoxycarbonyl)((2S)-2-((tert-butoxycarbonyl)amino)-3-(4-(trifluoromethyl)phenyl)propyl)amino)-1,3,4-thiadiazol-2-yl)-2-nitrophenyl)acetate. To a 500 mL round bottom flask was added diethyl 2-(5-(5-((S)-2-(tert-butoxycarbonyl)-3-(4-(trifluoromethyl)phenyl)propyl-boc-amino)-1,3,4-thiadiazol-2-yl)-2-nitrophenyl)malonate (3.60 g, 4.60 mmol), lithium chloride (0.390 g, 9.21 mmol), distilled water (0.0830 g, 4.60 mmol) and 50 mL DMSO. The reaction mixture was heated to 100° C. and stirred at this temperature for 3 hours. LC-MS indicated the reaction was not complete. Another 4 equivalents of LiCl was added. The reaction mixture was stirred at 100° C. overnight. The reaction mixture was cooled to ambient temperature, and 200 mL EtOAc and 200 mL brine were added. The organic portion was separated. The aqueous portion was extracted with EtOAc. The combined organic portions were washed with brine and dried over sodium sulfate. The crude mixture (3.40 g) was used in the following reaction without further purification.

tert-Butyl (S)-1-(5-(2-oxoindolin-5-yl)-1,3,4-thiadiazol-2-ylamino)-3-(4-(trifluoromethyl)phenyl)propan-2-ylcarbamate. Ethyl 2-(5-(5-(tert-butoxycarbonyl)-1,3,4-thiadiazol-2-yl)-2-nitrophenyl)acetate (3.40 g, 4.79 mmol) from the previous step was dissolved in 70 mL of acetic acid. Iron powder (1.07 g, 19.2 mmol) was added, and the reaction mixture was heated to 100° C. and stirred at this temperature for 1 hour. LC-MS indicated that the reaction was complete. Acetic acid was removed. To the residue was added 200 mL of EtOAc. The mixture was sonicated for 15 minutes. The solid was removed by filtration. The filtrate was washed with saturated ammonium chloride, brine, and dried over sodium sulfate. The crude product was purified by flash column chromatography using 100% EtOAc to yield the product as a white solid (360 mg, 12%). LCMS (API-ES) m/z (%): 534.0 (100%, M$^+$+H).

5-(5-((S)-2-Amino-3-(4-(trifluoromethyl)phenyl)propylamino)-1,3,4-thiadiazol-2-yl)indolin-2-one. A mixture of tert-butyl (S)-1-(5-(2-oxoindolin-5-yl)-1,3,4-thiadiazol-2-ylamino)-3-(4-(trifluoromethyl)phenyl)propan-2-ylcarbamate (350 mg) and TFA (10 mL) in DCM (10 mL) was stirred at room temperature for 1 hour. The solvent was removed under vacuum. The residue was partitioned between saturated sodium bicarbonate and DCM. The combined organic portions were washed with brine and then dried over sodium sulfate. Removal of the solvent gave the title compound 5-(5-((S)-2-amino-3-(4-(trifluoromethyl)phenyl)propylamino)-1,3,4-thiadiazol-2-yl)indolin-2-one as an off-white amorphous solid (137 mgs, 48%). LCMS (API-ES) m/z (%): 434.1 (100%, $M^++H$); $^1$H NMR (400 MHz, $CD_3OD$) δ ppm 3.05-3.16 (m, 2H) 3.54-3.64 (m, 3H) 3.68-3.76 (m, 1H) 3.90 (td, J=7.14, 4.30 Hz, 1H) 6.96 (d, J=8.22 Hz, 1H) 7.54 (d, J=8.02 Hz, 2H) 7.60-7.65 (m, 1H) 7.65-7.71 (m, 3H).

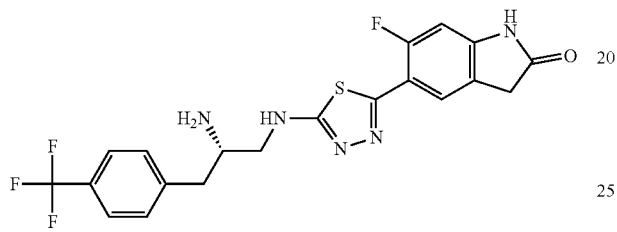

Example 3

5-(5-((S)-2-Amino-3-(4-(trifluoromethyl)phenyl)propylamino)-1,3,4-thiadiazol-2-yl)-6-fluoroindolin-2-one. The title compound was prepared according to the procedure described for Example 2 starting with N—((S)-2-amino-3-(4-(trifluoromethyl)phenyl)propyl)-5-(2,5-difluoro-4-nitrophenyl)-1,3,4-thiadiazol-2-amine, which was prepared in a similar manner as shown in Scheme 1 with 2,5-difluoro-4-nitrobenzenecarboxylic acid as the starting material. 2,5-Difluoro-4-nitrobenzenecarboxylic acid was purchased from Ryan Scientific Inc. LCMS (API-ES) m/z (%): 452.5 (100%, $M^++H$); $^1$H NMR (400 MHz, $CD_3OD$): δ ppm 3.13-3.26 (m, 2H), 3.62-3.71 (m, 3H), 3.78-3.84 (m, 1H), 3.85-4.10 (m, 1H), 3.99 (d, J=2.35 Hz, 4H), 6.83-6.89 (m, 1H), 7.61 (d, J=8.02 Hz, 2H), 7.75 (d, J=8.02 Hz, 2H), 7.99 (d, J=6.85 Hz, 1H).

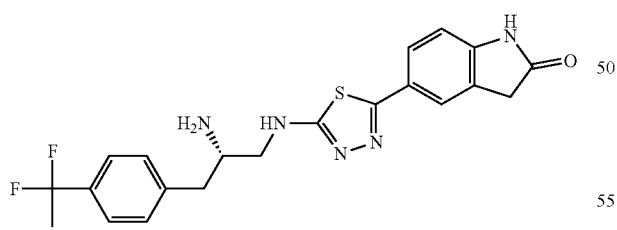

Example 4

5-(5-((S)-2-Amino-3-(4-(1,1-difluoroethyl)phenyl)propylamino)-1,3,4-thiadiazol-2-yl)indolin-2-one. LCMS (API-ES) m/z (%): 430.0 (100%, $M^++H$); $^1$H NMR (300 MHz, $CD_3OD$) δ ppm 1.81 (t, J=18.11 Hz, 3H), 2.72 (m, 1H), 2.83 (m, 1H), 3.22 (s, 2H), 3.35 (m, 1H), 3.48 (m, 2H), 6.86 (d, J=8.19 Hz, 1H), 7.26 (d, J=6.11 Hz, 2H), 7.42 (d, J=4.50 Hz, 2H), 7.52 (d, J=4.5 Hz, 1H), 7.59 (d, J=1.5 Hz, 1H). This compound was prepared according to a procedure similar to that of Example 2 shown in Scheme 2 starting with tert-butyl (S)-3-(4-(1,1-difluoroethyl)phenyl)-1-(5-(3-fluoro-4-nitrophenyl)-1,3,4-thiadiazol-2-yl-boc-amino)propan-2-ylcarbamate. tert-Butyl (S)-3-(4-(1,1-difluoroethyl)phenyl)-1-(5-(3-fluoro-4-nitrophenyl)-1,3,4-thiadiazol-2-yl-boc-amino)propan-2-ylcarbamate was prepared in a similar manner to that shown in Schemes 1a and 1b using the mixture of (R) and (S)-tert-butyl-(S)-4-(4-(1,1-difluoroethyl)benzyl)-1,2,3-oxathiazolidine-3-carboxylate-2-oxide as the starting material in stead of (S)-tert-Butyl 4-(4-(trifluoromethyl)benzyl)-1,2,3-oxathiazolidine-3-carboxylate-2,2-dioxide to react with tert-butyl 5-(3-fluoro-4-nitrophenyl)-1,3,4-thiadiazol-2-yl-carbamate. The (R),(S)-tert-butyl-(S)-4-(4-(1,1-difluoroethyl)benzyl)-1,2,3-oxathiazolidine-3-carboxylate-2-oxide was prepared as shown in Scheme 3 starting from (S)-methyl 3-(4-acetylphenyl)-2-(tert-butoxycarbonyl)propanoate which was purchased from RSP Amino Acids.

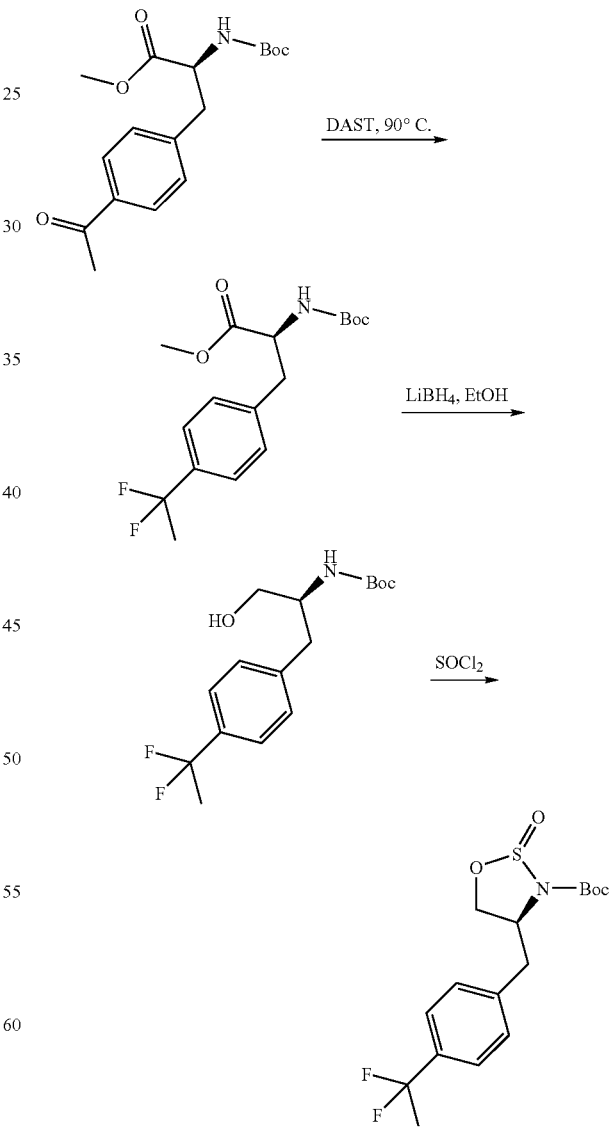

Scheme 3

(S)-Methyl 2-(tert-butoxycarbonylamino)-3-(4-(1,1-difluoroethyl)phenyl)propanoate. To a solution of (S)-methyl 3-(4-acetylphenyl)-2-(tert-butoxycarbonyl)propanoate (1.82 g, 5.66 mmol) in 1 mL DCM in a 5 mL sealable tube was added DAST (1.5 mL, 11.3 mmol) and 2 drops of EtOH. The tube was sealed, and the mixture was stirred at 90° C. for 20 hours. The reaction mixture was cooled, diluted with DCM (20 mL) and transferred to a separation funnel. After washing with a saturated NaHCO$_3$ aqueous solution (2×10 mL), the organic phase was separated and dried over Na$_2$SO$_4$. After filtration and concentration, the desired product was obtained through a silica gel flash column chromatography (eluted with hexane:EtOAc, 4:1) as an oil (120 mg, 6.2% yield). LCMS (API-ES) m/z: 366 (M$^+$+Na); $^1$H NMR (300 MHz, CDCl$_3$) δ ppm 1.41 (s, 9H), 1.90 (t, J=18.12 Hz, 3H), 3.21 (m, 2H), 3.73 (s, 3H), 4.71 (m, 1H), 4.95 (br., 1H), 7.18 (d, J=7.89 Hz, 2H), 7.44 (d, J=8.18 Hz, 2H).

(S)-tert-Butyl 3-(4-(1,1-difluoroethyl)phenyl)-1-hydroxypropan-2-ylcarbamate. To a solution of (S)-methyl 2-(tert-butoxycarbonyl)-3-(4-(1,1-difluoroethyl)phenyl)propanoate (200 mg, 582 µmol) in THF (1 mL) and EtOH (1.02 mL, 17.5 mmol) cooled over an ice bath was slowly added LiBH$_4$ (25 mg, 1.16 mmol). The resulting reaction mixture was stirred at 0° C. for 1 hour and at room temperature for 1 hour. The resulting mixture was quenched with a saturated NaH$_2$PO$_4$ aqueous solution, extracted with EtOAc, and dried over Na$_2$SO$_4$. After filtration and concentration, the desired product was obtained as a solid (130 mg, 71%) using silica gel flash column chromatography (eluted with hexane:EtOAc, 4:1). LCMS (API-ES) m/z: 338 (M$^+$+Na); $^1$H NMR (300 MHz, CDCl$_3$) δ ppm 1.41 (s, 9H), 1.91 (t, J=18.12 Hz, 3H), 2.18 (br, 1H), 2.88 (d, J=7.02 Hz, 2H), 3.55 (m, 1H), 3.68 (m, 1H), 3.88 (m, 1H), 4.73 (br, 1H), 7.26 (d, J=6.21 Hz, 2H), 7.45 (d, J=8.18 Hz, 2H).

(S)-tert-Butyl 4-(4-(1,1-difluoroethyl)benzyl)-1,2,3-oxathiazolidine-3-carboxylate-2-oxide. To a solution of (S)-tert-butyl 3-(4-(1,1-difluoroethyl)phenyl)-1-hydroxypropan-2-ylcarbamate (250 mg, 793 µmol) in ACN (0.5 mL) and DCM (0.5 mL) was slowly added thionyl chloride (145 µl, 1982 µmol) through a syringe. After addition, the reaction mixture was stirred at −60° C. for 10 minutes. To this mixture was added pyridine (321 µl, 3964 µmol) through a syringe while the reaction mixture was kept at −60° C. Upon completion of addition, the reaction mixture was warmed to room temperature and stirred overnight. The reaction mixture was quenched with a saturated NaH$_2$PO$_4$ aqueous solution, extracted with EtOAc, and dried over Na$_2$SO$_4$. After filtration and concentration, the desired product was obtained as a solid (243 mg, 85% yield) using silica gel flash column chromatography (eluted with hexane:EtOAc, 4:1) The desired product included a minor impurity and was used in the next step without further purification. LCMS (API-ES) m/z: 384 (M$^+$+Na).

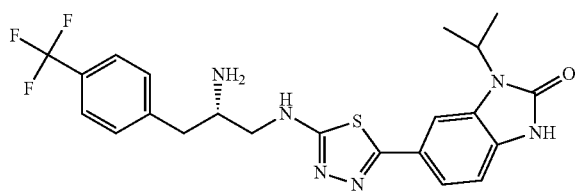

Example 5

6-(5-((S)-2-Amino-3-(4-(trifluoromethyl)phenyl)propylamino)-1,3,4-thiadiazol-2-yl)-1-isopropyl-1H-benzo[d]imidazol-2(3H)-one. LCMS (API-ES) m/z (%): 477.0 (100%, M$^+$+H); $^1$H NMR (400 MHz, CD$_3$OD) δ ppm 1.58 (d, J=7.03 Hz, 6 H) 2.77 (dd, J=13.30, 7.28 Hz, 1H) 2.99 (dd, J=13.30, 5.27 Hz, 1H) 3.38-3.45 (m, 2H) 3.47-3.55 (m, 1H) 4.65-4.76 (m, 1H) 7.12 (d, J=8.53 Hz, 1H) 7.40 (d, J=8.03 Hz, 1H) 7.48 (d, J=8.03 Hz, 2H) 7.62 (d, J=8.03 Hz, 2H) 7.72 (s, 1H). The title compound was prepared in a similar manner to that described for Example 1, using isopropylamine instead of methylamine.

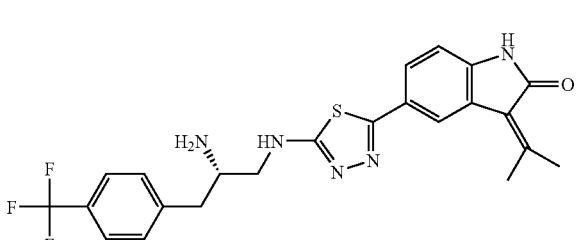

Example 6

5-(5-((S)-2-Amino-3-(4-(trifluoromethyl)phenyl)propylamino)-1,3,4-thiadiazol-2-yl)-3-(propan-2-ylidene)indolin-2-one. Example 2 (5-(5-((S)-2-amino-3-(4-(trifluoromethyl)phenyl)propylamino)-1,3,4-thiadiazol-2-yl)indolin-2-one) (40 mg, 46 µmol) was dissolved in 1 mL of anhydrous acetone. To the resulting solution was added 2.0 mL of 2.0M ammonia in MeOH. The resulting mixture was stirred for one hour. After removing the solvent, the title compound was obtained as a white solid (20 mg, 48%). LCMS (API-ES) m/z (%): 474.1 (100%, M$^+$+H); $^1$H NMR (400 MHz, CD$_3$OD) δ ppm 2.45 (s, 3H) 2.59 (s, 3H) 3.06-3.18 (m, 2H) 3.54-3.65 (m, 1H) 3.66-3.76 (m, 1H) 3.86-3.96 (m, 1H) 6.94 (d, J=8.22 Hz, 1H) 7.49-7.57 (m, 3H) 7.62-7.70 (m, 2H) 8.00 (s, 1H).

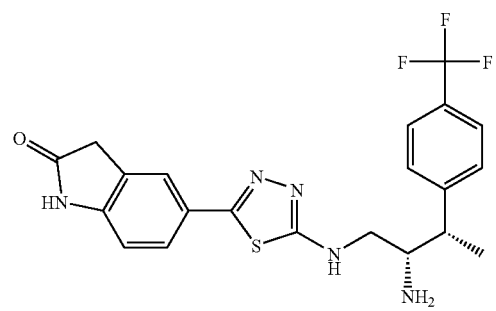

Example 7

5-(5-((2S,3S)-2-Amino-3-(4-(trifluoromethyl)phenyl)butylamino)-1,3,4-thiadiazol-2-yl)indolin-2-one. LCMS (API-ES) m/z (%): 448.1 (100%, M$^+$+H); $^1$H NMR (400 MHz, CD$_3$OD) δ ppm 1.41 (d, J=7.03 Hz, 3H) 2.93-3.02 (m, 1H) 3.26-3.31 (m, 4H) 3.58-3.69 (m, 1H) 6.97 (d, J=8.53 Hz, 1H) 7.51 (d, J=8.03 Hz, 2H) 7.64 (t, J=7.28 Hz, 3H) 7.70 (s, 1H). The title compound was synthesized in a similar manner as Example 2 starting with tert-butyl (2S,3S)-1-(5-(3-fluoro-4-nitrophenyl)-1,3,4-thiadiazol-2-yl-Boc-amino)-3-(4-(trifluoromethyl)phenyl)butan-2-ylcarbamate, which was synthesized in a similar manner to described for Example 1 using tert-butyl 5-(3-fluoro-4-nitrophenyl)-1,3,4-thiadiazol-2-ylcarbamate to react with (S)-tert-butyl 4-((S)-1-(4-(trifluoromethyl)phenyl)ethyl)-1,2,3-oxathiazolidine-3-carboxylate, 2,2-dioxide. (S)-tert-Butyl 4-((S)-1-(4-(trifluoromethyl)phenyl)ethyl)-1,2,3-oxathiazolidine-3-carboxylate, 2,2-dioxide was synthesized as shown in Scheme 4.

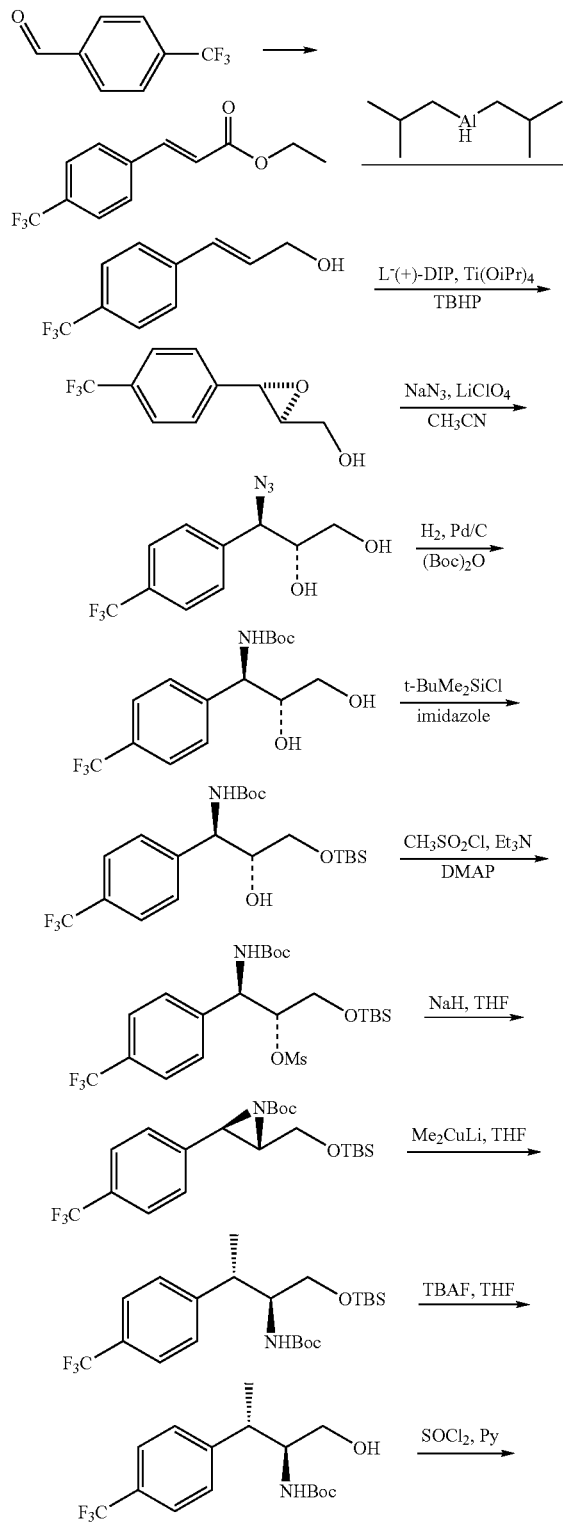

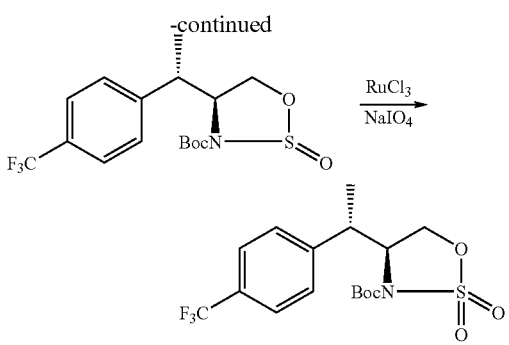

(E)-Ethyl 3-(4-(trifluoromethyl)phenyl)acrylate. To a solution of (carbethoxymethylene)triphenylphosphorane (55.3 g, 159 mmol) in 150 mL DCM, was added α,α,α-trifluoro-p-tolualdehyde (25.00 g, 144 mmol)(commercially available from 3B Scientific Corporation Product List (Order Number 3B4-3644)) in 75 mL DCM. The reaction was exothermic. The mixture was heated at reflux for 90 minutes. After removing the solvent, hexane was added to the resulting residue. A precipitate appeared and was collected by filtration through filter paper. The collected solid was subjected to silica gel chromatography with 100% hexane as the elutant to afford a white solid ((E)-ethyl 3-(4-(trifluoromethyl)phenyl)acrylate (25.0 g, yield=71%). LCMS (API-ES) m/z(%): 245.1 (100%, M$^+$+H); $^1$H NMR (400 MHz, CD$_3$OD) δ ppm 1.35 (t, J=7.14 Hz, 3H) 4.28 (q, J=7.04 Hz, 2H) 6.68 (d, J=16.04 Hz, 1H) 7.70-7.77 (m, 3H) 7.80-7.84 (m, 2H).

(E)-3-(4-(Trifluoromethyl)phenyl)prop-2-en-1-ol. (E)-Ethyl 3-(4-(trifluoromethyl)phenyl)acrylate (25.00 g, 102 mmol) in 100 mL ether was cooled in an ice-water bath. To this solution, di-iso-butylaluminum hydride (205 mL, 205 mmol) in hexane was added. After addition, the ice-water bath was removed. After 2 hours of stirring at room temperature, the reaction mixture was diluted with 200 mL diethyl ether, cooled to 0° C. and quenched with careful addition of 200 mL brine and 200 mL of 5.0 M HCl. The aqueous solution was extracted twice with diethyl ether (200 mL each time). The combined organic phases were washed with brine and dried over sodium sulfate. The product was chromatographed eluting with 20% EtOAc in hexane. After removing the solvent, a white solid was obtained as the desired product (15.3 g, yield=74%). $^1$H NMR (400 MHz, CD$_3$OD) δ ppm 4.28 (dd, J=5.28, 1.57 Hz, 2H) 6.55 (dt, J=15.94, 5.23 Hz, 1H) 6.67-6.75 (m, 1H) 7.58-7.67 (m, 4H).

((2S,3S)-3-(4-(Trifluoromethyl)phenyl)oxiran-2-yl)methanol. Into a 2000 mL flame-dried flask were introduced dry powdered 4 Å molecular sieves (9.0 g) and anhydrous DCM (1000 mL) under nitrogen. After cooling to −20° C., the following reagents were introduced sequentially via cannula under stirring: (diisopropyl 1-tartrate (5 g, 21 mmol); titanium tetraisopropoxide (4 mL, 14 mmol); and a 5.5 M solution of t-butylhydroperoxide (101 mL, 554 mmol). The mixture was stirred 1 hour at −20° C., and a solution of (E)-3-(4-(trifluoromethyl)phenyl)prop-2-en-1-ol (56.0 g, 277 mmol) in 150 mL DCM was added over a 30 minute period. After 8 hours of stirring at the same temperature, the reaction was quenched by addition of 24 mL of a 10% aqueous solution of NaOH saturated with NaCl (100 mL of a 10% solution were prepared by adding 10 g of NaCl to a solution of 10 g of NaOH in 95 mL water). Ether (300 mL) was added dropwise while the cold bath was maintained at −20° C. After the ether addition, the cold bath was removed, and the mixture was allowed to warm to 110° C. Stirring was maintained for an additional 15 minutes at 10° C., and anhydrous MgSO₄ (24 g) and Celite (3 g) were added. After a final 30 minutes of stirring, the mixture was allowed to settle, and the upper portion was filtered through a pad of Celite. The Celite was washed with 20 mL ether. The solvents were evaporated, and tert-butyl hydroperoxide was removed by azeotropic evaporation with toluene (3×100 mL) under high vacuum. The resulting product was then chromatographed eluting with 30% EtOAc in hexane. After removing the solvent, a colorless oil was obtained as the desired product (54 g, yield=90%). ¹H NMR (400 MHz, CD₃OD) δ ppm 3.17 (ddd, J=4.74, 2.89, 2.15 Hz, 1H) 3.72 (dd, J=12.72, 4.70 Hz, 1H) 3.90 (dd, J=12.72, 2.93 Hz, 1H) 3.96 (d, J=1.96 Hz, 1H) 7.50 (d, J=8.02 Hz, 2H) 7.66 (d, J=8.22 Hz, 2H).

(2R,3R)-3-Azido-3-(4-(trifluoromethyl)phenyl)propane-1,2-diol. To a mixture of ((2S,3S)-3-(4-(trifluoromethyl)phenyl)oxiran-2-yl)methanol (15.00 g, 68.8 mmol) in 400 mL ACN was added lithium perchlorate (75.3 mL, 1719 mmol). The reaction mixture was a suspension. After stirring for 15 minutes, sodium azide (12.1 mL, 344 mmol) was added, and the mixture was heated at 65° C. for 24 hours under nitrogen. The reaction mixture was then cooled, and the solvent was evaporated under reduced pressure. Distilled water (500 mL) was added, and the resulting mixture was extracted 3 times (3×400 mL) with diethyl ether. The combined ether layers were directly dried over MgSO₄. After removing the solvent, a colorless oil was obtained as the desired product (14.5 g, yield=81%). ¹H NMR (400 MHz, CD₃OD) δ ppm 3.50-3.56 (m, 1H) 3.58-3.63 (m, 1H) 3.84-3.90 (m, 1H) 4.78 (d, J=6.53 Hz, 1H) 7.62 (d, J=8.03 Hz, 2H) 7.67-7.73 (m, 2H).

tert-Butyl (1R,2R)-2,3-dihydroxy-1-(4-(trifluoromethyl)phenyl)-propylcarbamate. To (2R,3R)-3-azido-3-(4-(trifluoromethyl)phenyl)propane-1,2-diol (14.50 g, 56 mmol) in 120 mL EtOAc, was added di-t-butyldicarbonate (17 g, 78 mmol) and 10% Pd/C (1.45 g, 14 mmol). The mixture was hydrogenated at atmospheric pressure until no starting material could be observed by TLC (about 36 hours). The reaction mixture was filtered through Celite. The filtrate was washed twice with water and twice with brine solution and then dried over sodium sulfate. After removing the solvent, 100 mL hexane was added into the residue and a precipitate appeared. The resulting precipitate was filtered and washed with cold hexane. The white solid was air-dried and was obtained as the desired product (11.0 g, yield=60%). ¹H NMR (400 MHz, CD₃OD) δ ppm 1.42 (s, 9H) 3.43-3.52 (m, 2H) 3.84 (q, J=5.41 Hz, 1H) 4.75 (d, J=5.67 Hz, 1H) 7.52-7.57 (m, 2H) 7.60-7.64 (m, 2H).

tert-Butyl (1R,2R)-3-(tert-butyldimethylsilyloxy)-2-hydroxy-1-(4-(trifluoromethyl)phenyl)propylcarbamate. tert-Butyl (1R,2R)-2,3-dihydroxy-1-(4-(trifluoromethyl)phenyl)-propylcarbamate (11 g, 32.8 mol) in 100 mL DMF was cooled in an ice-water bath. 1H-imidazole (8.2 mL, 72 mol) was added in one portion, and the mixture was stirred for 10 minutes under nitrogen. tert-Butyldimethylsilylchloride (5.43 g, 36.0 mmol) in 20 mL DMF was then added via syringe. The reaction was monitored by TLC. After 16 hours, DMF was evaporated under high vacuum. Distilled water (150 mL) was added, and the resulting mixture was extracted into diethyl ether (2×200 mL). The ether layer was washed with saturated aqueous ammonia chloride and dried over sodium sulfate. After removing the solvent, the product was obtained as a white solid (14.0 g, yield=95%). ¹H NMR (400 MHz, CD₃OD) δ ppm 0.08-0.12 (m, 6 H) 0.97 (s, 9 H) 1.43 (s, 9 H) 3.50 (s, 1H) 3.63 (s, 1H) 3.85 (s, 1H) 4.81 (s, 1H) 7.53-7.58 (m, 2H) 7.60-7.66 (m, 2H).

(1R,2R)-1-((tert-Butoxycarbonyl)amino)-3-(tert-butyldimethylsilyloxy)-1-(4-(trifluoromethyl)phenyl)propan-2-yl methanesulfonate. To a solution of tert-butyl (1R,2R)-3-(tert-butyldimethylsilyloxy)-2-hydroxy-1-(4-(trifluoromethyl)phenyl)-propylcarbamate (14.50 g, 32.3 mmol) in 50 mL DCM at −15° C. were added TEA (4.57 g, 45.2 mmol), N,N-dimethylpyridin-4-amine (0.197 g, 1.61 mmol), and methanesulfonyl chloride (3.26 mL, 41.9 mmol). The mixture was allowed to warm to room temperature. Distilled water (200 mL) was added, and the aqueous phase was extracted into DCM (2×200 mL). The combined organic layers were washed with cold 5% HCl, saturated sodium bicarbonate, and water. The resulting product was then chromatographed eluting with 15% EtOAc in hexane. After removing the solvent, the product was obtained as a colorless oil (15 g, yield=88%). ¹H NMR (400 MHz, CD₃OD) δ ppm 0.11 (d, J=3.91 Hz, 6 H) 0.93-0.98 (m, 9 H) 1.44 (s, 9 H) 2.84 (s, 3H) 3.80-3.87 (m, 2H) 4.84-4.86 (m, 1H) 5.13 (d, J=5.28 Hz, 1H) 7.58 (d, J=8.02 Hz, 2H) 7.69 (d, J=8.22 Hz, 2H).

(2R,3R)-tert-Butyl 2-((tert-butyldimethylsilyloxy)methyl)-3-(4-(trifluoromethyl)phenyl)aziridine-1-carboxylate. To a suspension of 4.0 g sodium hydride (60% dispersion in mineral oil) in 50 mL THF at 0° C. was added a solution (1R,2R)-1-((tert-butoxycarbonyl)amino)-3-(tert-butyldimethylsilyloxy)-1-(4-(trifluoromethyl)phenyl)-propan-2-yl methanesulfonate (13.5 g, 25.6 mmol) in 60 mL THF. The reaction progress was monitored by TLC (20% EtOAc in hexane). When no more starting material could be detected, 4 grams of MeOH was added to the mixture to remove the excess sodium hydride. The solvent was then removed at reduced pressure, and 200 mL of distilled water was added to the residue. The aqueous phase was extracted (3×150 mL) with EtOAc. The combined organic layers were washed with brine and dried over sodium sulfate. The crude product was then chromatographed eluting with 3% EtOAc in hexane. After removing the solvent, the product was obtained as a colorless oil (6.5 g, yield=58%). ¹H NMR (400 MHz, CD₃OD) o ppm 0.14-0.18 (m, 6 H) 0.95-0.98 (m, 9 H) 1.46 (s, 9 H) 2.78 (q, J=2.80 Hz, 1H) 3.64 (d, J=2.93 Hz, 1H) 4.11 (ddd, J=18.19, 11.93, 2.54 Hz, 2H) 7.48 (d, J=8.22 Hz, 2H) 7.66 (d, J=8.02 Hz, 2H).

tert-Butyl (2S,3S)-1-(tert-butyldimethylsilyloxy)-3-(4-(trifluoromethyl)phenyl)butan-2-ylcarbamate. To a stirred slurry of cuprous iodide (7.9 g, 42 mmol) in 150 mL ether at 0° C. was added methyllithium (1.6 M solution in diethyl ether (52 mL, 83 mmol)). The mixture was stirred at this temperature for 20 minutes. A solution of (2R,3R)-tert-butyl 2-((tert-butyldimethylsilyloxy)methyl)-3-(4-(trifluoromethyl)phenyl)aziridine-1-carboxylate (6.00 g, 14 mmol) in 150 mL ether was then added via cannula to the lithium dimethylcuprate solution. The mixture was stirred at 0° C. and monitored by TLC. When no starting material could be detected (about 7 hours), 250 mL of an 8:1 mixture of saturated aqueous ammonia chloride and ammonia hydroxide (28-30% in water) was added to the reaction. The resulting reaction mixture was extracted with diethyl ether (2×300 mL). The combined organic layers were washed twice with brine and dried over sodium sulfate. The crude product was then chromatographed eluting with 3% EtOAc in hexane. After removing the solvent, the desired product was obtained as a colorless oil (2.0 g, yield=32%). ¹H NMR (400 MHz, CD₃OD) δ ppm 0.09 (s, 6 H) 0.90-0.96 (m, 9 H) 1.25-1.33 (m, 12 H) 3.00-3.11 (m, 1H) 3.68-3.80 (m, 3H) 7.43 (d, J=8.02 Hz, 2H) 7.56 (d, J=8.02 Hz, 2H).

tert-Butyl (2S,3S)-1-hydroxy-3-(4-(trifluoromethyl)phenyl)butan-2-ylcarbamate. To tert-butyl (2S,3S)-1-(tert-butyldimethylsilyloxy)-3-(4-(trifluoromethyl)phenyl)butan-2-ylcarbamate (2000 mg, 4.5 mmol) in 25 mL ether at 0° C. was added 1.0 M tetrabutylammonium fluoride in THF (8.9 mL, 8.9 mmol). After the addition, the ice-bath was taken away. The reaction progress was monitored by TLC. After 60 minutes, the solvent was evaporated and 100 mL diethyl ether was added. The organic layer was washed with water and brine solution, and then dried over sodium sulfate. The crude product was then chromatographed eluting with 30% EtOAc in hexane. After removing the solvent, the desired product was obtained as a white solid (1.25 g, 84%). ¹H NMR (400 MHz, CD₃OD) δ ppm 1.26-1.31 (m, 9 H) 1.34 (d, J=7.04 Hz, 3H) 3.02-3.13 (m, 1H) 3.61-3.67 (m, 2H) 3.75 (dd, J=8.71, 4.60 Hz, 1H) 7.44 (d, J=8.02 Hz, 2H) 7.57 (d, J=8.22 Hz, 2H).

Mixture of (R)-tert-butyl 4-((S)-1-(4-(trifluoromethyl)phenyl)-1-S-ethyl)-1,2,3-oxathiazolidine-3-carboxylate, 2-oxide and (S)-tert-butyl 4-((S)-1-(4-(trifluoromethyl)phenyl)-1-S-ethyl)-1,2,3-oxathiazolidine-3-carboxylate, 2-oxide. To a solution of thionyl chloride (0.6 mL, 8 mmol) in 10 mL of ACN at −60° C. was added tert-butyl (2S,3S)-1-hydroxy-3-(4-(trifluoromethyl)phenyl)butan-2-ylcarbamate (1.1 g, 3 mmol) in 20 mL of ACN dropwise via syringe. After 10 minutes, pyridine (1 mL, 16 mmol) was added dropwise while keeping the cold bath temperature at −60° C. The mixture was then allowed to warm to room temperature and stirred overnight. During the warm up period, the reaction mixture remained a suspension. After overnight stirring, the reaction became a clear brown solution. The solvent was then removed under reduced pressure. The residue was taken up in 100 mL of EtOAc. The mixture was transferred to a separatory funnel and washed twice with 100 mL of water and once with 100 mL of brine. The organic layer was dried over Na₂SO₄. Filtration and concentration under reduced pressure, followed by flash chromatography on silica gel (5% to 10% EtOAc/hexanes) afforded 1.0 g of the mixture of diastereomers. The product is a yellow solid, and 900 mg product was obtained. ¹H NMR (400 MHz, CDCl₃) δ ppm 1.40-1.44 (m, 9 H) 1.51 (m, 3H) 3.62-3.70 (m, 1H) 4.37-4.46 (m, 2H) 4.79-4.89 (m, 1H) 7.38-7.43 (m, 2H) 7.59 (t, J=8.90 Hz, 2H).

(S)-tert-Butyl 4-((S)-1-(4-(trifluoromethyl)phenyl)ethyl)-1,2,3-oxathiazolidine-3-carboxylate, 2,2-dioxide. Sodium periodate (2.30 g, 9.5 mmol), ruthenium(III) chloride hydrate (2.67 mg, 0.012 mmol) and a mixture of (R)-tert-butyl 4-((S)-1-(4-(trifluoromethyl)phenyl)-1-S-ethyl)-1,2,3-oxathiazolidine-3-carboxylate, 2-oxide and (S)-tert-butyl 4-((S)-1-(4-(trifluoromethyl)phenyl)-1-S-ethyl)-1,2,3-oxathiazolidine-3-carboxylate, 2-oxide (900 mg, 2.37 mmol) were mixed together in a 500 mL round bottom flask. The ratio of the solvent by volume was as follows: ACN:water:EtOAc=30:10:5. 45 mL ACN was used. The mixture was sonicated for 17 minutes and turned into a nice suspension. The mixture was filtered through filter paper and washed with DCM. The solvent was evaporated. The resulting mixture was taken up in DCM and washed with water and brine solution. The organic layer was dried over sodium sulfate. 840 mg of the white solid product was obtained. ¹H NMR (400 MHz, CDCl₃) δ ppm 1.44-1.49 (m, 12H) 3.51-3.59 (m, J=6.90, 6.90, 6.90, 6.90 Hz, 1H) 4.40-4.50 (m, 3H) 7.43 (d, J=8.22 Hz, 2H) 7.61 (d, J=8.22 Hz, 2H).

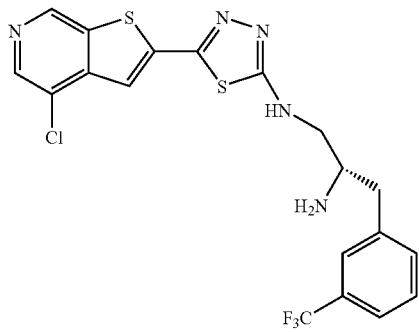

Example 8

N-((S)-2-amino-3-(3-(trifluoromethyl)phenyl)propyl)-5-(4-chlorothieno[2,3-c]pyridin-2-yl)-1,3,4-thiadiazol-2-amine. The title compound was synthesized as shown in Scheme 5.

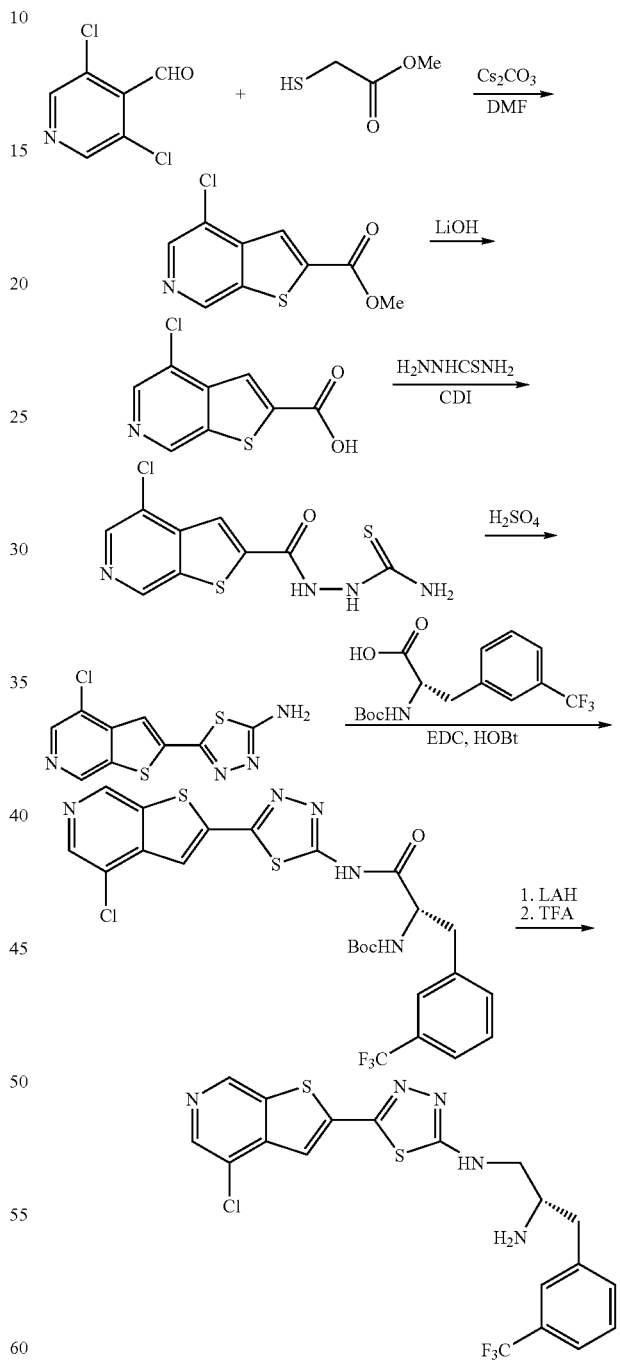

Methyl 4-chlorothieno[2,3-c]pyridine-2-carboxylate. 3,5-Dichloroisonicotinaldehyde (20.39 g, 115.8 mmol) obtained from Aldrich was dissolved in 250 mL DMF. To this solution was added Cs₂CO₃ (12.9 g, 121.59 mmol) and then methyl 2-mercaptoacetate (56.6 g, 173.7 mmol). The mixture was stirred at room temperature for 3 hours. After removing 200 mL DMF under a reduced pressure, the remaining residue was mixed with 100 mL water. After filtration, the filter cake was washed thoroughly with water and air dried. An off-white solid was obtained as the pure product (23.15 g, y=88%). LCMS (API-ES) m/z (%): 228.2 (100%, M$^+$+H); $^1$H NMR (300 MHz, DMSO-d$_6$) δ ppm 3.96 (s, 3H) 8.12 (s, 1H) 8.64 (s, 1H) 9.36 (s, 1H).

4-Chlorothieno[2,3-c]pyridine-2-carboxylic acid. Methyl 4-chlorothieno[2,3-c]pyridine-2-carboxylate (19.76 g) was dissolved in 100 mL THF and treated with 100 mL 2M LiOH at room temperature for 3 hours. The reaction mixture was acidified with concentrated HCl to pH=4. A white solid (17.93 g, y=97%) was obtained after filtration, washing with MeOH and air drying. LCMS (API-ES) m/z (%): 214.1 (100%, M$^+$+H); $^1$H NMR (300 MHz, CD$_3$OD) δ ppm 8.35 (s, 1H) 8.71 (s, 1H) 9.54 (s, 1H).

1-(4-Chlorothieno[2,3-c]pyridine-2-carbonyl)thiosemicarbazide. 4-Chlorothieno[2,3-c]pyridine-2-carboxylic acid (4.2 g, 19.7 mmol) was dissolved in 110 mL DMF in a round bottom flask. To this flask was added CDI (7.68 g, 47.4 mmol). After the flask was heated at 70° C. for 30 minutes, thiosemicarbazide (4.32 g, 47.4 mmol) dissolved in 5 mL DMF was added and the resulting mixture was heated at 70° C. for 30 minutes. After removing the DMF under reduced pressure, the remaining residue was mixed with 50 mL 1N HCl. After filtration and washing with water, the product was dried in a vacuum oven at 80° C. for 4 hours. The resulting product (6.0 g) was used directly in the next step. LCMS (API-ES) m/z (%): 287.1 (100%, M$^+$+H).

5-(4-Chlorothieno[2,3-c]pyridin-2-yl)-1,3,4-thiadiazol-2-amine. The above produced 1-(4-chlorothieno[2,3-c]pyridine-2-carbonyl)thiosemicarbazide was mixed with 2 mL concentrated H$_2$SO$_4$, and the resulting mixture was stirred at room temperature for 16 hours. A solution of 50 mL ice and 50 mL concentrated ammonia (30%) was prepared. To the ammonia solution was added the sulfuric acid solution portion by portion with stirring. A yellow solid formed immediately. After addition, the suspension was stirred at 0° C. for 30 minutes. After filtration, the yellow solid was washed with more water. The solid was mixed with 100 mL MeOH and heated to reflux. After it was cooled to 20° C., the pure product was obtained as a light yellow solid (2.93 g). LCMS (API-ES) m/z (%): 269.2 (100%, M$^+$+H); $^1$H NMR (300 MHz, DMSO-d$_6$) δ ppm 7.84 (s, 1H) 7.86 (bs, 2H) 8.55 (s, 1H) 9.21 (s, 1H).

tert-Butyl (S)-1-(5-(4-chlorothieno[2,3-c]pyridin-2-yl)-1,3,4-thiadiazol-2-ylamino)-1-oxo-3-(3-(trifluoromethyl)phenyl)propan-2-ylcarbamate. (S)-2-((tert-Butoxycarbonyl)amino)-3-(3-(trifluoromethyl)phenyl)propanoic acid (1 g, 3 mmol) purchased from Peptech was mixed with EDC (0.766 g, 4 mmol) and HOBt (0.810 g, 6 mmol) in 5 mL DMF in a round bottom flask. The mixture was stirred at room temperature for 30 minutes. 5-(4-Chlorothieno[2,3-c]pyridin-2-yl)-1,3,4-thiadiazol-2-amine (0.268 g, 1 mmol) was added to the flask followed by addition of DIEA (1.4 mL, 8 mmol). The mixture was heated at 50° C. for one hour. After the DMF was removed under reduced pressure, the remaining residue was mixed with 200 mL EtOAc. The EtOAc solution was washed three times with saturated ammonium chloride aqueous solution, three times with saturated aqueous NaHCO$_3$, and then dried over Na$_2$SO$_4$. After removing the solvent, the product was obtained and used directly in the next step.

tert-Butyl (S)-1-(5-(4-chlorothieno[2,3-c]pyridin-2-yl)-1,3,4-thiadiazol-2-ylamino)-3-(3-(trifluoromethyl)phenyl)propan-2-ylcarbamate. tert-Butyl (S)-1-(5-(4-chlorothieno[2,3-c]pyridin-2-yl)-1,3,4-thiadiazol-2-ylamino)-1-oxo-3-(3-(trifluoromethyl)phenyl)propan-2-ylcarbamate was dissolved in 10 mL THF and cooled to 0° C. in a round bottom flask under nitrogen. To this flask was added 5 mL of a 1 N LiAlH$_4$ THF solution dropwise. The resulting mixture was stirred from 0° C. to 20° C. in 2 hours and then at 20° C. for 3 hours. The reaction mixture was diluted with 20 mL THF and quenched with addition of 2 grams of Na$_2$SO$_4$.10H$_2$O. After the mixture was stirred for 16 hours, it was filtered through a pad of celite. THF was removed under reduced pressure, and the remaining residue was subjected to a silica gel flash column chromatograph separation using 40% EtOAc in hexane as the eluant to yield the desired product (0.075 g, two steps y=13%) as a white solid. LCMS (API-ES) m/z (%): 570.2 (100%, M$^+$+H).

N—((S)-2-Amino-3-(3-(trifluoromethyl)phenyl)propyl)-5-(4-chlorothieno[2,3-c]pyridin-2-yl)-1,3,4-thiadiazol-2-amine. tert-Butyl (S)-1-(5-(4-chlorothieno[2,3-c]pyridin-2-yl)-1,3,4-thiadiazol-2-ylamino)-3-(3-(trifluoromethyl)phenyl)propan-2-ylcarbamate (0.070 g, 0.12 mmol) was treated with 1 mL TFA in 1 mL DCM for 30 minutes. After removing the solvent, the residue was mixed with 10 mL 2M ammonia in MeOH. The solvent was removed again and the remaining residue was subjected to a silica gel flash chromatography separation using 3.5% 2M ammonia MeOH solution in DCM as the eluant. An off white solid was obtained as the pure product (0.03 g, y=52%). LCMS (API-ES) m/z (%): 470.1 (100%, M$^+$+H); $^1$H NMR (300 MHz, CDCL$_3$) δ ppm 1.48-1.82 (b, 3H) 2.72 (dd, J=13.56, 8.48 Hz, 1H) 3.00 (dd, J=13.66, 4.99 Hz, 1H) 3.26-3.35 (m, 1H) 3.40-3.50 (m, 1H) 3.61 (dd, J=12.72, 3.67 Hz, 1H) 7.41-7.56 (m, 6H) 8.46 (s, 1H) 8.95 (s, 1H).

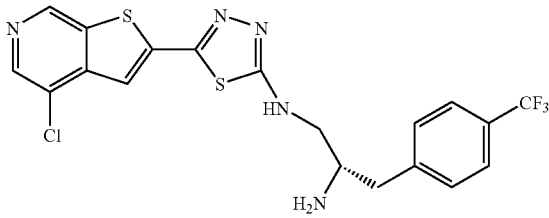

Example 9

N-((S)-2-amino-3-(4-(trifluoromethyl)phenyl)propyl)-5-(4-chlorothieno[2,3-c]pyridin-2-yl)-1,3,4-thiadiazol-2-amine. The title compound was prepared in a similar manner as that described for Example 8 using (S)-2-((tert-butoxycarbonyl)amino)-3-(4-(trifluoromethyl)phenyl)propanoic acid, commercially available from 3B Scientific Corporation Product List (Order Number 3B3-007199), instead of (S)-2-((tert-butoxycarbonyl)amino)-3-(3-(trifluoromethyl)phenyl)propanoic acid. LCMS (API-ES) m/z (%): 470.1 (100%, M$^+$+H); $^1$H NMR (400 MHz, CD$_3$OD) δ ppm 2.77 (dd, J=13.60, 7.34 Hz, 1H) 2.94-3.01 (m, 1H) 3.38-3.46 (m, 2H) 3.54 (d, J=8.22 Hz, 1H) 7.47 (d, J=8.02 Hz, 2H) 7.62 (d, J=8.02 Hz, 2H) 7.71 (s, 1H) 8.42 (s, 1H) 9.03 (s, 1H).

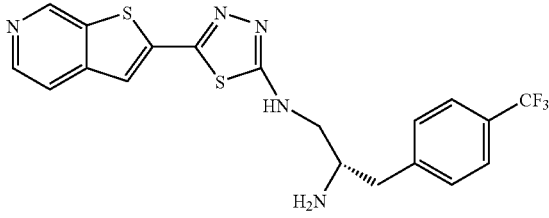

Example 10

N-((S)-2-Amino-3-(4-(trifluoromethyl)phenyl)propyl)-5-(thieno[2,3-c]pyridin-2-yl)-1,3,4-thiadiazol-2-amine.

LCMS (API-ES) m/z (%): 436.0 (100%, M$^+$+H); $^1$H NMR (400 MHz, CD$_3$OD) δ ppm 2.75 (dd, J=13.40, 7.53 Hz, 1H) 2.96 (dd, J=13.60, 4.99 Hz, 1H) 3.37-3.43 (m, 2H) 3.47-3.57 (m, 1H) 7.45 (d, J=8.02 Hz, 2H) 7.60 (d, J=8.02 Hz, 2H) 7.69 (s, 1H) 7.79 (d, J=5.48 Hz, 1H) 8.41 (d, J=5.67 Hz, 1H) 9.10 (s, 1H). This compound was prepared in a similar manner to that described for Example 8 using methyl thieno[2,3-c]pyridine-2-carboxylate as the starting material. Methyl thieno[2,3-c]pyridine-2-carboxylate was prepared by a hydrogenation reaction of methyl 4-chlorothieno[2,3-c]pyridine-2-carboxylate using 10% Pd/C as the catalyst under 60 psi H$_2$ pressure in a par shaker at 60° C. for 16 hours.

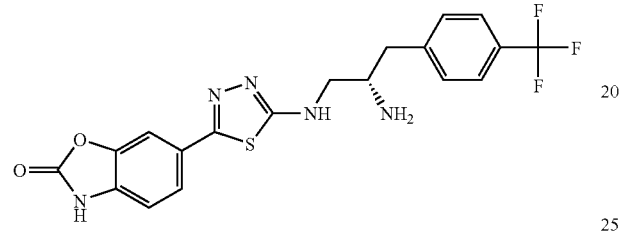

Example 11

6-(5-((S)-2-Amino-3-(4-(trifluoromethyl)phenyl)propylamino)-1,3,4-thiadiazol-2-yl)benzo[d]oxazol-2(3H)-one. The title compound was synthesized as shown in Scheme 6.

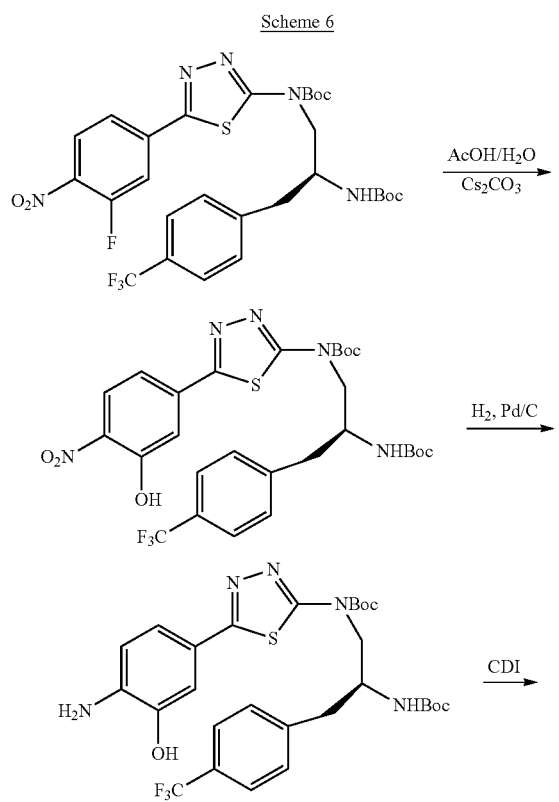

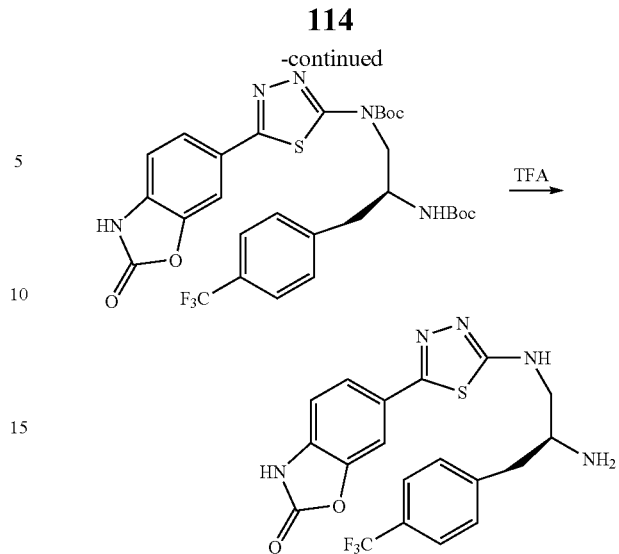

tert-Butyl (S)-1-(5-(3-hydroxy-4-nitrophenyl)-1,3,4-thiadiazol-2-yl-boc-amino)-3-(4-(trifluoromethyl)phenyl)propan-2-ylcarbamate. To a solution of tert-butyl (S)-1-(5-(3-fluoro-4-nitrophenyl)-1,3,4-thiadiazol-2-yl-boc-amino)-3-(4-(trifluoromethyl)phenyl)propan-2-ylcarbamate (630 mg, 982 μmol) (prepared as described in Example 1) in 15 mL DMF were added cesium carbonate (3199 mg, 9819 μmol) and acetic acid (590 mg, 9819 μmol). The mixture was heated at 70° C. for 45 minutes. The reaction mixture was concentrated, and the resulting residue was diluted with 100 mL EtOAc. The organic phase was washed with water and saturated aqueous ammonium chloride twice and then dried over sodium sulfate. Removal of the solvent gave the compound as a tan solid (500 mg, 79%). LCMS (API-ES) m/z (%): 640.0 (100%, M$^+$+H); $^1$H NMR (400 MHz, DMSO-d$_6$) δ ppm 1.13 (s, 9H) 1.54 (s, 9H) 2.84-2.94 (m, 2H) 4.23-4.31 (m, 3H) 7.47 (t, J=8.78 Hz, 3H) 7.62-7.69 (m, 3H) 8.01 (d, J=8.53 Hz, 1H).

tert-Butyl (S)-1-(5-(3-hydroxy-4-aminophenyl)-1,3,4-thiadiazol-2-yl-boc-amino)-3-(4-(trifluoromethyl)phenyl)propan-2-ylcarbamate. tert-Butyl (S)-1-(5-(3-hydroxy-4-nitrophenyl)-1,3,4-thiadiazol-2-yl-boc-amino)-3-(4-(trifluoromethyl)phenyl)propan-2-ylcarbamate (400 mg, 625 μmol) was dissolved in 100 mL MeOH in a 500 mL round bottom flask. To this flask was added 10% Pd/C (100 mg pre-wet with water) and 1.5 mL acetic acid. The mixture was stirred under an atmosphere of hydrogen under balloon pressure for 2 hours. After filtration through a pad of celite, the solution was evaporated to dryness. The residue was re-dissolved in 150 mL EtOAc. The solution was washed with saturated ammonia chloride twice and dried over sodium sulfate. After removing the solvent, the remaining residue was subjected to silica gel column chromatograph separation using 20% to 40% EtOAc in hexane as the eluant. After removing the solvent, the desired product (200 mg, 53%) was obtained as a tan solid. LCMS (API-ES) m/z (%): 610.0 (100%, M$^+$+H); $^1$H NMR (400 MHz, CD$_3$OD) δ ppm 1.21 (s, 9H) 1.55 (s, 9H) 2.80-2.95 (m, 1H) 2.95-3.06 (m, 1H) 4.00-4.25 (m, 1H) 4.25-4.57 (m, 2H) 6.77 (d, J=8.22 Hz, 1H) 7.18 (dd, J=8.02, 1.96 Hz, 1H) 7.25 (d, J=1.76 Hz, 1H) 7.44-7.53 (m, 2H) 7.60 (d, J=8.02 Hz, 2H).

tert-Butyl (S)-1-(5-(2-oxo-2,3-dihydrobenzo[d]oxazol-6-yl)-1,3,4-thiadiazol-2-yl-boc-amino)-3-(4-(trifluoromethyl)phenyl)propan-2-ylcarbamate. tert-Butyl (S)-1-(5-(3-hydroxy-4-aminophenyl)-1,3,4-thiadiazol-2-yl-boc-amino)-3-(4-(trifluoromethyl)phenyl)propan-2-ylcarbamate (200 mg, 328 μmol) was dissolved in 50 mL THF in a round bottom flask. To this flask was added CDI (213 mg, 1312 μmol). The mixture was stirred at 70° C. for 16 hours. After removing the solvent under reduced pressure, the remaining residue was mixed with 100 mL EtOAc. The organic solution was washed with water, saturated ammonium chloride twice and dried over sodium sulfate. After removing the solvent, the desired product (140 mg, 67%) was obtained as a tan solid. LCMS (API-ES) m/z (%): 636.0 (100%, M$^+$+H); $^1$H NMR (400 MHz, CD$_3$OD) δ ppm 1.23 (s, 9H) 1.58 (s, 9H) 2.82-2.96 (m, 1H) 2.95-3.08 (m, 1H) 4.12-4.27 (m, 1H) 4.32-4.43 (m, 2H) 7.15-7.25 (m, 1H) 7.49 (d, J=8.02 Hz, 2H) 7.60 (d, J=7.83 Hz, 2H) 7.70 (dd, J=8.12, 1.47 Hz, 1H) 7.76 (s, 1H).

6-(5-((S)-2-Amino-3-(4-(trifluoromethyl)phenyl)propylamino)-1,3,4-thiadiazol-2-yl)benzo[d]oxazol-2(3H)-one. tert-Butyl (S)-1-(5-(2-oxo-2,3-dihydrobenzo[d]oxazol-6-yl)-1,3,4-thiadiazol-2-yl-boc-amino)-3-(4-(trifluoromethyl)phenyl)propan-2-ylcarbamate (130 mg, 205 μmol) in 10 mL DCM was treated with 10 mL TFA for 60 minutes. After removing the solvent, the remaining residue was dissolved in 100 mL EtOAc. The resulting solution was washed with a mixture of aqueous saturated sodium bicarbonate plus 5% 5N NaOH, then twice with saturated sodium bicarbonate. The organic layer was dried over sodium sulfate. Removal of the solvent gave the title compound 6-(5-((S)-2-amino-3-(4(trifluoromethyl)phenyl)propylamino)-1,3,4-thiadiazol-2-yl) benzo[d]oxazol-2(3H)-one as an off-white amorphous solid (47 mgs, 53%). LCMS (API-ES) m/z (%): 436.0 (100%, M$^+$+H); $^1$H NMR (400 MHz, CD$_3$OD) δ ppm 2.78 (dd, J=13.60, 7.53 Hz, 1H) 2.99 (dd, J=13.60, 5.58 Hz, 1H) 3.35-3.40 (m, 1H) 3.40-3.47 (m, 1H) 3.48-3.55 (m, 1H) 7.13 (d, J=8.22 Hz, 1H) 7.48 (d, J=8.02 Hz, 2H) 7.53 (dd, J=8.12, 1.47 Hz, 1H) 7.62 (d, J=7.24 Hz, 3H).

Examples 12-14

These compounds were prepared in a manner similar to that described for Example 8 as shown in Scheme 5 using the appropriately substituted amino acid starting materials which were commercially available.

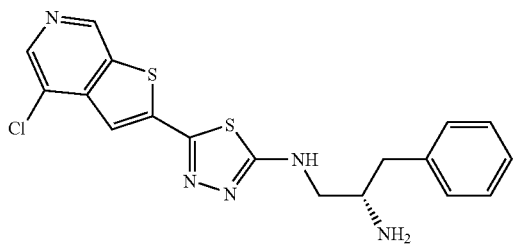

Example 12

N-((S)-2-Amino-3-phenylpropyl)-5-(4-chlorothieno[2,3-c]pyridin-2-yl)-1,3,4-thiadiazol-2-amine. This compound was synthesized as shown for Example 8 using (S)-2-(tert-butoxycarbonyl)-3-phenylpropanoic acid, commercially available from Acros Organics (Order Number 27564), instead of (S)-2-((tert-Butoxycarbonyl)amino)-3-(3-(trifluoromethyl)phenyl)propanoic acid. LCMS (API-ES) m/z (%) 402.1 (100%, M$^+$+H); $^1$H NMR (400 MHz, CD$_3$OD) δ ppm 2.68 (dd, J=13.40, 7.34 Hz, 1H) 2.88 (td, J=8.71, 4.11 Hz, 1H) 3.35-3.43 (m, 2H) 3.45-3.56 (m, 1H) 7.21-7.28 (m, 3H) 7.29-7.34 (m, 2H) 7.79 (s, 1H) 8.46 (s, 1H) 9.06 (s, 1H).

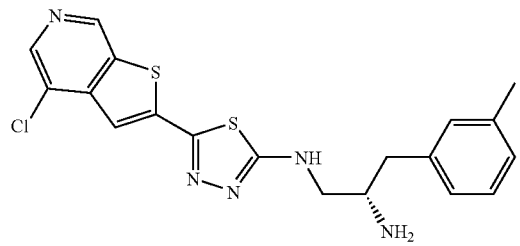

Example 13

N-((S)-2-Amino-3-m-tolylpropyl)-5-(4-chlorothieno[2,3-c]pyridin-2-yl)-1,3,4-thiadiazol-2-amine. This compound was synthesized as shown for Example 8 using (S)-2-(tert-butoxycarbonyl)-3-m-tolylpropanoic acid, commercially available from 3B Scientific Corporation Product List (Order Number 3B3-015489), instead of (S)-2-((tert-butoxycarbonyl)amino)-3-(3-(trifluoromethyl)phenyl)propanoic acid. LCMS (API-ES) m/z (%): 416.1 (100%, M$^+$+H); $^1$H NMR (400 MHz, CD$_3$OD) δ ppm 2.34 (s, 3H) 2.64 (d, J=13.11 Hz, 1H) 2.85 (d, J=18.98 Hz, 1H) 3.34-3.41 (m, 2H) 3.46-3.57 (m, 1H) 7.03-7.13 (m, 3H) 7.20 (t, J=7.53 Hz, 1H) 7.77 (s, 1H) 8.45 (s, 1H) 9.06 (s, 1H).

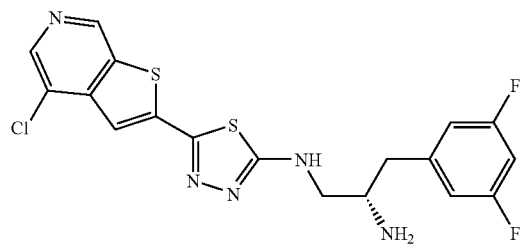

Example 14

N-((S)-2-Amino-3-(3,5-difluorophenyl)propyl)-5-(4-chlorothieno[2,3-c]pyridin-2-yl)-1,3,4-thiadiazol-2-amine. This compound was synthesized as shown for Example 8 using (S)-2-(tert-butoxycarbonyl)-3-(3,5-difluorophenyl)propanoic acid, commercially available from 3B Scientific Corporation Product List (Order Number 3B3-015704), instead of (S)-2-((tert-butoxycarbonyl)amino)-3-(3-(trifluoromethyl)phenyl)propanoic acid. LCMS (API-ES) m/z (%): 438.1 (100%, M$^+$+H); $^1$H NMR (400 MHz, CD$_3$OD) δ ppm 2.71-2.75 (m, 1H) 2.89-2.93 (m, 1H) 3.34-3.39 (m, 2H) 3.47-3.56 (m, 1H) 6.75-6.85 (m, 1H) 6.85-6.96 (m, 2H) 7.79 (s, 1H) 8.45 (s, 1H) 9.06 (s, 1H).

Scheme 7

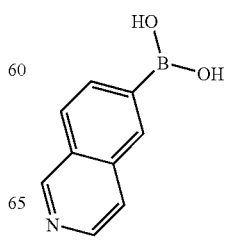

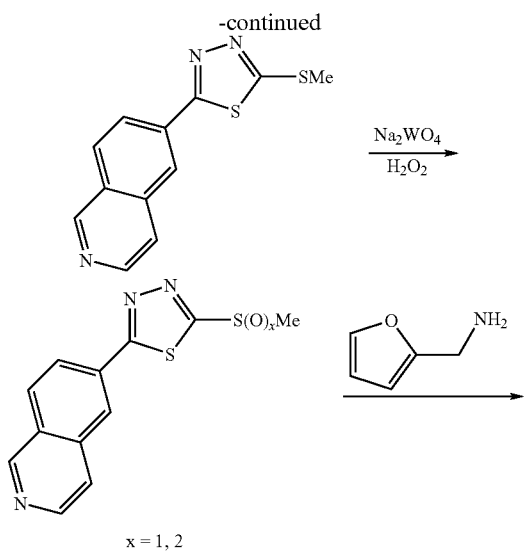

6-(5-(Methylthio)-1,3,4-thiadiazol-2-yl)isoquinoline. To a stirred mixture or isoquinolin-6-ylboronic acid (83 mg, 0.33 mmol) (prepared as described in US Patent Publication No. US 2007/0173506), 2-bromo-5-(methylthio)-1,3,4-thiadiazole (82 mg, 0.39 mmol) (prepared as described in WO 97/30981) and Pd(PPh$_3$)$_4$ (19 mg, 0.016 mmol) was added dimethoxyethane (5.0 mL) and sodium carbonate (0.41 mM, 2.0 M aq, 0.82 mmol). The mixture was heated at 90° C. under a reflux condenser overnight. After cooling, the mixture was filtered through a short path of Celite and washed with EtOAc (3×10 mL). The combined organic layers were evaporated and purified by flash column chromatography (eluting with a gradient of 1:1 EtOAc in hexanes to pure EtOAc) to provide 6-(5-(methylthio)-1,3,4-thiadiazol-2-yl)isoquinoline (80 mg, 95%) as a pale yellow solid. LCMS (M+H) 260.4 calc. for C$_{12}$H$_{10}$N$_3$S$_2$ 260.0. $^1$H NMR (400 MHz, CDCl$_3$): δ ppm 9.33 (d, J=1.17 Hz, 1H) 8.62 (s, 1H) 8.31 (s, 1H) 8.23 (d, J=8.80 Hz, 1H) 8.11 (d, J=8.80 Hz, 1H) 7.74-7.83 (m, 1H) 2.88 (s, 3H).

6-(5-(Methylsulfonyl)-1,3,4-thiadiazol-2-yl)isoquinoline and 6-(5-(methylsulfinyl)-1,3,4-thiadiazol-2-yl)isoquinoline. To 6-(5-(methylthio)-1,3,4-thiadiazol-2-yl)isoquinoline (0.0464 g, 0.18 mmol) and sodium tungstate (0.0026 g, 0.0089 mmol) in glacial acetic acid (0.27 mL, 4.7 mmol) was added dropwise hydrogen peroxide (0.025 mL, 0.52 mmol). The mixture was stirred at room temperature 2 hours. Tlc (1:1 hexane:EtOAc) and LCMS showed no starting material and a 1:1 mixture of two slower spots. After 6 hours, the ratio of products was 2:1. The reaction was partitioned between EtOAc (50 mL) and brine/bicarbonate (1:1 100 mL), the organic layer was dried over sodium sulfate, and the mixture was evaporated to provide 58.8 mg of a 2:1 mixture of 6-(5-(methylsulfonyl)-1,3,4-thiadiazol-2-yl)isoquinoline and 6-(5-(methylsulfinyl)-1,3,4-thiadiazol-2-yl)isoquinoline (0.058 g, quantitative yield) and was used without further purification. LCMS (M+H) 276.0 calc. for C$_{12}$H$_{10}$N$_3$OS$_2$ 276.3. LCMS (M+H) 292.0 calc. for C$_{12}$H$_{10}$N$_3$O$_2$S$_2$ 292.3.

N-(furan-2-ylmethyl)-5-(isoquinolin-6-yl)-1,3,4-thiadiazol-2-amine. A stirred mixture of 6-(5-(methylsulfonyl)-1,3,4-thiadiazol-2-yl)isoquinoline and 6-(5-(methylsulfinyl)-1,3,4-thiadiazol-2-yl)isoquinoline (44 mg, 0.16 mmol) and furan-2-ylmethanamine (78 mg, 0.8 mmol) (commercially available from Acros Organics (Order Number 11980)) was heated at 80-100° C. for 3 hours. The resulting mixture was cooled to room temperature, diluted with EtOAc and washed with 2M aqueous Na$_2$CO$_3$ solution and water. The organic layer was dried over Na$_2$SO$_4$, filtered, and concentrated in vacuo. The residue was purified by flash chromatography on silica gel (eluting with gradients of EtOAc in hexanes) to provide N-(furan-2-ylmethyl)-5-(isoquinolin-6-yl)-1,3,4-thiadiazol-2-amine as an amphorous solid (32 mg, 65%). LCMS (M+H) 309.3 calc for C$_{16}$H$_{13}$N$_4$OS 309.1. $^1$H NMR (300 MHz, DMSO-d$_6$): δ ppm 9.34 (s, 1H), 8.54 (m, 2H), 8.29 (s, 1H), 8.17 (m, 2H), 7.92 (d, J=5.8 Hz, 1H), 7.64 (s, 1H), 6.43 (m, 2H), 4.58 (d, J=5.2 Hz, 2H).

Examples 15-23

Examples 15-23 were prepared in a manner similar to that shown in Scheme 7 with the appropriate amine nucleophiles in place of the furan-2-ylmethanamine in the last step.

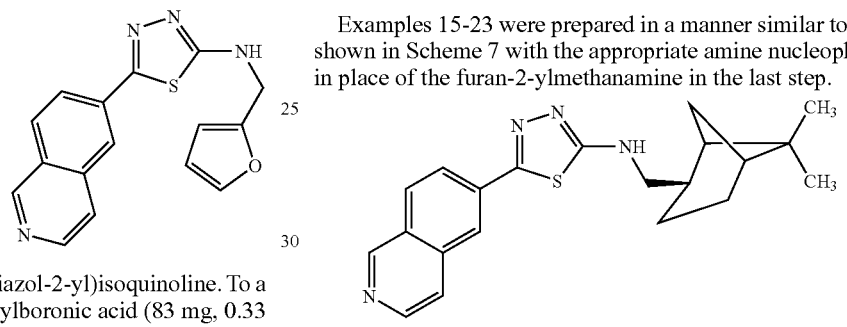

Example 15

N-(((2S)-6,6-Dimethylbicyclo[3.1.1]heptan-2-yl)methyl)-5-(isoquinolin-6-yl)-1,3,4-thiadiazol-2-amine. The title compound was prepared using ((2S)-6,6-dimethylbicyclo[3.1.1]heptan-2-yl)methanamine commercially available from SinoChemexper Product List (Order Number SE-153847). LCMS (M+H) 365 calc. for C$_{21}$H$_{25}$N$_4$S 365.2. $^1$H-NMR (300 MHz, DMSO-d$_6$): δ ppm 9.33 (s, 1H), 8.54 (d, J=5.8, 1H), 8.26 (s, 1H), 8.13-8.21 (m, 3H), 7.93 (d, J=5.8 Hz, 1H), 3.36 (m, 2H), 2.32-2.42 (m, 2H), 1.83-2.01 (m, 6H), 1.54 (m, 1H), 1.19 (s, 3H), 1.06 (s, 3H).

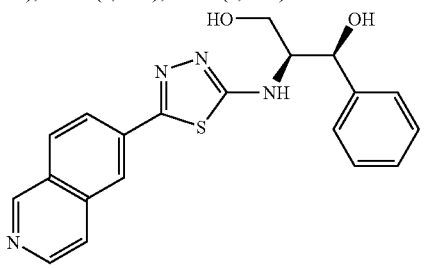

Example 16

(1S,2S)-2-(5-(Isoquinolin-6-yl)-1,3,4-thiadiazol-2-ylamino)-1-phenylpropane-1,3-diol. The addition step was performed in DMA (0.3 M) using (1S,2S)-2-amino-1-phenylpropane-1,3-diol commercially available from 3B Scientific Corporation Product List (Order Number 3B3-011348). LCMS (M+H) 379 calc. for C$_{20}$H$_{19}$N$_4$O$_2$S 379.1. $^1$H-NMR (300 MHz, DMSO-d$_6$): δ ppm 9.37 (s, 1H), 8.59 (d, J=5.7 Hz, 1H), 8.08-8.25 (m, 4H), 7.98 (d, J=5.7 Hz, 1H), 7.46 (d, J=7.2

Hz, 1H), 7.25-7.38 (m, 3H), 5.73 (d, J=4.3 Hz, OH), 5.05 (m, 1H), 4.97 (m, 2H), 4.10 (m, 1H), 3.70 (m, 1H), 3.55 (m, 1H).

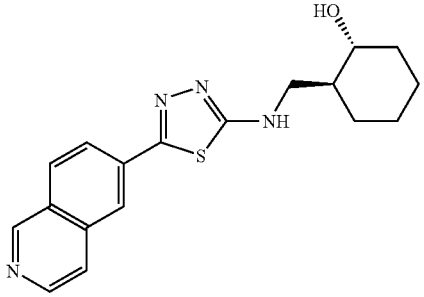

Example 17

(1R,2S)-2-((5-(Isoquinolin-6-yl)-1,3,4-thiadiazol-2-ylamino)methyl)cyclohexanol. The addition step was performed in DMA (0.3 M) using (1R,2S)-2-(aminomethyl)cyclohexanol commercially available from 3B Scientific Corporation Product List (Order Number 3B3-059206). LCMS (M+H) 341 calc. for $C_{18}H_{21}N_4OS$ 341.1. $^1$H-NMR (300 MHz, DMSO-$d_6$): δ ppm 9.33 (s, 1H), 8.56 (d, J=5.7 Hz, 1H), 8.26 (s, 1H), 8.17 (m, 2H), 7.93 (d, J=5.7 Hz, 1H), 8.10 (br.s., NH), 4.74 (d, J=5.2 Hz, OH), 3.65-3.75 (m, 1H), 1.86 (m, 2H), 1.65 (m, 2H), 1.50 (m, 1H), 1.03-1.24 (m, 4H). 2H missing, covered by water signal.

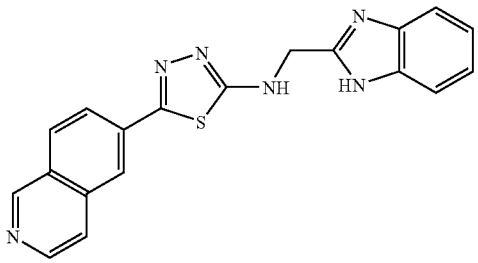

Example 18

N-((1H-Benzo[d]imidazol-2-yl)methyl)-5-(isoquinolin-6-yl)-1,3,4-thiadiazol-2-amine. The addition step was performed in DMA (0.3 M) with DEA (8.5 equiv) and (1H-benzo[d]imidazol-2-yl)methanamine commercially available from 3B Scientific Corporation Product List (Order Number 3B3-066238). LCMS (M+H) 359 calc. for $C_{19}H_{15}N_6S$ 359.1. $^1$H-NMR (300 MHz, DMSO-$d_6$): δ ppm 12.45 (br.s., NH), 9.34 (s, 1H), 8.80 (br.s., NH), 8.56 (d, J=5.7 Hz, 1H), 8.31 (s, 1H), 8.18 (m, 2H), 7.93 (d, J=5.7 Hz, 1H), 7.60 (m, 1H), 7.49 (m, 1H), 7.18 (m, 2H), 4.83 (d, J=5.5 Hz, 2H).

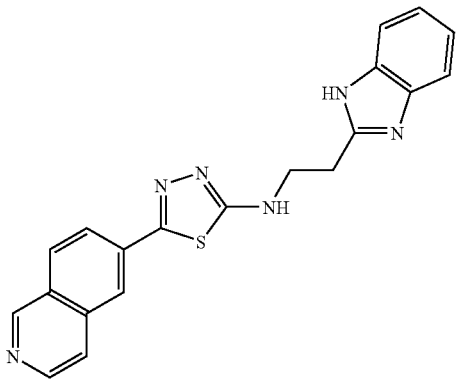

Example 19

N-(2-(1H-Benzo[d]imidazol-2-yl)ethyl)-5-(isoquinolin-6-yl)-1,3,4-thiadiazol-2-amine. The addition step was performed in DMA (0.3 M) with DEA (8.5 equiv) and 2-(1H-benzo[d]imidazol-2-yl)ethanamine commercially available from Ryan Scientific Product List (Order Number EN300-13505). LCMS (M+H) 373 calc. for $C_{20}H_{17}N_6S$ 373.1. $^1$H-NMR (300 MHz, DMSO-$d_6$): δ ppm 12.30 (br.s., NH), 9.34 (s, 1H), 8.56 (d, J=5.7 Hz, 1H), 8.18-8.28 (m, 4H), 7.93 (d, J=5.7 Hz, 1H), 7.55 (m, 1H), 7.45 (m, 1H), 7.14 (m, 2H), 3.87 (m, 2H), 3.23 (m, 2H).

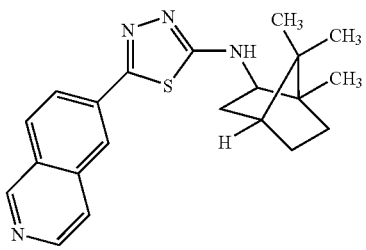

Example 20

5-(Isoquinolin-6-yl)-N-(1,7,7-trimethylbicyclo[2.2.1]heptan-2-yl)-1,3,4-thiadiazol-2-amine. The addition step was performed in DMA (0.3 M) with DEA (8.5 equiv) and 1,7,7-trimethylbicyclo[2.2.1]heptan-2-amine commercially available from Affinitis Pharma Product List (Order Number AF-0664). LCMS (M+H) 365 calc. for $C_{21}H_{25}N_4S$ 365.2. $^1$H-NMR (300 MHz, DMSO-$d_6$): δ ppm 9.34 (s, 1H), 8.56 (d, J=5.7 Hz, 1H), 8.25 (s, 1H), 8.14-8.18 (m, 2H), 7.93 (d, J=5.7 Hz, 1H), 7.81 (d, J=7.1 Hz, 1H), 3.85 (m, 1H), 1.89 (m, 1H), 1.59-1.76 (m, 4H), 1.15-1.31 (m, 2H), 0.98 (s, 3H), 0.92 (s, 3H), 0.83 (s, 3H).

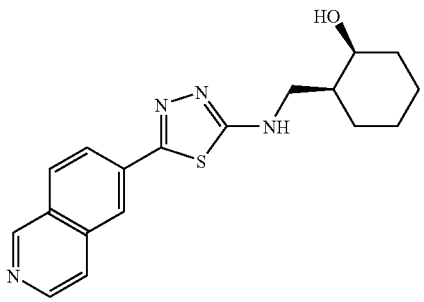

Example 21

(1S,2S)-2-((5-(Isoquinolin-6-yl)-1,3,4-thiadiazol-2-ylamino)methyl)cyclohexanol. The addition step was performed in DMA (0.3 M) with DIEA (8.5 equiv) and (1S,2S)-2-(aminomethyl)cyclohexanol commercially available from 3B Scientific Corporation Product List (Order Number 3B3-056698). LCMS (M+H) 341 calc. for $C_{18}H_{21}N_4OS$ 341.1. $^1$H-NMR (300 MHz, DMSO-$d_6$): δ ppm 9.33 (s, 1H), 8.56 (d, J=5.7 Hz, 1H), 8.26 (s, 1H), 8.10-8.17 (m, 3H), 7.93 (d, J=5.7 Hz, 1H), 8.10 (br.s., N—H), 4.43 (d, J=4.1 Hz, OH), 3.83 (m, 1H), 1.52-1.73 (m, 4H), 1.18-1.47 (m, 4H). 2H missing, covered by water signal.

121

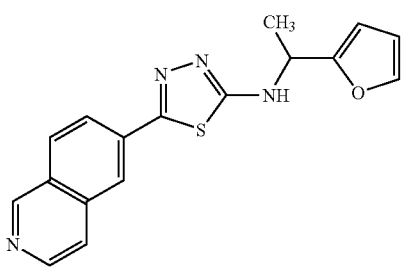

Example 22

(±)-N-(1-(Furan-2-yl)ethyl)-5-(isoquinolin-6-yl)-1,3,4-thiadiazol-2-amine. The addition step was performed in DMA (0.3 M) at 130° C. for 30 minutes with microwave heating using 1-(furan-2-yl)ethanamine commercially available from 3B Scientific Corporation Product List (Order Number 3B3-075175). LCMS (M+H) 323 calc. for $C_{17}H_{15}N_4OS$ 323.1. $^1$H-NMR (300 MHz, DMSO-$d_6$): δ ppm 9.39 (s, 1H), 8.59 (d, J=5.7 Hz, 2H), 8.33 (s, 1H), 8.19-8.27 (m, 2H), 7.98 (d, J=5.7 Hz, 1H), 7.68 (d, J=1.0 Hz, 1H), 6.48 (s, 1H), 6.42 (s, 1H), 5.12 (m, 1H), 1.61 (d, J=6.9 Hz, 3H).

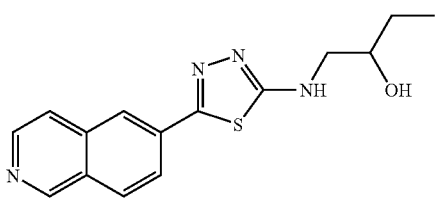

Example 23

(±)-1-(5-(Isoquinolin-6-yl)-1,3,4-thiadiazol-2-ylamino)butan-2-ol. The addition step was performed in DMF (0.09 M) at 150° C. for 20 minutes with microwave heating using 1-aminobutan-2-ol commercially available from 3B Scientific Corporation Product List (Order Number 3B3-046360). LCMS (M+H) 301 calc for $C_{15}H_{17}N_4OS$ 301.4. $^1$H NMR (400 MHz, CD$_3$OD): δ ppm 9.26 (s, 1H), 8.48 (d, J=6.5 Hz, 1H), 8.22 (s, 1H), 8.18 (s, 2H), 7.89 (d, J=6.0 Hz, 1H), 4.63 (s, 1H), 3.82-3.75 (m, 1H), 3.57 (dd, J=4.1 Hz, 13.6 Hz, 1H), 3.37 (dd, J=7.6 Hz, 13.5 Hz, 1H), 1.65-1.50 (m, 2H), (1.25 (t, J=7.1 Hz, 1H), 1.04 (t, J=7.6 Hz, 3H).

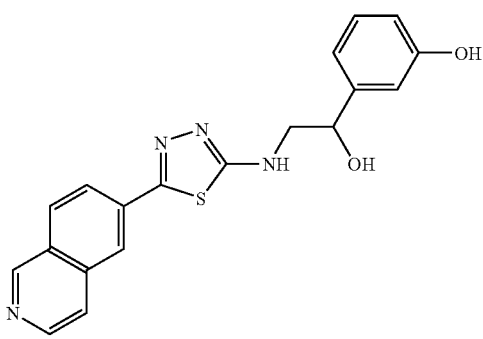

122

Example 24

(±)-3-(1-Hydroxy-2-(5-(isoquinolin-6-yl)-1,3,4-thiadiazol-2-ylamino)ethyl)phenol. Example 24 was synthesized as shown in Scheme 8.

Scheme 8

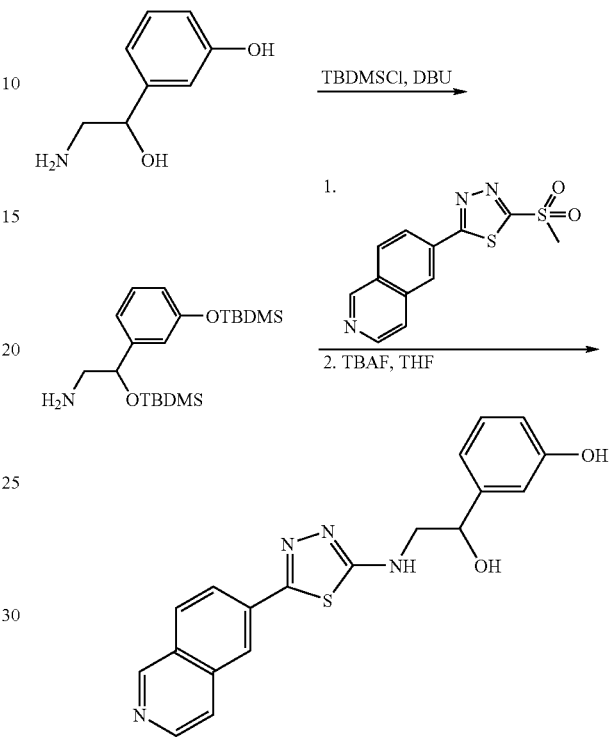

(±)-2-(tert-Butyldimethylsilyloxy)-2-(3-(tert-butyldimethylsilyloxy)phenyl)ethanamine. To a mixture of (±)-3-(2-amino-1-hydroxyethyl)phenol (500 mg, 3.26 mg)(commercially available from Interbioscreen Building Blocks (Order Number BB_NC-2015)) and DBU (1.95 mL, 13.1 mmol) in ACN (6 mL) at 0° C. was added TBDMSCI (1.67 g, 11.1 mmol). The mixture was stirred at room temperature for 16 hours. The mixture was diluted with DCM, washed with 2 M aqueous Na$_2$CO$_3$ solution, and water. The organic layer was dried over Na$_2$SO$_4$, filtered and concentrated in vacuo. The resulting residue was purified by flash chromatography on silica gel (eluting with gradients of MeOH in DCM) to provide 2-(tert-butyldimethylsilyloxy)-2-(3-(tert-butyldimethylsilyloxy)phenyl)ethanamine (1.1 g, 87%) as a brown oil. LCMS (M+H) 382 calc. for $C_{20}H_{40}NO_2Si_2$ 382.2. $^1$H NMR (300 MHz, DMSO-$d_6$): δ ppm 7.22 (t, J=7.8, 1H), 6.93 (m, 1H), 6.83 (m, 1H), 6.75 (m, 1H), 4.61 (t, J=5.8 Hz, 1H), 2.63 (d, J=5.8 Hz, 2H), 1.29 (br.s, NH$_2$), 0.97 (s, 9H), 0.88 (s, 9H), 0.20 (s, 6H), 0.07 (s, 3H), −0.08 (s, 3H).

(±)-3-(1-Hydroxy-2-(5-(isoquinolin-6-yl)-1,3,4-thiadiazol-2-ylamino)ethyl)phenol. (±)-2-(tert-Butyldimethylsilyloxy)-2-(3-(tert-butyldimethylsilyloxy)phenyl)ethanamine and 6-(5-(methylsulfonyl)-1,3,4-thiadiazol-2-yl)isoquinoline and 6-(5-(methylsulfinyl)-1,3,4-thiadiazol-2-yl)isoquinoline (prepared as in Scheme 7) was heated at 80-100° C. for 3 hours in DMA (0.3 M) to provide (±)-N-(2-(tert-butyldimethylsilyloxy)-2-(3-(tert-butyldimethylsilyloxy)phenyl)ethyl)-5-(isoquinolin-6-yl)-1,3,4-thiadiazol-2-amine. This intermediate was dissolved in THF and TBAF (1M in THF, 1.24 mmol) was added. After 16 hours, the mixture was concentrated in vacuo and the residue purified by flash chromatography on silica (eluting with DCM/MeOH gradients) to provide (±)-3-(1-hydroxy-2-(5-(isoquinolin-6-yl)-1,3,4-thiadiazol-2-ylamino)ethyl)phenol (20 mg, 8%). LCMS (M+H) 365 calc. for $C_{19}H_{17}N_4O_2S$ 365.1. $^1$H NMR (300 MHz, DMSO-$d_6$): δ ppm 9.33 (s, 1H+OH), 8.56 (d, J=5.8 Hz, 1H), 8.27 (m, 2H), 8.18 (m, 2H), 7.92 (d, J=5.8 Hz, 1H), 7.14 (t, J=7.6, 1H), 6.84 (m, 2H), 6.65 (m, 1H), 5.58 (d, J=4.0 Hz, OH), 4.80 (m, 1H), 3.60 (m, 1H). 1H missing, covered by water signal.

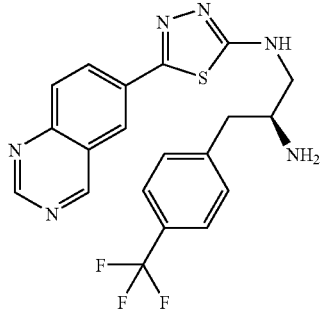

Example 25

N-((S)-2-Amino-3-(4-(trifluoromethyl)phenyl)propyl)-5-(quinazolin-6-yl)-1,3,4-thiadiazol-2-amine. Example 25 was synthesized as shown in Scheme 9.

Scheme 9

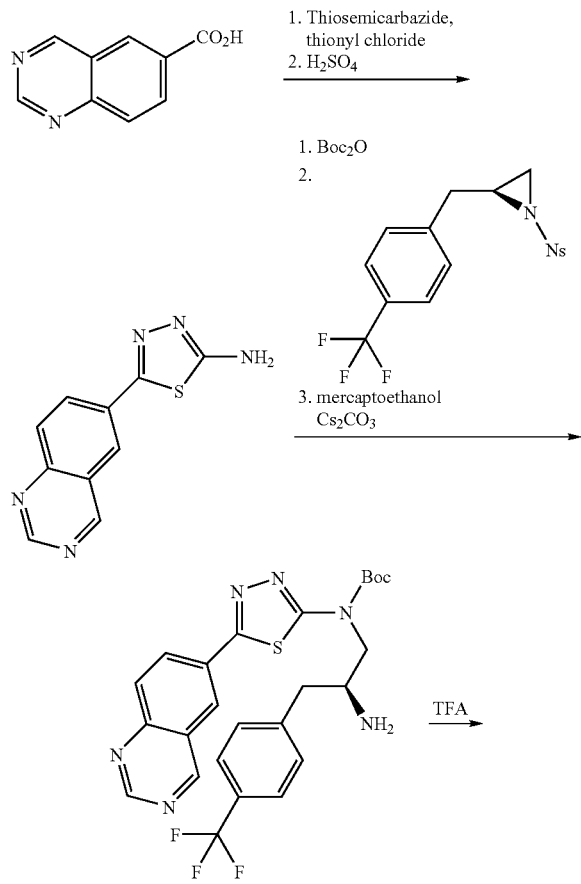

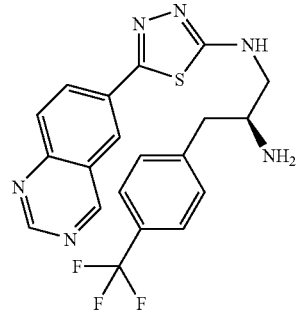

5-(Quinazolin-6-yl)-1,3,4-thiadiazol-2-amine. This compound was prepared as shown in Scheme 5 using 6-quinazolinecarboxylic acid, commercially available from ACES Pharma Product List (Order Number 36021) instead of 4-chlorothieno[2,3-c]pyridine-2-carboxylic acid. LCMS (M+H) 230.3 calc. for $C_{10}H_8N_5S$ 230.0. $^1$H NMR (400 MHz, DMSO-$d_6$): δ ppm 9.70 (s, 1H) 9.33 (s, 1H) 8.47-8.53 (m, 2H) 8.09 (d, J=8.80 Hz, 1H) 7.63 (s, 2H).

tert-Butyl 5-(quinazolin-6-yl)-1,3,4-thiadiazol-2-ylcarbamate. To a stirred mixture of 5-(quinazolin-6-yl)-1,3,4-thiadiazol-2-amine (0.132 g, 0.58 mmol) in DMF (5 mL) was added Boc$_2$O (188 mg, 0.86 mmol) and commercially available N,N-dimethylpyridin-4-amine (4 mg, 0.029 mmol). The mixture was heated at 100° C. 15 hours. After cooling, the mixture was concentrated. The resulting residue was purified by flash column chromatography (eluting with a gradient of DCM to 5% MeOH in DCM) to provide tert-butyl 5-(quinazolin-6-yl)-1,3,4-thiadiazol-2-ylcarbamate (33 mg, 17%) as a yellow solid.

N—((S)-2-Amino-3-(4-(trifluoromethyl)phenyl)propyl)-5-(quinazolin-6-yl)-1,3,4-thiadiazol-2-amine. tert-Butyl (S)-2-amino-3-(4-(trifluoromethyl)phenyl)propyl(5-(quinazolin-6-yl)-1,3,4-thiadiazol-2-yl)carbamate was obtained as a semi-pure yellow solid from tert-butyl 5-(quinazolin-6-yl)-1,3,4-thiadiazol-2-ylcarbamate using the procedure described previously. To a stirred mixture of tert-butyl (S)-2-amino-3-(4-(trifluoromethyl)phenyl)propyl(5-(quinazolin-6-yl)-1,3,4-thiadiazol-2-yl)carbamate (17 mg, 32 μmol) in DCM (2.0 mL) was added TFA (2.0 mL). The overall mixture was stirred at room temperature for 1 hour. The reaction mixture was concentrated and the residue taken up in DCM. The mixture was washed with aqueous NaHCO$_3$ (5 mL) and water (5 mL). The separated aqueous layer was extracted with DCM (2×5 mL). The combined organic layers were washed with brine, dried over Na$_2$SO$_4$, and concentrated. The residue was purified by flash column chromatography (eluting with a gradient of DCM to 10% MeOH in DCM) to provide N—((S)-2-amino-3-(4-(trifluoromethyl)phenyl)propyl)-5-(quinazolin-6-yl)-1,3,4-thiadiazol-2-amine as a white solid (1.0 mg, 7% yield). LCMS (M+H) 431.1 calc. for $C_{20}H_{18}F_3N_6S$ 431.1. $^1$H NMR (400 MHz, CDCl$_3$): δ ppm 9.43 (d, J=2.74 Hz, 1H) 9.35 (d, J=3.13 Hz, 1H) 8.46 (d, J=8.22 Hz, 1H) 8.19 (s, 1H) 8.09 (d, J=5.87 Hz, 1H) 7.60 (d, J=5.87 Hz, 1H) 7.36 (d, J=6.65 Hz, 2H) 3.66 (d, J=13.89 Hz, 1H) 3.40-3.51 (m, 1H) 2.07 (s, 1H) 1.38-1.79 (m, 2H) 1.26 (s, 2H). 2H obscured.

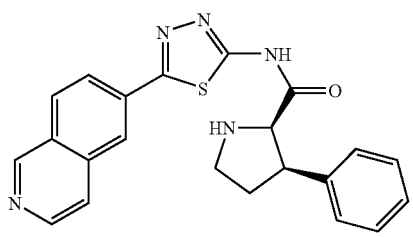

Example 26

(±)-cis-N-(5-(Isoquinolin-6-yl)-1,3,4-thiadiazol-2-yl)-3-phenylpyrrolidine-2-carboxamide. Example 26 was synthesized as shown in Scheme 10.

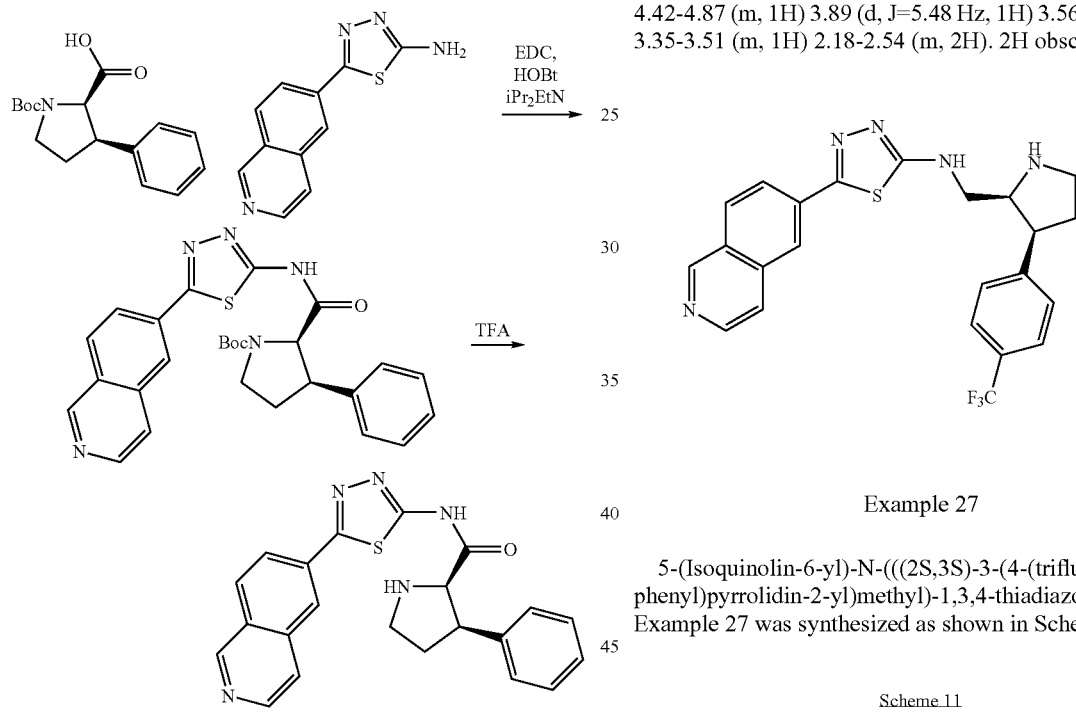

(±)-cis-tert-Butyl 2-((5-(isoquinolin-6-yl)-1,3,4-thiadiazol-2-yl)carbamoyl)-3-phenylpyrrolidine-1-carboxylate. To a stirred mixture of 5-(isoquinolin-6-yl)-1,3,4-thiadiazol-2-amine (97 mg, 0.42 mmol) (prepared as shown in Scheme 5 using isoquinoline-6-carboxylic acid, commercially available from AstaTech Product List (Order Number 62874), instead of 4-chlorothieno[2,3-c]pyridine-2-carboxylic acid) and (±)-cis-1-(tert-butoxycarbonyl)-3-phenylpyrrolidine-2-carboxylic acid ((Damour et al. Synlett 1999, 2, 189-192), 149 mg, 0.51 mmol) in DMF (5.0 mL) was added EDC (122 mg, 0.64 mmol), HOBt (86 mg, 0.64 mmol) and DIEA (0.22 mL, 1.3 mmol). The mixture was stirred at room temperature for 24 hours. Aqueous NH$_4$Cl (5 mL), water (5 mL) and DCM (10 mL) were added. The aqueous layer was extracted with DCM (3×10 mL). The combined organic layers were washed with brine, dried over Na$_2$SO$_4$, and concentrated. The crude residue was purified by flash column chromatography (eluting with a gradient from DCM to 5% MeOH in DCM) to provide (±)-cis-tert-butyl 2-((5-(isoquinolin-6-yl)-1,3,4-thiadiazol-2-yl)carbamoyl)-3-phenylpyrrolidine-1-carboxylate as a white foam (64 mg, 30%). LCMS (M+H) 502.2 calc. for C$_{27}$H$_{28}$N$_5$O$_3$S 502.2.

(±)-cis-N-(5-(Isoquinolin-6-yl)-1,3,4-thiadiazol-2-yl)-3-phenylpyrrolidine-2-carboxamide. To a stirred mixture of (±)-cis-tert-butyl 2-((5-(isoquinolin-6-yl)-1,3,4-thiadiazol-2-yl)carbamoyl)-3-phenylpyrrolidine-1-carboxylate (54 mg, 0.11 mmol) in DCM (3.0 mL) was added TFA (3.0 mL). The mixture was stirred at room temperature for 1 hour. The reaction mixture was concentrated. The crude residue was purified by flash column chromatography (eluting with a gradient of DCM to DCM containing 5% of 10% MeOH in ammonia) to provide (±)-cis-N-(5-(isoquinolin-6-yl)-1,3,4-thiadiazol-2-yl)-3-phenylpyrrolidine-2-carboxamide as a white solid (3.0 mg, 7%). LCMS (M+H) 402.2 calc. for C$_{22}$H$_{20}$N$_5$OS 402.1. $^1$H NMR (400 MHz, CDCl$_3$): δ ppm 9.23 (s, 1H) 8.55 (d, J=4.89 Hz, 1H) 8.08-8.29 (m, 2H) 7.97 (d, J=7.63 Hz, 1H) 7.65 (d, J=5.48 Hz, 1H) 7.15-7.24 (m, 5H) 4.42-4.87 (m, 1H) 3.89 (d, J=5.48 Hz, 1H) 3.56-3.72 (m, 1H) 3.35-3.51 (m, 1H) 2.18-2.54 (m, 2H). 2H obscured.

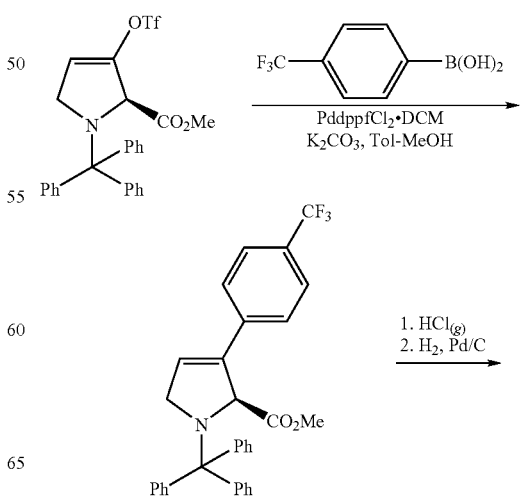

Example 27

5-(Isoquinolin-6-yl)-N-(((2S,3S)-3-(4-(trifluoromethyl)phenyl)pyrrolidin-2-yl)methyl)-1,3,4-thiadiazol-2-amine. Example 27 was synthesized as shown in Scheme 11.

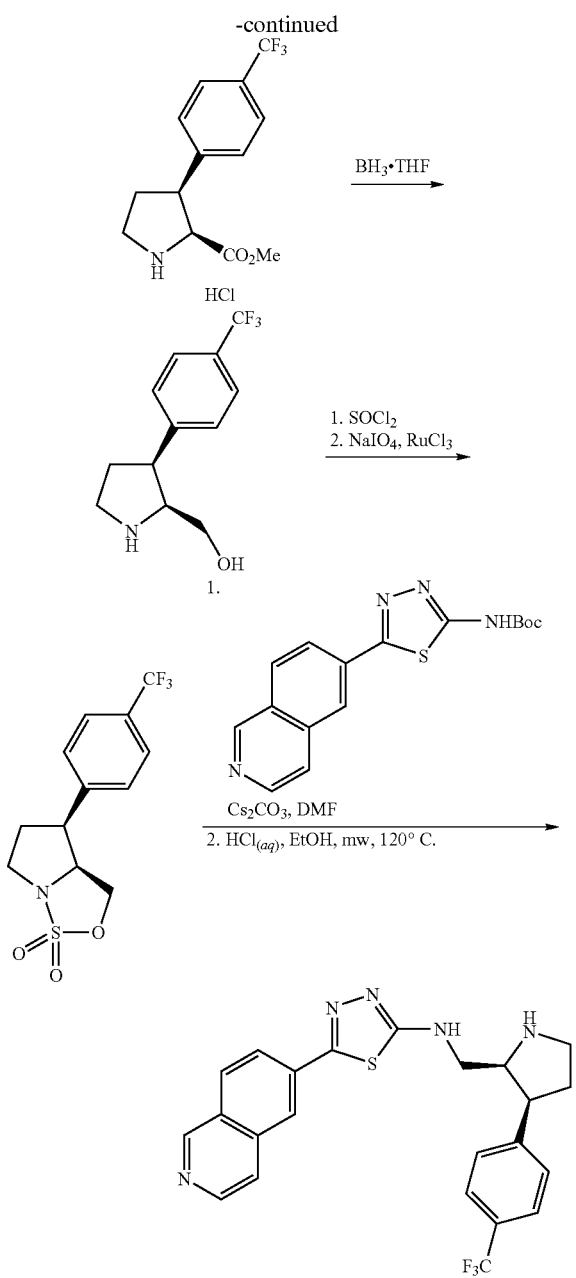

(S)-Methyl 3-(4-(trifluoromethyl)phenyl)-1-trityl-2,5-dihydro-1H-pyrrole-2-carboxylate. To a stirred mixture of (S)-methyl 3-(trifluoromethylsulfonyloxy)-1-trityl-2,5-dihydro-1H-pyrrole-2-carboxylate ((Tetrahedron Lett. 2001, 8571) 1.71 g, 3.3 mmol), 4-(trifluoromethyl)phenylboronic acid (1.3 g, 6.6 mmol), K$_2$CO$_3$ (0.68 mg, 5.0 mmol) and dichloro [1,1'-bis(diphenylphosphino)ferrocene]dichloride palladium (II) DCM adduct (0.12 g, 0.16 mmol) was added toluene (10 mL) and MeOH (1.0 mL). The mixture was stirred under nitrogen at 85° C. 15 hours. The mixture was cooled and evaporated in vacuo. The residue was dissolved in DCM, adsorbed onto silica gel and purified by flash column chromatography (eluting first with 1:5 EtOAc in hexanes and second with a gradient of hexanes to 30% DCM in hexanes) to give (S)-methyl 3-(4-(trifluoromethyl)phenyl)-1-trityl-2, 5-dihydro-1H-pyrrole-2-carboxylate as a white solid (1.06 g, 62%). LCMS (M+H) 514.5 calc. for C$_{32}$H$_{27}$F$_3$NO$_2$ 514.2. $^1$H NMR (400 MHz, CDCl$_3$): δ ppm 6.67-8.21 (a series of m, 19H) 5.85 (s, 1H) 5.01 (d, J=4.11 Hz, 1H) 4.39 (dd, J=17.61, 2.54 Hz, 1H) 3.82 (dd, J=17.70, 2.64 Hz, 1H) 3.64 (s, 3H).

(2S,3S)-Methyl 3-(4-(trifluoromethyl)phenyl)pyrrolidine-2-carboxylate. (S)-Methyl 3-(4-(trifluoromethyl)phenyl)-1-trityl-2,5-dihydro-1H-pyrrole-2-carboxylate (0.22 g, 0.43 mmol) was stirred in MeOH (5.0 mL). Anhydrous HCl$_{(g)}$ was bubbled through the solution at 0° C. for 5 minutes. The mixture was stirred an additional 5 minutes at 0° C. and at room temperature for 10 minutes. The mixture was evaporated in vacuo. The residue was redissolved in MeOH (5.0 mL) and Pd/C (0.10 g, 0.05 mmol) was added. The resulting suspension was stirred under 1 atm H$_2$ at room temperature overnight. The mixture was passed through a short path of Celite washing with MeOH (3×10 mL). The filtrate was evaporated in vacuo. The residue was dissolved in DCM/MeOH (10% with NH$_3$) and adsorbed onto silica gel. The crude residue was purified by flash column chromatography (eluting with a gradient of pure DCM to 5% MeOH in DCM) to provide (2S,3S)-methyl 3-(4-(trifluoromethyl)phenyl)pyrrolidine-2-carboxylate as a colorless oil (66 mg, 56%). LCMS (M+H) 274.2 calc. for C$_{13}$H$_{15}$F$_3$NO$_2$ 274.1. $^1$H NMR (400 MHz, CDCl$_3$): δ ppm 2.01-2.35 (m, 3H), 3.02-3.12 (m, 1H), 3.24 (s, 3H), 3.43-3.53 (m, 1H), 3.68 (q, J=8.22 Hz, 1H), 4.10 (d, J=8.61 Hz, 1H), 7.30 (d, J=8.02 Hz, 2H), 7.54 (d, J=8.02 Hz, 2H).

((2S,3S)-3-(4-(Trifluoromethyl)phenyl)pyrrolidin-2-yl) methanol. To a stirred mixture of (2S,3S)-methyl 3-(4-(trifluoromethyl)phenyl)pyrrolidine-2-carboxylate (0.33 g, 1.21 mmol) in THF (5.0 mL) was added BH$_3$-THF (12 mL, 12 mmol) at 0° C. The mixture was heated at reflux for 4 hours. The mixture was cooled to 0° C., the reaction carefully quenched with MeOH, and the mixture was evaporated in vacuo. The residue was diluted with saturated aqueous NaHCO$_3$, water and extracted with EtOAc (3×50 mL). The combined organic layers were washed with brine, dried over Na$_2$SO$_4$, and concentrated. The crude residue was purified by flash column chromatography (ISCO Combiflash system, eluting with a gradient from pure DCM to 5% MeOH in DCM) to provide ((2S,3S)-3-(4-(trifluoromethyl)phenyl) pyrrolidin-2-yl)methanol as a white solid (45 mg, 15%).

(3aS,4S)-4-(4-(Trifluoromethyl)phenyl)tetrahydro-3H-pyrrolo[1,2-c][1,2,3]oxathiazole 1,1-dioxide. This compound was made using the same procedure used previously in 15% yield from ((2S,3S)-3-(4-(trifluoromethyl)phenyl)pyrrolidin-2-yl)methanol. The product was used directly without further purification.

5-(Isoquinolin-6-yl)-N-(((2S,3S)-3-(4-(trifluoromethyl) phenyl)pyrrolidin-2-yl)methyl)-1,3,4-thiadiazol-2-amine. To a stirred mixture of tert-butyl 5-(isoquinolin-6-yl)-1,3,4-thiadiazol-2-ylcarbamate (99 mg, 0.30 mmol) and cesium carbonate (154 mg, 0.47 mmol) in DMF (1.0 mL) was added slowly a solution of (3aS,4S)-4-(4-(trifluoromethyl)phenyl) tetrahydro-3H-pyrrolo[1,2-c][1,2,3]oxathiazole 1,1-dioxide (58 mg, 0.19 mmol) in DMF (1.0 mL) at 50° C. The mixture was stirred for 1 hour and then concentrated. The residue was dissolved in EtOH and acidified with 5 N HCl (~pH 2). The mixture was heated at 120° C. for 20 minutes under microwave irradiation. The mixture was concentrated, and the residue was taken up in DCM (2 mL) and water (2 mL). The aqueous layer was made basic with 5 N NaOH and extracted with EtOAc (3×5 mL). The combined organic layers were washed with brine, dried over Na$_2$SO$_4$, and concentrated. The residue was purified by flash column chromatography (ISCO Combiflash system, eluting with a gradient of DCM to 10% MeOH in DCM) to provide 5-(isoquinolin-6-yl)-N-(((2S, 3S)-3-(4-(trifluoromethyl)phenyl)pyrrolidin-2-yl)methyl)-1, 3,4-thiadiazol-2-amine as a pale yellow solid (8.8 mg, 10%). LCMS (M+H) 456.1 calc. for $C_{23}H_{21}F_3N_5S$ 456.1. $^1$H NMR (400 MHz, CDCl$_3$): δ ppm 2.14-2.29 (m, 1H), 2.48-2.54 (m, 2H), 3.72-3.81 (m, 1H), 3.82-3.92 (m, 1H), 4.04-4.23 (m, 1H), 4.54-4.67 (m, 1H), 7.48 (d, J=7.53 Hz, 2H), 7.70 (d, J=8.03 Hz, 2H), 7.78 (d, J=5.02 Hz, 2H), 7.86-8.02 (m, 1H), 8.30 (d, J=3.01 Hz, 1H), 8.42-8.54 (m, 2H), 9.24 (s, 1H). 2H obscured.
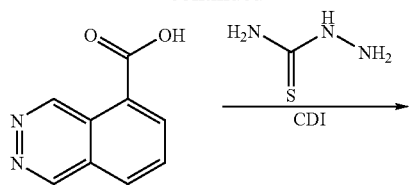
Example 28
N-((S)-2-amino-3-(4-(trifluoromethyl)phenyl)propyl)-5-(phthalazin-5-yl)-1,3,4-thiadiazol-2-amine. Example 28 was synthesized as shown in Scheme 12 starting with 3-bromobenzaldehyde purchased from Aldrich.
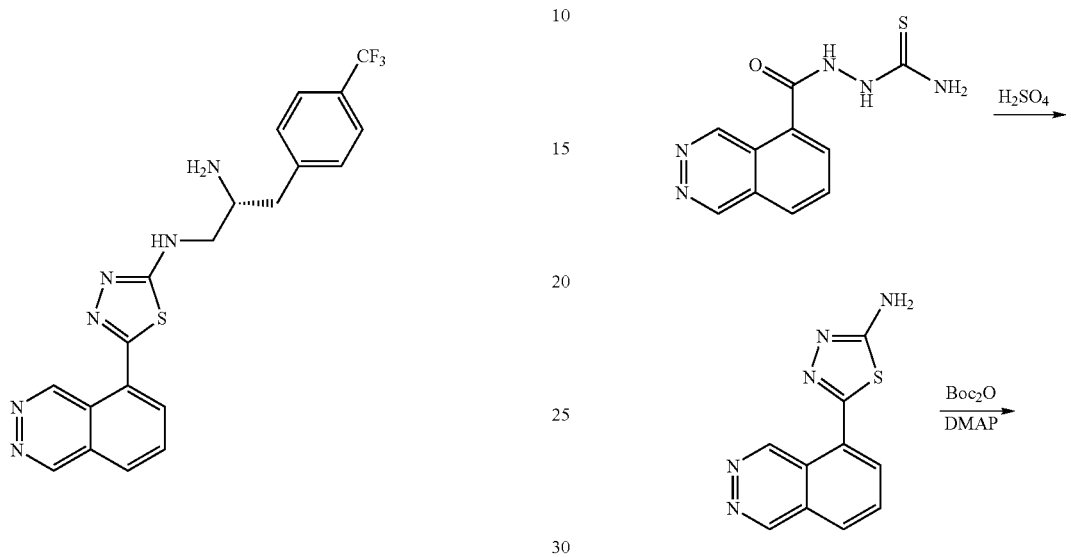
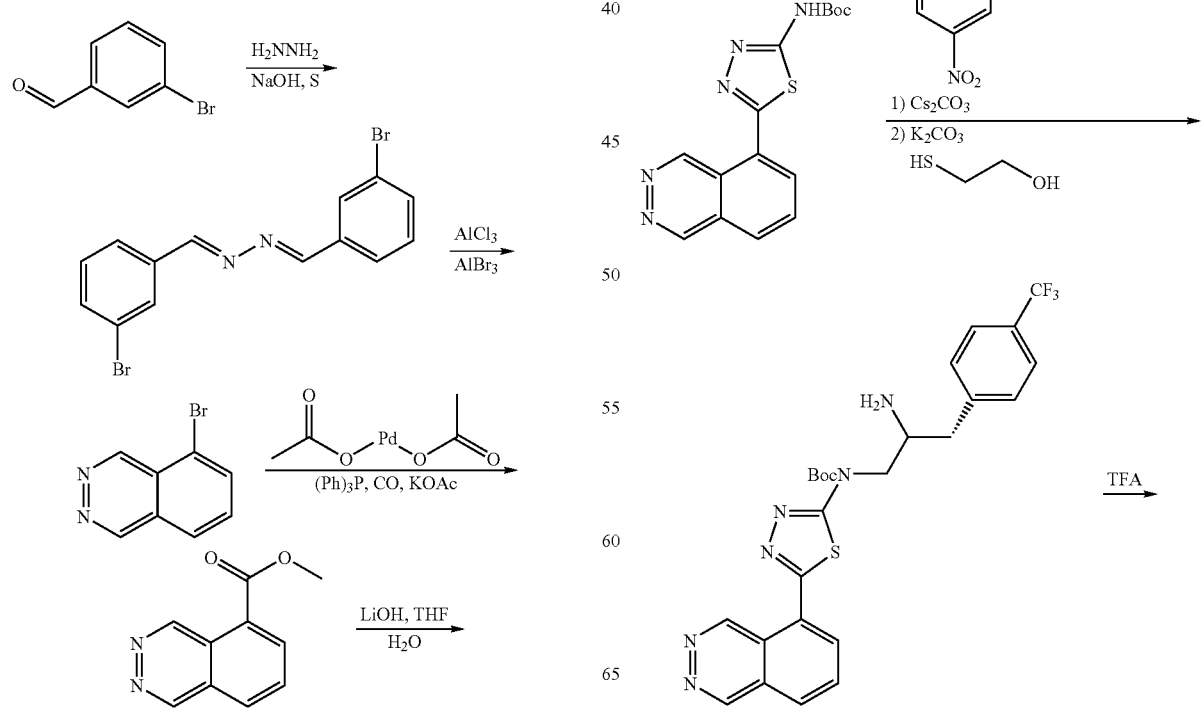

-continued

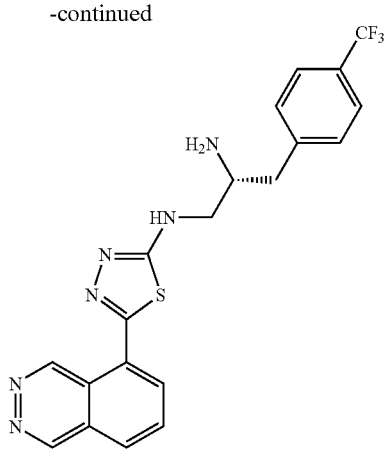

(1E,2E)-1,2-Bis(3-bromobenzylidene)hydrazine. To a 250 mL 3-neck round-bottom flask equipped with condenser was added sodium hydroxide (6.2 g, 156 mmol), sulfur (5.0 g, 156 mmol), and hydrazine (5.0 g, 156 mmol). The mixture was stirred at reflux 85° C. for 2 hours. The solution was cooled to room temperature and treated dropwise via syringe with 3-bromobenzaldehyde (18 mL, 156 mmol). The precipitate was recovered by filtration, washed with water and dried in an oven to provide (1E,2E)-1,2-bis(3-bromobenzylidene)hydrazine (23 g, 40%). LCMS (M+H) 367.1 calc. for $C_{14}H_{\;}Br_2N_2$ 366.9. $^1H$ NMR (400 MHz, CDCl$_3$): δ ppm 7.30-7.35 (m, 2H) 7.59 (d, J=7.82 Hz, 2H) 7.70-7.73 (d, 2H) 8.03 (s, 2H) 8.56 (s, 2H).

5-Bromophthalazine. To a 250 mL 3-neck round-bottom flask was added (1E,2E)-1,2-bis(3-bromobenzylidene)hydrazine (13.0 g, 35.5 mmol), aluminum(III) chloride (71.0 g, 533 mmol), and aluminum(III) bromide (71.0 g, 266 mmol). The mixture was stirred at 185-200° C. for 1 hour. The dark gum was cooled in an ice bath and slowly treated with 1.5 L of water. The suspension was filtered, and the precipitate was washed with 5% HCl. The solution was made basic with 15% potassium hydroxide and extracted with EtOAc three times. The organic extracts were dried over sodium sulfate, filtered and concentrated in vacuo. The residue was recrystallized from EtOAc and hexane to provide 5-bromophthalazine (3.12 g, 42%). LCMS (M+H) 209.2 calc. for $C_8H_6BrN_2$ 209.0. $^1H$ NMR (400 MHz, CDCl$_3$): δ ppm 7.78-7.83 (m, 1H) 7.95 (d, J=8.02 Hz, 1H) 8.14 (d, 1H) 9.49 (s, 2H).

Methyl phthalazine-5-carboxylate. To a 140 mL pressure flask was added 5-bromophthaiazine (3.5 g, 17 mmol), palladium (II) acetate (0.98 g, 4.4 mmol), triphenylphosphine (1.3 g, 5.0 mmol), potassium acetate (2.1 g, 21 mmol), MeOH (20 mL) and DMF (20 mL). The flask was sealed and purged with CO (3×). The flask was charged with CO to 40 PSI and stirred at 100° C. 15 hours. The suspension was filtered through Celite, the cake was washed with MeOH, and the filtrate was concentrated. The residue was taken up in DCM and washed with saturated sodium bicarbonate (2×), saturated sodium chloride (2×) and water (2×). The organic layer was dried over sodium sulfate, filtered and concentrated in vacuo. The residue was adsorbed on to a plug of silica gel and purified by chromatography through a Redi-Sep pre-packed silica gel column, eluting with a gradient of EtOAc in hexane to provide methyl phthalazine-5-carboxylate (1.0 g, 32%). LCMS (M+H) 189.2 calc. for $C_{10}H_9N_2O_2$ 189.1. $^1H$ NMR (400 MHz, CDCl$_3$): δ ppm 4.05 (s, 3H) 8.06 (d, J=8.41 Hz, 1H) 8.51-8.56 (m, 1H) 8.71 (d, 1H) 9.64 (s, 2H).

Phthalazine-5-carboxylic acid. To a 50 mL round bottom flask was added methyl phthalazine-5-carboxylate (1.0 g, 5 mmol), lithium hydroxide (0.3 g, 11 mmol), THF (4 mL) and water (4 mL). The resulting solution was stirred for 1 hour at room temperature. After removal of THF, the residue was acidified with 1N HCl until a precipitate was formed. The precipitate was filtered to provide phthalazine-5-carboxylic acid, used directly for next step. LCMS (M+H) 175.1 calc. for $C_9H_7N_2O_2$ 175.0. $^1H$ NMR (400 MHz, CDCl$_3$): δ ppm 8.06 (d, J=8.41 Hz, 1H) 8.51-8.56 (d, 1H) 8.71 (d, 1H) 9.64 (s, 2H). Carboxylic acid H not detected.

1-(Phthalazine-5-carbonyl)thiosemicarbazide. To a 100 mL round bottom flask was added phthalazine-5-carboxylic acid (0.50 g, 2.9 mmol) 1,1'-carbonyldiimidazole (0.93 g, 5.7 mmol) and DMF (2.2 mL). The mixture was stirred at 70° C. for 1 hour and treated with thiosemicarbazide (0.81 g, 8.9 mmol). The resulting mixture was stirred at 70° C. for 30 minutes. The mixture was concentrated under vacuum to remove almost all of the DMF. The remaining residue was treated with 2 N HCl with stirring until the solution reached pH 4. Upon standing, a yellow solid formed. The precipitate was recovered by filtration, washing with water and air dried to provide 1-(phthalazine-5-carbonyl)thiosemicarbazide (0.45 g, 63%).

5-(Phthalazine-5yl)-1,3,4-thiadiazol-2-amine. To a 100 mL round bottom flask was added 1-(phthalazine-5-carbonyl)thiosemicarbazide (0.20 g, 0.81 mmol) and concentrated sulfuric acid (10 mL). The resulting solution was stirred at room temperature for 3 hours. The reaction mixture was poured into a mixture of 10 mL 33% aqueous ammonia and 10 mL ice with stirring. The resulting solution was adjusted to pH 8 with additional ammonia solution. The product was obtained as a yellow solid via filtration and washing with water. The solid was dried in a vacuum oven for 24 hours at 50° C. to provide 5-(phthalazine-5yl)-1,3,4-thiadiazol-2-amine. LCMS (M+H) 230.1 calc. $C_{10}H_8N_5S$ for 230.0. $^1H$ NMR (400 MHz, CDCl$_3$): δ ppm 8.23 (m, J=8.41 Hz, 1H) 8.46 (d, 1H) 8.53 (d, 1H) 9.63 (d, J=16.24 Hz, 2H). NH$_2$ not detected.

tert-Butyl 5-(phthalazin-5-yl)-1,3,4-thiadiazol-2-ylcarbamate. To a 100 mL round bottom flask was added 5-(phthalazine-5yl)-1,3,4-thiadiazol-2-amine (0.25 g, 1.1 mmol), di-tert-butylpyrocarbonate (0.48 g, 2.2 mmol), DMF (50 mL) and 4-(dimethylamino)pyridine (0.002 g, 0.02 mmol). The mixture was heated at 60° C. for 2 hours. EtOAc (200 mL) was added and the mixture was washed with saturated aqueous ammonium chloride. The organic layer was dried over sodium sulfate and the solution was evaporated to a yellow solid. The product was recovered by filtration and washing with EtOAc to provide tert-butyl 5-(phthalazin-5-yl)-1,3,4-thiadiazol-2-ylcarbamate (0.14 g, 39%). LCMS (M+H) 330.2 calc. for $C_{15}H_{16}N_5O_2S$ 330.1. $^1H$ NMR (400 MHz, CDCl$_3$): δ ppm 1.54 (s, 9H) 8.23 (d, J=8.41 Hz, 1H) 8.46 (s, 1H) 8.53 (d, 1H) 9.63 (d, J=16.24 Hz, 2H)). NH not detected.

tert-Butyl (S)-2-amino-3-(4-(trifluoromethyl)phenyl)propyl(5-(phthalazin-5-yl)-1-3,4-thiadiazol-2-yl)carbamate. To a 50 mL round bottom flask was added tert-butyl 5-(phthalazin-5-yl)-1,3,4-thiadiazol-2-ylcarbamate (0.13 g, 0.41 mmol), cesium carbonate (0.27 g, 0.82 mmol) and DMF (10 mL). The mixture was heated at 50° C. and treated with (S)-2-(4-(trifluoromethyl)benzyl)-1-4-nitrophenylsulfonyl) aziridine (0.32 g, 0.82 mmol) in 10 mL DMF dropwise. The mixture was heated at 50° C. for 30 minutes. To the resulting suspension was added potassium carbonate (0.28 g, 2.0 mmol) and 2-mercaptoethanol (0.096 g, 1.23 mmol) and the mixture was stirred for 30 minutes. The crude product was adsorbed on to a plug of silica gel and purified by chromatography through a Redi-Sep pre-packed silica gel column, eluting with a gradient of DCM in MeOH to provide tert-butyl (S)-2-amino-3(4-(trifluoromethyl)phenyl)propyl(5-(phthalazin-5-yl)-1-3,4-thiadiazol-2-yl)carbamate (70 mg, 32%). LCMS (M+H) 531.2 calc. for $C_{25}H_{26}F_3N_6O_2S$ 531.2. $^1H$ NMR (400 MHz, CDCl$_3$): δ ppm 1.54 (s, 9H) 2.83 (m, J=14.28, 8.61 Hz, 1H) 3.10 (m, J=14.28, 4.50 Hz, 1H) 3.71 (b, 1H) 4.22-4.36 (m, 2H) 7.12-7.16 (d, 2H) 7.38 (d, J=8.02 Hz, 2H) 7.56-7.63 (d, 1H) 7.90-7.97 (d, 2H) 8.14 (d, 1H) 9.56 (s, 1H) 9.91 (s, 1H). NH not detected.

N—((S)-2-Amino-3-(4-(trifluoromethyl)phenyl)propyl)-5-(phthalazin-5-yl)-1,3,4-thiadiazol-2-amine. To a 50 mL round bottom flask was added tert-butyl (S)-2-amino-3(4-(trifluoromethyl)phenyl)propyl(5-(phthalazin-5-yl)-1,3,4-thiadiazol-2-yl)carbamate (0.025 g, 0.0476 mmol) DCM (5 mL) and TFA (5 mL). The resulting solution was stirred for 30 minutes and evaporated. The residue was dissolved in EtOAc (100 mL), washed with a mixture of aqueous saturated sodium bicarbonate plus 5% 5N NaOH, and saturated sodium bicarbonate (2×). The organic layer was dried over sodium sulfate and evaporated to provide N—((S)-2-amino-3-(4-(trifluoromethyl)phenyl)propyl)-5-(phthalazin-5-yl)-1,3,4-thiadiazol-2-amine as a tan solid (15 mg, 75%). LCMS (M+H) 431.2 calc. for $C_{20}H_{18}F_3N_6S$ 431.1. $^1$H NMR (400 MHz, CDCl$_3$): δ ppm 2.83 (dd, J=14.28, 8.61 Hz, 2H) 3.10 (dd, J=14.28, 4.50 Hz, 1H) 3.71 (m, 1H) 4.22 (d, 2H) 7.12-7.15 (d, 2H) 7.39 (d, J=8.22 Hz, 1H) 7.60 (d, 1H) 8.07 (m, J=1.17 Hz, 1H) 8.11 (d, 1H) 8.17 (d, 1H) 9.70 (s, 1H) 9.87 (s, 1H). 2H not detected.

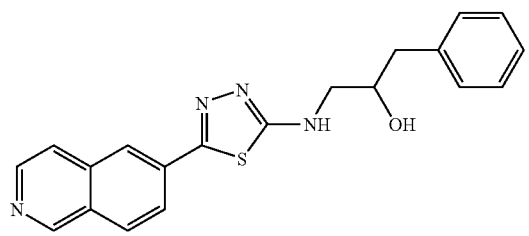

Example 29

(±)-1-(5-(isoquinolin-6-yl)-1,3,4-thiadiazol-2-ylamino)-3-phenylpropan-2-ol. Example 29 was synthesized as shown in Scheme 13.

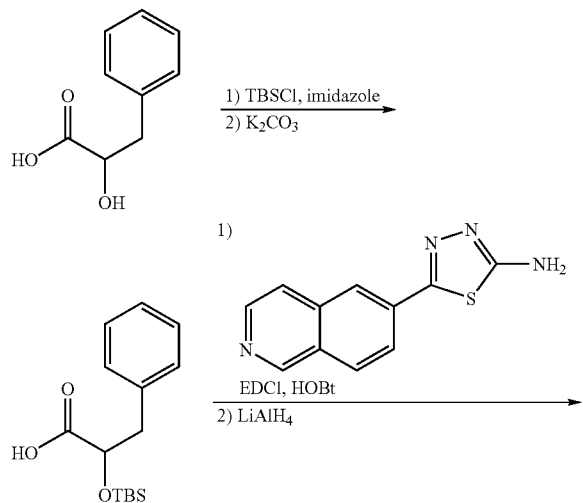

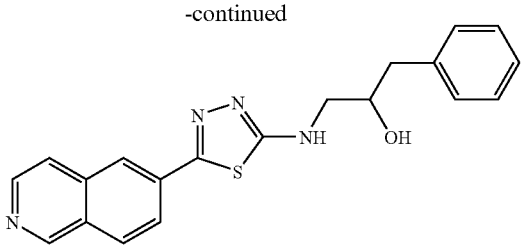

(±)-2-(tert-Butyldimethylsilyloxy)-3-phenylpropanoic acid. (±)-2-Hydroxy-3-phenylpropanoic acid (Sigma, 3.0 g, 18 mmol) was dissolved in 13 mL of DMF and chilled to 0° C. Imidazole (2.5 g, 36 mmol) and tert-butyldimethylsilylchloride (10 g, 69 mmol) were added. The mixture was allowed to warm to room temperature. After 12 hours, the mixture was diluted with 450 mL of 1:1 EtOAc:hexanes. The mixture was washed with 300 mL of 1M citric acid, 300 mL of water, and 150 mL of sat. Na$_2$SO$_4$, and the organic layer was evaporated. The residue was taken up in 170 mL of MeOH. The resulting mixture was chilled to 0° C. and potassium carbonate (5.7 g, 42 mmol) and 60 mL of water were added. The mixture was warmed to room temperature and stirred for 4 hours. The solvent was evaporated under reduced pressure. The residue was taken up in 5 mL of water and 1 M citric acid was added until the mixture reached pH 4.0. The mixture was extracted with EtOAc (3×100 mL), and the combined organic extracts were dried over MgSO$_4$. The mixture was filtered and evaporated under reduced pressure. The residue was purified by flash chromatography on silica gel (eluting with a gradient of 10% to 30% EtOAc in hexanes) to afford (±)-2-(tert-butyldimethylsilyloxy)-3-phenylpropanoic acid (2.0 g, 40%) as a clear oil. $^1$H NMR (400 MHz, CDCl$_3$): δ ppm 7.49-7.37 (m, 5H), 4.60 (dd, J=3.7 Hz, 7.6 Hz, 1H), 3.30 (dd, J=3.7 Hz, 13.7 Hz, 1H), 3.12 (dd, J=7.8 Hz, 13.6 Hz, 1H), 1.03 (s, 9H), 0.12 (s, 3H), 0.00 (s, 3H). Carboxyl H was not detected.

(±)-2-(tert-Butyldimethylsilyloxy)-N-(5-(isoquinolin-6-yl)-1,3,4-thiadiazol-2-yl)-3-phenylpropanamide. (±)-2-(tert-Butyldimethylsilyloxy)-3-phenylpropanoic acid (1.2 g, 4.3 mmol) was taken up in 18 mL of DMF. N1-((ethylimino)methylene)-N3,N3-dimethylpropane-1,3-diamine hydrochloride (1.4 g, 7.1 mmol) and HOBt (1.4 g, 11 mmol) were added. After 10 minutes, 5-(isoquinolin-6-yl)-1,3,4-thiadiazol-2-amine (0.81 g, 3.6 mmol) (prepared as shown in Scheme 5 using isoquinoline-6-carboxylic acid, commercially available from AstaTech Product List (Order Number 62874), instead of 4-chlorothieno[2,3-c]pyridine-2-carboxylic acid) was added. The mixture was stirred overnight. It was then partitioned between 50 mL of EtOAc and 50 mL of aq. NH$_4$Cl. The aqueous portion was extracted twice with 50 mL of EtOAc. The combined organic extracts were washed with water (3×50 mL) and brine (50 mL) and dried over MgSO$_4$. The mixture was filtered and evaporated under reduced pressure. The residue was purified by flash chromatography on silica gel (eluting with a gradient of 10% to 50% EtOAc in hexanes) to provide (±)-2-(tert-butyldimethylsilyloxy)-N-(5-(isoquinolin-6-yl)-1,3,4-thiadiazol-2-yl)-3-phenylpropanamide (0.45 g, 26%) as a yellow solid.

1-(5-(Isoquinolin-6-yl)-1,3,4-thiadiazol-2-ylamino)-3-phenylpropan-2-ol. (±)-2-(tert-Butyldimethylsilyloxy)-N-(5-(isoquinolin-6-yl)-1,3,4-thiadiazol-2-yl)-3-phenylpropanamide (0.44 g, 0.9 mmol) was taken up in 9 mL of THF and chilled to 0° C. Lithium aluminum hydride (4 mL, 1.0 M in THF) was added. After 1 hour, the mixture was poured into 50 mL of ½ saturated aqueous Rochelle's salt and diluted with 25 mL of ether. The mixture was stirred for 1 hour. The mixture was partitioned in a separatory funnel, and the aqueous portion was extracted twice with 50 mL of EtOAc. The combined organic extracts were washed with 50 mL of brine and dried over MgSO$_4$. Filtration and concentration under reduced pressure, followed by purification by flash chromatography on silica gel (eluting with a gradient of 2% to 10% MeOH in DCM) afforded (±)-1-(5-(isoquinolin-6-yl)-1,3,4-thiadiazol-2-ylamino)-3-phenylpropan-2-ol (0.005 g, 2%) as a yellow oil. LCMS (M+H) 363 calc. for C$_{20}$H$_{19}$N$_4$OS 363.1. $^1$H NMR (400 MHz, CD$_3$OD): δ ppm 9.27 (s, 1H), 8.50 (d, J=5.2 Hz, 1H), 8.24 (s, 1H), 8.20 (d, J=1.5 Hz, 2H), 7.90 (d, J=5.8 Hz, 1H) 7.33-7.29 (m, 5H), 7.26-7.22 (m, 1H), 4.14-4.10 (m, 1H), 3.60 (dd, J=3.9 Hz, 13.5 Hz, 1H), 3.40 (dd, J=7.5 Hz, 13.5 Hz, 1H), 2.91 (dd, J=5.4 Hz, 13.7 Hz, 1H), 2.82 (dd, J=7.6 Hz, 13.7 Hz, 1H). 1H not detected.

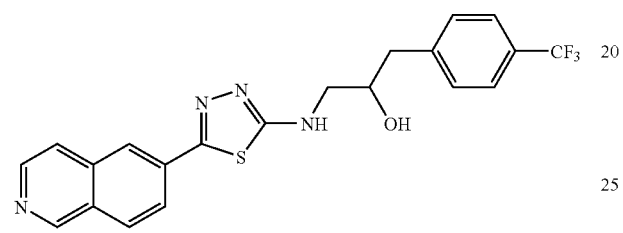

Example 30

(±)-1-(5-(Isoquinolin-6-yl)-1,3,4-thiadiazol-2-ylamino)-3-(4-(trifluoromethyl)phenyl)propan-2-ol. The title compound was synthesized as shown in Scheme 7 using 1-amino-3-(4-(trifluoromethyl)phenyl)propan-2-ol (prepared as described in J. Org. Chem. 46(20), 4051-4057, 1981) instead of furan-2-ylmethanamine. HRMS (M+H) 431.11548 calc. for C$_{21}$H$_{18}$F$_3$N$_4$OS 431.11479. $^1$H NMR (400 MHz, CD$_3$OD): δ ppm 9.27 (s, 1H), 8.50 (d, J=5.7 Hz, 1H), 8.25 (s, 1H), 8.20 (s, 2H), 7.90 (d, J=5.7 Hz, 1H), 7.61 (d, J=8.2 Hz, 2H), 7.50 (d, J=8.2 Hz, 2H), 4.20-4.11 (m, 1H), 3.63 (dd, J=4.1 Hz, 13.7 Hz, 1H), 3.44 (dd, J=7.4 Hz, 13.5 Hz, 1H), 3.02 (dd, J=4.9 Hz, 13.7 Hz, 1H), 2.88 (dd, J=8.4 Hz, 13.7 Hz, 1H), 1.78 (d, J=6.9 Hz, 1H). 1H not detected.

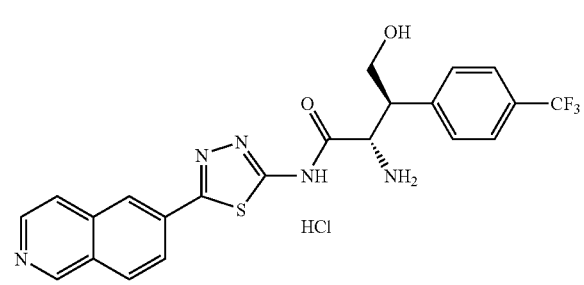

Example 31

(2S,3S)-2-Amino-4-hydroxy-N-(5-(isoquinolin-6-yl)-1,3,4-thiadiazol-2-yl)-3-(4-(trifluoromethyl)phenyl)butanamide hydrochloride. Example 31 was synthesized as shown in Scheme 14.

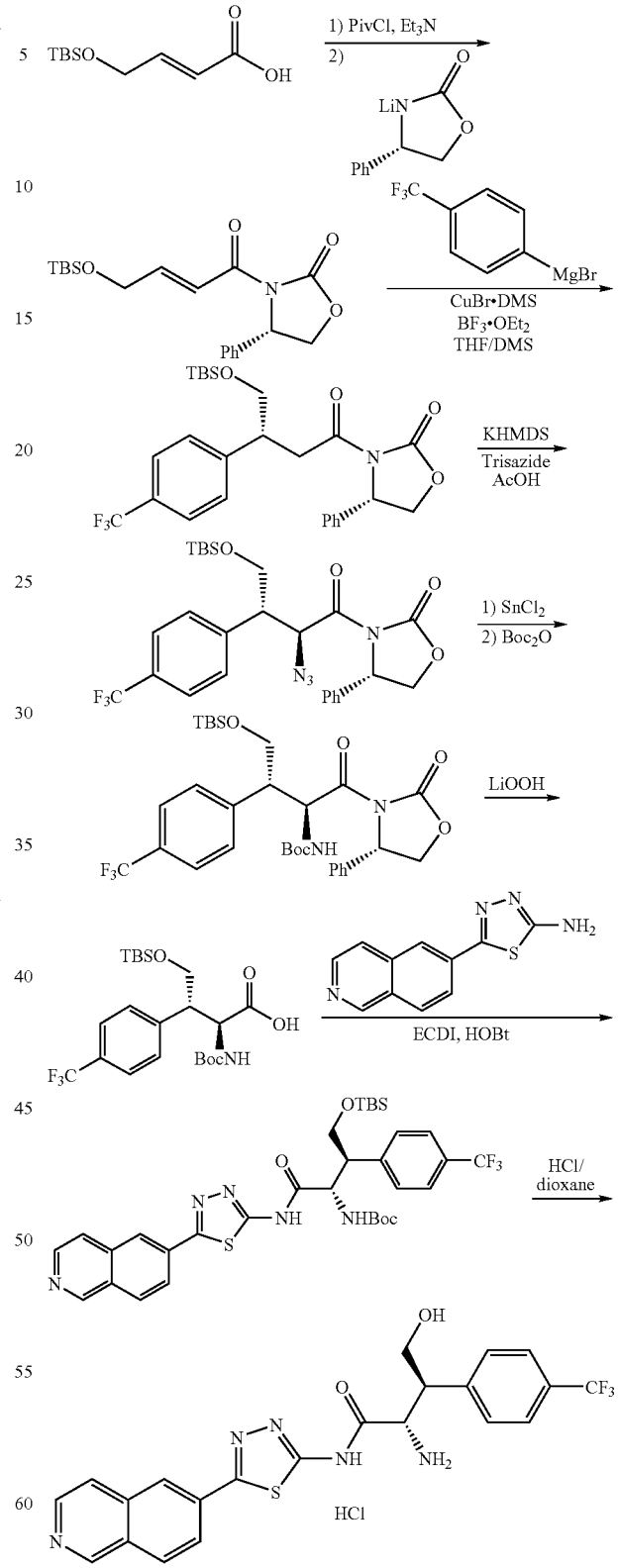

(S,E)-3-(4-(tert-Butyldimethylsilyloxy)but-2-enoyl)-4-phenyloxazolidin-2-one. To a solution of (E)-4-(tert-butyldimethylsilyloxy)but-2-enoic acid (18.0 g, 83.6 mmol)

(prepared as described in Angewandte Chemie, International Edition (2002), 41(9), 1603-1607) in 400 mL of THF was added TEA (13.2 mL, 95 mmol). The mixture was chilled to −78° C. Pivaloyl chloride (10.2 mL, 83 mmol) (commercially available from Aldrich, Milwaukee, Wis.) was added. After 10 minutes, the mixture was warmed to room temperature and stirred for 45 minutes. The mixture was then chilled to −78° C. In a separate flask, (S)-4-phenyloxazolidin-2-one (12.3 g, 79 mmol) was taken up in 125 mL of THF and chilled to −78° C. n-Butyllithium (32 mL, 2.5 M in hexanes)(commercially available from Acros Organics (Order Number 30385)) was added to the (S)-4-phenyloxazolidin-2-one mixture, and the mixture was stirred for 20 minutes. The metallated oxazolidinone was then cannulated into the pivaloyl anhydride mixture. The combined mixture was then warmed to 0° C. and stirred for 1 hour. The reaction was quenched with 250 mL of aq NH$_4$Cl and diluted with 250 mL of water. The mixture was extracted with EtOAc (2×250 mL) and the combined organic extracts were washed with brine (150 mL) and dried over MgSO$_4$. Filtration and concentration under reduced pressure afforded a yellow solid that was recrystallized from DCM/hexanes to afford (S,E)-3-(4-(tert-butyldimethylsilyloxy)but-2-enoyl)-4-phenyloxazolidin-2-one (17.8 g, 62%) as a white solid. $^1$H NMR (400 MHz, CDCl$_3$): δ ppm 7.46 (dt, J=2.1, 15.1 Hz, 1H), 7.31-7.20 (m, 5H), 7.02 (dt, J=3.4, 15.3 Hz, 1H), 5.40 (dd, J=3.9, 8.6 Hz, 1H), 4.61 (t, J=8.8 Hz, 1H), 4.19 (dd, J=3.9 Hz, 8.8 Hz, 1H), 0.85 (s, 9H), 0.00 (s, 6H). 2H were obscured.

(4S)-3-((3R)-4-((tert-Butyl(dimethyl)silyl)oxy)-3-(4-(trifluoromethyl)phenyl)butanoyl)-4-phenyl-1,3-oxazolidin-2-one. Magnesium turnings (1.3 g, 55 mmol) were flattened with a hammer into small pieces. The pieces were transferred to a flask equipped with a reflux condenser. THF (5 mL) was added, followed by a crystal of iodine. 4-Trifluoromethylbromobenzene (3.9 mL, 27.7 mmol)(commercially available from Ryan Scientific Product List (Order Number SB 01902)) was then added slowly (approximately 0.20 mL per minute). Once the reaction initiated (exotherm) an additional 50 mL of THF was added slowly along with the aryl bromide until the reaction was complete (about 30 minutes). The solution was then cannulated into a new flask, leaving the residual solid magnesium behind. The solution was further diluted with 30 mL of THF and chilled to −40° C. Copper(I) bromide dimethyl sulfide complex (5.7 g, 27.7 mmol) was then added to the mixture in 70 mL of dimethyl sulfide. The dark mixture was stirred for 1 hour and then chilled to −78° C. BF$_3$.OEt$_2$ (3.4 mL, 27.2 mmol) was added to the mixture. After 5 minutes, (S,E)-3-(4-(tert-butyldimethylsilyloxy)but-2-enoyl)-4-phenyloxazolidin-2-one (5.0 g, 13.9 mmol) was added in 5 mL of THF. The mixture was then warmed to −20° C. and stirred for 2 hours. The reaction was quenched with 200 mL of aq. NH$_4$Cl and diluted with 100 mL of water. The mixture was extracted twice with 200 mL of EtOAc and the combined organic extracts were washed with 100 mL of brine and dried over MgSO$_4$. The mixture was filtered and evaporated under reduced pressure. The residue was purified by flash chromatography on silica gel (eluting with a gradient of 5% to 25% EtOAc in hexanes) to provide (S)-3-((R)-4-(tert-butyldimethylsilyloxy)-3-(trifluoromethylphenyl)butanoyl)-4-phenyloxazolidin-2-one (4.4 g, 62%) as a yellow solid. $^1$H NMR (400 MHz, CDCl$_3$): δ ppm 7.51 (d, J=8.2 Hz, 2H), 7.25-7.23 (m, 5H), 7.03 (d, J=7.1 Hz, 2H), 5.42 (dd, J=4.1 Hz, 8.8 Hz, 1H), 4.69 (t, J=8.8 Hz, 1H), 4.24 (dd, J=4.1 Hz, 9.0 Hz, 1H), 3.78 (dd, J=5.3 Hz, 9.8 Hz, 1H), 3.74 (dd, J=6.6 Hz, 9.9 Hz, 1H), 3.63 (dd, J=8.0 Hz, 16.0 Hz, 1H), 3.49-3.42 (m, 1H), 3.40 (5.9 Hz, 16.1 Hz, 1H), 0.89 (s, 9H), 0.00 (s, 6H).

(S)-3-((2S,3S)-2-Azido-4-(tert-butyldimethylsilyloxy)-3-(4-trifluoromethyl phenyl)butanoyl)-4-phenyloxazolidin-2-one. (S)-3-((R)-4-(tert-Butyldimethylsilyloxy)-3-(trifluoromethylphenyl)butanoyl)-4-phenyloxazolidin-2-one (1.5 g, 3.0 mmol) was taken up in 10 mL of THF and chilled to −78° C. KHMDS (6.6 mL, 0.5 M in toluene) was added by cannula at −78° C. The mixture was stirred for 30 minutes. Trisyl azide (1.3 g, 4.2 mmol) was then added by cannula in 5 mL of THF at −78° C. After 1 minute, acetic acid (0.77 mL, 13.5 mmol) was added to the mixture, and the flask was warmed to 30° C. with a water bath. The mixture was stirred for 90 minutes. The mixture was then diluted with 10 mL of water and 10 mL of brine. The mixture was extracted three times with 20 mL of EtOAc, and the combined organic extracts were washed with 20 mL of brine and dried over MgSO$_4$. The mixture was filtered and evaporated under reduced pressure. The residue was purified by flash chromatography on silica gel (eluting with a gradient of 5% to 30% EtOAc in hexanes) to provide (S)-3-((2S,3S)-2-azido-4-(tert-butyldimethylsilyloxy)-3-(4-trifluoromethyl phenyl)butanoyl)-4-phenyloxazolidin-2-one (0.97 g, 61%) as a yellow solid. $^1$H NMR (400 MHz, CDCl$_3$): δ ppm 7.59 (d, J=8.1 Hz, 2H), 7.46 (d, J=8.2 Hz, 2H), 7.41-7.29 (m, 5H), 5.69 (d, J=9.7 Hz, 1H), 5.42 (dd, J=4.3 Hz, 8.8 Hz, 1H), 4.70 (t, J=9.0 Hz, 1H), 4.32 (dd, J=4.3 Hz, 9.0 Hz, 1H), 3.86 (dd, J=7.2 Hz, 10.3 Hz, 1H), 3.79 (dd, J=4.7 Hz, 10.3 Hz, 1H), 3.52-2.47 (m, 1H), 0.87 (s, 9H), 0.00 (s, 6H).

(S)-3-((2S,3S)-2-Boc-amino-4-(tert-butyldimethylsilyloxy)-3-(4-trifluoromethylphenyl)butanoyl)-4-phenyloxazolidin-2-one. SnCl$_2$ (0.46 g, 2.4 mmol) in 6 mL of MeOH was chilled to 0° C. After 10 minutes, (S)-3-((2S,3S)-2-azido-4-(tert-butyldimethylsilyloxy)-3-(4-trifluoromethyl phenyl)butanoyl)-4-phenyloxazolidin-2-one (0.65 g, 1.2 mmol) was added in 6 mL of MeOH. After 5 minutes, the mixture was warmed to room temperature and stirred for 4 hours. The solvent was then removed under reduced pressure. The residue was taken up in 12 mL of dioxane. NaHCO$_3$ (0.43 g, 4.8 mmol) was then added in 1.2 mL of water, followed by di-tert-butyl dicarbonate (0.39 g, 1.8 mmol). The mixture was stirred for 12 hours and then was quenched with 5 mL of NH$_4$Cl. The mixture was diluted with 10 mL of water and extracted twice with 20 mL of EtOAc. The combined organic extracts were washed with 10 mL of brine and dried over MgSO$_4$. The mixture was filtered and evaporated under reduced pressure. The residue was purified by flash chromatography on silica gel (eluting with a gradient of 5% to 15% EtOAc in hexanes) to afford (S)-3-((2S,3S)-2-boc-amino-4-(tert-butyldimethylsilyloxy)-3-(4-trifluoromethylphenyl)butanoyl)-4-phenyloxazolidin-2-one (0.54 g, 72%) as a thick oil. $^1$H NMR (400 MHz, CDCl$_3$): δ ppm 7.56 (d, J=8.2 Hz, 2H), 7.36-7.26 (m, 7H), 6.00 (t, J=8.8 Hz, 1H), 5.37 (dd, J=4.5 Hz, 8.8 Hz, 1H), 5.03 (m, 1H), 4.67 (t, J=8.9 Hz, 1H), 4.30-4.23 (m, 1H), 4.09-4.02 (m, 1H), 3.79 (dd, J=5.7 Hz, 10.3 Hz, 1H), 3.42-3.34 (m, 1H), 1.38 (s, 9H), 0.83 (s, 9H), −0.03 (s, 6H).

(2S,3S)-2-(tert-Butoxycarbonylamino)-4-(tert-butyldimethylsilyloxy)-3-(4-(trifluoromethyl)phenyl)butanoic acid. (S)-3-((2S,3S)-2-Boc-amino-4-(tert-butyldimethylsilyloxy)-3-(4-trifluoromethyl phenyl)butanoyl)-4-phenyloxazolidin-2-one (0.50 g, 0.80 mmol) was taken up in 9 mL of THF and chilled to 0° C. Lithium hydroxide (0.067 g, 1.6 mmol) and 30% hydrogen peroxide (0.37 mL, 3.2 mmol) were added. After 2.5 hours, the reaction was quenched with 0.50 g of Na$_2$S$_2$O$_3$. The mixture was then diluted with 10 mL of aq NH$_4$Cl and extracted three times with 15 mL of EtOAc. The combined organic extracts were washed with 10 mL of brine and dried over MgSO$_4$. The mixture was filtered and concentrated under reduced pressure to afford (2S,3S)-2-(tert-butoxycarbonyl)-4-(tert-butyldimethylsilyloxy)-3-(4-(trifluoromethyl)phenyl)butanoic which was used without further purification.

tert-Butyl (2S,3S)-4-(tert-butyldimethylsilyloxy)-1-(5-(isoquinolin-6-yl)-1,3,4-thiadiazol-2-ylamino)-1-oxo-3-(4-(trifluoromethyl)phenyl)butan-2-ylcarbamate. To (2S,3S)-2-(tert-butoxycarbonyl)-4-(tert-butyldimethylsilyloxy)-3-(4-(trifluoromethyl)phenyl)butanoic acid (0.11 g, 0.23 mmol) in 3 mL of DMF was added EDCI (0.065 g, 0.34 mmol) and HOBt (0.062 g, 0.46 mmol). After 10 minutes, 5-(isoquinolin-6-yl)-1,3,4-thiadiazol-2-amine (0.057 g, 0.25 mmol) was added. 5-(isoquinolin-6-yl)-1,3,4-thiadiazol-2-amine was prepared as shown in Scheme 5 using isoquinoline-6-carboxylic acid, commercially available from AstaTech Product List (Order Number 62874), instead of 4-chlorothieno[2,3-c]pyridine-2-carboxylic acid. The mixture was stirred for 12 hours. The solvent was removed under reduced pressure and the residue was taken up in 20 mL of EtOAc. The mixture was washed with aq NH$_4$Cl (5 mL), water (5×5 mL), and brine (5 mL), then dried over MgSO$_4$. The mixture was filtered and concentrated under reduced pressure. The residue was purified by flash chromatography on silica gel (eluting with a gradient from 0 to 2.5% MeOH in DCM) to provide tert-butyl (2S,3S)-4-(tert-butyldimethylsilyloxy)-1-(5-(isoquinolin-6-yl)-1,3,4-thiadiazol-2-ylamino)-1-oxo-3-(4-trifluoromethylphenyl)butan-2-ylcarbamate (0.086 g, 54%) as a yellow solid. $^1$H NMR (400 MHz, CD$_3$OD): δ ppm 9.38 (s, 1H), 8.61-8.58 (m, 2H), 8.40 (d, J=8.9, 1H), 8.32 (d, 8.6 Hz, 1H), 8.06 (s, 1H), 8.04 (d, J=5.8 Hz, 1H), 7.70 (d, J=7.9 Hz, 2H), 7.61 (d, J=8.1 Hz, 2H), 5.01-4.95 (m, 1H), 4.11-3.96 (m, 2H), 3.62-3.55 (m, 1H), 1.38 (s, 9H), 0.87 (s, 9H), 0.02 (s, 3H), 0.00 (s, 3H). 1H not detected.

(2S,3S)-2-Amino-4-hydroxy-N-(5-(isoquinolin-6-yl)-1,3,4-thiadiazol-2-yl)-3-(4-(trifluoromethyl)phenyl)butanamide hydrochloride. tert-Butyl (2S,3S)-4-(tert-butyldimethylsilyloxy)-1-(5-(isoquinolin-6-yl)-1,3,4-thiadiazol-2-ylamino)-1-oxo-3-(4-trifluoromethylphenyl)butan-2-ylcarbamate (0.014 g, 0.020 mmol) was taken up in 2 mL of 4 N HCl in dioxane. After 1.5 hours, a white precipitate formed. The precipitate was collected by filtration to provide (2S,3S)-2-amino-4-hydroxy-N-(5-(isoquinolin-6-yl)-1,3,4-thiadiazol-2-yl)-3-(4-(trifluoromethyl)phenyl)butanamide hydrochloride (1.2 mg, 12%). LCMS (M+H) 474 calc. for C$_{22}$H$_{19}$F$_3$N$_5$O$_2$S 474.1. $^1$H NMR (400 MHz, CD$_3$OD): δ ppm 9.84-9.78 (m 1H), 8.90-8.55 (m, 6H), 7.80-6.58 (m, 3H), 4.83-4.72 (m 2H), 4.09-3.90 (m, 1H), 3.72-3.54 (m, 1H). 4H not detected.

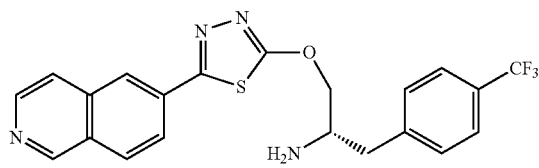

Example 32

(2S)-1-(5-(isoquinolin-6-yl)-1,3,4-thiadiazol-2-yloxy)-3-(4-(trifluoromethyl)phenyl)propan-2-amine. Example 32 was synthesized as shown in Scheme 15.

Scheme 15

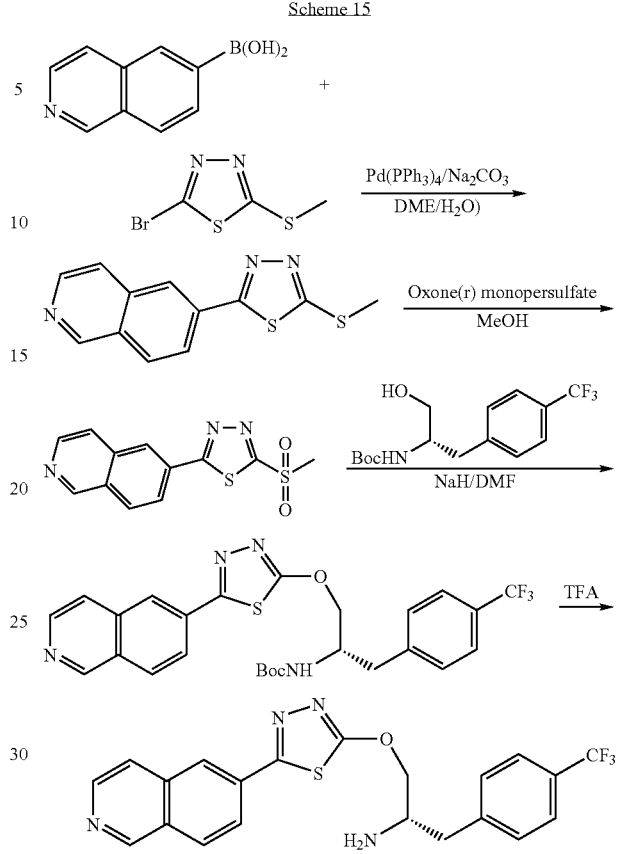

6-(5-(Methylthio)-1,3,4-thiadiazol-2-yl)isoquinolines. To a 25 mL round bottom flask was added 2-bromo-5-(methylthio)-1,3,4-thiadiazole (0.40 g, 1.9 mmol) (prepared as described in WO 97/30981, isoquinolin-6-ylboronic acid (0.39 g, 2.3 mmol) (prepared as described in US Patent Publication No. US 2007/0173506), Pd(PPh$_3$)$_4$ (0.11 g, 0.095 mmol), 2.4 mL of a 2 M Na$_2$CO$_3$ aqueous solution and 2 mL of DME. The reaction was heated at reflux for 16 hours. The reaction mixture was concentrated, and the residue was purified by column chromatography on silica gel (eluting with a gradient from 0 to 70% EtOAc in hexanes) to provide 6-(5-(methylthio)-1,3,4-thiadiazol-2-yl)isoquinoline (0.29 g, 59%) as a yellow solid. LCMS (M+H) 260 calc. for C$_{12}$H$_{10}$N$_3$S$_2$ 260.0.

6-(5-(Methylsulfonyl)-1,3,4-thiadiazol-2-yl)isoquinolines. To a 25 mL round bottom flask was added 6-(5-(methylthio)-1,3,4-thiadiazol-2-yl)isoquinoline (0.28 g, 1.1 mmol), Oxone® monopersulfate (2.7 g, 4.3 mmol) and 10 mL of MeOH. The reaction mixture was heated at reflux for 4 hours. Sodium thiosulfate solution (25 mL, 1 M) was added to the mixture. The mixture was then extracted with EtOAc (3×30 mL). The combined organic layers were concentrated in vacuo. The residue was purified by column chromatography on silica gel (eluting with a gradient of 0 to 90% EtOAc in hexanes) to provide 6-(5-(methylsulfonyl)-1,3,4-thiadiazol-2-yl)isoquinoline (0.19 g, 60%) as a yellow solid. LCMS (M+H) 292 calc. for C$_{12}$H$_{10}$N$_3$O$_2$S$_2$ 292.0. $^1$H NMR (400 MHz, CD$_3$OD): δ ppm 2.77-2.79 (m, 3H), 7.19 (d, J=5.67 Hz, 1H), 7.49-7.53 (m, 1H), 7.54-7.58 (m, 1H), 7.78 (d, J=5.87 Hz, 1H), 7.92 (s, 1H), 8.57 (s, 1H).

tert-Butyl (S)-1-(5-(isoquinolin-6-yl)-1,3,4-thiadiazol-2-yloxy)-3-(4-(trifluoromethyl)phenyl)propan-2-ylcarbamate.

A 25 mL round bottom flask was charged with sodium hydride (60% dispersion in mineral oil, 0.2 g), (S)-2-amino-3-(4-(trifluoromethyl)phenyl)propan-1-ol (90 mg, 0.41 mmol) and 1 mL of DMF at 0° C. After 10 minutes, 6-(5-(methylsulfonyl)-1,3,4-thiadiazol-2-yl)isoquinoline (80 mg, 0.27 mmol) in 1 mL of DMF was added dropwise. The reaction mixture was stirred at room temperature 3 hours. The mixture was evaporated. The residue was purified by reversed phase C-18 HPLC chromatography to provide tert-butyl (S)-1-(5-(isoquinolin-6-yl)-1,3,4-thiadiazol-2-yloxy)-3-(4-(trifluoromethyl)phenyl)propan-2-ylcarbamate in aqueous fractions that were not fully evaporated. LCMS (M+H) 531 calc. for $C_{26}H_{26}F_3N_4O_3S$ 531.2.

(2S)-1-(5-(Isoquinolin-6-yl)-1,3,4-thiadiazol-2-yloxy)-3-(4-(trifluoromethyl)phenyl)propan-2-amine. A 50% TFA/DCM mixture (2 mL) was added to tert-butyl (S)-1-(5-(isoquinolin-6-yl)-1,3,4-thiadiazol-2-yloxy)-3-(4-(trifluoromethyl)phenyl)propan-2-ylcarbamate. After 30 minutes, the reaction mixture was concentrated. The residue was purified by reverse phase C-18 HPLC chromatography to provide (2S)-1-(5-(isoquinolin-6-yl)-1,3,4-thiadiazol-2-yloxy)-3-(4-(trifluoromethyl)phenyl)propan-2-amine (50 mg, 42% over two steps). LCMS 431 (M+H) calc. for $C_{21}H_{18}F_3N_4OS$ 431.1. $^1$H NMR (400 MHz, CDCl$_3$): δ ppm 3.14 (d, J=6.46 Hz, 2H) 3.81-3.88 (m, 2H) 3.95-4.00 (m, 1H) 7.43 (d, J=8.02 Hz, 2H) 7.60 (d, J=8.22 Hz, 2H) 8.03 (d, J=6.26 Hz, 1H) 8.17 (s, 1H) 8.22-8.28 (m, 2H) 8.62 (d, J=6.26 Hz, 1H) 9.58 (s, 1H). 2H not detected.

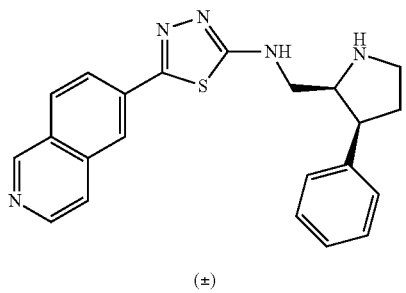

(±)

Example 33

Racemic mixture of 5-(isoquinolin-6-yl)-N-(((2S,3S)-3-phenylpyrrolidin-2-yl)methyl)-1,3,4-thiadiazol-2-amine and 5-(isoquinolin-6-yl)-N-(((2R,3R)-3-phenylpyrrolidin-2-yl)methyl)-1,3,4-thiadiazol-2-amine. This compound was synthesized as shown in Scheme 16.

Scheme 16

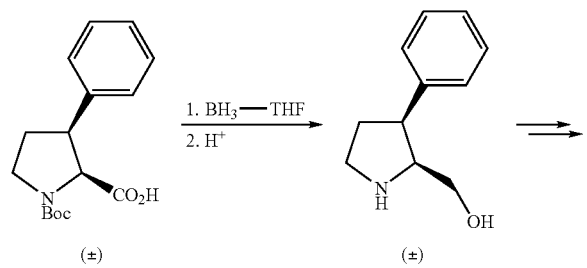

(±) (±)

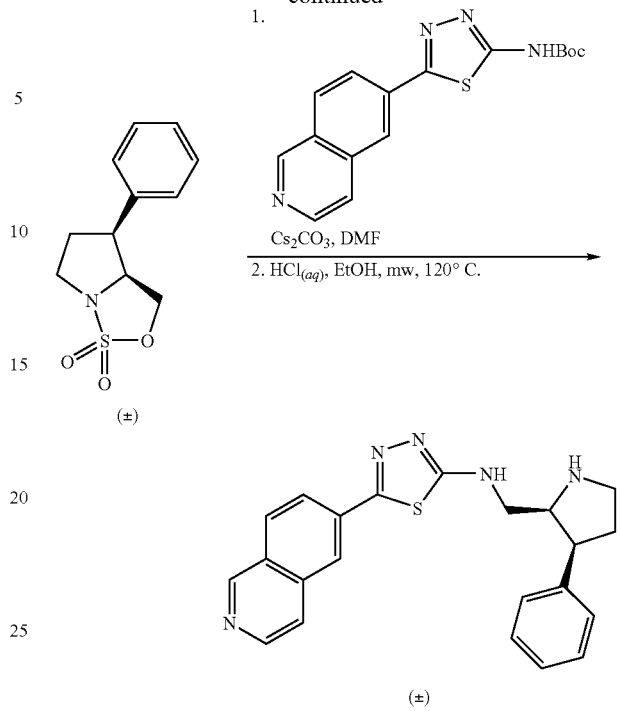

rac-(cis)-tert-Butyl 2-(hydroxymethyl)-3-phenylpyrrolidine-1-carboxylate. To a stirred mixture of rac-(cis)-1-(tert-butoxycarbonyl)-3-phenylpyrrolidine-2-carboxylic acid (0.77 g, 2.6 mmol) (prepared as described by Damour et al. Synlett 1999, 2, 189-192) in THF (10.00 mL, 122 mmol) was added BH$_3$●THF (9.3 mL, 1.0 M in THF, 9.3 mmol) slowly at 0° C. The resulting mixture was stirred at room temperature overnight. The mixture was then cooled to 0° C., and the resulting mixture was quenched with MeOH, concentrated, and the remaining residue was diluted with 1.0 N aqueous NaOH (10 mL), and extracted with EtOAc (10 mL×3). The organic layers were washed with brine, dried over Na$_2$SO$_4$, and concentrated to give a residue which was purified with flash column chromatography (pure hexane→30% EtOAc in hexanes) to obtain the desired product as a colorless sticky syrup, which solidified upon standing. LCMS (API-ES) m/z (%): 278.4 (100%, M+H); $^1$H NMR (400 MHz, CDCl$_3$) δ ppm (mixture of rotatomers) 1.50 (s, 9H) 2.10-2.17 (m, 2H), 3.33 (d, J=4.70 Hz, 2H), 3.42-3.51 (m, 1H), 3.60-3.67 (m, 2H), 4.26-4.33 (m, 1H) 7.23 (d, J=11.74 Hz, 2H), 7.30-7.39 (m, 3H).

rac-(cis)-3-Phenylpyrrolidin-2-yl)methanol. To a stirred solution of rac-(cis)-tert-butyl-2-(hydroxymethyl)-3-phenylpyrrolidine-1-carboxylate, racemic (0.2133 g, 769 μmol) in THF (2.0 mL, 24409 μmol) was added hydrogen chloride (4.0 N solution in 1,4-dioxane) (1.9 mL, 7690 μmol) at room temperature. The resulting mixture was stirred at room temperature for 1 hour. The entire mixture was neutralized with 5N NaOH and concentrated to give rac-(cis)-3-phenylpyrrolidin-2-ylmethanol (76 mg, 56% yield) as a white solid, which was pure enough to be used without further purification.

rac-(3aS,4S)-4-Phenyltetrahydro-3H-pyrrolo[1,2-c][1,2,3]oxathiazole 1,1-dioxide. The preparation of the cyclic sulfamidate derivative from rac-(cis)-3-phenylpyrrolidin-2-yl)methanol via the corresponding cyclic sulfamidite was accomplished using the general sequence as that described for Example 1 in Schemes 1a and 1b in an overall 24% yield. The product was used directly without further purification.

5-(Isoquinolin-6-yl)-N-(3-phenylpyrrolidin-2-yl)methyl)-1,3,4-thiadiazol-2-amine. To a stirred mixture of tert-butyl 5-(isoquinolin-6-yl)-1,3,4-thiadiazol-2-ylcarbamate (0.12 g, 0.37 mmol) and cesium carbonate (0.30 g, 0.91 mmol) in DMF (1.00 mL, 13 mmol) was added slowly a solution of crude cyclic sulfamidate (0.13 g, 0.55 mmol) in DMF (1.0 mL) at 50° C. The resulting mixture was stirred at the same temperature for 1 hour. After cooling, the overall dark mixture was concentrated to give the crude rac-(cis)-2-((tert-butoxycarbonyl)methyl)-3-phenylpyrrolidine-1-sulfonic acid (0.21 g, 370 μmol). EtOH (0.022 mL, 370 μmol) was added and then 6N aqueous HCl (3.00 mL, 98736 μmol) was slowly added until the pH was about 2. The resulting almost homogeneous light brown solution was sealed and irradiated under microwave at 120° C. for 20 minutes. After cooling, the solution was extracted with DCM (5 mL×3) and the aqueous layer was neutralized with 5N NaOH until slightly basic and extracted with EtOAc (10 mL×3). The combined organic layers were washed with brine, dried over $Na_2SO_4$, and concentrated to give a residue which was purified with preparative TLC (5% MeOH in DCM) to obtain the desired product as a light yellow solid (26 mg, 18% in 4 steps). LCMS (API-ES) m/z (%): 388.5 (100%, M$^+$+H); $^1$H NMR (400 MHz, DMSO-d$_6$) δ ppm 9.22 (s, 1H) 8.51 (s, 1H) 8.43 (d, J=5.67 Hz, 1H) 8.35 (dd, J=8.71, 1.47 Hz, 1H) 7.91 (d, J=8.80 Hz, 1H) 7.78 (d, J=5.87 Hz, 1H) 7.31-7.39 (m, 2H) 7.22-7.29 (m, 3H) 4.53-4.61 (m, 1H) 4.39 (t, J=9.68 Hz, 1H) 3.79-3.87 (m, 1H) 3.68 (q, J=7.56 Hz, 1H) 3.49 (dd, J=9.88, 7.14 Hz, 1H) 3.34-3.44 (m, 1H) 2.51 (m, buried under DMSO peak, 1H) 2.30-2.40 (m, 1H) 2.11-2.21 (m, 1H).

Example 34

5-(5-((S)-2-Amino-3-(4-chlorophenyl)propylamino)-1,3,4-thiadiazol-2-yl)indolin-2-one. This compound was synthesized in a similar manner as that described for Example 2 using (S)-2-amino-3-(4-chlorophenyl)propanoic acid instead of (S)-2-amino-3-(4-(trifluoromethyl)phenyl)propanoic acid. LCMS (API-ES) m/z (%): 400.0 (100%, M$^+$+H); $^1$H NMR (400 MHz, DMSO-d$_6$): δ ppm 2.92 (d, J=7.1 Hz, 2H), 3.53 (m, 2H), 3.56 (s, 2H), 3.68 (bs, 1H), 3.96 (s, 1H), 6.90 (d, J=8.2 Hz, 1H), 7.35 (d, J=8.5 Hz, 2H), 7.43 (d, J=8.4 Hz, 2H), 7.57-7.62 (m, 4H), 10.62 (s, 1H).

Examples 35-41

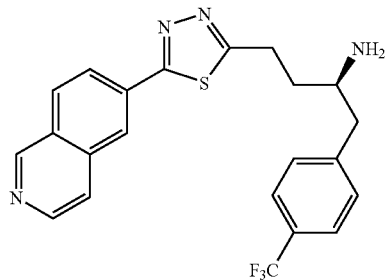

Example 35

(2R)-4-(5-(Isoquinolin-6-yl)-1,3,4-thiadiazol-2-yl)-1-(4-(trifluoromethyl)phenyl)butan-2-amine. This compound was synthesized in a similar manner as that described for Example 45 using isoquinoline-6-carboxylic acid instead of 3-fluoroisoquinoline-6-carboxylic acid and (R)-tert-butyl 2-(4-(trifluoromethyl)benzyl)-5-oxopyrrolidine-1-carboxylate instead of (R)-tert-butyl 2-oxo-5-((6-(trifluoromethyl)pyridin-3-yl)methyl)pyrrolidine-1-carboxylate. LCMS (API-ES) m/z: 429.1 (M+H$^+$).

Scheme 17

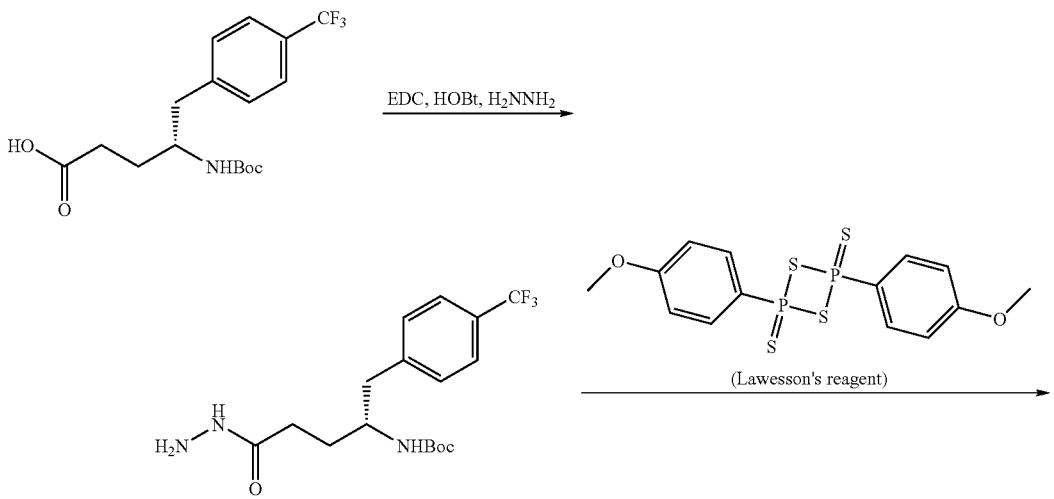

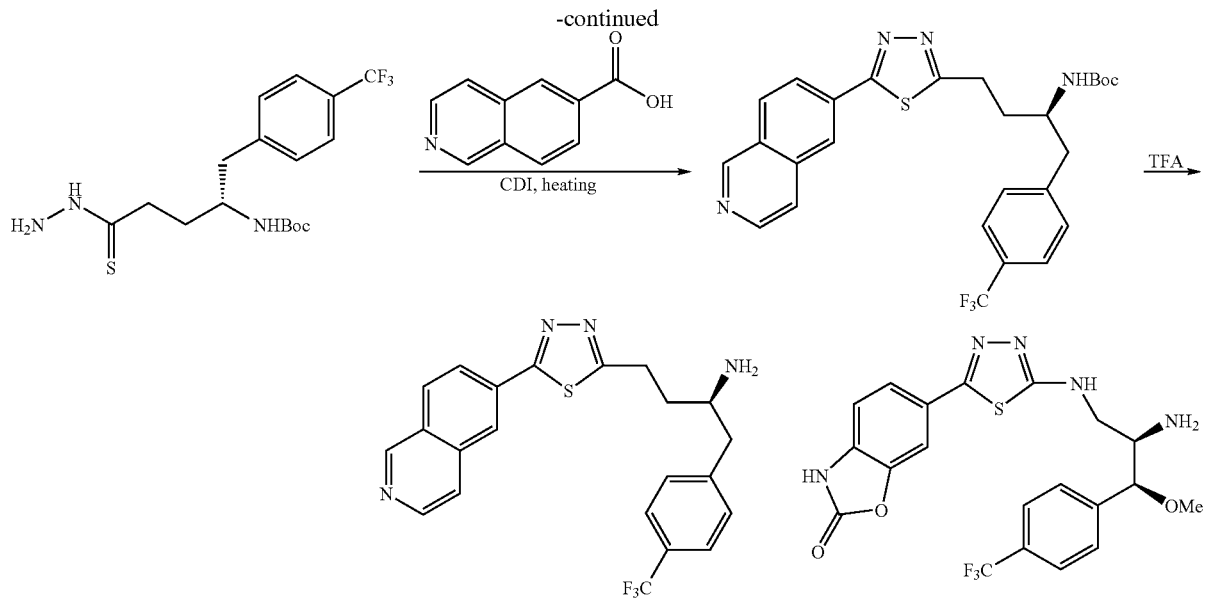

Example 36

6-(5-((2R,3S)-2-amino-3-methoxy-3-(4-(trifluoromethyl)phenyl)propylamino)-1,3,4-thiadiazol-2-yl)benzoloxazol-2(3H)-one. This compound is synthesized in a similar manner to that shown in Schemes 1 and 6, but using tert-butyl (1S, 2R)-3-hydroxy-1-methoxy-1-(4-(trifluoromethyl)phenyl)propan-2-ylcarbamate, as prepared in Scheme 18, instead of (S)-tert-butyl 1-hydroxy-3-(4-(trifluoromethyl)phenyl)propan-2-ylcarbamate.

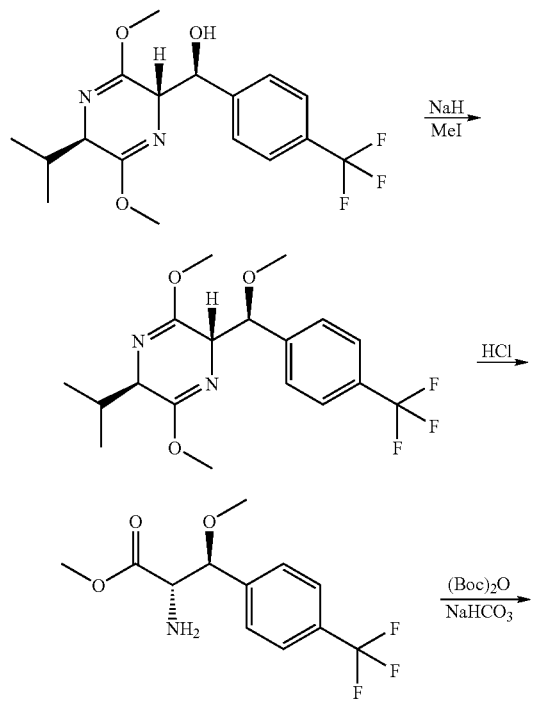

Scheme 18

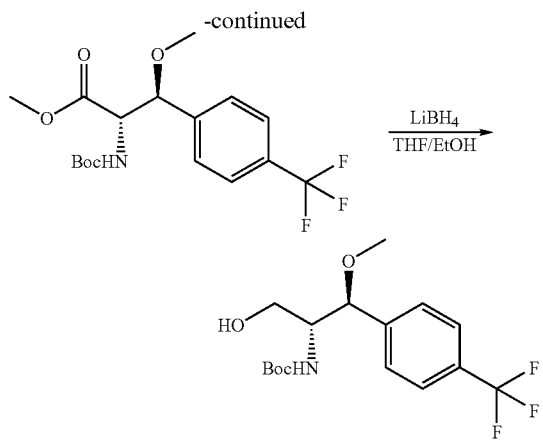

(2R,5S)-2-Isopropyl-3,6-dimethoxy-5-((S)-methoxy(4-(trifluoromethyl)phenyl)methyl)-2,5-dihydropyrazine: To a mixture of (S)-((2S,5R)-5-isopropyl-3,6-dimethoxy-2,5-dihydropyrazin-2-yl)(4-(trifluoromethyl)phenyl)methanol (4.09 g, 11.4 mmol) (prepared as shown in Scheme 27) and THF (60 mL) at 0° C., was added methyl iodide (4.28 mL, 68.5 mmol) and sodium hydride (60% dispersion in mineral oil, 0.55 g, 13.7 mmol). The mixture was stirred and gradually warmed to 10° C., then diluted with EtOAc and washed with saturated NH₄Cl. The aqueous layer was extracted with EtOAc three times. The combined organic layers were washed with water and brine, dried over Na₂SO₄ and concentrated in vacuo. The resulting product was purified by chromatography on silica gel (0-10% EtOAc-hexane) to provide the title product as a white solid (3.7 g, 88%). LCMS (API-ES) m/z: 373 (M+H⁺).

(2S,3S)-Methyl 2-amino-3-methoxy-3-(4-(trifluoromethyl)phenyl)propanoate: To a solution of (2R,5S)-2-isopropyl-3,6-dimethoxy-5-((S)-methoxy(4-(trifluoromethyl)phenyl)methyl)-2,5-dihydropyrazine (3.40 g, 9.1 mmol) in THF (25 mL) and CH₃CN (50 mL) was added 0.25 N hydrochloric acid (73 mL, 18 mmol) at room temperature. The mixture was stirred overnight and the solvent was removed in vacuo. The residue was neutralized with saturated NaHCO₃ and extracted with ether. The organic layer was dried over Na₂SO₄ and concentrated in vacuo. The resulting residue was purified by silica gel chromatography (30%-50% EtOAc-hexane) to provide the product as a colorless oil (1.1 g, 43%). LCMS (API-ES) m/z (%): 278 (M+H).

(2S,3S)-Methyl 2-(tert-butoxycarbonylamino)-3-methoxy-3-(4-(trifluoromethyl)phenyl)propanoate: To a solution of (2S,3S)-methyl 2-amino-3-methoxy-3-(4-(trifluoromethyl)phenyl)propanoate (0.94 g, 3.39 mmol) in THF (10 mL) was added di-tert-butyl dicarbonate (0.89 g, 4.07 mmol) and sodium bicarbonate (0.56 g, 6.78 mmol) at room temperature. The mixture was stirred over the weekend and filtered through a funnel. The filtrate was concentrated in vacuo. The residue was purified by silica gel chromatography (0-14% EtOAc-hexane) to provide the product as a white solid (1.1 g, 83%). LCMS (API-ES) m/z: 278, 322 (M+H⁺).

tert-Butyl (1S,2R)-3-hydroxy-1-methoxy-1-(4-(trifluoromethyl)phenyl)propan-2-ylcarbamate: To a solution of (2S, 3S)-methyl 2-(tert-butoxycarbonyl)-3-methoxy-3-(4-(trifluoromethyl)phenyl)propanoate (0.96 g, 2.5 mmol) in THF (15 mL) and EtOH (4.5 mL, 76 mmol) was added lithium borohydride (2.0 M solution in THF, 2.5 mL, 5.1 mmol) at 0° C. The reaction mixture was stirred at 0° C. for 1 hour and then the cooling bath was removed. The mixture was stirred for 1 hour at room temperature. The reaction was quenched with 5% citric acid in water. The mixture was concentrated in vacuo and the residue was extracted with EtOAc twice. The organic phase was washed with saturated NaHCO₃, water and brine, dried over Na₂SO₄ and concentrated in vacuo. The product was obtained as a white solid (0.79 g, 89%). LCMS (API-ES) m/z: 250 (M+H-100).

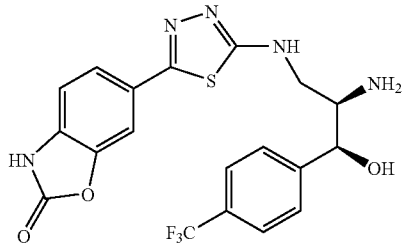

Example 37

6-(5-((2R,3S)-2-amino-3-hydroxy-3-(4-(trifluoromethyl)phenyl)propylamino)-1,3,4-thiadiazol-2-yl)benzo[d]oxazol-2(3H)-one: The title compound is synthesized in a similar manner to that shown in Schemes 1a and 6, using tert-butyl (4R)-4-((S)-((tert-butyl(dimethyl)silyl)oxy)(4-(trifluoromethyl)phenyl)methyl)-1,2,3-oxathiazolidine-3-carboxylate 2,2-dioxide, as prepared in Scheme 27, instead of (S)-tert-butyl 4-(4-(trifluoromethyl)benzyl)-1,2,3-oxathiazolidine-3-carboxylate-2,2-dioxide.

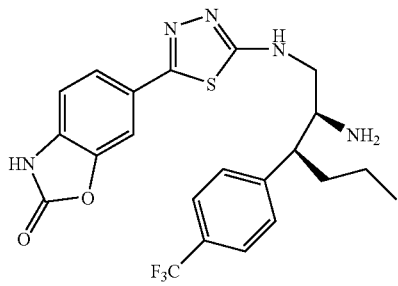

Example 38

6-(5-((2S,3S)-2-Amino-3-(4-(trifluoromethyl)phenyl)hexylamino)-1,3,4-thiadiazol-2-yl)benzo[d]oxazol-2(3H)-one. This compound is synthesized in a similar manner to that described for Example 36. The starting material, tert-butyl (2S,3S)-1-hydroxy-3-(4-(trifluoromethyl)phenyl)hexan-2-ylcarbamate, was synthesized as shown in Scheme 19.

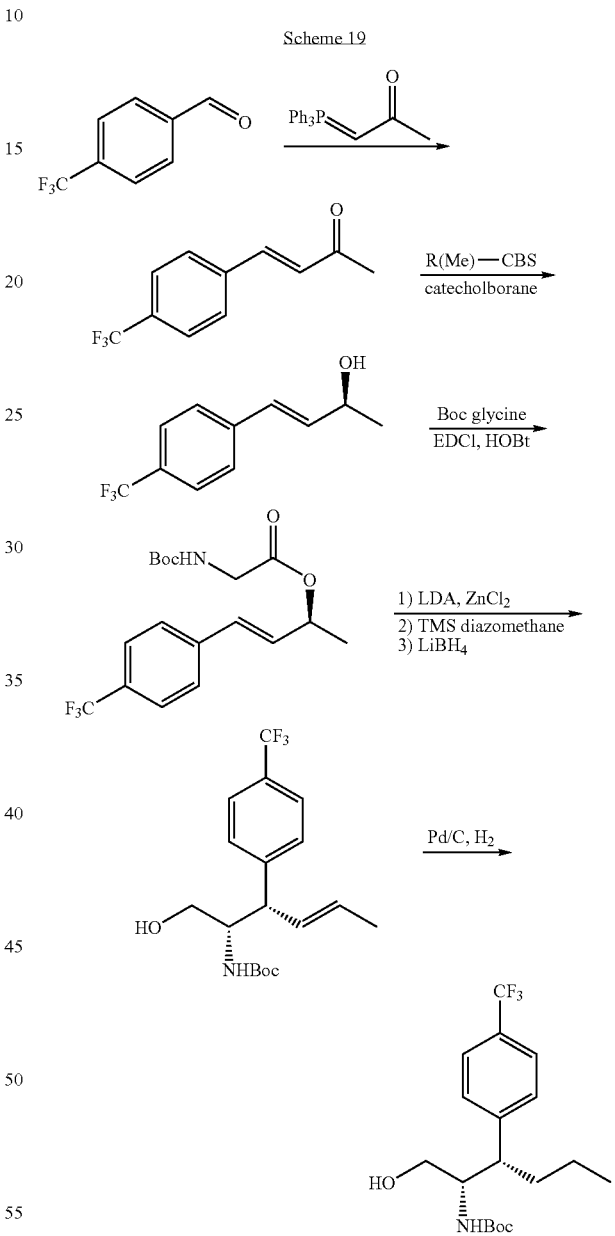

E-4-(4-(Trifluoromethyl)phenyl)but-3-en-2-one. 4-(Trifluoromethyl)benzaldehyde (25.0 g, 144 mmol)(commercially available from 3B Scientific Corporation Product List (Order Number 3B4-3644)) was taken up in 500 mL of DCM. 1-Triphenylphosphoranylidene-2-propanone (48.0 g, 151 mmol) was added. After 5 hours, an additional 3 g of the Wittig reagent was added. The mixture was stirred for 10 hours. The solvent was removed under reduced pressure, and the residue was triturated with 500 mL of 5% EtOAc/hexanes. The mixture was filtered, removing a large amount of P(O)

Ph₃. The residue was taken up in 300 mL of 2.5% EtOAc/hexanes and filtered through a pad of silica. The mixture was concentrated under reduced pressure, and the residue was found to be (E)-4-(4-(trifluoromethyl)phenyl)but-3-en-2-one (28.3 g, 92.0% yield). $^1$H NMR (400 MHz, CDCl₃) δ ppm 7.68-7.60 (m, 3H), 7.52 (d, J=16.43 Hz, 1H), 6.78 (d, J=16.4 Hz, 1H), 2.41 (s, 3H).

(S,E)-4-(4-(Trifluoromethyl)phenyl)but-3-en-2-ol. (E)-4-(4-(Trifluoromethyl)phenyl)but-3-en-2-one (15 g, 70 mmol) was taken up in 500 mL of toluene. (R)-(+)-2-Methyl-CBS-oxazaborolidine (1.09 M in toluene) (6.4 mL, 7.0 mmol) was added, and the mixture was chilled to −78° C. Catecholborane (13 mL, 119 mmol) was added dropwise via addition funnel in 125 mL of toluene. The mixture was stirred for 25 minutes and then gradually warmed to −45° C. and stirred for 2 hours. The yellow color taken on during the catecholborane addition faded during this time and the solution cleared. The mixture was quenched with 300 mL of water and warmed to room temperature. The mixture was partitioned in a separatory funnel. The organic portion was washed 3 times with 200 mL of 5% aq. KOH (to remove the catechol), twice with 200 mL of 10% aqueous HCl (to remove the CBS catalyst), and once with 200 mL of brine, and then dried over MgSO₄. Filtration and concentration under reduced pressure afforded (S,E)-4-(4-(trifluoromethyl)phenyl)but-3-en-2-ol (15 g, 99% yield) as a yellow oil that slowly crystallized. $^1$H NMR (400 MHz, CDCl₃) δ ppm 7.57 (d, J=8.22 Hz, 2H) 7.50-7.45 (m, 2H) 6.62 (d, J=16.04 Hz, 1H) 6.36 (dd, J=16.04, 6.06 Hz, 1H) 4.49-4.57 (m, 1H) 1.61 (d, J=4.30 Hz, 1H) 1.39 (d, J=6.46 Hz, 3H).

(S,E)-4-(4-(Trifluoromethyl)phenyl)but-3-en-2-yl 2-(tert-butoxycarbonylamino)acetate. (S,E)-4-(4-(Trifluoromethyl)phenyl)but-3-en-2-ol (11.2 g, 51.8 mmol) was taken up in 240 mL of DMF. N-Boc glycine (22.7 g, 130 mmol), N1-((ethylimino)methylene)-N3,N3-dimethylpropane-1,3-diamine hydrochloride (29.8 g, 155 mmol), HOBt (21.0 g, 155 mmol), and Hunig's base (27.1 mL, 155 mmol) were added. After 12 hours, the solvent was removed under reduced pressure. The residue was taken up in 500 mL of EtOAc and transferred to a separatory funnel. The mixture was washed with 200 mL of 1 N aqueous HCl, 200 mL of aqueous NaHCO₃, and 200 mL of brine, and then dried over MgSO₄. Filtration and concentration under reduced pressure, followed by flash chromatography on silica gel (2.5% to 15% EtOAc/hexanes) afforded (S,E)-4-(4-(trifluoromethyl)phenyl)but-3-en-2-yl 2-(tert-butoxycarbonyl)acetate (16.5 g, 85.3% yield) as a thick oil. $^1$H NMR (400 MHz, CDCl₃) δ ppm 7.59-7.52 (m, 2 H) 7.47 (d, J=8.22 Hz, 2 H) 6.64 (d, J=15.85 Hz, 1 H) 6.26 (dd, J=15.94, 6.55 Hz, 1 H) 5.60 (dq, J=6.55, 6.29 Hz, 1 H) 5.00 (s, 1 H) 3.85-4.00 (m, 2 H), 1.46-1.43 (m, 12 H).

tert-Butyl (2S,3S,E)-1-hydroxy-3-(4-(trifluoromethyl)phenyl)hex-4-en-2-ylcarbamate. Diisopropylamine (8.3 mL, 59 mmol) was taken up in 45 mL of THF and chilled to −20° C. Butyllithium, (2.5 M in hexane) (19 mL, 48 mmol) was added, and the mixture was stirred for 20 minutes. The mixture was then chilled to −78° C. (S,E)-4-(4-(Trifluoromethyl)phenyl)but-3-en-2-yl 2-(tert-butoxycarbonyl)acetate (8.1 g, 22 mmol) was added in 22 mL of THF at −78° C. by cannula. The mixture immediately turned purple. After 5 minutes, zinc(II) chloride (0.5 M in THF) (50 mL, 25 mmol) was added slowly to the mixture. The mixture was then gradually warmed to room temperature over 1.5 hours. The mixture was quenched with 30 mL of 10% aq. HCl. The solvent was removed under reduced pressure. The residue was taken up in 400 mL of ether. The mixture was washed with 100 mL of 10% aqueous HCl. The mixture was then extracted twice with 125 mL of 1 M aq NaOH. The combined basic extracts were acidified with concentrated HCl. The mixture was then extracted three times with 200 mL of ether. The combined ethereal extracts were dried over MgSO₄. Filtration and concentration under reduced pressure afforded (2S,3S,E)-2-(tert-butoxycarbonyl)-3-(4-(trifluoromethyl)phenyl)hex-4-enoic acid (5.3 g, 65% yield) which was carried on in the next reaction directly without any further purification.

(2S,3S,E)-Methyl 2-(tert-butoxycarbonylamino)-3-(4-(trifluoromethyl)phenyl)hex-4-enoate. (2S,3S,E)-2-(tert-Butoxycarbonyl)-3-(4-(trifluoromethyl)phenyl)hex-4-enoic acid (5.3 g, 14 mmol) was taken up in 70 mL of 3.5:1 benzene:MeOH. TMS diazomethane, (2M in hexane)(7.8 mL, 16 mmol) was added slowly to the mixture. Bubbling ensued. Approximately 2 mL excess of the TMS diazomethane reagent was added, presumably due to loss of titer of the reagent. The bubbling was monitored, and the addition was stopped when the bubbling ceased. The solvent was removed under reduced pressure. The mixture was triturated twice with 50 mL of 10% ether:hexanes, affording (2S,3S,E)-methyl 2-(tert-butoxycarbonyl)-3-(4-(trifluoromethyl)phenyl)hex-4-enoate (5.4 g, 98% yield) as a white solid. $^1$H NMR (400 MHz, CDCl₃) δ ppm 7.59 (d, J=8.22 Hz, 2H) 7.34 (d, J=8.22 Hz, 2H) 5.75-5.59 (m, 2H) 4.92-4.84 (m, 1H) 4.70-4.63 (m, 1H) 3.78-3.72 (m, 1H) 3.68 (s, 3H) 1.72 (d, J=5.28 Hz, 3H) 1.37 (s, 9H).

tert-Butyl (2S,3S,E)-1-hydroxy-3-(4-(trifluoromethyl)phenyl)hex-4-en-2-ylcarbamate. (2S,3S,E)-Methyl 2-(tert-butoxycarbonyl)-3-(4-(trifluoromethyl)phenyl)hex-4-enoate (5.4 g, 14 mmol) was taken up in 140 mL of Et₂O and chilled to 0° C. Lithium borohydride (1.2 g, 56 mmol) was added to the mixture. After 1.5 hours, about 10 mL of MeOH was added to the reaction. The mixture was stirred an additional 20 minutes and then carefully quenched by dropwise addition of aqueous NH₄Cl (20 mL). The mixture was then diluted with 50 mL of aq NH₄Cl and 50 mL of water. The mixture was partitioned, and the aqueous portion was extracted with 120 mL of ether. The combined organic extracts were washed with 100 mL of brine and dried over MgSO₄. Filtration and concentration under reduced pressure, followed by flash chromatography on silica gel (5% to 30% EtOAc/hexanes) afforded tert-butyl (2S,3S,E)-1-hydroxy-3-(4-(trifluoromethyl)phenyl)hex-4-en-2-ylcarbamate (3.9 g, 78% yield) as a sticky solid. $^1$H NMR (400 MHz, CDCl₃) δ ppm 7.56 (d, J=8.03 Hz, 2 H) 7.34 (d, J=8.03 Hz, 2 H) 5.59-5.69 (m, 2 H) 4.60-4.50 (m, 1H) 3.94 (s, 1 H) 3.75 (d, J=4.02 Hz, 2 H) 3.59 (s, 1 H) 2.15-2.07 (s, 1H) 1.69 (d, J=4.52 Hz, 4 H) 1.29 (s, 9 H).

(2S,3S,E)-2-Amino-3-(4-(trifluoromethyl)phenyl)hex-4-en-1-ol. tert-Butyl (2S,3S,E)-1-hydroxy-3-(4-(trifluoromethyl)phenyl)hex-4-en-2-ylcarbamate (0.10 g, 0.28 mmol) was taken up in 3 mL of DCM. 1 mL of TFA was added. The mixture was stirred for 1 hour. The solvent was removed under reduced pressure, and the residue was taken up in 5 mL of DCM and 5 mL of 5% aq NaOH. The mixture was partitioned, and the aqueous portion was extracted three times with 5 mL of DCM. The combined organic extracts were dried over MgSO₄. Filtration and concentration under reduced pressure afforded (2S,3S,E)-2-amino-3-(4-(trifluoromethyl)phenyl)hex-4-en-1-ol, which was used without further purification.

tert-Butyl (2S,3S)-1-hydroxy-3-(4-(trifluoromethyl)phenyl)hexan-2-ylcarbamate. tert-Butyl (2S,3S,E)-1-hydroxy-3-(4-(trifluoromethyl)phenyl)hex-4-en-2-ylcarbamate (0.51 g, 1.4 mmol) was taken up in 10 mL of MeOH. 0.10 g of 10% Pd on carbon was added, and hydrogen was bubbled through the mixture. After 2 minutes, the bubbling ceased and the reaction was kept under a balloon of hydrogen. After 2 hours, the mixture was filtered through celite and concentrated under reduced pressure, affording tert-butyl (2S,3S)-1-hydroxy-3-(4-(trifluoromethyl)phenyl)hexan-2-ylcarbamate (0.50 g, 97% yield) as a white solid.

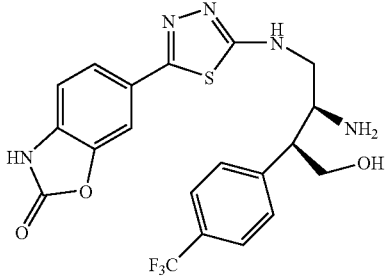

Example 39

6-(5-((2S,3S)-2-Amino-4-hydroxy-3-(4-(trifluoromethyl)phenyl)butylamino)-1,3,4-thiadiazol-2-yl)benzo[d]oxazol-2(3H)-one. This compound is synthesized in a similar manner to that described for Example 36. The starting material (2S,3S)-3-(tert-butoxycarbonyl)-4-hydroxy-2-(4-(trifluoromethyl)phenyl)butyl pivalate was synthesized as shown in Scheme 20.

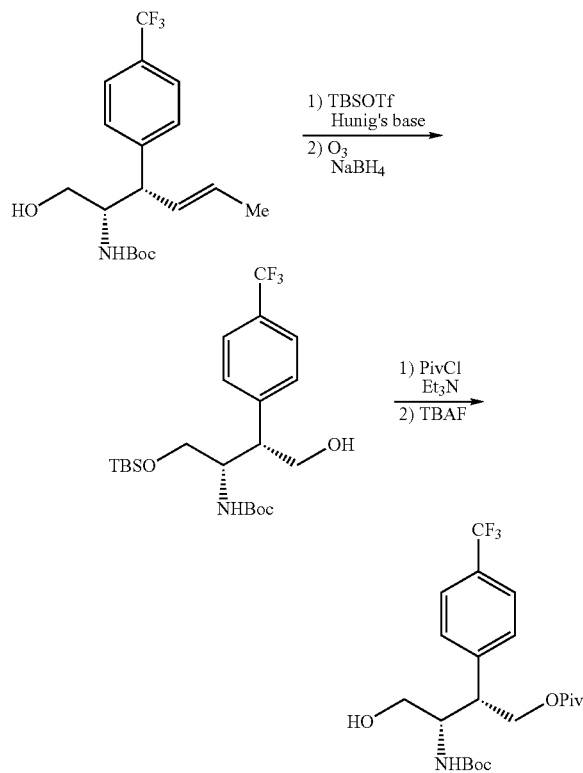

tert-Butyl (2S,3S)-1-(tert-butyldimethylsilyloxy)-4-hydroxy-3-(4-(trifluoromethyl)phenyl)butan-2-ylcarbamate. tert-Butyl (2S,3S,E)-1-hydroxy-3-(4-(trifluoromethyl)phenyl)hex-4-en-2-ylcarbamate (1.94 g, 5.4 mmol) (prepared as shown in Scheme 19) was taken up in 50 mL of DCM and chilled to 0° C. DIEA (2.4 mL, 13 mmol) was added, followed by slow addition of tert-butyldimethylsilyl trifluoromethanesulfonate (TBSOTf) (1.5 mL, 6.5 mmol). After 45 minutes, an additional 0.20 mL of TBSOTf was added. After an additional 20 minutes, the reaction was quenched with 50 mL of aq NaHCO$_3$. The mixture was partitioned, and the aqueous portion was extracted twice with 50 mL of DCM. The combined organic extracts were dried over MgSO$_4$. Filtration and concentration under reduced pressure, followed by flash chromatography on silica gel (1% to 7.5% EtOAc/hexanes), afforded tert-butyl (2S,3S,E)-1-(tert-butyldimethylsilyloxy)-3-(4-(trifluoromethyl)phenyl)hex-4-en-2-ylcarbamate (2.0 g, 78% yield) as a clear oil. The oil crystallized over 12 hours. $^1$H NMR (400 MHz, CDCl$_3$) δ ppm 7.54 (d, J=8.02 Hz, 2 H) 7.35 (d, J=8.02 Hz, 2 H) 5.61 (s, 1 H) 5.59 (d, J=5.87 Hz, 1 H) 4.62-4.60 (m, 1H) 3.97-3.92 (m, 1H) 3.79-3.76 (m, 1H) 3.66-3.59 (m, 2H) 1.69 (d, J=5.28 Hz, 3 H) 1.26 (s, 9 H) 0.92-0.97 (m, 9 H) 0.06 (s, 6 H).

tert-Butyl (2S,3S)-1-(tert-butyldimethylsilyloxy)-4-hydroxy-3-(4-(trifluoromethyl)phenyl)butan-2-ylcarbamate. tert-Butyl (2S,3S,E)-1-(tert-butyldimethylsilyloxy)-3-(4-(trifluoromethyl)phenyl)hex-4-en-2-ylcarbamate (2.0 g, 4.2 mmol) was taken up in 40 mL of 1:1 MeOH/DCM and the mixture was chilled to −78° C. Ozone was bubbled through the mixture until a blue color persisted. Nitrogen was then bubbled through the mixture for 15 minutes. NaBH$_4$ (0.80 g, 21 mmol) was added, and the mixture was warmed to room temperature. After 3 hours, the mixture was quenched with aq NH$_4$Cl. The mixture was extracted three times with 50 mL of DCM. The combined organic extracts were dried over MgSO$_4$. Filtration and concentration under reduced pressure afforded tert-butyl (2S,3S)-1-(tert-butyldimethylsilyloxy)-4-hydroxy-3-(4-(trifluoromethyl)phenyl)butan-2-ylcarbamate (1.9 g, 97% yield) as a white solid. $^1$H NMR (400 MHz, CDCl$_3$) δ ppm 7.56 (d, J=8.03 Hz, 2 H) 7.32 (d, J=8.03 Hz, 1 H) 4.51 (s, 1 H) 4.22-4.16 (m, 1H) 3.90-3.66 (m, 3H) 3.47 (d, J=5.52 Hz, 2 H) 3.15-3.20 (m, 1 H) 1.45 (s, 9 H) 0.84 (s, 9 H) 0.01 (s, 3H) −0.01 (s, 3H).

(2S,3S)-3-(tert-Butoxycarbonyl)-4-hydroxy-2-(4-(trifluoromethyl)phenyl)butyl pivalate. (2S,3S)-3-(tert-Butoxycarbonylamino)-4-hydroxy-2-(4-(trifluoromethyl)phenyl)butyl pivalate. tert-Butyl (2S,3S)-1-(tert-butyldimethylsilyloxy)-4-hydroxy-3-(4-(trifluoromethyl)phenyl)butan-2-ylcarbamate (1.9 g, 4.1 mmol) was taken up in 40 mL of DCM and chilled to 0° C. TEA (1.1 mL, 8.2 mmol), N,N-dimethylpyridin-4-amine (0.025 g, 0.20 mmol), and pivaloyl chloride (0.76 mL, 6.1 mmol) were added. The mixture was warmed to room temperature. After 12 hours, the reaction was quenched with 50 mL of aq NaHCO$_3$ and stirred for 10 minutes. The mixture was partitioned, and the aqueous portion was extracted twice with 50 mL of DCM. The combined organic extracts were washed with 50 mL of aq NaCHO$_3$ and 50 mL of aq NH$_4$Cl, and then dried over MgSO$_4$. Filtration and concentration under reduced pressure afforded a yellow oil that was used without any further purification.

(2S,3S)-3-(tert-Butoxycarbonyl)-4-(tert-butyldimethylsilyloxy)-2-(4-(trifluoromethyl)phenyl)butyl pivalate (2.2 g, 4.0 mmol) was taken up in 40 mL of THF and chilled to 0° C. TBAF, (1 M in THF) (6.0 mL, 6.0 mmol) was added slowly. After 20 minutes, the mixture was warmed to room temperature and stirred for 1 hour. 0.5 mL of additional TBAF was added, and the mixture was stirred for 20 minutes. The mixture was quenched with 20 mL of aq NH$_4$Cl. The mixture was then diluted with 40 mL of water and extracted twice with 50 mL of EtOAc. The combined organic extracts were washed with 50 mL of brine and dried over MgSO$_4$. Filtration and concentration under reduced pressure, followed by flash chromatography on silica gel (5% to 40% EtOAc/hexanes) afforded (2S,3S)-3-(tert-butoxycarbonyl)-4-hydroxy-2-(4-(trifluoromethyl)phenyl)butyl pivalate (1.5 g, 86% yield) as a yellow solid. $^1$H NMR (400 MHz, CDCl$_3$) δ ppm 7.59 (d, J=8.22 Hz, 2H) 7.37 (d, J=8.02 Hz, 2H) 4.57 (d, J=6.4 Hz, 1H)

4.45-4.35 (m, 2H) 4.06 (apparent s, 1H) 3.70 (apparent s, 1H) 3.46 (d, J=5.6 Hz, 1H), 1.75 (broad s, 1H) 1.33 (s, 9H) 1.08 (s, 9H).

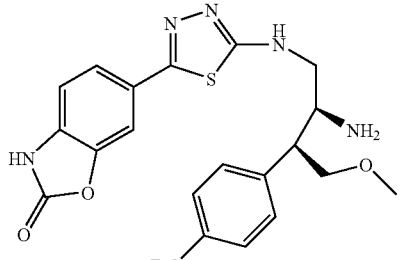

Example 40

6-(5-((2S,3S)-2-Amino-4-methoxy-3-(4-(trifluoromethyl)phenyl)butylamino)-1,3,4-thiadiazol-2-yl)benzo[d]oxazol-2(3H)-one. This compound is synthesized in a similar manner to that described for Example 39. The starting material, tert-butyl (2S,3S)-1-hydroxy-4-methoxy-3-(4-(trifluoromethyl)phenyl)butan-2-ylcarbamate, was prepared by a methylation reaction of tert-butyl (2S,3S)-1-(tert-butyldimethylsilyloxy)-4-hydroxy-3-(4-(trifluoromethyl)phenyl)butan-2-ylcarbamate which was prepared as shown in Scheme 20.

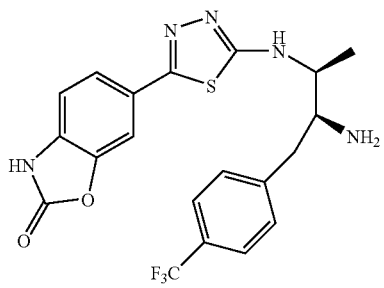

Example 41

6-(5-((2S,3S)-3-Amino-4-(4-(trifluoromethyl)phenyl)butan-2-ylamino)-1,3,4-thiadiazol-2-yl)benzo[d]oxazol-2(3H)-one. This compound is synthesized in a similar manner to that described for Example 36. The starting material tert-butyl (2S,3R)-3-hydroxy-1-(4-(trifluoromethyl)phenyl)butan-2-ylcarbamate was synthesized as shown in Scheme 21.

Scheme 21

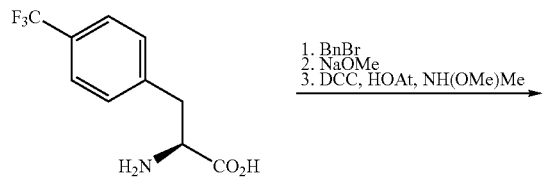

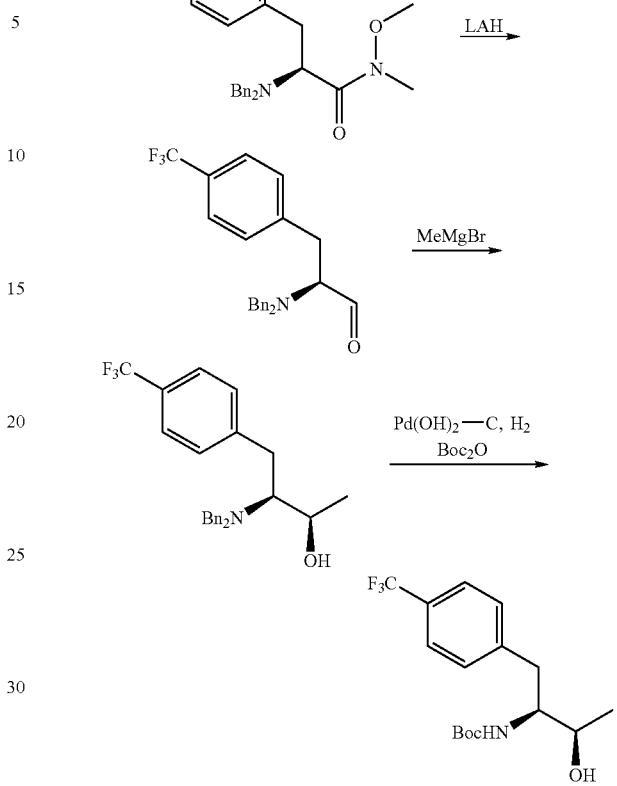

(S)-2-(Dibenzylamino)-N-methoxy-N-methyl-3-(4-(trifluoromethyl)phenyl)propanamide. To a 1 L round bottom flask, was added (S)-2-amino-3-(4-(trifluoromethyl)phenyl)propanoic acid (20.12 g, 86.28 mmol) (commercially available from Peptech (CAS No. 114873-07-3)), 1-(bromomethyl)benzene (35.84 mL, 302.0 mmol), potassium carbonate (53.66 g, 388.3 mmol), and EtOH (500 mL). The mixture was heated at 80° C. under a reflux condenser for 5 hours. The mixture was filtered through a coarse scintered glass funnel washing with EtOAc, and the filtrate was evaporated. The residue was taken up in DCM (500 mL) and washed with brine (100 mL), dried over sodium sulfate, and evaporated to a yellow oil. The crude product was stirred in 6:1:3 (dioxane 360 mL:MeOH 60 mL:2 N NaOH 120 mL, 600 mL) for 5 hours, and 200 mL ether was added, but the phases did not separate. The mixture was evaporated to an aqueous solution and ether (300 mL) was added. The aqueous layer was extracted again with ether (100 mL), the ether was washed with brine (100 mL), dried over sodium sulfate, and evaporated to provide the product as a yellow oil that was used without purification. LCMS m/z 414.2 (M+H).

(S)-2-(Dibenzylamino)-N-methoxy-N-methyl-3-(4-(trifluoromethyl)phenyl)propanamide. To a 250 mL round bottom flask was added crude (S)-2-(dibenzylamino)-3-(4-(trifluoromethyl)phenyl)propanoic acid, DMF (700 mL), N,O-dimethylhydroxylamine hydrochloride (25.3 g, 259 mmol), TEA (36.0 mL, 259 mmol), 3H-[1,2,3]triazolo[4,5-b]pyridin-3-ol (17.6 g, 130 mmol), and 1,3-dicyclohexylcarbodiimide (26.7 g, 130 mmol) at 0° C. The mixture was allowed to warm to room temperature. After 18 hours, the mixture was diluted with 1 L ether, and the precipitate was filtered through a coarse scintered glass funnel washing with ether. The filtrate was washed with brine (4×200 mL), and the organic layer was again passed through a coarse scintered glass funnel. The aqueous layer was extracted with ether (200 mL), and the combined ether layers were washed with brine (100 mL) and passed through a coarse scintered glass funnel. The organic layers were dried over sodium sulfate and evaporated providing a cloudy yellow oil. The oil was passed through a medium scintered glass funnel washing with ether, and the filtrate was evaporated to provide a clear yellow oil. The crude product was loaded onto a 1.5 kg silica gel column in hexane and eluted at 400 mL/minute 0% to 70% EtOAc in hexane to provide (S)-2-(dibenzylamino)-N-methoxy-N-methyl-3-(4-(trifluoromethyl)phenyl)propanamide (26.52 g, 67.3% yield) as a light yellow oil. LCMS (ES+) m/z=457.3 (M+H). $^1$H NMR (400 MHz, DMSO-d$_6$) δ ppm 2.50 (dt, J=3.67, 1.79 Hz, 3H) 3.09-3.19 (m, 3H) 3.31 (s, 3H) 3.68-3.76 (m, 2H) 3.77-3.85 (m, 2H) 7.16-7.34 (m, 12H) 7.63 (d, J=8.22 Hz, 2H).

(S)-2-(Dibenzylamino)-3-(4-(trifluoromethyl)phenyl)propanal. To a 500 mL round-bottomed flask was added (S)-2-(dibenzylamino)-N-methoxy-N-methyl-3-(4-(trifluoromethyl)phenyl)propanamide (6.22 g, 13.6 mmol), THF (100 mL), and lithium aluminum hydride (1.0 M solution in THF (27.3 mL, 27.3 mmol)), dropwise at 0° C. After 30 minutes, TLC (2:1 hexanes:EtOAc) showed that no starting material remained. The mixture was quenched by dropwise addition of water (6.82 mL), 2 N NaOH (6.82 mL), and water (9.83 mL). The solids were removed by filtration through a medium scintered glass funnel. The filtrate was dried over sodium sulfate and evaporated. The residue was taken up in EtOAc (200 mL) and washed with brine (50 mL). The organic layer was dried over sodium sulfate and evaporated to provide (S)-2-(dibenzylamino)-3-(4-(trifluoromethyl)phenyl)propanal (4.51 g, 83.3% yield) as a light yellow oil. LCMS (ES+) m/z=398.2. $^1$H NMR (400 MHz, CDCl$_3$) δ ppm 2.96 (dd, J=13.89, 5.67 Hz, 1H) 3.18 (dd, J=13.89, 7.43 Hz, 1H) 3.52-3.55 (m, 1H) 3.66-3.72 (m, 2H) 3.82-3.88 (m, 2H) 7.21-7.33 (m, 12H) 7.50 (d, J=8.02 Hz, 2H) 9.74 (s, 1H).

(2R,3S)-3-(Dibenzylamino)-4-(4-(trifluoromethyl)phenyl)butan-2-ol. Ether (100 mL) was added to a 500 mL round-bottom flask containing (S)-2-(dibenzylamino)-3-(4-(trifluoromethyl)phenyl)propanal (4.51 g, 11.3 mmol). The mixture was cooled to −78° C., and methylmagnesium bromide (3.16 M in ether, 35.9 mL, 113 mmol) was added dropwise over 15 minutes. After 5 hours, ammonium chloride (50 mL) was added dropwise, and the mixture was warmed to room temperature. The mixture was extracted with EtOAc (2×500 mL), washed with brine (250 mL), dried over sodium sulfate, and purified by chromatography through a 300 g column eluting with a gradient of 0% to 70% EtOAc in hexane, to provide (2R,3S)-3-(dibenzylamino)-4-(4-(trifluoromethyl)phenyl)butan-2-ol (3.09 g, 65.9% yield) as a yellow oil. LCMS (ES+) m/z=414.3 (M+H). $^1$H NMR (400 MHz, CDCl$_3$) δ ppm 1.23-1.28 (m, 3H) 2.84-2.94 (m, 2H) 3.08 (dd, J=12.81, 6.36 Hz, 1H) 3.66-3.76 (m, 4H) 4.03 (dt, J=10.66, 6.41 Hz, 1H) 7.15-7.28 (m, 12H) 7.51 (d, J=8.02 Hz, 2H).

tert-Butyl (2S,3R)-3-hydroxy-1-(4-(trifluoromethyl)phenyl)butan-2-ylcarbamate. To a 1 L flask containing (2R,3S)-3-(dibenzylamino)-4-(4-(trifluoromethyl)phenyl)butan-2-ol (3.09 g, 7.5 mmol), was added palladium hydroxide, 20 wt % Pd (dry basis) on carbon, wet, degussa type e101 ne/w (0.52 g, 0.75 mmol), and MeOH (70 mL). The flask was purged with a balloon of hydrogen and then stirred under a balloon of hydrogen. After 3 hours, the hydrogen was purged with a stream of nitrogen, and di-tert-butyldicarbonate (3.3 g, 15 mmol) and DMAP (0.091 g, 0.75 mmol) were added. After 1 hour, the mixture was filtered through Celite, washing with EtOAc to provide a colorless clear filtrate which was evaporated to a pale yellow solid. The solid was triturated with boiling hexane and allowed to cool to room temperature before being placed in a freezer at −20° C. After 16 hours, the solid was recovered by filtration through a medium scintered glass funnel to provide tert-butyl (2S,3R)-3-hydroxy-1-(4-(trifluoromethyl)phenyl)butan-2-ylcarbamate (1.922 g, 77% yield) as a white crystalline solid. LCMS (ES+) m/z=234.2 (M-Boc). $^1$H NMR (400 MHz, DMSO-d$_6$) δ ppm 1.08 (d, J=6.06 Hz, 3H) 1.22 (s, 9H) 2.56 (dd, J=13.50, 10.56 Hz, 1H) 3.09 (dd, J=13.40, 2.64 Hz, 1H) 3.40-3.54 (m, 2H) 4.72 (d, J=5.48 Hz, 1H) 6.59 (d, J=9.19 Hz, 1H) 7.39 (d, J=8.02 Hz, 2H) 7.59 (d, J=8.02 Hz, 2H).

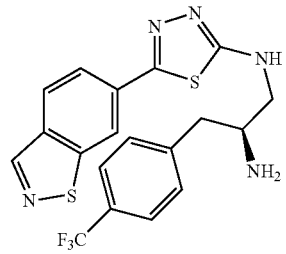

Example 42

N-((S)-2-Amino-3-(4-(trifluoromethyl)phenyl)propyl)-5-(benzo[d]isothiazol-6-yl)-1,3,4-thiadiazol-2-amine. This compound was prepared according to the procedure described for Example 1 starting with tert-butyl 5-(benzo[d]isothiazol-6-yl)-1,3,4-thiadiazol-2-ylcarbamate instead of tert-butyl 5-(3-fluoro-4-nitrophenyl)-1,3,4-thiadiazol-2-ylcarbamate. LCMS (API-ES) m/z (%): 436.5 (100%, M+H$^+$); $^1$H NMR (400 MHz, CD$_3$OD) δ ppm 9.03 (s, 1 H) 8.49 (s, 1 H) 8.26 (d, J=8.53 Hz, 1 H) 7.98 (d, J=8.53 Hz, 1 H) 7.64 (d, J=7.53 Hz, 2 H) 7.49 (d, J=7.53 Hz, 2 H) 3.48-3.64 (m, 1 H) 3.40-3.49 (m, 2 H) 2.92-3.06 (m, 1 H) 2.79 (dd, J=13.30, 7.28 Hz, 1 H). tert-Butyl 5-(benzo[d]isothiazol-6-yl)-1,3,4-thiadiazol-2-ylcarbamate was prepared as shown in Scheme 22.

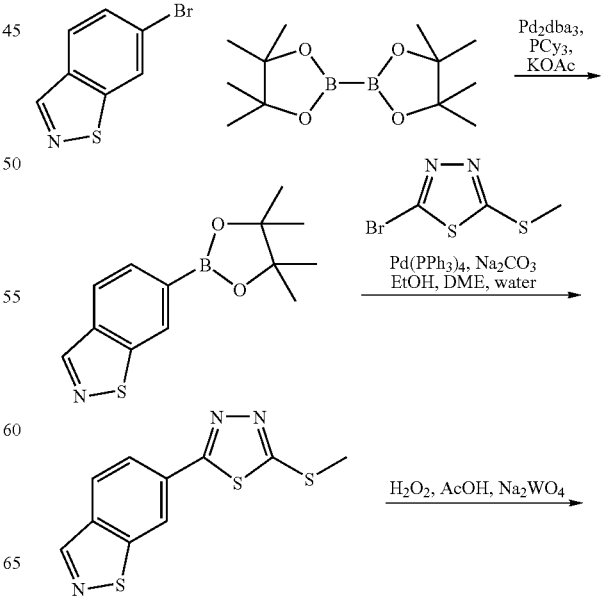

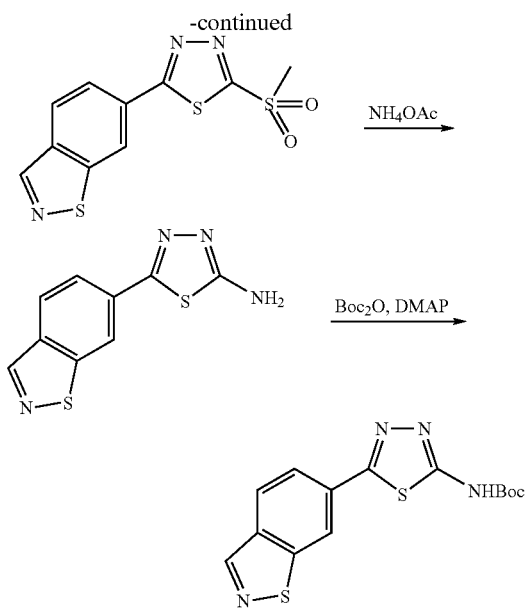

6-(4,4,5,5-Tetramethyl-1,3,2-dioxaborolan-2-yl)benzo[d]isothiazole. To a mixture of 6-bromobenzo[d]isothiazole (0.86 g, 4.0 mmol) (prepared as described in WO 2008/036308), potassium acetate (0.38 mL, 6.0 mmol), bis(pinacolato)diboron (1.3 g, 5.2 mmol), tris(dibenzylideneacetone)dipalladium (0) (0.18 g, 0.20 mmol), and tricyclohexylphosphine (0.12 g, 0.44 mmol) was added dioxane (5 mL). The resulting mixture was sealed and heated at 110° C. for 30 minutes under microwave irradiation. The mixture was cooled and passed through a short path of Celite, washing with DCM (3×10 mL). The combined organic phases were concentrated to give a residue that was purified by chromatography on silica gel (hexanes-50% EtOAc in hexanes) and trituration with hexanes provided the product as a white powder (0.59 g, 56%). LCMS (API-ES) m/z (%): 230.2 (100%, M+H$^+$); $^1$H NMR (400 MHz, CDCl$_3$) δ ppm 8.95 (s, 1 H) 8.58 (s, 1 H) 7.91-8.02 (m, 2 H) 1.41 (s, 12 H).

6-(5-(Methylthio)-1,3,4-thiadiazol-2-yl)benzo[d]isothiazole. To a stirred mixture of 2-bromo-5-(methylthio)-1,3,4-thiadiazole (0.22 g, 1.0 mmol) (prepared as described in WO 97/30981), 5-(4,4,5,5-tetramethyl-1,3,2-dioxaborolan-2-yl)benzo[d]isothiazole (0.18 g 0.69 mmol), Na$_2$CO$_3$ (0.22 g, 2.1 mmol), and Pd(PPh$_3$)$_4$ (80 mg, 0.07 mmol) was added EtOH (1.0 mL), water (1.0 mL) and DME (3.0 mL). The resulting mixture was heated at 90° C. overnight and at 140° C. for 30 minutes. The mixture was cooled and passed through a short path of Celite, washing with DCM (3×10 mL). The combined organic phases were concentrated to give the crude residue. Purification by chromatography on silica gel (DCM—5% MeOH in DCM) gave the product as an off-white powder (0.16 g, 87%). LCMS (API-ES) m/z (%): 266.4 (100%, M+H$^+$); $^1$H NMR (400 MHz, CDCl$_3$): δ ppm 8.97 (s, 1 H) 8.48 (s, 1 H) 8.16 (d, J=8.53 Hz, 1 H) 8.00 (d, J=8.03 Hz, 1 H) 2.87 (s, 3 H).

6-(5-(Methylsulfonyl)-1,3,4-thiadiazol-2-yl)benzo[d]isothiazole. To a stirred mixture of 6-(5-(methylthio)-1,3,4-thiadiazol-2-yl)benzo[d]isothiazole (0.20 g, 0.75 mmol) and hydrogen peroxide (0.19 mL, 1.9 mmol) in AcOH (2.00 mL, 35 mmol) was added sodium tungstate (0.0026 mL, 0.038 mmol). The resulting mixture was stirred at room temperature 16 hours. The mixture was diluted with aqueous NaHCO$_3$ (10 mL), water (10 mL) and EtOAc (5 mL). The separated aqueous layer was extracted with EtOAc (2×10 mL) and the combined organic layers were washed with brine, dried over Na$_2$SO$_4$, and concentrated to give the product as a residue which was used without further purification.

5-(Benzo[d]isothiazol-6-yl)-1,3,4-thiadiazol-2-amine. A mixture of 6-(5-(methylsulfonyl)-1,3,4-thiadiazol-2-yl)benzo[d]isothiazole (0.16 g, 0.54 mmol) and excess ammonium acetate (1.93 mL, 26.9 mmol) was heated in a microwave-safe reaction vessel at 140° C. for 30 minutes under microwave irradiation. The mixture was cooled, 5% MeOH in DCM (with NH$_3$) was added, and the mixture was adsorbed onto silica gel. The residue was purified by flash column chromatography (DCM—10% MeOH in DCM) to obtain the desired product as an off-white solid (89 mg, 71%). LCMS (API-ES) m/z (%): 235.3 (100%, M+H$^+$); $^1$H-NMR (400 MHz, CD$_3$OD) δ ppm 9.02 (s, 1 H) 8.49 (s, 1 H) 8.25 (d, J=8.53 Hz, 1 H) 7.98 (d, J=9.03 Hz, 1 H).

tert-Butyl 5-(benzo[d]isothiazol-6-yl)-1,3,4-thiadiazol-2-ylcarbamate. To a suspension of 5-(benzo[d]isothiazol-6-yl)-1,3,4-thiadiazol-2-amine (88 mg, 0.38 mmol) and DMAP (4.6 mg, 38 μmol) in CH$_3$CN (3 mL) was added Boc$_2$O (0.17 mL, 0.75 mmol) and the mixture was stirred at 50° C. for 1 hour. LiBr (0.17 g, 1.9 mmol) was added, and the mixture was heated for 2 hours, cooled, and adsorbed onto silica gel. The residue was purified by column chromatography (DCM—2% MeOH in DCM) to obtain the desired product as a white solid (65 mg, 52%). LCMS (API-ES) m/z (%): 335.4 (100%, M+H$^+$); $^1$H NMR (400 MHz, CDCl$_3$) δ ppm 8.97 (s, 1 H) 8.51 (s, 1 H) 8.17 (d, J=8.53 Hz, 1 H) 8.00 (d, J=8.03 Hz, 1 H) 1.60 (s, 9 H).

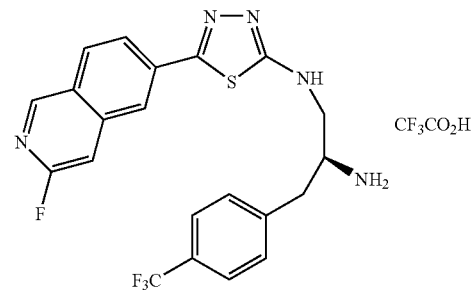

Example 43

N-((S)-2-Amino-3-(4-(trifluoromethyl)phenyl)propyl)-5-(3-fluoroisoquinolin-6-yl)-1,3,4-thiadiazol-2-amine trifluoroacetate. This compound was synthesized as shown in Scheme 23.

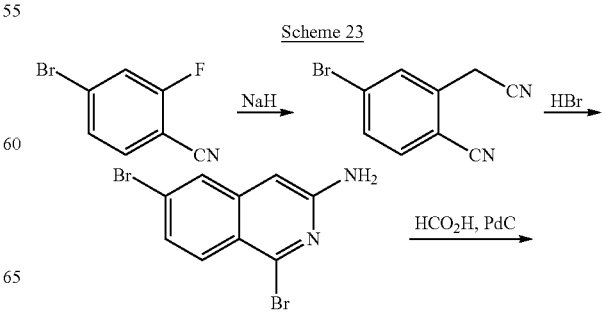

Scheme 23

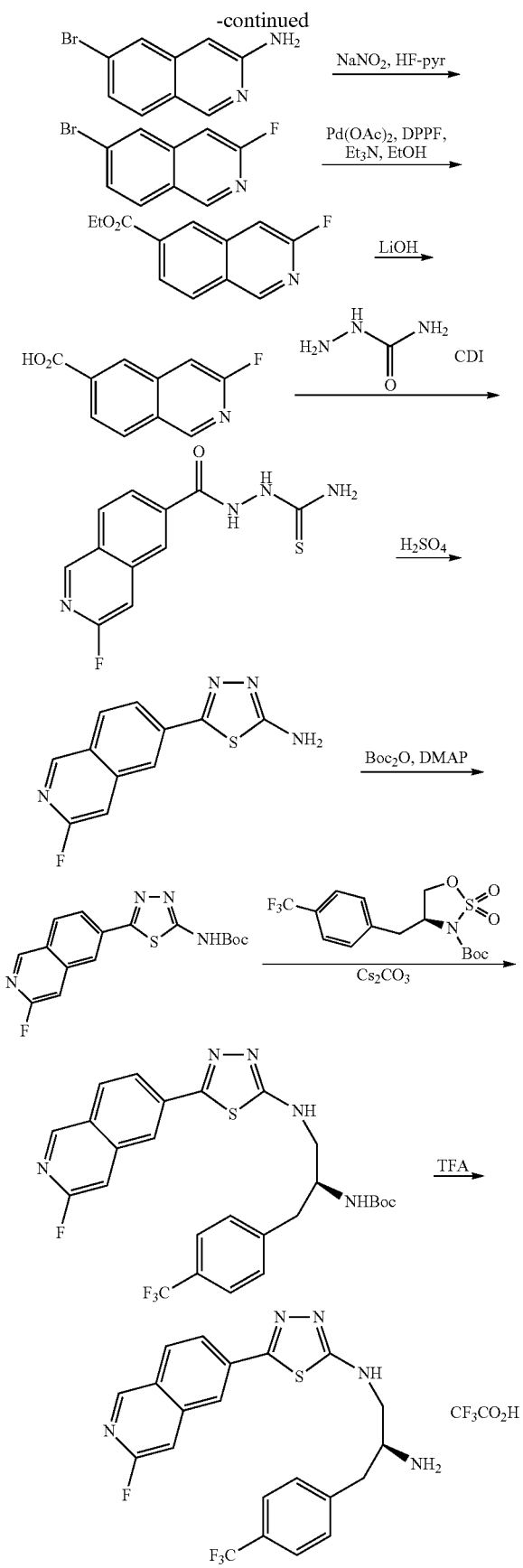

4-Bromo-2-(cyanomethyl)benzonitrile. Sodium hydride (47.2 g, 1.18 mol) was suspended in 320 mL DMSO and cooled to 0° C. in an ice-water bath. The mixture became viscous as the DMSO began to freeze. Methyl cyanoacetate (104 mL, 1.18 mol) was added slowly causing a slight temperature increase and thus a more easily stirrable solution. The mixture was stirred for 30 minutes at room temperature. 4-Bromo-2-fluorobenzonitrile (118 g, 590 mmol) (commercially available from Acros Organics (Order Number 29049)) was added via cannula as a solution in 500 mL DMSO. The mixture was heated to an internal temperature of 90° C. The mixture was cooled and allowed to stand overnight. 1.2 L of water was added to the reaction mixture. The mixture was heated to an internal temperature of 104° C. over 3 hours. 2.3 L of water were added, and the mixture was heated at reflux 16 hours. The mixture was cooled to 5° C. HCl (700 mL, 0.2 N) was added, and the mixture was allowed to stir at 5° C. for 30 minutes. The resulting precipitate was filtered, washed with water, and dried to provide the product (102 g, 78%). LCMS (API-ES) m/z: 223, 221 (M+H$^+$).

1,6-Dibromoisoquinolin-3-amine. 4-Bromo-2-(cyanomethyl)benzonitrile (75 g, 339 mmol) was added to 2,2-dichloroacetic acid (150 mL, 339 mmol). The resulting solution was cooled to 0° C. in an ice-water bath. HBr (27.5 g, 339 mmol) was bubbled through the cold solution until a yellow precipitate crashed out of solution, resulting in a yellow slurry. HBr was bubbled through the slurry for an additional 5 minutes. The solution was allowed to warm to room temperature over 1 hour. The slurry was then cooled to 0° C. in an ice-water bath and diethyl ether (200 mL) was added. The mixture was stirred for 20 minutes at 5° C. The product was recovered as a yellow solid by filtration (42 g, 41%). LCMS (API-ES) m/z: 303 (M+H$^+$).

6-Bromoisoquinolin-3-amine: A mixture of 1,6-dibromoisoquinolin-3-amine (13.5 g, 45 mmol), ammonium formate (10.8 g, 172 mmol) and tetrakis(triphenylphosphine) palladium (0) (3.45 g, 3.0 mmol) in 50 mL of DMF was sealed in a 350 mL screw-cap flask and heated at 50° C. for 48 h. To the reaction was added tetrakis(triphenylphosphine)palladium (0) (950 mg) and ammonium formate (3.0 g) and the mixture was heated at 50° C. for 48 h. The mixture was cooled to room temperature and the solid was filtered, washed with a minimal amount of DMF, washed with Et$_2$O and dried in vacuo at 50° C. to give the product as a yellow amorphous solid (10.4 g, 90%) LCMS (API-ES) m/z: 222.9, 224.9 [M+1]. $^1$H NMR (300 MHz, DMSO-d$_6$) δ ppm 8.81 (s, 1 H), 7.80 (d, J=1.6 Hz, 1 H), 7.73 (d, J=8.8 Hz, 1 H), 7.22 (dd, J=8.6, 1.9 Hz, 1 H), 6.55 (s, 1 H), 6.12 (s, 2 H).

6-Bromo-3-fluoroisoquinoline. To a mixture of 6-bromoisoquinolin-3-amine (0.710 g, 3.18 mmol) in pyridine hydrofluoride (10 mL, 3.18 mmol) at −78° C. was carefully added sodium nitrite (0.26 g, 3.82 mmol). The reaction mixture was stirred at −78° C. for 5 minutes. The reaction mixture was warmed to room temperature over 40 minutes. The mixture was poured into an ice bath, and the pH was adjusted to >9 with Na$_2$CO$_3$. The mixture was filtered to recover a yellow-purple solid. The solid was dissolved in EtOAc-water with stirring. The mixture was extracted with EtOAc (3×200 mL). The EtOAc was washed with brine, dried over Na$_2$SO$_4$, filtered and concentrated. The residue was taken up in DCM-MeOH and adsorbed onto silica gel. Purification by chromatography on silica gel (EtOAc 0-7% in hexane) provided the product (500 mg, 70%). LCMS (API-ES) m/z: 226, 228 (M+H$^+$).

Ethyl 3-fluoroisoquinoline-6-carboxylate. To a round-bottomed flask was added 6-bromo-3-fluoroisoquinoline (0.54 g, 2.4 mmol), palladium (II) acetate (0.027 g, 0.12 mmol), DPPF (0.13 g, 0.24 mmol), EtOH (2.1 mL, 36 mmol), and DMSO (4.8 mL, 2.4 mmol). The reaction flask was evacuated and filled with carbon monoxide (2×) and stirred at room temperature under 1 atm carbon monoxide for 20 hours. The mixture was evaporated. The residue was partitioned between water and DCM. The aqueous layer was extracted with DCM (4×100 mL). The combined extracts were washed with brine, dried over sodium sulfate and evaporated. The residue was purified by column chromatography on silica gel to provide the product as a white solid (294 mg, 56%).

LCMS (API-ES) m/z: 220 (M+H$^+$).

3-Fluoroisoquinoline-6-carboxylic acid. A mixture of methyl 3-fluoroisoquinoline-6-carboxylate (0.257 g, 1.25 mmol) and lithium hydroxide, monohydrate (105 mg, 2.51 mmol) in THF:MeOH:H$_2$O (3:2:1, 4 mL) was stirred at room temperature for 3 hours. The MeOH and THF were evaporated. 5% citric acid was added, and the mixture was further acidified to pH=4 with NaHSO$_4$. The precipitate was recovered by filtration. The filtrate was extracted with chloroform-isopropanol. The organic extracts were washed with water, brine, dried over sodium sulfate and evaporated. The solids were combined to provide the product as a white solid (1.12 g, 100%). LCMS (API-ES) m/z: 192 (M+H$^+$).

1-(3-Fluoroisoquinoline-6-carbonyl)thiosemicarbazide. A mixture of 3-fluoroisoquinoline-6-carboxylic acid (0.71 g, 3.72 mmol) and di(1H-imidazol-1-yl)methanone (1.21 g, 7.44 mmol) in DMF (9.0 mL) was stirred at room temperature for 1 hour and 20 minutes until no gas was evolved. The reaction mixture was heated at 70° C. for 40 minutes. Thiosemicarbazide (1.02 g, 11.2 mmol) was added, and the reaction mixture was stirred at 70° C. for another 30 minutes. The solvents were removed under reduced pressure. HCl (1.0 N, 50 mL) was added, and the solids were recovered by filtration, and washed with water to provide the product as an off-white solid (0.86 g, 89%). LCMS (API-ES) m/z: 265 (M+H$^+$).

5-(3-Fluoroisoquinolin-6-yl)-1,3,4-thiadiazol-2-amine. A mixture of 1-(3-fluoroisoquinoline-6-carbonyl)thiosemicarbazide (0.98 g, 3.71 mmol) in sulfuric acid (10 mL) was stirred at room temperature for 3 hours. The mixture was poured into ice-ammonium hydroxide (33%). The pH was adjusted to >9 with additional ammonium hydroxide. The precipitate was recovered by filtration and washed with water (4×) to provide the product as an off-white solid (0.84 g, 92%). LCMS (API-ES) m/z: 247 (M+H$^+$).

tert-Butyl 5-(3-fluoroisoquinolin-6-yl)-1,3,4-thiadiazol-2-ylcarbamate. A mixture of 5-(3-fluoroisoquinolin-6-yl)-1,3,4-thiadiazol-2-amine (0.87 g, 3.53 mmol), di-tert-butyl dicarbonate (0.810 g, 3.71 mmol) and 4-dimethylaminopyridine (0.00432 g, 0.0353 mmol) in THF (15 mL) was stirred at 70° C. for 4 hours. Additional di-tert-butyl dicarbonate (0.40 g, 1.83 mmol) was added, and the mixture was stirred at 70° C. 16 hours. The solvent was evaporated. The residue was taken up in ACN (20 mL) and lithium bromide (1.18 g, 13.6 mmol) was added. The mixture was stirred at room temperature for 4 hours and at 70° C. for 2 hours. The solvent was evaporated. The residue was stirred with saturated NaHCO$_3$ and water for 5 minutes. The precipitate was recovered by filtration and washed with water. The precipitate was triturated with ether by sonication and the solid was recovered by filtration, washing with ether to provide the product as an off-white solid (1.22 g, 78%). LCMS (API-ES) m/z: 347 (M+H$^+$).

tert-Butyl (S)-1-(5-(3-fluoroisoquinolin-6-yl)-1,3,4-thiadiazol-2-ylamino)-3-(4-(trifluoromethyl)phenyl)propan-2-ylcarbamate. tert-Butyl 5-(3-fluoroisoquinolin-6-yl)-1,3,4-thiadiazol-2-ylcarbamate (0.30 g, 0.860 mmol) and cesium carbonate (0.56 g, 1.72 mmol) in DMF (5.0 mL) were stirred under nitrogen at 55° C. for 10 minutes. tert-Butyl (4S)-4-(4-(trifluoromethyl)benzyl)-1,2,3-oxathiazolidine-3-carboxylate 2,2-dioxide (0.362 g, 0.946 mmol) as prepared in Schemes 1a and 1b for Example 1 was added as a solid. The resulting reaction mixture was stirred at 55° C. for 1.5 hours. The solvent was removed and the residue was partitioned between water and EtOAc. The aqueous layer was extracted with EtOAc (3×140 mL), the combined organic extracts were washed with brine, dried over sodium sulfate and evaporated. The residue was partially purified by chromatography on silica gel (0-35% EtOAc:hexane) to provide the product contaminated with tert-butyl ((2Z)-3-((2S)-2-((tert-butoxycarbonyl)amino)-3-(6-(trifluoromethyl)-3-pyridinyl)propyl)-5-(3-fluoro-6-isoquinolinyl)-1,3,4-thiadiazol-2(3H)-ylidene)carbamate. The mixture was taken up in DMSO (6 mL) and water (0.019 mL). Lithium chloride (0.15 g, 3.5 mmol) was added and the mixture was heated at 100° C. with stirring 16 hours. Saturated NH$_4$Cl was added, and the mixture was extracted with EtOAc (120 mL×3). The organic extracts were washed with water (3×100 mL), brine, dried over sodium sulfate and evaporated. The residue was purified by chromatography on silica gel (0-3% MeOH-DCM) to provide the product as an off-white solid (57 mg, 30%). LCMS (API-ES) m/z: 548 (M+H$^+$).

N—((S)-2-Amino-3-(4-(trifluoromethyl)phenyl)propyl)-5-(3-fluoroisoquinolin-6-yl)-1,3,4-thiadiazol-2-amine trifluoroacetate. A mixture of tert-butyl (S)-1-(5-(3-fluoroisoquinolin-6-yl)-1,3,4-thiadiazol-2-ylamino)-3-(4-(trifluoromethyl)phenyl)propan-2-ylcarbamate (0.047 g, 0.086 mmol) in TFA/DCM (1:1, 4.0 mL) was stirred at room temperature for 30 minutes. The solvent was evaporated to provide the product as an off-white solid (50.3 mg, 100%). LCMS (API-ES) m/z: 449 (M+H$^+$); $^1$H NMR (400 MHz, DMSO-d$_6$) δ ppm 3.05 (d, J=6.85 Hz, 2H), 3.54-3.65 (m, 2 H), 7.57 (d, J=8.02 Hz, 2 H), 7.72 (d, J=7.82 Hz, 3 H), 7.76 (s, 1 H), 8.03 (s, 3 H), 8.11 (dd, J=8.61, 1.57 Hz, 1 H), 8.28 (d, J=8.80 Hz, 1 H), 8.33-8.39 (m, 2 H).

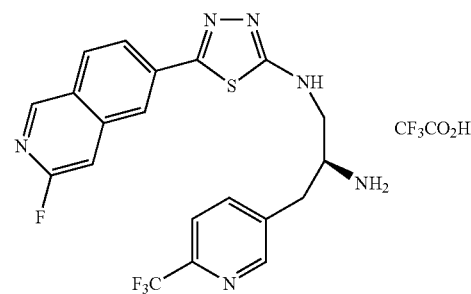

Example 44

N-((S)-2-Amino-3-(6-(trifluoromethyl)pyridin-3-yl)propyl)-5-(3-fluoroisoquinolin-6-yl)-1,3,4-thiadiazol-2-amine trifluoroacetate. This compound was prepared in a similar manner to Example 42, but using tert-butyl (4S)-4-((6-(trifluoromethyl)-3-pyridinyl)methyl)-1,2,3-oxathiazolidine-3-carboxylate 2,2-dioxide (prepared as described in US Patent Publication No. US 2007/0173506) instead of tert-butyl (4S)-4-(trifluoromethyl)benzyl)-1,2,3-oxathiazolidine-3-carboxylate 2,2-dioxide. LCMS (API-ES) m/z: 448 (M+H$^+$); $^1$H NMR (400 MHz, DMSO-d$_6$) δ ppm 3.04-3.17 (m, 2 H), 3.57-3.71 (m, 2 H), 3.87 (s, 1 H), 7.72 (s, 1 H), 7.91 (d, J=8.02

Hz, 1 H), 8.03-8.13 (m, 5 H), 8.26-8.35 (m, 2 H), 8.42 (t, J=5.77 Hz, 1 H), 8.74 (s, 1 H).

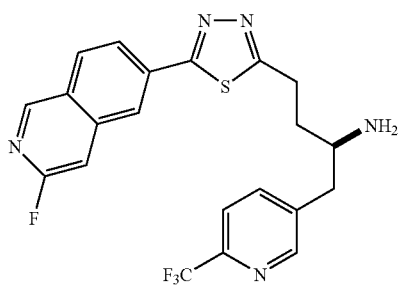

Example 45

(2R)-4-(5-(3-Fluoroisoquinolin-6-yl)-1,3,4-thiadiazol-2-yl)-1-(6-(trifluoromethyl)pyridin-3-yl)butan-2-amine. This compound was prepared as shown in Scheme 24.

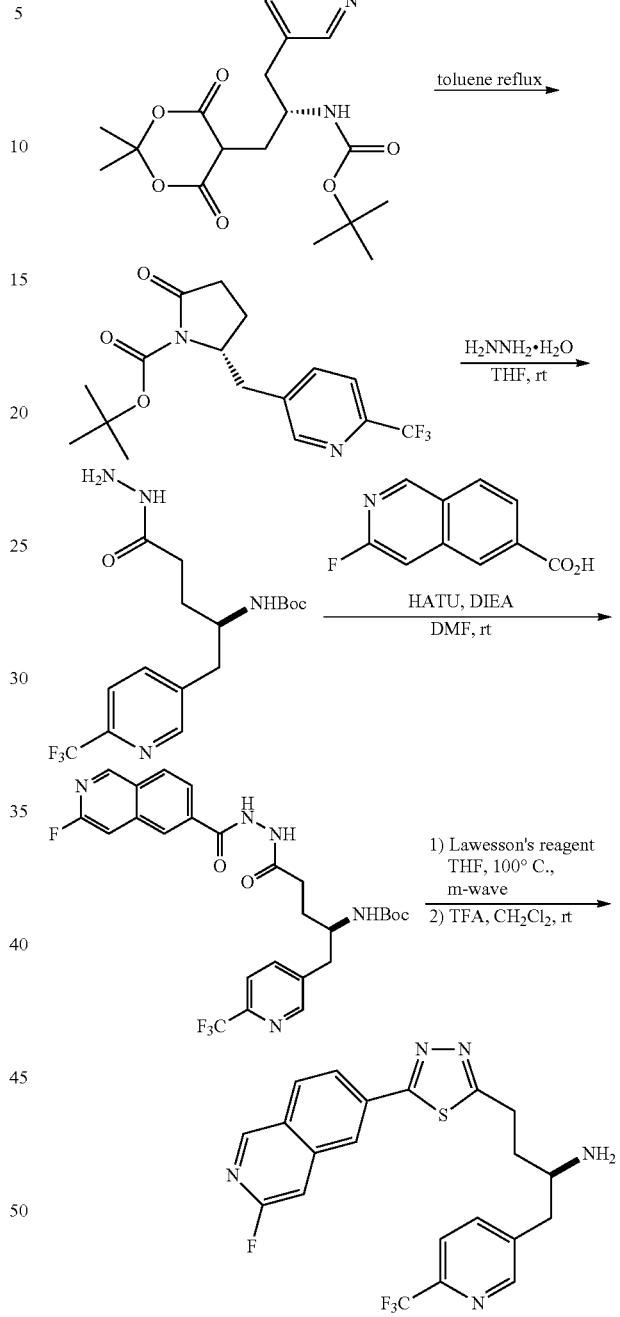

(S)-Methyl 2-(tert-butoxycarbonylamino)-3-(6-(trifluoromethyl)pyridin-3-yl)propanoate. Zinc (12 g, 186 mmol) and methylene dibromide (1.6 g, 9.3 mmol) were stirred in DMF (45 mL) at 90° C. for 30 minutes. After cooling to room temperature, trimethylsilyl chloride (0.24 mL, 1.9 mmol) was added, and the mixture was stirred at room temperature 30 minutes. Boc-3-iodo-1-alanine methyl ester (13 g, 40 mmol) (commercially available from 3B Scientific Corporation Product List (Order Number 3B3-063312)) in 15 mL DMF was added in one portion. After stirring at room temperature for 4 hours, dichlorobis(triphenyl-phosphine)palladium (ii) (1.2 g, 1.7 mmol) and 5-bromo-2-(trifluoromethyl)pyridine (7.0 g, 31.0 mmol) (commercially available from 3B Scientific Product List (Order Number 3B3-009312)) in 20 mL DMF were added. The reaction mixture was stirred at room temperature 16 hours. The reaction mixture was filtered through a pad of Celite and washed with EtOAc (3×). The solvent was evaporated. The residue was taken up in EtOAc and the organic layer was washed with saturated ammonium chloride (300 mL) and brine, dried over sodium sulfate, and evaporated. The residue was purified by chromatography on silica gel (20% EtOAc in hexane) to provide the product as a tan solid (4.0 g, 37%). LCMS (API-ES) m/z (%): 349.1 (100%, M+H$^+$).

(S)-2-(tert-Butoxycarbonylamino)-3-(6-(trifluoromethyl)pyridin-3-yl)propanoic acid. To a LiOH solution (1.0 M in 1:1:1 water:MeOH:THF, 75 mL) was added (S)-methyl 2-(tert-butoxycarbonylamino)-3-(6-(trifluoromethyl)pyridin-3-yl)propanoate (3.8 g, 10.9 mmol). The reaction was stirred at room temperature for 30 minutes. The organic solvent in the reaction mixture was evaporated. The residue was diluted with EtOAc, washed with saturated ammonium chloride (2×100 mL), and dried over sodium sulfate. The solvent was removed to provide the product as a white solid (2.4 g, 66%). LCMS (API-ES) m/z (%): 335.0 (100%, M+H$^+$).

(S)-tert-Butyl 1-(2,2-dimethyl-4,6-dioxo-1,3-dioxan-5-yl)-1-oxo-3-(6-(trifluoromethyl)pyridin-3-yl)propan-2-ylcarbamate. (S)-2-(tert-Butoxycarbonylamino)-3-(6-(trifluoromethyl)pyridin-3-yl)propanoic acid (2.4 g, 7.2 mmol), 2,2-dimethyl-1,3-dioxane-4,6-dione (1.1 g, 7.9 mmol), and N,N-dimethylpyridin-4-amine (1.4 g, 11 mmol) in 30 mL DCM were cooled in an ice-water-sodium chloride bath (−5° C.). N-((cyclohexylimino)methylene)cyclohexanamine (1.6 g, 7.9 mmol) in 50 mL DCM was added dropwise in about 40 minutes. The reaction mixture was stirred for 16 hours at room temperature. The suspension was filtered, and the solid was washed with DCM. The filtrate was washed with 5% KHSO$_4$ (4×50 mL) and once with brine, and dried over MgSO$_4$. After removing the solvent, the product was obtained as a white solid (3.0 g, 91%). LCMS (API-ES) m/z (%): 461.0 (100%, M+H$^+$).

(R)-tert-Butyl 3-(2,2-dimethyl-4,6-dioxo-1,3-dioxan-5-yl)-1-(6-(trifluoromethyl)pyridin-3-yl)propan-2-ylcarbamate. (S)-tert-Butyl 1-(2,2-dimethyl-4,6-dioxo-1,3-dioxan-5-yl)-1-oxo-3-(6-(trifluoromethyl)pyridin-3-yl)propan-2-ylcarbamate in 100 mL DCM was cooled to −5° C. Acetic acid (4.45 g, 74.1 mmol) was added in one portion. The resulting mixture was stirred for 5 minutes and sodium borohydride (0.637 g, 16.8 mmol) was added portion-wise over 40 minutes. After stirring for another 40 minutes, the reaction mixture was washed with brine (3×150 mL) and water (2×100 mL). The organic layer was dried over MgSO$_4$. After removing the solvent, the desired product compound (2.5 g, 83%) was obtained as a white solid. LCMS (API-ES) m/z (%): 447.0 (100%, M+H$^+$).

(R)-tert-Butyl 2-oxo-5-((6-(trifluoromethyl)pyridin-3-yl)methyl)pyrrolidine-1-carboxylate. (R)-tert-Butyl 3-(2,2-dimethyl-4,6-dioxo-1,3-dioxan-5-yl)-1-(6-(trifluoromethyl)pyridin-3-yl)propan-2-ylcarbamate (2.5 g, 5.6 mmol) in 100 mL toluene was heated at 105° C. for 8 hours. After removing the solvent, the residue was purified by chromatography on silica gel (20-40% EtOAc in hexane) to provide the product (1.3 g, 67%) as a white solid. LCMS (API-ES) m/z (%): 345.0 (100%, M+H$^+$).

(R)-4-(tert-Butoxycarbonylamino)-5-(6-(trifluoromethyl)pyridin-3-yl)pentanehydrazide. Hydrazine monohydrate (0.93 mL, 18.6 mmol) was added to a solution of (R)-tert-butyl 2-oxo-5-((6-(trifluoromethyl)pyridin-3-yl)methyl)pyrrolidine-1-carboxylate (1.6 g, 4.65 mmol) in THF (23 mL), and the mixture was stirred at room temperature for 1 hour. Saturated aqueous NH$_4$Cl (20 mL) was added and the mixture was extracted with EtOAc (3×20 mL). The combined organic layers were dried (MgSO$_4$) and concentrated under reduced pressure. The resulting off-white solid was purified by recrystallization from EtOAc to provide (R)-4-(tert-butoxycarbonylamino)-5-(6-(trifluoromethyl)pyridin-3-yl)pentanehydrazide (1.40 g, 80%) as a white solid. LCMS (API-ES) m/z: 399.1 (M+Na$^+$).

(R)—N'-(4-(tert-Butoxycarbonylamino)-5-(6-(trifluoromethyl)pyridin-3-yl)pentanoyl)-3-fluoroisoquinoline-6-carbohydrazide. A mixture of 3-fluoroisoquinoline-6-carboxylic acid (123 mg, 644 µmol)(prepared as shown in Scheme 23), HATU (245 mg, 644 µmol), and DIEA (122 µl, 698 µmol) in DMF (5 mL) was stirred at room temperature for 15 minutes. This mixture was added dropwise to a mixture of (R)-4-(tert-butoxycarbonylamino)-5-(6-(trifluoromethyl)pyridin-3-yl)pentanehydrazide (202 mg, 537 µmol) and DIEA (122 µL, 698 µmol) in DMF (5 mL), and the resulting mixture was stirred at room temperature for 1 hour. The solvent was removed under reduced pressure and the residue was partitioned between saturated aqueous NaHCO$_3$ (20 mL) and DCM (20 mL). The layers were separated and the aqueous layer was extracted with DCM (2×20 mL). The combined organic layers were dried (MgSO$_4$) and concentrated under reduced pressure. The resulting white solid was recrystallized from EtOAc to deliver (R)—N'-(4-(tert-butoxycarbonylamino)-5-(6-(trifluoromethyl)pyridin-3-yl)pentanoyl)-3-fluoroisoquinoline-6-carbohydrazide (218 mg, 74%) as a white solid. LCMS (API-ES) m/z: 572.0 (M+Na$^+$).

tert-Butyl (R)-4-(5-(3-fluoroisoquinolin-6-yl)-1,3,4-thiadiazol-2-yl)-1-(6-(trifluoromethyl)pyridin-3-yl)butan-2-ylcarbamate. A mixture of (R)—N'-(4-(tert-butyloxycarbonylamino)-5-(6-(trifluoromethyl)pyridin-3-yl)pentanoyl)-3-fluoroisoquinoline-6-carbohydrazide (108 mg, 207 µmol) and Lawesson's reagent (101 mg, 249 µmol) in THF (2 mL) was heated in a Biotage® microwave reactor at 100° C. for 10 minutes. The mixture was diluted with DCM, absorbed onto silica gel, and purified by flash chromatography (silica gel, 2-8% MeOH/DCM) providing tert-butyl (R)-4-(5-(3-fluoroisoquinolin-6-yl)-1,3,4-thiadiazol-2-yl)-1-(6-(trifluoromethyl)pyridin-3-yl)butan-2-ylcarbamate (96 mg, 88%) as a white solid. LCMS (API-ES) m/z: 548.1 (M+H$^+$).

(2R)-4-(5-(3-Fluoroisoquinolin-6-yl)-1,3,4-thiadiazol-2-yl)-1-(6-(trifluoromethyl)pyridin-3-yl)butan-2-amine. TFA (1 mL) was added to a solution of tert-butyl (R)-4-(5-(3-fluoroisoquinolin-6-yl)-1,3,4-thiadiazol-2-yl)-1-(6-(trifluoromethyl)pyridin-3-yl)butan-2-ylcarbamate (85 mg, 155 µmol) in DCM (1 mL), and the mixture was stirred at room temperature for 2 hours. The mixture was concentrated under reduced pressure, and the resulting yellow oil was purified by reversed phase HPLC (Shimadsu Valiant, Phenomenex Gemini C18 5 µm 100×30 mm, 5% to 50% H$_2$O/MeCN, 0.1% TFA) to deliver a colorless oil. The oil was dissolved in MeOH, absorbed onto ISOLUTE Si-TsOH(SCX-3) (5 g), and washed with MeOH (50 mL) and then with 2 N NH$_3$ in MeOH (30 mL) providing (2R)-4-(5-(3-fluoroisoquinolin-6-yl)-1,3,4-thiadiazol-2-yl)-1-(6-(trifluoromethyl)pyridin-3-yl)butan-2-amine (57 mg, 82%) as a light yellow solid. $^1$H NMR (300 MHz, CD$_3$OD) δ ppm 1.88-2.16 (m, 2 H), 2.85 (d, J=13.6, 7.6 Hz, 1 H), 3.02 (dd, J=13.6, 5.8 Hz, 1 H), 3.15-3.28 (m, 1 H), 3.34-3.49 (m, 2 H), 7.53 (s, 1 H), 7.76 (d, J=8.0 Hz, 1 H), 7.95 (d, J=8.0 Hz, 1 H), 8.15 (dd, J=8.7, 1.3 Hz, 1 H), 8.23 (d, J=8.7 Hz, 1 H), 8.45 (s, 1 H), 8.63 (s, 1 H), 9.05 (s, 1 H). LCMS (API-ES) m/z: 470.0 (M+Na$^+$).

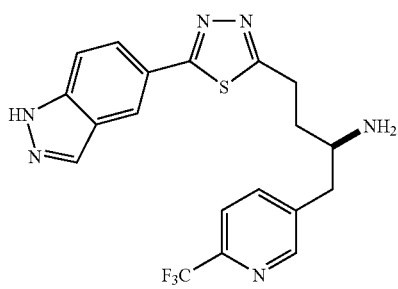

Example 46

(2R)-4-(5-(1H-Indazol-5-yl)-1,3,4-thiadiazol-2-yl)-1-(6-(trifluoromethyl)pyridin-3-yl)butan-2-amine. The title compound was prepared in a similar manner to Example 45, using 1H-indazole-5-carboxylic acid commercially available from SpeedChemical Product List (Order Number SP-37040) instead of 3-fluoroisoquinoline-6-carboxylic acid. $^1$H NMR (300 MHz, CD$_3$OD) δ ppm 1.86-2.15 (m, 2 H), 2.84 (dd, J=13.7, 7.6 Hz, 1 H) 2.96-3.07 (m, J=13.7, 5.8 Hz, 1 H), 3.15-3.30 (m, 2 H), 3.35-3.44 (m, 1 H), 7.66 (d, J=8.8 Hz, 1 H), 7.76 (d, J=8.0 Hz, 1 H), 7.90-8.03 (m, 2 H), 8.18 (d, J=0.7 Hz, 1 H) 8.34 (m, 1 H), 8.63 (d, J=0.9 Hz, 1 H). LCMS (API-ES) m/z: 441.0 (M+Na$^+$).

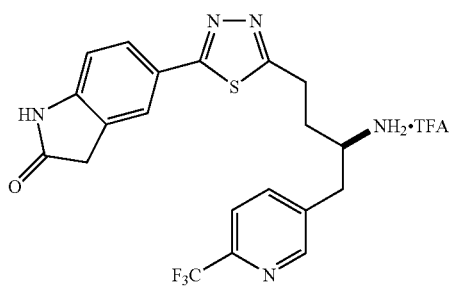

Example 47

5-(5-((R)-3-Amino-4-(6-(trifluoromethyl)pyridin-3-yl)butyl)-1,3,4-thiadiazol-2-yl)indolin-2-one trifluoroacetate. This compound was prepared as shown in Scheme 25.

Scheme 25

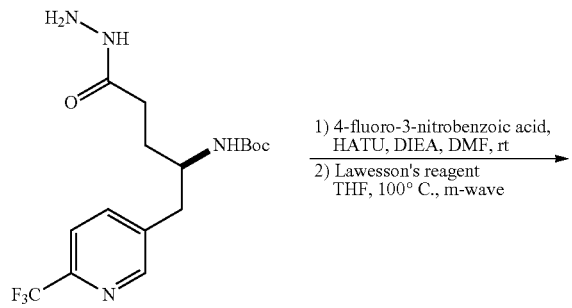

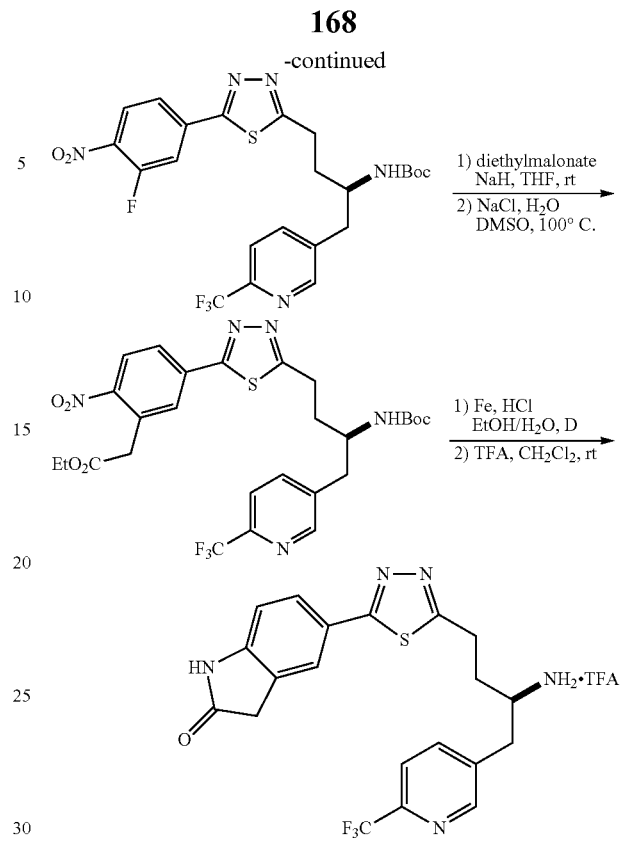

tert-Butyl ((1R)-4-(2-((3-fluoro-4-nitrophenyl)carbonyl)hydrazino)-4-oxo-1-((6-(trifluoromethyl)-3-pyridinyl)methyl)butyl)carbamate: A mixture of 3-fluoro-4-nitrobenzoic acid (130 mg, 701 μmol) (commercially available from 3B Scientific Corporation Product List (Order Number 3B3-068221)), HATU (267 mg, 701 μmol), and N,N-diisopropylethylamine (132 μL, 760 μmol) in DMF (4 mL) was stirred at room temperature for 1 hour. This mixture was added dropwise to a mixture of tert-butyl ((1R)-4-hydrazino-4-oxo-1-((6-(trifluoromethyl)-3-pyridinyl)methyl)butyl)carbamate (220 mg, 585 μmol), prepared as shown in Scheme 24, and N,N-diisopropylethylamine (132 μL, 760 μmol) in DMF (3 mL) and the resulting mixture was stirred at room temperature for 1 hour. The solvent was removed under reduced pressure and the remaining residue partitioned between saturated aqueous NaHCO$_3$ (20 mL) and DCM (20 mL). The layers were separated and the aqueous layer was extracted with DCM (3×20 mL). The combined organic layers were dried (MgSO$_4$) and concentrated under reduced pressure. The resulting colorless solid was dissolved in MeOH/DCM, absorbed onto silica gel and purified by flash chromatography (silica gel, 2% to 8% MeOH/DCM) to provide tert-butyl ((1R)-4-(2-((3-fluoro-4-nitrophenyl)carbonyl)hydrazino)-4-oxo-1-((6-(trifluoromethyl)-3-pyridinyl)methyl)butyl)carbamate (834 mg, 77%) as a light yellow solid. LCMS (API-ES) m/z: 566.0 (M+Na$^+$).

tert-Butyl (R)-4-(5-(3-fluoro-4-nitrophenyl)-1,3,4-thiadiazol-2-yl)-1-(6-(trifluoromethyl)pyridin-3-yl)butan-2-ylcarbamate: A mixture of tert-butyl ((1R)-4-(2-((3-fluoro-4-nitrophenyl)carbonyl)hydrazino)-4-oxo-1-((6-(trifluoromethyl)-3-pyridinyl)methyl)butyl)carbamate (214 mg, 394 μmol) and Lawesson's reagent (207 mg, 512 μmol) in THF (3 mL) was heated in a Biotage® microwave reactor at 100° C. for 15 minutes. The mixture was concentrated under reduced pressure, and the resulting yellow solid was taken up in MeOH/DCM, absorbed onto silica gel, and purified by flash chromatography (silica gel, 2% to 6% MeOH/DCM) to provide tert-butyl (R)-4-(5-(3-fluoro-4-nitrophenyl)-1,3,4-thiadiazol-2-yl)-1-(6-(trifluoromethyl)pyridin-3-yl)butan-2-ylcarbamate (190 mg, 89.1% yield) as a light yellow solid. LCMS (API-ES) m/z: 564.0 (M+Na$^+$)

Diethyl 2-(5-(5-((R)-3-(tert-butoxycarbonylamino)-4-(6-(trifluoromethyl)pyridin-3-yl)butyl)-1,3,4-thiadiazol-2-yl)-2-nitrophenyl)malonate: A 60% dispersion of sodium hydride in mineral oil (48 mg, 1263 µmol) was added to a solution of diethyl malonate (191 µL, 1263 µmol) in THF (2 mL) and the mixture was stirred at room temperature for 15 minutes. This mixture was added to a solution of tert-butyl (R)-4-(5-(3-fluoro-4-nitrophenyl)-1,3,4-thiadiazol-2-yl)-1-(6-(trifluoromethyl)pyridin-3-yl)butan-2-ylcarbamate (171 mg, 316 µmol) in THF (3 mL) and the mixture was stirred at room temperature for 4 hours. The mixture was concentrated under reduced pressure, and the residue was partitioned between saturated aqueous NH$_4$Cl (15 mL) and DCM (15 mL). The layers were separated and the aqueous layer was extracted with DCM (2×15 mL). The combined organic layers were dried (MgSO$_4$) and concentrated under reduced pressure. The resulting yellow solid was dissolved in MeOH/DCM, absorbed onto silica gel, and purified by flash chromatography (silica gel, 40% to 70% EtOAc/hexanes) to provide diethyl 2-(5-(5-((R)-3-(tert-butoxycarbonylamino)-4-(6-(trifluoromethyl)pyridin-3-yl)butyl)-1,3,4-thiadiazol-2-yl)-2-nitrophenyl)malonate (204 mg, 95% yield) as a yellow solid. LCMS (API-ES) m/z: 703.6 (M+Na$^+$).

Ethyl 2-(5-(5-((R)-3-(tert-butoxycarbonylamino)-4-(6-(trifluoromethyl)pyridin-3-yl)butyl)-1,3,4-thiadiazol-2-yl)-2-nitrophenyl)acetate. A mixture of diethyl 2-(5-(5-((R)-3-(tert-butoxycarbonylamino)-4-(6-(trifluoromethyl)pyridin-3-yl)butyl)-1,3,4-thiadiazol-2-yl)-2-nitrophenyl)malonate (165 mg, 242 µmol), water (4 µL, 242 µmol), and lithium chloride (51 mg, 1210 µmol) in DMSO (2 mL) was heated at 100° C. for 24 hours. The mixture was cooled to room temperature and partitioned between saturated aqueous NH$_4$Cl (15 mL) and DCM (15 mL). The layers were separated, and the aqueous layer was extracted with DCM (2×15 mL). The combined organic layers were dried (MgSO$_4$) and concentrated under reduced pressure. The resulting yellow solid was dissolved in MeOH/DCM, absorbed onto silica gel, and purified by flash chromatography (silica gel, 40% to 70% EtOAc/hexanes) to provide ethyl 2-(5-(5-((R)-3-(tert-butoxycarbonylamino)-4-(6-(trifluoromethyl)pyridin-3-yl)butyl)-1,3,4-thiadiazol-2-yl)-2-nitrophenyl)acetate (117 mg, 79%) as a white solid. LCMS (API-ES) m/z: 610.0 (M+H$^+$).

tert-Butyl (R)-4-(5-(2-oxoindolin-5-yl)-1,3,4-thiadiazol-2-yl)-1-(6-(trifluoromethyl)pyridin-3-yl)butan-2-ylcarbamate. Iron powder (48 mg, 853 µmol) was added to a suspension of ethyl 2-(5-(5-((R)-3-(tert-butoxycarbonylamino)-4-(6-(trifluoromethyl)pyridin-3-yl)butyl)-1,3,4-thiadiazol-2-yl)-2-nitrophenyl)acetate (104 mg, 171 µmol) in EtOH (1.5 mL). 2N aqueous HCl (256 µL, 512 µmol) was added, and the mixture was heated under reflux for 4 hours. Saturated aqueous NaHCO$_3$ (5 mL) was added dropwise and the mixture was stirred at room temperature for 5 minutes. It was diluted with H$_2$O (5 mL) and extracted with DCM (3×15 mL). The combined organic layers were dried (MgSO$_4$) and concentrated under reduced pressure. The resulting light yellow oil was absorbed onto silica gel and purified by flash chromatography (silica gel, 2% to 6% MeOH/DCM) to deliver tert-butyl (R)-4-(5-(2-oxoindolin-5-yl)-1,3,4-thiadiazol-2-yl)-1-(6-(trifluoromethyl)pyridin-3-yl)butan-2-ylcarbamate (49 mg, 54%) as a white solid. LCMS (API-ES) m/z: 534.0 (M+H$^+$).

5-(5-((R)-3-Amino-4-(6-(trifluoromethyl)pyridin-3-yl)butyl)-1,3,4-thiadiazol-2-yl)indolin-2-one trifluoroacetate. TFA (1 mL) was added to a solution of tert-butyl (R)-4-(5-(2-oxoindolin-5-yl)-1,3,4-thiadiazol-2-yl)-1-(6-(trifluoromethyl)pyridin-3-yl)butan-2-ylcarbamate (185 mg, 347 µmol) in DCM (2 mL), and the mixture was stirred at room temperature for 2 hours. The mixture was concentrated under reduced pressure, and the resulting yellow oil was purified by reversed phase HPLC (Shimadsu Valiant, Phenomenex Gemini C18 5 µm 100×30 mm, 10% to 70% H$_2$O/MeCN, 0.1% TFA) to provide 5-(5-((R)-3-amino-4-(6-(trifluoromethyl)pyridin-3-yl)butyl)-1,3,4-thiadiazol-2-yl)indolin-2-one trifluoroacetate as a white solid (38 mg, 88%). LCMS (API-ES) m/z: 434.0 (M+H$^+$); $^1$H NMR (300 MHz, CD$_3$OD) δ ppm 2.24 (q, J=7.4 Hz, 2 H), 3.12 (dd, J=14.3, 7.4 Hz, 1 H), 3.24 (dd, J=14.3, 6.7 Hz, 1 H), 3.33-3.40 (m, 2 H), 3.61 (s, 2 H), 3.78 (quin, J=6.7 Hz, 1 H), 7.01 (d, J=8.0 Hz, 1 H), 7.76-7.83 (m, 2 H), 8.01 (dd, J=8.0, 1.1 Hz, 1 H), 8.68 (d, J=1.1 Hz, 1 H).

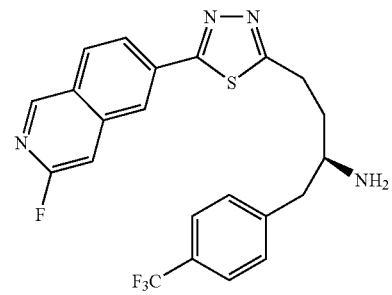

Example 48

(2R)-4-(5-(3-Fluoroisoquinolin-6-yl)-1,3,4-thiadiazol-2-yl)-1-(4-(trifluoromethyl)phenyl)butan-2-amine. This compound was prepared in a similar manner to Example 45 using (S)-2-(tert-butoxycarbonylamino)-3-(4-(trifluoromethyl)phenyl)propanoic acid instead of (S)-2-(tert-butoxycarbonyl)-3-(6-(trifluoromethyl)pyridin-3-yl)propanoic acid. (S)-2-(tert-Butoxycarbonylamino)-3-(4-(trifluoromethyl)phenyl)propanoic acid was obtained commercially from 3B Scientific Corporation Product List (Order Number 3B3-007199). LCMS (API-ES) m/z: 447 (M+H$^+$); $^1$H NMR (400 MHz, CD$_3$OD) δ ppm (m, 1 H), 2.01-2.10 (m, J=9.21, 9.21, 6.58, 4.82, 4.82 Hz, 1 H), 2.76-2.84 (m, 1 H), 2.90-3.02 (m, 1 H), 3.15-3.31 (m, 2 H), 3.34-3.43 (m, 1 H), 7.37-7.51 (m, 3 H), 7.60 (d, J=8.02 Hz, 2 H), 8.06-8.13 (m, 1 H), 8.14-8.20 (m, 1 H), 8.36 (s, 1 H), 9.00 (s, 1 H).

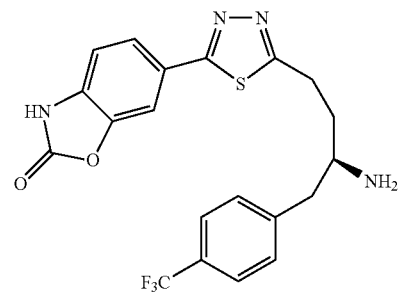

Example 49

6-(5-((R)-3-Amino-4-(4-(trifluoromethyl)phenyl)butyl)-1,3,4-thiadiazol-2-yl)benzo[d]oxazol-2(3H)-one. This compound was prepared in a similar manner to Example 45 using (S)-2-(tert-butoxycarbonylamino)-3-(4-(trifluoromethyl)phenyl)propanoic acid instead of (S)-2-(tert-butoxycarbonylamino)-3-(6-(trifluoromethyl)pyridin-3-yl)propanoic acid, and 2-oxo-2,3-dihydrobenzo[d]oxazole-6-carboxylic acid instead of 3-fluoroisoquinoline-6-carboxylic acid. LCMS (API-ES) m/z: 447 (M+H$^+$); $^1$H NMR (400 MHz, CD$_3$OD) d 1.91 (s, 1 H), 2.83 (s, 1 H), 2.94 (d, J=6.26 Hz, 1 H), 3.14-3.30 (m, 3 H), 7.17 (d, J=8.22 Hz, 1 H), 7.44 (d, J=8.02 Hz, 3 H), 7.62 (d, J=8.02 Hz, 2 H), 7.71 (s, 1 H), 7.77 (s, 1 H). (S)-2-(tert-butoxycarbonylamino)-3-(4-(trifluoromethyl)phenyl)propanoic acid was commercially available from 3B Scientific Corporation Product List (Order Number 3B3-007199). 2-Oxo-2,3-dihydrobenzo[d]oxazole-6-carboxylic acid was prepared as shown in Scheme 26.

Scheme 26

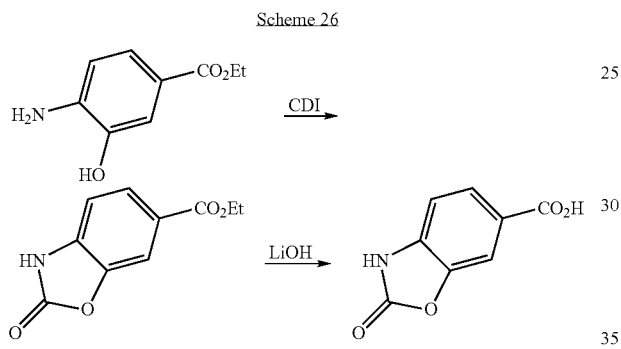

Ethyl 2-oxo-2,3-dihydrobenzo[d]oxazole-6-carboxylate. Methyl 4-amino-3-hydroxybenzoate (1.23 g, 7.36 mmol) (commercially available from Pfaltz & Bauer Chemicals Catalog (Order Number A22677)) and 1,1'-carbonyldiimidazole (1.19 g, 7.36 mmol) in 20 mL THF were heated by microwave at 100° C. for 10 minutes. The reaction mixture was used directly for next step. LCMS (API-ES) m/z: 194 (M+H$^+$).

2-Oxo-2,3-dihydrobenzo[d]oxazole-6-carboxylic acid. To ethyl 2-oxo-2,3-dihydrobenzo[d]oxazole-6-carboxylate in THF (20 mL) was added LiOH (2 g in 10 mL water). The mixture was stirred at room temperature for 20 hours. The solvent was evaporated. The residue was taken up in water and acidified with 5 N HCl to pH=5. The solid was recovered by filtration, washing with water, to provide the pure product as a tan solid (1.44 g, 80%). LCMS (API-ES) m/z: 180 (M+H$^+$).

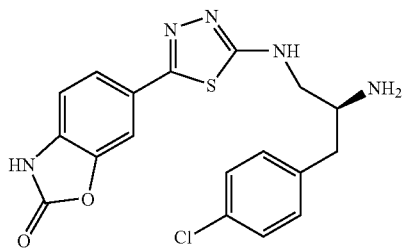

Example 50

6-(5-((S)-2-Amino-3-(4-chlorophenyl)propylamino)-1,3,4-thiadiazol-2-yl)benzo[d]oxazol-2(3H)-one: The title compound was synthesized in a similar manner to that described for Example 11, by alkylating tert-butyl 5-(3-fluoro-4-nitrophenyl)-1,3,4-thiadiazol-2-ylcarbamate, prepared as in Example 1, with tert-butyl (4S)-4-(4-chlorobenzyl)-1,2,3-oxathiazolidine-3-carboxylate 2,2-dioxide instead of tert-butyl (4S)-4-(4-(trifluoromethyl)benzyl)-1,2,3-oxathiazolidine-3-carboxylate 2-oxide. tert-Butyl (4S)-4-(4-chlorobenzyl)-1,2,3-oxathiazolidine-3-carboxylate 2,2-dioxide was prepared as shown in Scheme 1b but using (S)-2-amino-3-(4-chlorophenyl)propanoic acid instead of (S)-2-amino-3-(4-(trifluoromethyl)phenyl)propanoic acid. LCMS (API-ES) m/z: 402 (M+H$^+$); $^1$H NMR (400 MHz, CD$_3$OD): δ ppm 2.95-3.07 (m, 2H), 3.55-3.60 (m, 1H), 3.70-3.75 (m, 1H), 3.80-3.86 (m, 1H), 7.17 (d, J=8 Hz, 1H), 7.33 (d, J=8 Hz, 2H), 7.40 (d, J=8 Hz, 2H), 7.59 (d, J=8 Hz, 1H), 7.69 (s, 1H).

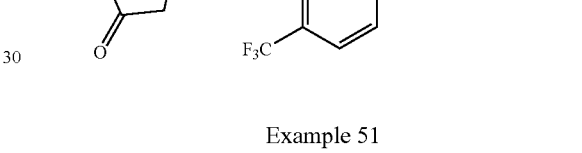

Example 51

5-(5-((2R,3S)-2-Amino-3-hydroxy-3-(4-(trifluoromethyl)phenyl)propylamino)-1,3,4-thiadiazol-2-yl)indolin-2-one trifluoroacetate: The title compound was synthesized as shown in Scheme 27.

Scheme 27

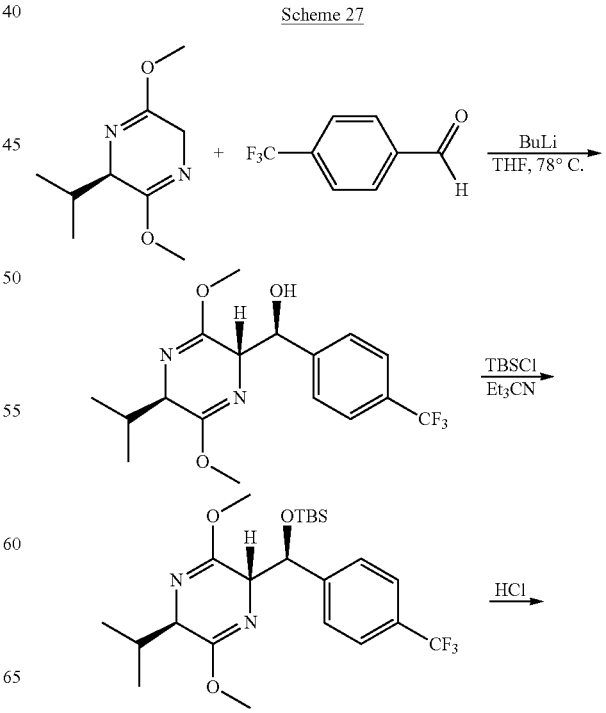

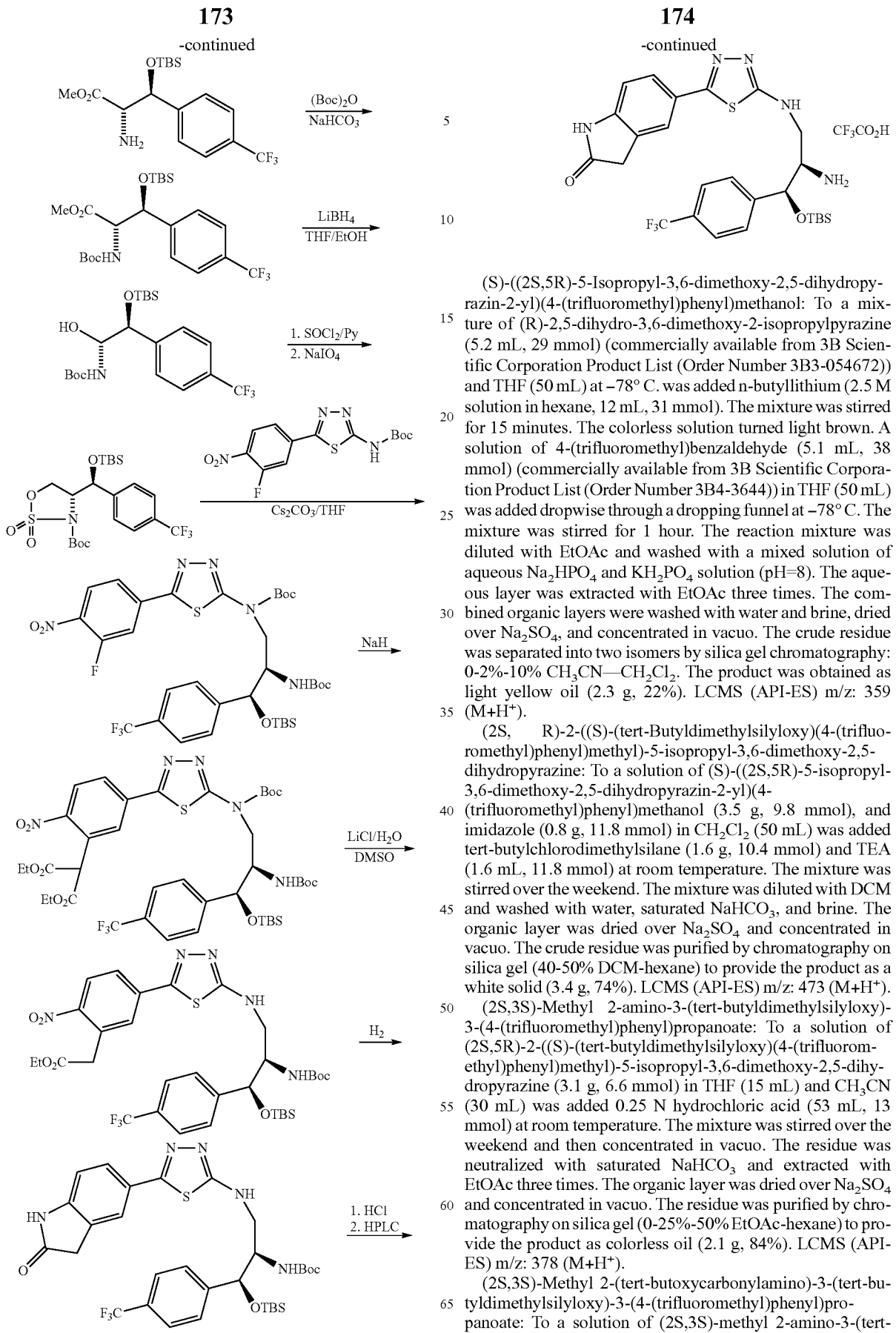

(S)-((2S,5R)-5-Isopropyl-3,6-dimethoxy-2,5-dihydropyrazin-2-yl)(4-(trifluoromethyl)phenyl)methanol: To a mixture of (R)-2,5-dihydro-3,6-dimethoxy-2-isopropylpyrazine (5.2 mL, 29 mmol) (commercially available from 3B Scientific Corporation Product List (Order Number 3B3-054672)) and THF (50 mL) at −78° C. was added n-butyllithium (2.5 M solution in hexane, 12 mL, 31 mmol). The mixture was stirred for 15 minutes. The colorless solution turned light brown. A solution of 4-(trifluoromethyl)benzaldehyde (5.1 mL, 38 mmol) (commercially available from 3B Scientific Corporation Product List (Order Number 3B4-3644)) in THF (50 mL) was added dropwise through a dropping funnel at −78° C. The mixture was stirred for 1 hour. The reaction mixture was diluted with EtOAc and washed with a mixed solution of aqueous Na$_2$HPO$_4$ and KH$_2$PO$_4$ solution (pH=8). The aqueous layer was extracted with EtOAc three times. The combined organic layers were washed with water and brine, dried over Na$_2$SO$_4$, and concentrated in vacuo. The crude residue was separated into two isomers by silica gel chromatography: 0-2%-10% CH$_3$CN—CH$_2$Cl$_2$. The product was obtained as light yellow oil (2.3 g, 22%). LCMS (API-ES) m/z: 359 (M+H$^+$).

(2S, R)-2-((S)-(tert-Butyldimethylsilyloxy)(4-(trifluoromethyl)phenyl)methyl)-5-isopropyl-3,6-dimethoxy-2,5-dihydropyrazine: To a solution of (S)-((2S,5R)-5-isopropyl-3,6-dimethoxy-2,5-dihydropyrazin-2-yl)(4-(trifluoromethyl)phenyl)methanol (3.5 g, 9.8 mmol), and imidazole (0.8 g, 11.8 mmol) in CH$_2$Cl$_2$ (50 mL) was added tert-butylchlorodimethylsilane (1.6 g, 10.4 mmol) and TEA (1.6 mL, 11.8 mmol) at room temperature. The mixture was stirred over the weekend. The mixture was diluted with DCM and washed with water, saturated NaHCO$_3$, and brine. The organic layer was dried over Na$_2$SO$_4$ and concentrated in vacuo. The crude residue was purified by chromatography on silica gel (40-50% DCM-hexane) to provide the product as a white solid (3.4 g, 74%). LCMS (API-ES) m/z: 473 (M+H$^+$).

(2S,3S)-Methyl 2-amino-3-(tert-butyldimethylsilyloxy)-3-(4-(trifluoromethyl)phenyl)propanoate: To a solution of (2S,5R)-2-((S)-(tert-butyldimethylsilyloxy)(4-(trifluoromethyl)phenyl)methyl)-5-isopropyl-3,6-dimethoxy-2,5-dihydropyrazine (3.1 g, 6.6 mmol) in THF (15 mL) and CH$_3$CN (30 mL) was added 0.25 N hydrochloric acid (53 mL, 13 mmol) at room temperature. The mixture was stirred over the weekend and then concentrated in vacuo. The residue was neutralized with saturated NaHCO$_3$ and extracted with EtOAc three times. The organic layer was dried over Na$_2$SO$_4$ and concentrated in vacuo. The residue was purified by chromatography on silica gel (0-25%-50% EtOAc-hexane) to provide the product as colorless oil (2.1 g, 84%). LCMS (API-ES) m/z: 378 (M+H$^+$).

(2S,3S)-Methyl 2-(tert-butoxycarbonylamino)-3-(tert-butyldimethylsilyloxy)-3-(4-(trifluoromethyl)phenyl)propanoate: To a solution of (2S,3S)-methyl 2-amino-3-(tert-butyldimethylsilyloxy)-3-(4-(trifluoromethyl)phenyl)

propanoate (2.1 g, 5.5 mmol) in THF (14 mL) was added di-tert-butyl dicarbonate (1.4 g, 6.7 mmol) and sodium carbonate monohydrate (1.4 g, 11.1 mmol) at room temperature. The mixture was stirred overnight and then filtered through a scintered glass funnel. The filtrate was concentrated in vacuo and the residue was purified by chromatography on a short silica gel column(0-10% EtOAc-hexane. The product was obtained as colorless oil (2.6 g, 100%). LCMS (API-ES) m/z: 378 (M+H$^+$).

tert-Butyl (1S,2R)-1-(tert-butyldimethylsilyloxy)-3-hydroxy-1-(4-(trifluoromethyl)phenyl)propan-2-ylcarbamate: To a solution of (2S,3S)-methyl 2-(tert-butoxycarbonyl)-3-(tert-butyldimethylsilyloxy)-3-(4-(trifluoromethyl)phenyl)propanoate (2.6 g, 5.5 mmol) in THF (32.4 mL, 400 mmol) and EtOH (9.7 mL, 166 mmol) was added lithium borohydride (2.0 M solution in THF, 5.6 mL, 11.1 mmol) at 0° C. The reaction mixture was stirred at 0° C. for 1 hour. The cooling bath was removed. HPLC-MS showed over 90% conversion after 24 hours. The reaction was quenched with 5% citric acid in water. The mixture was then concentrated in vacuo and the residue was extracted with EtOAc twice. The organic phase was washed with saturated NaHCO$_3$, water and brine, dried over Na$_2$SO$_4$, and then concentrated in vacuo. The residue was purified by chromatography on silica gel (0-10% to remove the starting material, then 10%-20% EtOAc-hexane) to provide the product as a white solid (1.80 g, 73%). LCMS (API-ES) m/z: 350 (M+H$^+$).

tert-Butyl (4R)-4-((S)-((tert-butyl(dimethyl)silyl)oxy)(4-(trifluoromethyl)phenyl)methyl)-1,2,3-oxathiazolidine-3-carboxylate 2-oxide: To a solution of thionyl chloride (0.74 mL, 10.1 mmol) in MeCN (12 mL) and DCM (12 mL) at −78° C. was added a solution of tert-butyl (1S,2R)-1-(tert-butyldimethylsilyloxy)-3-hydroxy-1-(4-(trifluoromethyl)phenyl)propan-2-ylcarbamate (1.82 g, 4.05 mmol) in MeCN (20 mL), DCM (20 mL) and THF (4 mL) dropwise via a dropping funnel. After 10 minutes, pyridine (1.82 mL, 22.3 mmol) was added dropwise at −78° C. The mixture was allowed to warm to room temperature and stirred overnight. The solvent was removed in vacuo. The residue was taken up in EtOAc (60 mL), washed with water and brine, dried over Na$_2$SO$_4$ and concentrated in vacuo. The residue was purified by chromatography on silica gel (0%-10% EtOAc-hexane) to provide the product as a white solid (1.80 g, 90%).

tert-Butyl (4R)-4-((S)-((tert-butyl(dimethyl)silyl)oxy)(4-(trifluoromethyl)phenyl)methyl)-1,2,3-oxathiazolidine-3-carboxylate 2,2-dioxide: A mixture of tert-butyl (4R)-4-((S)-((tert-butyl(dimethyl)silyl)oxy)(4-(trifluoromethyl)phenyl)methyl)-1,2,3-oxathiazolidine-3-carboxylate 2-oxide (1.80 g, 3.63 mmol), sodium periodate (3.11 g, 14.5 mmol), ruthenium(III) chloride hydrate (0.0164 g, 0.0726 mmol) in CH$_3$CN:water:EtOAc (51 mL:17 mL:9 mL) was put in a sonicator for 17 minutes. The dark mixture became a yellow suspension. HPLC-MS showed no more starting material. The reaction mixture was filtered through celite and the solid was washed with EtOAc. The organic phase was washed with water and brine, dried over Na$_2$SO$_4$, and then concentrated in vacuo. The residue was purified by chromatography on silica gel (0-4%-10% EtOAc-hexane) to provide the product as a white solid (1.75 g, 94%). LCMS (API-ES) m/z: 456 (M+H$^+$-56).

tert-Butyl ((2R,3S)-2-((tert-butoxycarbonyl)amino)-3-((tert-butyl(dimethyl)silyl)oxy)-3-(4-(trifluoromethyl)phenyl)propyl)(5-(3-fluoro-4-nitrophenyl)-1,3,4-thiadiazol-2-yl)carbamate: To a mixture of tert-butyl 5-(3-fluoro-4-nitrophenyl)-1,3,4-thiadiazol-2-ylcarbamate (0.64 g, 1.89 mmol) in THF (6 mL) was added cesium carbonate (1.07 g, 3.28 mmol). The mixture was heated to 55° C. for 10 minutes and then tert-butyl (4R)-4-((S)-((tert-butyl(dimethyl)silyl)oxy)(4-(trifluoromethyl)phenyl)methyl)-1,2,3-oxathiazolidine-3-carboxylate 2,2-dioxide (0.84 g, 1.64 mmol) in THF (4 mL) was added. The mixture was heated for 1 hour after the addition. HPLC-MS showed the product and thiadiazole starting material. The reaction was concentrated in vacuo and EtOAc (75 mL) was added. The mixture was cooled to 0° C. and 5% HCl (50 mL) was slowly added. The mixture was stirred for 1 hour. The organic phase was separated, and the aqueous phase was extracted twice with EtOAc. To the combined EtOAc solution was added saturated NaHCO$_3$ and Na$_2$CO$_3$ until it was basic (pH=9). The organic layer was washed with brine, dried over Na$_2$SO$_4$, and then concentrated in vacuo. The residue was purified by chromatography on silica gel (50%-100% DCM-hexane) to provide the product as a yellow solid (1.18 g, 93%). LCMS (API-ES) m/z: 772 (M+H$^+$).

Diethyl (5-(5-((tert-butoxycarbonyl)((2R,3S)-2-((tert-butoxycarbonyl)amino)-3-((tert-butyl(dimethyl)silyl)oxy)-3-(4-(trifluoromethyl)phenyl)propyl)amino)-1,3,4-thiadiazol-2-yl)-2-nitrophenyl)propanedioate: To a solution of sodium hydride (60% dispersion in mineral oil, 0.15 g, 3.74 mmol) in dioxane (2 mL) was added a solution of diethyl malonate (0.57 mL, 3.74 mmol) in dioxane (3 mL). The mixture was stirred for 15 minutes and then a solution of tert-butyl ((2R,3S)-2-((tert-butoxycarbonyl)amino)-3-((tert-butyl(dimethyl)silyl)oxy)-3-(4-(trifluoromethyl)phenyl)propyl)(5-(3-fluoro-4-nitrophenyl)-1,3,4-thiadiazol-2-yl)carbamate (0.58 g, 0.75 mmol) in dioxane (3 mL) was added. The reaction mixture was stirred 16 hours, concentrated in vacuo, and the reaction was quenched with saturated NH$_4$Cl. The mixture was extracted with EtOAc three times. The organic phase was dried over Na$_2$SO$_4$, concentrated in vacuo and purified by chromatography on silica gel (0-15% EtOAc-hexane) to provide the product as a yellow solid (0.68 g, 99%). LCMS (API-ES) m/z: 856 (M+H$^+$-56).

Ethyl 2-(5-(5-((2R,3S)-2-(tert-butoxycarbonyl)-3-(tert-butyldimethylsilyloxy)-3-(4-(trifluoromethyl)phenyl)propylamino)-1,3,4-thiadiazol-2-yl)-2-nitrophenyl)acetate: To a solution of diethyl 2-(5-(5-(tert-butoxycarbonyl)-1,3,4-thiadiazol-2-yl)-2-nitrophenyl)malonate (0.68 g, 0.75 mmol) in DMSO (10 mL) was added lithium chloride (0.19 g, 4.48 mmol) and water (0.14 mL, 7.47 mmol). The mixture was heated to 100° C. and stirred overnight. The reaction mixture was cooled and diluted with EtOAc (60 mL) and brine (60 mL). The organic layer was separated, washed with brine, dried over Na$_2$SO$_4$, and then concentrated in vacuo. The product was purified by chromatography on silica gel (10-45-50% EtOAc-hexane) to provide the product as a yellow solid. (0.12 g, 21%). LCMS (API-ES) m/z: 740 (M+H$^+$).

tert-Butyl (1S,2R)-1-(tert-butyldimethylsilyloxy)-3-(5-(2-oxoindolin-5-yl)-1,3,4-thiadiazol-2-ylamino)-1-(4-(trifluoromethyl)phenyl)propan-2-ylcarbamate: To a solution of ethyl 2-(5-(5-((2R,3S)-2-(tert-butoxycarbonyl)-3-(tert-butyldimethylsilyloxy)-3-(4-(trifluoromethyl)phenyl)propylamino)-1,3,4-thiadiazol-2-yl)-2-nitrophenyl)acetate (0.11 g, 0.15 mmol) in EtOH (5 mL) was added palladium (10 wt. % on activated carbon, 0.016 g, 0.015 mmol). The mixture was connected to a hydrogen balloon and stirred at room temperature for 1.5 hours to give the aniline intermediate. The catalyst was filtered through celite. The celite was washed with MeOH, and the solution was concentrated in vacuo. The yellow solid was dissolved in EtOH (10 mL) and cooled to 0° C. 1.0 N hydrochloric acid (0.21 mL, 0.21 mmol) and palladium (10 wt. % on activated carbon, 0.0158 g, 0.0149 mmol) were added. The mixture was connected to a H$_2$ balloon and stirred 16 hours. The mixture was concentrated in vacuo and diluted with EtOAc and saturated NaHCO$_3$. The organic phase was washed with water and brine, dried over Na$_2$SO$_4$, and concentrated in vacuo. The crude product was purified by chromatography on silica gel (50-65-70% EtOAc-hexane) to provide the product as a yellow solid (22 mg, 21%). LCMS (API-ES) m/z: 664 (M+H$^+$).

5-(5-((2R,3S)-2-Amino-3-hydroxy-3-(4-(trifluoromethyl)phenyl)propylamino)-1,3,4-thiadiazol-2-yl)indolin-2-one trifluoroacetate: To a solution of tert-butyl (1S,2R)-1-(tert-butyldimethylsilyloxy)-3-(5-(2-oxoindolin-5-yl)-1,3,4-thiadiazol-2-ylamino)-1-(4-(trifluoromethyl)phenyl)propan-2-ylcarbamate (0.018 g, 0.027 mmol) in 1,4-dioxane (2 mL) was added hydrochloric acid (4.0 M solution in dioxane, 0.81 mL, 3.3 mmol). The mixture was stirred at room temperature overnight. HPLC-MS showed the product as the major peak. The solvent was removed in vacuo and the residue was purified by preparative HPLC (25%-100% CH$_3$CN (with 0.1% TFA)-water (with 0.1% TFA) in 12 min, Phenomenex Luna C18 5 μm 150×30 mm). The product was obtained as a white solid (12 mg, 77%). LCMS (API-ES) m/z: 450 (M+H$^+$).

2.1 PKB Assay Testing

The kinase assay for evaluating PKB activity comprises active PKB enzymes, a PKB specific substrate, and P$^{33}$-labeled ATP. Two form of PKBα enzymes were used, the full length PKBα and a kinase domain of PKBα with pleckstrin domain (amino acids 1-117) deleted. Both PKB enzymes were obtained from Upstate cell signaling solutions (Cat. #14-276 and 14-341). The PKB substrate used is a synthetic peptide (ARKRERTYSFGHHA (SEQ ID NO: 1)) as described in Obata et al., J. Biol. Chem. 275 (46), 36108-36115 (2000). The phosphorylated substrate was captured by a phosphocellulose membrane filter plate (MILLIPORE) and measured by a Wallac Microbeta liquid scintillation counter (Perkin Elmer). Table 1 provides the IC$_{50}$ values obtained for each of the examples with respect to PKBα.

PKB activity in cells was assayed in a PTEN null human breast tumor cell line MDA-MB-468 and U87-MG. The phosphorylation status of PKB substrate PRAS40, FKHRL1, GSK3a/b, and Tuberin is measured by immunoassays utilizing phospho-specific antibodies (Invitrogen, Cell signaling technology).

The effect of PKB inhibition on cell viability is measured in a range of human tumor cell lines including, but not limiting to, MDA-MB-468, MDA-MB-231, U87-MG, LN-229, PC3, DU145. The cells are treated in regular growth media for 72 hours and cell viability was measured by Alamar Blue (Invitrogen).

The effect of PKB inhibition on tumor growth in vivo is assessed in an established U87MG xenograft model. Athymic nude mice bearing U87MG tumors (approximately 200 mm$^3$) in the right flank are treated with the compound orally at the dosage of 15, 30, and 60 mg/kg/day (n=10) for 17 days. Tumor volume and body weight are measured twice per week. Data are expressed as means plus or minus standard errors and plotted as a function of time. Statistical significance of the effect is evaluated by Repeated Measures Analysis of Variance (RMANOVA) followed by Scheffe post hoc testing for multiple comparisons. Tumor stasis and regression are observed.

TABLE 1

| Example | Structure[a] | IC$_{50}$[b] |
|---|---|---|
| 1 | | ++++ |
| 2 | | ++++ |
| 3 | | +++ |

TABLE 1-continued

| Example | Structure | IC$_{50}$ |
|---|---|---|
| 4 | | ++++ |
| 5 | | ++ |
| 6 | | ++ |
| 7 | | ++++ |
| 8 | | +++ |
| 9 | | +++ |

TABLE 1-continued

| Example | Structure[a] | IC$_{50}$[b] |
|---|---|---|
| 10 | | ++++ |
| 11 | | ++++ |
| 12 | | +++ |
| 13 | | +++ |
| 14 | | +++ |
| 15 | | +++ |

TABLE 1-continued
| Example | Structure | IC$_{50}$[b] |
|---|---|---|
| 16 | 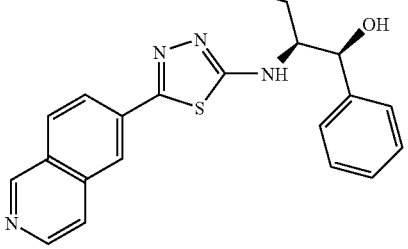 | ++ |
| 17 | 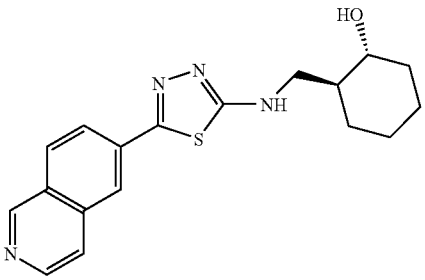 | +++ |
| 18 | 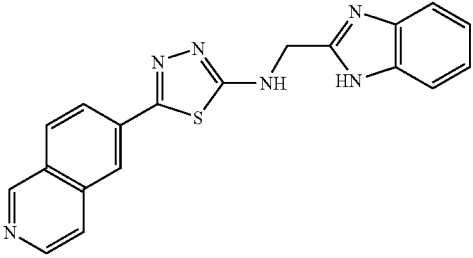 | ++ |
| 19 | 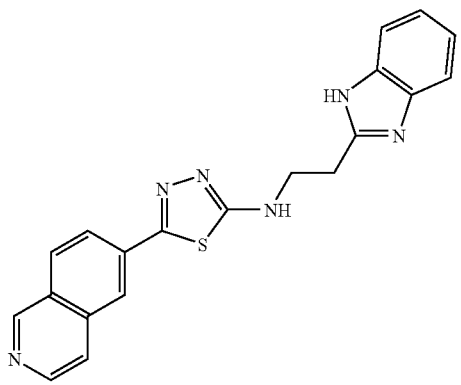 | ++ |
| 20 | 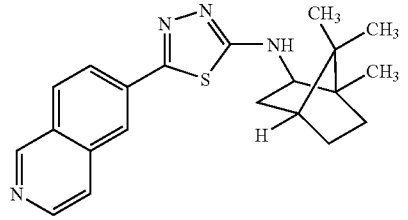 | ++ |

TABLE 1-continued

| Example | Structure<sup>a</sup> | IC<sub>50</sub><sup>b</sup> |
|---------|-----------------------|-----------------------------|
| 21 | | +++ |
| 22 | | ++ |
| 23 | | ++ |
| 24 | | ++ |
| 25 | | +++ |

TABLE 1-continued

| Example | Structure[a] | IC$_{50}$[b] |
|---|---|---|
| 26 | | +++ |
| 27 | | ++ |
| 28 | | ++ |
| 29 | | +++ |
| 30 | | +++ |

TABLE 1-continued

| Example | Structure | IC$_{50}$ |
|---|---|---|
| 31 | | ++ |
| 32 | | +++ |
| 33 | | +++ |
| 34 | | ++++ |
| 35 | | ++++ |
| 36 | | ND |

TABLE 1-continued

| Example | Structure[a] | IC$_{50}$[b] |
|---|---|---|
| 37 | | [c]ND |
| 38 | | [c]ND |
| 39 | | [c]ND |
| 40 | | [c]ND |
| 41 | | [c]ND |

TABLE 1-continued

| Example | Structure | IC$_{50}$ |
|---|---|---|
| 42 | | ++++ |
| 43 | | ++++ |
| 44 | | ++++ |
| 45 | | ++++ |
| 46 | | ++++ |

TABLE 1-continued

| Example | Structure[a] | IC$_{50}$[b] |
|---|---|---|
| 47 | | +++ |
| 48 | | ++++ |
| 49 | | ++++ |
| 50 | | ++++ |
| 51 | | ++++ |

[a]When the stereochemistry is not specified at a carbon bonded to four different groups, this indicates a mixture of stereoisomers is present.
[b]IC$_{50}$ Ranges:
+ IC$_{50}$ > 10 μM
++ 1 μM ≤ IC$_{50}$ ≤ 10 μM
+++ 0.05 μM ≤ IC$_{50}$ < 1μM
++++ IC$_{50}$ < 0.05 μM
[c]IC$_{50}$ value for this compound has not yet been determined.

Each of the compounds in the above table and tautomers, salts, neutral forms, solvates including hydrates, and stereoisomers thereof is preferred both individually and as a member of a group. Each of the groups in these compounds that corresponds to any of the variables in the compounds of Formula I, Formula II, Formula IV, and/or Formula V is also preferred.

The foregoing has demonstrated the pertinent and important features of the present invention. Many modifications and variations of the present invention can be made without departing from its spirit and scope, as will be apparent to those skilled in the art. The specific embodiments described herein are offered by way of example only, and the invention is to be limited only by the terms of the appended claims along with the full scope of equivalents to which such claims are entitled.

All references cited herein are incorporated herein by reference in their entireties and for all purposes as if specifically set forth herein and to the same extent as if each individual publication or patent or patent application was specifically and individually indicated to be incorporated by reference in its entirety for all purposes.

$R^5$ is selected from —H, —OR$^{10}$, —O—(C$_1$-C$_6$ alkyl)-O—R$^{10}$, C$_1$-C$_6$ alkyl, C$_1$-C$_6$ alkenyl, —(C$_1$-C$_6$ alkyl)-O—R$^{10}$, or —(C$_1$-C$_6$ alkyl)-O—C(O)—R$^{10}$;

$R^6$ is selected from —H, or C$_1$-C$_6$ alkyl;

$R^7$ is selected from —H, —OR$^{10}$, —O—(C$_1$-C$_6$ alkyl)—O—R$^{10}$, C$_1$-C$_6$ alkyl, C$_1$-C$_6$ alkenyl, —(C$_1$-C$_6$ alkyl)-O—R$^{10}$, or —(C$_1$-C$_6$ alkyl)-O—C(O)—R$^{10}$;

$R^8$ and $R^9$, in each instance, are independently selected from —H, C$_1$-C$_6$ alkyl, or aryl;

$R^{10}$ is selected from —H, C$_1$-C$_6$ alkyl, C$_1$-C$_6$ haloalkyl, —(C$_1$-C$_6$ alky)aryl, aryl, heteroaryl, C$_1$-C$_6$ hydroxyalkyl, or —(C$_1$-C$_6$ alkyl)-O—(C$_1$-C$_6$ alkyl), cycloalkyl, or heterocyclyl;

each t is independently selected from 0, 1, 2, or 3; and

Z is selected from aryl or heteroaryl;

wherein each of the above alkyl, aryl, heteroaryl, cycloalkyl, and heterocyclyl moieties and heterocyclic and carbocyclic rings are optionally and independently substituted by 1-3 substituents selected from amino, aryl, heteroaryl, cycloalkyl, or heterocyclyl optionally substituted by 1-5 substituents selected from

---

---

What is claimed is:

1. A compound of Formula V

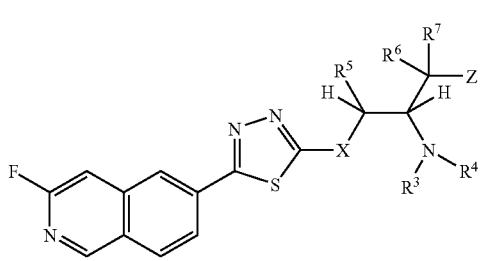

V wherein:

X is selected from NR$^2$ or CR$^{2a}$R$^{2b}$;

$R^2$ may be absent or is selected from —H, C$_1$-C$_8$ alkyl, —(C$_1$-C$_6$ alkyl)aryl, or —C(O)(C$_1$-C$_6$ alkyl);

$R^{2a}$ and $R^{2b}$ may both be absent or are independently selected from —H, C$_1$-C$_8$ alkyl, —(C$_1$-C$_6$)alkyl)aryl, or —C(O)(C$_1$-C$_6$alkyl);

$R^3$ is selected from —H, C$_1$-C$_8$ alkyl, —C(O)(CR$^8$R$^9$)$_t$N(R$^7$)$_2$, —(CR$^8$R$^9$)$_t$(aryl), —(CR$^8$R$^9$)$_t$(heteroaryl), —(CR$^8$R$^9$)$_t$(cycloalkyl), or —(CR$^8$R$^9$)$_t$(heterocyclyl);

$R^4$ is selected from —H, C$_1$-C$_8$ alkyl, —(C$_1$-C$_6$ alkyl)aryl, or —C(O)(C$_1$-C$_6$ alkyl);

C$_1$-C$_6$ alkoxy,
C$_1$-C$_6$ alkyl optionally substituted by halo,
aryl,
halo,
hydroxyl,
heteroaryl,
C$_1$-C$_6$ hydroxyalkyl, or
—NHS(O)$_2$—(C$_1$-C$_6$ alkyl);

C$_1$-C$_6$ alkyl, C$_1$-C$_6$ haloalkyl, C$_1$-C$_6$ hydroxyalkyl, C$_1$-C$_6$ alkoxy, C$_1$-C$_6$ haloalkoxy, C$_1$-C$_6$ hydroxyalkoxy, C$_1$-C$_6$ alkylamino, C$_2$-C$_6$ alkenyl, or C$_2$-C$_6$ alkynyl, wherein each of which may be interrupted by one or more hetero atoms, cyano,
halo,
hydroxyl,
nitro,
oxo,
—NH(CO)—O—(C$_1$-C$_6$ alkyl)aryl, —NH(CO)—O—(C$_1$-C$_6$ alkyl), —N(C$_1$-C$_6$ alkyl)(CO)—O—(C$_1$-C$_6$ alkyl)aryl, —N(C$_1$-C$_6$ alkyl)(CO)—O—(C$_1$-C$_6$ alkyl), —C(O)OH, —C(O)O(C$_1$-C$_6$ alkyl), —C(O)NH$_2$, —C(O)N(H)—(C$_1$-C$_6$ alkyl), —C(O)N(C$_1$-C$_6$ alkyl)$_2$, —NH(C$_1$-C$_6$ alkyl), —N(C$_1$-C$_6$ alkyl)$_2$, —(C$_2$-C$_4$ alkenyl)heterocyclyl, or —(C$_2$-C$_4$ alkenyl)cycloalkyl, or
—O—aryl;

or a pharmaceutically acceptable salt, stereoisomer, or mixture thereof.

2. The compound of claim 1, wherein the compound has the Formula VA

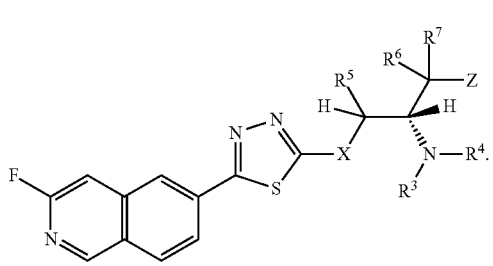

3. The compound of claim 1, wherein X is $NR^2$.
4. The compound of claim 3, wherein $R^2$ is —H.
5. The compound of claim 1, wherein X is $CR^{2a}R^{2b}$.
6. The compound of claim 5, wherein $R^{2a}$ and $R^{2b}$ are both —H.
7. The compound of claim 1, wherein $R^5$ is —H or $C_1$-$C_6$ alkyl.
8. The compound of claim 1, wherein $R^6$ is —H.
9. The compound of claim 1, wherein $R^7$ is —H.
10. The compound of claim 1, wherein $R^7$ is —$OR^{10}$, —O—($C_1$-$C_6$ alkyl)-O—$R^{10}$, $C_1$-$C_6$ alkyl, $C_1$-$C_6$ alkenyl, —($C_1$-$C_6$ alkyl)-O—$R^{10}$, or —($C_1$-$C_6$ alkyl)-O—C(O)—$R^{10}$.
11. The compound of claim 1, wherein $R^7$ is selected from —H, methyl, ethyl, propyl, ethenyl, propenyl, hydroxymethyl, methoxymethyl, —$CH_2$—O—C(O)—($C_1$-$C_6$ alkyl), 1-hydroxyethyl, or methoxymethoxy.
12. The compound of claim 1, wherein Z is selected from optionally substituted phenyl, optionally substituted indolyl, optionally substituted naphthyl, optionally substituted pyridyl. or optionally substituted thiophenyl.
13. The compound of claim 1, wherein Z is selected from phenyl, indolyl, naphthyl, pyridyl, or thiophenyl, each of which is optionally substituted with 1-3 substituents selected from —Cl, —F, —$CF_3$, —OH, —O—($C_1$-$C_6$ alkyl), —O—($C_1$-$C_6$ alkyl)-Cl, —O—($C_1$-$C_6$ alkyl)-OH, —$C_1$-$C_6$ alkyl, —$OCF_3$, —NH(CO)—O—($C_1$-$C_6$ alkyl)aryl, or —NH(CO)—O—($C_1$-$C_6$ alkyl).
14. The compound of claim 1, wherein Z is selected from phenyl, indolyl, naphthyl, pyridyl, thiophenyl, 4-chlorophenyl, 4-trifluoromethylphenyl, 3-chlorophenyl, 3-trifluoromethylphenyl, 4-methoxyphenyl, 3-fluoro-4-trifluoromethylphenyl, 4-chloro-3-fluorophenyl, 4-(3-chloropropoxy)phenyl, 4-(3-hydroxypropoxy)phenyl, 3,4-dichlorophenyl, 4-fluorophenyl, 2,4-dichlorophenyl, 4-methylphenyl, 3,4-difluorophenyl, 3-fluoro-4-methoxyphenyl, 3,5-difluorophenyl, 6-trifluoromethylmidin-3-yl, 5-methoxy-6-trifluoromethylpyridin-3-yl, 2-fluoro-4-trifluoromethylphenyl, 4-trifluoromethoxyphenyl, 2,3-difluoro-4-trifluoromethylphenyl, 4-hydroxyphenyl, 3-methoxy-4-trifluoromethylphenyl, 3-hydroxy-4-trifluoromethylphenyl, 5-chlorothiophen-2-yl, 3-fluoro-4-hydroxyphenyl, or a phenyl substituted in the 4 position with —NH—C(O)—O—$CH_2$-phenyl.
15. The compound of claim 1, wherein $R^3$ and $R^4$ are each H.
16. A pharmaceutical composition, comprising: a pharmaceutically-acceptable carrier and the compound of claim 1.

* * * * *

SEQUENCE LISTING

<160> NUMBER OF SEQ ID NOS: 1

<210> SEQ ID NO 1
<211> LENGTH: 14
<212> TYPE: PRT
<213> ORGANISM: Artificial Sequence
<220> FEATURE:
<223> OTHER INFORMATION: Synthetic peptide

<400> SEQUENCE: 1

Ala Arg Lys Arg Glu Arg Thr Tyr Ser Phe Gly His His Ala
1               5                   10